US009175069B2

(12) United States Patent
Garcia-Sastre et al.

(10) Patent No.: US 9,175,069 B2
(45) Date of Patent: Nov. 3, 2015

(54) MONOCLONAL ANTIBODIES AGAINST INFLUENZA VIRUS GENERATED BY CYCLICAL ADMINISTRATION AND USES THEREOF

(71) Applicant: Icahn School of Medicine at Mount Sinai, New York, NY (US)

(72) Inventors: Adolfo Garcia-Sastre, New York, NY (US); Peter Palese, New York, NY (US); Taia T. Wang, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/162,354

(22) Filed: Jan. 23, 2014

(65) Prior Publication Data

US 2014/0170163 A1    Jun. 19, 2014

Related U.S. Application Data

(62) Division of application No. 12/788,103, filed on May 26, 2010, now Pat. No. 8,673,314.

(60) Provisional application No. 61/181,263, filed on May 26, 2009, provisional application No. 61/224,302, filed on Jul. 9, 2009, provisional application No. 61/305,898, filed on Feb. 18, 2010.

(51) Int. Cl.
*C07K 16/10* (2006.01)
*G01N 33/569* (2006.01)
*A61K 39/00* (2006.01)

(52) U.S. Cl.
CPC ...... *C07K 16/1018* (2013.01); *G01N 33/56983* (2013.01); *A61K 2039/505* (2013.01); *C07K 2317/33* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,182,192 A | 1/1993 | Steplewski et al. |
| 5,413,923 A | 5/1995 | Kucherlapati et al. |
| 5,545,806 A | 8/1996 | Lonberg et al. |
| 5,569,825 A | 10/1996 | Lonberg et al. |
| 5,571,709 A | 11/1996 | Devauchelle et al. |
| 5,589,174 A | 12/1996 | Okuno et al. |
| 5,625,126 A | 4/1997 | Lonberg et al. |
| 5,631,350 A | 5/1997 | Okuno et al. |
| 5,633,425 A | 5/1997 | Lonberg et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,916,771 A | 6/1999 | Hori et al. |
| 6,001,634 A | 12/1999 | Palese et al. |
| 6,337,070 B1 | 1/2002 | Okuno et al. |
| 6,720,409 B2 | 4/2004 | Okuno et al. |
| 6,887,699 B1 | 5/2005 | Palese et al. |
| 8,367,077 B2 | 2/2013 | Zurbriggen et al. |
| 8,603,467 B2 | 12/2013 | Chen et al. |
| 8,673,314 B2 | 3/2014 | Garcia-Sastre et al. |
| 8,828,406 B2 | 9/2014 | Garcia-Sastre et al. |
| 2003/0134338 A1 | 7/2003 | Makarovskiy |
| 2005/0009008 A1 | 1/2005 | Robinson et al. |
| 2005/0064391 A1 | 3/2005 | Segal et al. |
| 2005/0106178 A1 | 5/2005 | O'Hagan |
| 2005/0201946 A1 | 9/2005 | Friede et al. |
| 2006/0008473 A1 | 1/2006 | Yang et al. |
| 2007/0020238 A1 | 1/2007 | Baltimore et al. |
| 2007/0036809 A1 | 2/2007 | Michl et al. |
| 2008/0019998 A1 | 1/2008 | Wang et al. |
| 2008/0032921 A1 | 2/2008 | Alexander et al. |
| 2008/0152657 A1 | 6/2008 | Horowitz et al. |
| 2008/0176247 A1 | 7/2008 | Chou et al. |
| 2009/0081255 A1 | 3/2009 | Bublot et al. |
| 2009/0291472 A1 | 11/2009 | Lu et al. |
| 2009/0304730 A1 | 12/2009 | Arnon et al. |
| 2009/0304739 A1 | 12/2009 | Rappuoli et al. |
| 2010/0297174 A1 | 11/2010 | Garcia-Sastre et al. |
| 2011/0027270 A1 | 2/2011 | Garcia-Sastre et al. |
| 2012/0039898 A1 | 2/2012 | Throsby et al. |
| 2012/0122185 A1 | 5/2012 | Palese et al. |
| 2012/0244183 A1 | 9/2012 | Garcia-Sastre et al. |
| 2013/0129747 A1 | 5/2013 | Schrader |
| 2013/0129761 A1 | 5/2013 | Garcia-Sastre et al. |
| 2013/0209499 A1 | 8/2013 | Garcia-Sastre et al. |
| 2014/0170163 A1 | 6/2014 | Garcia-Sastre et al. |
| 2014/0328875 A1 | 11/2014 | Garcia-Sastre et al. |

FOREIGN PATENT DOCUMENTS

| | | |
|---|---|---|
| CA | 2121559 | 10/1994 |
| WO | WO 84/00687 | 3/1984 |

(Continued)

OTHER PUBLICATIONS

Wang et al (PNAS 107:18979-18984, 2010).*
Ekiert et al, Science 324:246-252, 2009.*
Schneeman et al, Journal of Virology 11686-11697, 2012.*
Vanlandschoot et al, Journal of General Virology 79:1781-1791, 1998.*
Vareckova et al, Virus Research 132:181-186, 2008.*
Ekiert et al., 2009, "Antibody recognition of a highly conserved influenza virus epitope", Science; 324(5924):246-251.
International Search Report of International application No. PCT/US2011/025467, dated Oct. 19, 2011.
International Search Report of International application No. PCT/US2010/036170, dated Aug. 17, 2010.

(Continued)

*Primary Examiner* — Mary E Mosher
(74) *Attorney, Agent, or Firm* — Jones Day

(57) ABSTRACT

Provided herein are methods of producing neutralizing monoclonal antibodies, by cyclical immunization, that cross-react with strains of Influenza virus of the same subtype or different subtypes. Also provided herein are compositions comprising such antibodies and methods of using such antibodies to diagnose, prevent or treat Influenza virus disease.

36 Claims, 32 Drawing Sheets

(56) References Cited

FOREIGN PATENT DOCUMENTS

Figure 1:
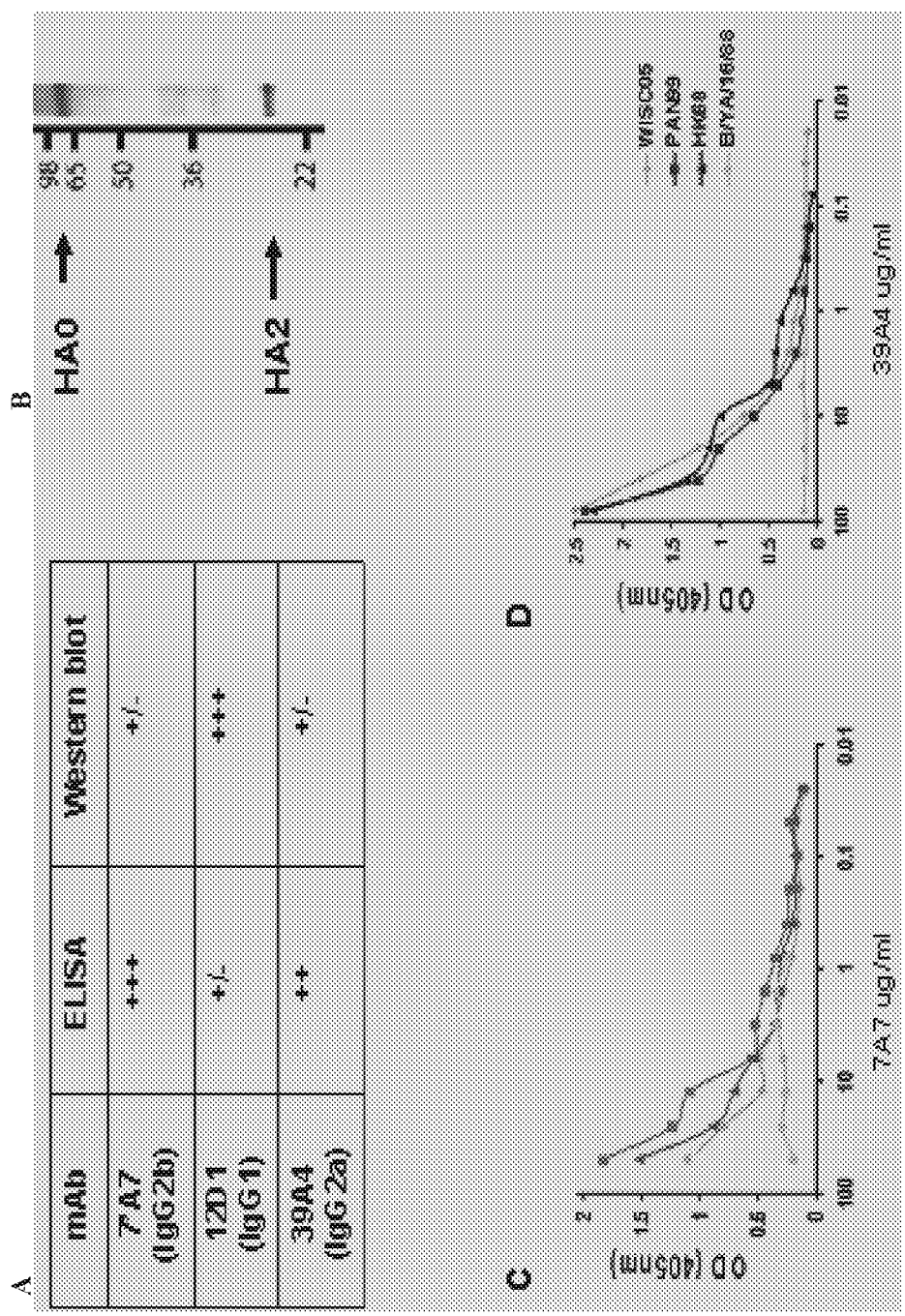

| WO | WO 92/01047 | 1/1992 |
|---|---|---|
| WO | WO 94/16109 | 7/1994 |
| WO | WO 94/17826 | 8/1994 |
| WO | WO 95/34324 | 12/1994 |
| WO | WO 96/33735 | 10/1996 |
| WO | WO 96/34096 | 10/1996 |
| WO | WO 98/24893 | 6/1998 |
| WO | WO 2007/045674 | 4/2007 |
| WO | WO 2007/064802 | 6/2007 |
| WO | WO 2007/134327 A2 | 11/2007 |
| WO | WO 2008/028946 A2 | 3/2008 |
| WO | WO 2008/032219 | 3/2008 |
| WO | WO 2009/025770 A2 | 2/2009 |
| WO | WO 2009/036157 A1 | 3/2009 |
| WO | WO 2009/068992 A1 | 6/2009 |
| WO | WO 2009/079259 A2 | 6/2009 |
| WO | WO 2009/121004 A2 | 10/2009 |
| WO | WO 2009/150532 A1 | 12/2009 |
| WO | WO 2010/117786 | 10/2010 |
| WO | WO 2010/130636 | 11/2010 |
| WO | WO 2010/138564 A1 | 12/2010 |
| WO | WO 2010/148511 | 12/2010 |
| WO | WO 2011/014645 | 2/2011 |
| WO | WO 2011/103453 | 8/2011 |
| WO | WO 2011/123495 | 10/2011 |
| WO | WO 2012/009790 | 1/2012 |
| WO | WO 2013/043729 | 3/2013 |
| WO | WO 2014/099931 | 6/2014 |

OTHER PUBLICATIONS

Kistner et al., 2007, "Cell culture (Vero) derived whole virus (H5N1) vaccine based on wild-type virus strain induces cross-protective immune responses", Vaccine; 25(32):6028-6036.

Leroux-Roels, et al., 2008, Broad Glade 2 cross-reactive immunity induced by an adjuvanted Glade 1 rH5N1 pandemic influenza vaccine; PLOS One 3(2):1-5.

Lowen et al. 2009, "Blocking interhost transmission of influenza virus by vaccination in the guinea pig model", Journal of Virology; 83(7):2803-2818.

Marasco et al., 2007, "The growth and potential of human antiviral monoclonal antibody therapeutics", Nat Biotechnol; 25(12):1421-1434.

Mo et al., 2003, "Coexpression of complementary fragments of CIC-5 and restoration of chloride channel function in a Dent's disease mutation", Am J Physiol Cell Physiol; 286:C79-C89.

Simmons et al., 2007, "Prophylactic and therapeutic efficacy of human monoclonal antibodies against H5N1 influenza", PLOS Medicine; 4(5):928-936.

Stephenson et al., 2005, "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy," The Journal of Infectious Diseases; 191:1210-1215.

Sui et al., 2009, "Structural and functional bases for broad-spectrum neutralization of avian and human influenza A viruses", Nat Struct Mol Biol; 16(3):265-273.

Thoennes et al., 2008, "Analysis of residues near the fusion peptide in the influenza hemagglutinin structure for roles in triggering membrane fusion", Virology; 370(2):403-414.

Throsby et al., 2008, "Heterosubtypic neutralizing monoclonal antibodies cross-protective against H5N1 and H1N1 recovered from human IgM+ memory B cells", PLoS ONE; 3(12):e3942.

Vanlandschoot et al., 1998, "An antibody which binds to the membrane-proximal end of influenza virus haemagglutinin (H3 subtype) inhibits the low-pH-induced conformational change and cell-cell fusion but does not neutralize virus", Journal of General Virology; 79:1781-1791.

Wang et al., 2009, "Universal epitopes of influenza virus hemagglutinins?", Nature Structural and Molecular Biology; 16(3):233-234.

Wang et al., 2010, "Broadly protective monoclonal antibodies against H3 influenza viruses following sequential immunization with different hemagglutinins", PLOS Pathogens; 6(2):1-9.

Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.

Written Opinion of International application No. PCT/US2011/25467, dated Oct. 19, 2011.

Written Opinion of International application No. PCT/US2010/036170, dated Aug. 17, 2010.

Yoshida et al., 2009, "Cross-Protective Potential of a Novel Monoclonal Antibody Directed against Antigenic Site B of the Hemagglutinin of Influenza A Viruses," PLOS Pathogens 5(3):1-9, e100350.

U.S. Appl. No. 14/345,816, filed Mar. 19, 2014, Garcia-Sastre et al.

Babai et al., "A novel liposomal influenza vaccine (INFLUSOM-VAC) containing hemagglutinin-neuraminidase and IL-2 or GM-CSF induces protective anti-neuraminidase antibodies cross-reacting with a wide spectrum of influenza A viral strains." Vaccine.,20(3-4);505-15 , 2002.

Berry, 2007, "Cross-reactive MAb to the binding domain of botulinum neurotoxin A, B, and E developed using a sequential immunization strategy: anti-botulinum neurotoxin", Hybridoma, 26(6):435-436.

Bianchi et al., 2005, "Universal influenza B vaccine based on the maturational cleavage site of the hemagglutinin precursor", Journal of Virology; 79(12):7380-7388.

Copeland et al., 2005, "Functional chimeras of human immunodeficiency virus type 1 Gp120 and influenza A virus (H3) hemagglutinin", Journal of Virology; 79:6459-6471.

Corti et al., 2011, "A neutralizing antibody selected from plasma cells that binds to group 1 and group 2 influenza A hemagglutinins", Science. 333(6044):850-856.

D'Aoust et al., 2008, "Influenza virus-like particles produced by transient expression in Nicotiana benthaminana induce a protective immune response against a lethal viral challenge in mice", J. Plant Biotechnology, 6(9):930-940.

Database Geneseq "Influenza A virus hemagglutinin protein, 1-11PR8", Accession No. AJG95109, dated Nov. 15, 2007.

Eda et al., 2006, "Sequential immunization with V3 peptides from primary human immunodeficiency virus type 1 produces cross-neutralizing antibodies against primary isolates with a matching narrow-neutralization sequence motif", J Virol, 80(11):5552-5562.

Ekiert et al., 2011, "A highly conserved neutralizing epitope on group 2 influenza A viruses", Science 333:843-850.

Ekiert et al., 2012, "Cross-neutralization of influenza A viruses mediated by a single antibody loop", Nature, 489:526-532.

Extended European Search Report for European Application No. 11763347.9, dated Feb. 2, 2015.

Fodor et al., 1999, "Rescue of influenza A virus from recombinant DNA", J Virol 73:9679-9682.

Fujii et al., 2003, "Selective incorporation of influenza virus RNA segments into virions", Proc. Natl. Acad. Sci. USA 100:2002-2007.

Gao & Palese, 2009, "Rewiring the RNAs of influenza virus to prevent reassortment", PNAS 106:15891-15896.

Gao et al., 2013, "Human infection with a novel avian-origin influenza A(H7N9) virus", N. Engl. J. Med. 368:1888-1897.

García-Sastre et al., 1994, "Introduction of foreign sequences into the genome of influenza A virus", Dev. Biol. Stand, 82:237-246.

García-Sastre et al., 1994, "Use of a mammalian internal ribosomal entry site element for expression of a foreign protein by a transfectant influenza virus", J. Virol. 68:6254-6261.

Gerhard et al., 2006, "Prospects for universal influenza virus vaccine", Emerging Infectious Diseases; 12(4):569-574.

Gocnik et al., 2008, "Antibodies Induced by the HA2 Glycopolypeptide of Influenza Virus Haemagglutinin Improve Recovery from Influenza A Virus Infection", J Gen Virol., 89:958-967.

Goff et al., 2013, "Adjuvants and immunization strategies to induce influenza virus hemagglutinin stalk antibodies", PLoS One 8:e79194.

(56) References Cited

OTHER PUBLICATIONS

Gould et al., 1987, "Mouse H-2k-Restricted Cytotoxic T Cells Recognize Antigenic Determinants in Both The HA1 and HA2 Subunits of the Influenza A/PR/8/34 Hemagglutinin," J. Exp. Med., 166:693-701.
Graves et al., 1983, "Preparation of influenza virus subviral particles lacking the HAI subunit of hemagglutinin: unmasking of cross-reactive HA2 determinants," Virology, 126(1):106-1 16).
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Horimoto et al., "Generation of influenza A viruses with chimeric (type AIR) hemagglutinins", J Virol. Jul. 2003;77(14):8031-8.
Horvath et al., 1998, "Hemagglutinin-based multipeptide construct elicits enhanced protective immune response in mice against influenza A virus infection", Immunology Letters; 60(2/03):127-136.
International Search Report issued on Feb. 19, 2013 or PCT Application No. PCT/US2012/056122, Published as WO 2013/043729.
International Search Report issued on Apr. 28, 2014 of PCT Application No. PCT/US2013/075697, Published as WO 2014/099931.
International Search Report issued on Jul. 13, 2011 of PCT Application No. PCT/US2011/030441, Published as WO 2011/123495.
International Search Report issued on Aug. 24, 2010 or PCT Application No. PCT/US2010/029202, Published as WO 2010/117786.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Krammer et al., 2010, "Trichoplusia ni cells (High Five) are highly efficient for the production of influenza A virus-like particles: a comparison of two insect cell lines as production platforms for influenza vaccines", Mol Biotechnol; 45:226-34.
Krammer et al., 2012, "A carboxy-terminal trimerization domain stabilizes conformational epitopes on the stalk domain of soluble recombinant hemagglutinin substrates", PLoS One. 7:e43603. doi:10.1371/j ournal.pone.0043603.
Krammer et al., 2013, "Chimeric hemagglutinin influenza virus vaccine constructs elicit broadly protective stalk-specific antibodies", J. Virol. 87:6542-6550.
Krammer et al., 2013, "Influenza virus hemagglutinin stalk-based antibodies and vaccines", Current Opinion in Virology 3:521-530.
Krause et al., 2012, "Human monoclonal antibodies to pandemic 1957 H2N2 and pandemic 1968 H3N2 influenza viruses", J. Virol. 86:6334-6340.
Landry et al., 2008, "Three-dimensional structure determines the pattern of CD4+ T-cell epitope dominance in influenza virus hemagglutinin", Journal of Virology; 82(3):1238-1248.
Lee et al., 2012, "Heterosubtypic antibody recognition of the influenza virus hemagglutinin receptor binding site enhanced by avidity", Proc. Natl. Acad. Sci. U.S.A. 109:17040-17045.
Li et al., 1992, "Influenza A virus transfectants with chimeric haemagglutinins containing epitopes from different subtypes", Journal of Virology, 66(1):399-404.
Margine et al., 2013, "H3N2 influenza virus infection induces broadly reactive hemagglutinin stalk antibodies in humans and mice", J. Virol. 87:4728-4737.
Miller et al., 2013, "1976 and 2009 H1N1 influenza virus vaccines boost anti-hemagglutinin stalk antibodies in humans", J. Infect. Dis. 207:98-105.
Mok et al., 2008, "Enhancement of the CD8<+> T cell response to a subdominant epitope respiratory syncytial virus by deletion of an immunodominant epitope", Vaccine: 26(37):4775-4782.
Neumann et al., 1999, "Generation of influenza A viruses entirely from cloned cDNAs", PNAS 96:9345-9350.

Okuno et al., 1993, "A common neutralizing epitope conserved between the hemagglutinins of influenza A virus H1 and H2 strains", J. Virol., 67(5):2552-2558.
Okuno et al., 1994, "Protection against the mouse-adapted A/FM/1/47 strain of influenza A virus in mice by a monoclonal antibody with cross-neutralizing activity among Ell and H2 strains", J. Virol., 68(1):517-520.
Ott et al., 2000. "The Adjuvant MF59: A 10-Year Perspective", p. 211-228. In O'Hagan DT (ed.), Vaccine Adjuvants, vol. 42. Springer.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Pica et al., "Hemagglutinin stalk antibodies elicited by the 2009 pandemic influenza virus as a mechanism for the extinction or seasonal H1N1 viruses", Proc Nat Acad Sci USA. 2012; 109(7):2573-8.
Pleschka et al., 1996, "A plasmid-based reverse genetics system for influenza A virus", J Virol 70:4188-92.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Roberts el al., "Role of conserved glycosylation sites in maturation and transport of influenza A virus hemagglutinin", J Virol, 1993; 67(6):3048-60.
Rudikoff et al., "Single amino acid substitution altering antigen-binding specificity", Proc Nat Acad Sci USA. 1982; 79(6): 1979-1983.
Sagawa et al., 1996, "The immunological activity of a deletion mutant of influenza virus haemagglutinin lacking the globular region", J Gen Virol; 77:1483-1487.
Salem, 2000, "In vivo acute depletion of CD8(+) T cells before murine cytomegalovirus infection upregulated innate antiviral activity of natural killer cells", Int. J. Immunopharmacol. 22:707-718.
Santak, M.,"Old and new ways to combat human influenza virus", Periodicus Biologorum, 2012; 114(2):221-34.
Shoji et al., 2008, "Plant-expressed HA as a seasonal influenza vaccine candidate", Vaccine, 26(23):2930-2934.
Song et al., 2007, "Influenza A Virus Hemagglutinin Protein, H1PR8," GENESEQ, XP002595511.
Stech et al., 2005, "A new approach to an influenza live vaccine: modification of the cleavage site of hemagglutinin", Nature Med. 11(6):683-689.
Steel et al., 2010. "Influenza Virus Vaccine Based on the Conserved Hemagglutinin Stalk Domain", mBIO, 1(0:1-9, pii: e00018-10.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Tamura et al., 1998, "Definition of amino acid residues on the epitope responsible for recognition by influenza A virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacy in vivo", J. Virol. 86:6179-6188.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3); 253-260.
Thomson et al., 2012, "Pandemic H1N1 Influenza Infection and Vaccination in Humans Induces Cross-Protective Antibodies that Target the Hemagglutinin Stem", Front. Immunol 3:87.
Vanlandschoot et al., 1995, A fairly conserved epitope on the hemagglutinin of influenza A (H3N2) virus with variable accessibility to neutralizing antibody. Virology. 212(2):526-34.
Wang et al., 2008, "Simplified recombinational approach for influenza A virus reverse genetics", J. Virol. Methods 151:74-78.
Wang et al., 2010, Broadly protective monoclonal antibodies against H3 influenza viruses following sequential immunization with different hemagglutinins PLoS Pathog. 6(2):e1000796.
Weldon et al., 2010, "Enhanced immunogenicity of stabilized trimeric soluble influenza hemagglutinin", PLoSONE 5(9): e12466.

(56) References Cited

OTHER PUBLICATIONS

Wrammert et al., 2011, "Broadly cross-reactive antibodies dominate the human B cell response against 2009 pandemic H1N1 influenza virus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.
Yang et al., 2006, "Targeting lentiviral vectors to specific cell types in vivo", PNAS 103: 11479-11484.
Yasugi et al., 2013, "Human monoclonal antibodies broadly neutralizing against influenza B virus", PLoS Pathog. 9(2): e1003150.
Zheng, et al., 1996, "Nonconserved nucleotides at the 3' and 5' ends of an influenza a virus RNA play an important role in viral RNA replication", Virology 217:242-251.
Sui et al.. 2009, "Structural and functional bases for broad-spectrum neutralization of avian and human influenza A viruses", Nat Struct Mol Biol; 16(3):265-273; Supplementary Information.

* cited by examiner

Variable region containing nucleic acid sequences for mAb 7A7

Nucleic acid sequence containing 7A7 heavy chain variable region:
>7A7_Heavy
ATGGACTCCAGGCTCAATTTAGTTTTCCTTGTCCTTATTTTAAAAGGTGTCCAGTG
TGATGTGCAGCTGGTGGAGTCTGGGGGAGGCTTAGTGCAGCCTGGAGGGTC
CCGGAAACTCTCCTGTGCAGCCTCT<u>GGATTCACTTTCAGTAGCTTTGGAATGC</u>
ACTGGGTTCGTCAGGCTCCAGAGAAGGGGCTGGAGTGGGTCGCATAC<u>ATTA</u>
<u>GTAGTGGCAGTAGTACCATC</u>TACTATGCAGACACAGTGAAGGGCCGATTCACC
ATCTCCAGAGACAATCCCAAGAACACCCTGTTCCTGCAAATGACCAGTCTAA
GGTCTGAGGACACGGCCATGTATTACTGT<u>GCAAGAAATTACGACGAGGACTTC</u>
<u>GATGTC</u>TGGGGCGCAGGGACCACGGTCACCGTCTCCTCAGCCAAAACAACAC
CCCCATCAGTCTATCCACTGGCCCCTGGGTGTGGAGATACAACTGGTTCCTCCGT
GACTCTGGGATGCCTGGTCAAGGGCTACTTCCCTGAGTCAGTGACTGTGACTTGG
AACTCTGGATCCCTGTCCAGCAGTGTGCACACCTTCCCAGCTCTCCTGCAGTCTG
GACTCTACACTATGAGCAGCTCAGTGACTGTCCCCTCCAGCACCTGGCCAAGTCA
GACCGTCACCTGCAGCGTTGCTCACCAGCCAGCAGCACCACGGTGGACAAAAA
ACTTGAGCCCAGCGGGCCCATTTCAACAATCAACCCCTGTCCTCCATGCAAGGAG
TGTCACAAATGCCCAGCTCCTAACCTCGAGGGTGGACCATCCGTCTTCATCTTC
(SEQ ID NO:2)

Junctional residues (amino acid) CARNYDEDFDVW (SEQ ID NO:3)

Nucleic acid sequence containing 7A7 light chain variable region:

>7A7_Kappa
ATGAAGTTGCCTGTTAGGCTGTTGGTGCTGATGTTCTGGATTCCTGCTTCCAGCAG
TGATGTTGTGATGACCCAAACTCCACTCTCCCTGCCTGTCAGTCTTGGAGAT
CAAGCCTCCATCTCTTGCAGATCTAGT<u>CAGAGCCTTGTACACAGTAATGGAAA</u>
<u>CACCTAT</u>TACATTGGTACCTGCAGAAGCCAGGCCAGTCTCCAAAGCTCCTG
ATCTAC<u>AAAGTTTCC</u>AACCGATTTTCTGGGGTCCCAGACAGGTTCAGTGGCA
GTGGATCAGGGACAGATTTCACACTCAAGATCAGCAGAGTGGAGGCTGAGG
ATCTGGGAGTTTATTTCTGC<u>TCTCAAAGTACACATGTTCCGTGGACGTTCGGTG</u>
GAGGCACCAAGCTGGAAATCAAACGGGCTGATGCTGCACCAACTGTATCCATC
TTCCCACCATCCAGTGAGCAGTTAACATCTGGAGGTGCCTCAGTCGTGTGCTTCT
TGAACAACTTCTACCCCAAAGACATCAATGTCAAGTGGAAGATTGATGGCAGTG
AACGACAAAATGGCGTCCTGAACAGTTGGACTGATCAGGACAGCAAAGACAGCA
CCTACAGCATGAGCAGCACCCTCACGTTGACCAAGGACGAGTATGAACGACATA
ACAGCTATACCTGTGAGGCCACTCACAAGACATCAACTTCACCCATTGTCAAGAG
CTTCAACAGGAATGAGTGTTAG (SEQ ID NO:4)

Junctional residues (amino acid): CSQSTHVPWTF (SEQ ID NO:5)

FIG 19

Variable region containing amino acid sequences for mAb 7A7

Amino acid sequence containing 7A7 heavy chain variable region:
>7A7_Heavy
MDSRLNLVFLVLILKGVQCDVQLVESGGGLVQPGGSRKLSCAASGFTFSSFGMHW
VRQAPEKGLEWVAYISSGSSTIYYADTVKGRFTISRDNPKNTLFLQMTSLRSEDT
AMYYCARNYDEDFDVWGAGTTVTVSSAKTTPPSVYPLAPGCGDTTGSSVTLGCLV
KGYFPESVTVTWNSGSLSSSVHTFPALLQSGLYTMSSSVTVPSSTWPSQTVTCSVAHP
ASSTTVDKKLEPSGPISTINPCPPCKECHKCPAPNLEGGPSVFIF (SEQ ID NO:6)

Amino acid sequence containing 7A7 light chain variable region:
>7A7_Kappa
MKLPVRLLVLMFWIPASSSDVVMTQTPLSLPVSLGDQASISCRSSQSLVHSNGNTY
LHWYLQKPGQSPKLLIYKVSNRFSGVPDRFSGSGSGTDFTLKISRVEAEDLGVYF
CSQSTHVPWTFGGGTKLEIKRADAAPTVSIFPPSSEQLTSGGASVVCFLNNFYPKDI
NVKWKIDGSERQNGVLNSWTDQDSKDSTYSMSSTLTLTKDEYERHNSYTCEATHKT
STSPIVKSFNRNEC (SEQ ID NO:7)

FIG 20

Variable region containing nucleic acid sequences for mAb 12D1

Nucleic acid sequence containing 12D1 heavy chain variable region:
>12D1_Heavy
ATGGCTGTCTTGGGGCTGCTCTTCTGCCTGGTGACATTCCCAAGCTGTGTCCTATC
CCAGGTGCACCTGGAGCAGTCAGGACCTGGCCTAGTGCAGCCCTCACAGAG
CCTGTCCATCACCTGCACAGTCTCTGGTTTCTCATTAACAACGTATGGTGTACA
CTGGGTTCGCCAGTCTCCAGGAAAGGGTCTGGAGTGGCTGGGAGTGATATG
GAGAGGTGGAAGCATAGACTATAATGCAGCTTTCATATCCAGACTGAGCATC
AGCAAGGACAATTCCAAGAGCCAAGTTTTCTTTAAAATGAACAGTCTGCAAG
CTAATGACACAGCCATATATTACTGTGCCAGAAATTGGGGTAGGTACGGATAC
TTCGATGTCTGGGGCGCAGGGACCACGGTCACCGTCTCCTCAGCCAAAACGA
CACCCCCATCTGTCTATCCACTGGCCCCTGGATCTGCTGCCCAAACTAACTCCAT
GGTGACCCTGGGATGCCTGGTCAAGGGCTATTTCCCTGAGCCAGTGACAGTGACC
TGGAACTCTGGATCCCTGTCCAGCGGTGTGCACACCTTCCCAGCTGTCCTGCAGT
CTGACCTCTACACTCTGAGCAGCTCAGTGACTGTCCCCTCCAGCACCTGGCCCAG
CGAGACCGTCACCTGCAACGTTGCCCACCCGGCCAGCAGCACCAAGGTGGACAA
GAAAATTGTGCCCAGGGATTGTGGTTGTAAGCCTTGCATATGTACAGTCCCAGAA
GTATCATCTGTCTTCATCTTCC (SEQ ID NO:8)

Junctional residues (amino acid): CARNWGRYGYFDVW (SEQ ID NO:9)

Nucleic acid sequence containing 12D1 light chain variable region:
>12D1_Kappa
ATGGAGACAGACACACTCCTGCTATGGGTGCTGCTGCTCTGGGTTCCAGGTTCCA
CAGGTGACATTGTGCTGACCCAATCTCCAGCTTCTTTGGCTGTGTCTCTAGG
GCAGAGGGCCACCATATCCTGCAGAGCCAGTGAAAGTGTTGATAGTTATGGC
AACAGTTTTATGCACTGGTACCAGCAGAAACCAGGACAGCCACCCAAAGTCC
TCATCTATCGTGCATCCAACCTAGAATCTGGGATCCCTGCCAGGTTCAGTGG
CAGTGGGTCTAGGACAGACTTCACCCTCACCATTAATCCTGTGGAGGCTGAT
GATGTTGCAACCTATTACTGTCAGCAAAGTAATGGGGATCCTCGGACGTTCGG
TGGAGGCACCAAGCTGGAAATCAAACGGGCTGATGCTGCACCAACTGTATCC
ATCTTCCCACCATCCAGTGAGCAGTTAACATCTGGAGGTGCCTCAGTCGTGTGCT
TCTTGAACAACTTCTACCCCAAAGACATCAATGTCAAGTGGAAGATTGATGGCAG
TGAACGACAAAATGGCGTCCTGAACAGTTGGACTGATCAGGACAGCAAAGACAG
CACCTACAGCATGAGCAGCACCCTCACGTTGACCAAGGACGAGTATGAACGACA
TAACAGCTATACCTGTGAGGCCACTCACAAGACATCAACTTCACCCATTGTCAAG
AGCTTCAACAGGAATGAGTGTTAG (SEQ ID NO:10)

Junctional residues (amino acid): CQQSNGDPRTF (SEQ ID NO:11)

Fig. 21

Variable region containing amino acid sequences for mAb 12D1

Amino acid sequence containing 12D1 heavy chain variable region:
>12D1_Heavy
MAVLGLLFCLVTFPSCVLSQVHLEQSGPGLVQPSQSLSITCTVSGFSLTTYGVHWV
RQSPGKGLEWLGVIWRGGSIDYNAAFISRLSISKDNSKSQVFFKMNSLQANDTAI
YYCARNWGRYGYFDVWGAGTTVTVSSAKTTPPSVYPLAPGSAAQTNSMVTLGCL
VKGYFPEPVTVTWNSGSLSSGVHTFPAVLQSDLYTLSSSVTVPSSTWPSETVTCNVA
HPASSTKVDKKIVPRDCGCKPCICTVPEVSSVFIF (SEQ ID NO:12)

Amino acid sequence containing 12D1 light chain variable region:
>12D1_Kappa
METDTLLLWVLLLWVPGSTGDIVLTQSPASLAVSLGQRATISCRASESVDSYGNSF
MHWYQQKPGQPPKVLIYRASNLESGIPARFSGSGSRTDFTLTINPVEADDVATYY
CQQSNGDPRTFGGGTKLEIKRADAAPTVSIFPPSSEQLTSGGASVVCFLNNFYPKDI
NVKWKIDGSERQNGVLNSWTDQDSKDSTYSMSSTLTLTKDEYERHNSYTCEATHKT
STSPIVKSFNRNEC (SEQ ID NO:13)

Fig. 22

Variable region containing nucleic acid sequences for mAb 66A6

Nucleic acid sequence containing 66A6 heavy chain variable region:
>66A6Heavy Chain AAGCTTGCCACCATGGAAACCGATACCCTGCTGCTGTGGGTGCTGCTGCTGTGGG
TGCCGGGCAGCTGGGCGCAGGTGCAGCTGCAGCAGAGCGGCCCGGAACTGAA
AAAACCGGGCGAAACCGTGAAAATTAGCTGCAAAGCGAGCGGCTATACCTTT
ACCAACTATGGCATGAACTGGGTGAAACAGGCGCCGGGCAAAGATCTGAAAT
GGCTGGGCTGGATTAACACCGATACCGGCGAACCGACCTATGCGGAAGAATT
TAAAGGCCGCTTTGCGTTTAGCCTGGAAACCAGCGCGAGCACCGCGTATCT
GGAAATTAACAACCTGAAAAACGAAGATGCGGCGACCTATTTTTGCGCGCGC
AACAAAAAATATGAAGCGTGGTTTACCCATTGGGGCCAGGGCACCCTGGTGAC
CGTGAGCAGCGCGAAAACCACCCCGCCGAGCGTGTATCCGCTGGCGCCGGGCA
GCGCGGCGCAGACCAACAGCATGGTGACCCTGGGCTGCCTGGTGAAAGGCTATT
TCCGGAACCGGTGACCGTGACCTGGAACAGCGGCAGCCTGAGCAGCGGCGTGC
ATACCTTTCCGGCGGTGCTGCAGAGCGATCTGTATACCCTGAGCAGCAGCGTGAC
CGTGCCGAGCAGCACCTGGCCGAGCCAGACCGTGACCTGCAACGTGGCGCATCC
GGCGAGCAGCACCAAAGTGGATAAAAAAATTGTGCCGCGCGATTGCGGCCATCA
TCATCATCATCATTAAGAATTC (SEQ ID NO:14)

Nucleic acid sequence containing 66A6 light chain variable region:
>66A6 Light Chain AAGCTTGCCACCATGGAAACCGATACCCTGCTGCTGTGGGTGCTGCTGCTGTGGG
TGCCGGGCAGCACCGGGAACATTGTGCTGACCCAGAGCCCGGCGAGCCTGGC
GGTGAGCCTGGGCCAGCGCGCGACCATTAGCTGCAAAGCGAGCGAAAGCGT
GGATAGCTATGGCACCAGCTTTATGCATTGGTATCAGCAGAAACCGGGCCAGC
CGCCGAAACTGCTGATTTATCTGGCGAGCAACCTGGAAAGCGGCGTGCCGGC
GCGCTTTAGCGGCAGCGGCAGCCGCACCGATTTTACCCTGACCATTGATCC
GGTGGAAGCGGATGATGCGGCGACCTATTATTGCCAGCAGAACAACGAACAT
CCGATGTTTGGCGGCGGCACCAAACTGGAAATTAAACGCGCGGATGCGGCGC
CGACCGTGAGCATTTTTCCGCCGAGCAGCGAACAGCTGACCAGCGGCGGCGCGA
GCGTGGTGTGCTTTCTGAACAACTTTTATCCGAAAGATATTAACGTGAAATGGAA
AATTGATGGCAGCGAACGCCAGAACGGCGTGCTGAACAGCTGGACCGATCAGGA
TAGCAAAGATAGCACCTATAGCATGAGCAGCACCCTGACCCTGACCAAAGATGA
ATATGAACGCCATAACAGCTATACCTGCGAAGCGACCCATAAAACCAGCACCAG
CCCGATTGTGAAGAGCTTTAACCGCAACGAATGCTAAGAATT (SEQ ID NO:15)

Fig. 28

Variable region amino acid sequences for mAb 66A6

Amino acid sequence containing 66A6 heavy chain variable region:
>66A6Heavy Chain SKLATMETDTLLLWVLLLWVPGSWAQVQLQQSGPELKKPGETVKISCKASGYTF
TNYGMNWVKQAPGKDLKWLGWINTDTGEPTYAEEFKGRFAFSLETSASTAYLEI
NNLKNEDAATYFCARNKKYEAWFTHWGQGTLVTVSSAKTTPPSVYPLAPGSAAQ
TNSMVTLGCLVKGYFPEPVTVTWNSGSLSSGVHTFPAVLQSDLYTLSSSVTVPSSTW
PSQTVTCNVAHPASSTKVDKKIVPRDCG (SEQ ID NO:16)

Amino acid sequence containing 66A6 light chain variable region:
>66A6Light Chain SKLATMETDTLLLWVLLLWVPGSTGNIVLTQSPASLAVSLGQRATISCKASESVDS
YGTSFMHWYQQKPGQPPKLLIYLASNLESGVPARFSGSGSRTDFTLTIDPVEADD
AATYYCQQNNEHPMFGGGTKLEIKRADAAPTVSIFPPSSEQLTSGGASVVCFLNNF
YPKDINVKWKIDGSERQNGVLNSWTDQDSKDSTYSMSSTLTLTKDEYERHNSYTCE
ATHKTSTSPIVKSFNRNEC (SEQ ID NO:17)

Fig. 29

MONOCLONAL ANTIBODIES AGAINST INFLUENZA VIRUS GENERATED BY CYCLICAL ADMINISTRATION AND USES THEREOF

This application is a divisional of U.S. application Ser. No. 12/788,103, filed May 26, 2010, which claims priority benefit of U.S. provisional application No. 61/181,263, filed May 26, 2009, U.S. provisional application No. 61/224,302, filed Jul. 9, 2009, and U.S. provisional application No. 61/305,898, filed Feb. 18, 2010, each of which is incorporated herein by reference in its entirety.

This invention was made with United States Government support under award numbers U01 AI70469 and U54 AI057158-06 awarded by the National Institutes of Health (NIH). The United States Government has certain rights in this invention.

1. INTRODUCTION

Provided herein are methods of producing neutralizing monoclonal antibodies, by cyclical administration, that cross-react with strains of Influenza virus of the same subtype or different subtypes. Also provided herein are compositions comprising such antibodies and methods of using such antibodies to diagnose, prevent or treat Influenza virus disease.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p1647-1689). The natural host of Influenza viruses are avians, but Influenza viruses (including those of avian origin) also can infect and cause illness in humans and other animal hosts (canines, pigs, horses, sea mammals, and mustelids). For example, the H5N1 avian Influenza virus circulating in Asia has been found in pigs in China and Indonesia and has also expanded its host range to include cats, leopards, and tigers, which generally have not been considered susceptible to Influenza A (CIDRAP—Avian Influenza: Agricultural and Wildlife Considerations). The occurrence of Influenza virus infections in animals could potentially give rise to human pandemic Influenza strains.

Influenza A and B viruses are major human pathogens, causing a respiratory disease that ranges in severity from sub-clinical infection to primary viral pneumonia which can result in death. The clinical effects of infection vary with the virulence of the Influenza strain and the exposure, history, age, and immune status of the host. The cumulative morbidity and mortality caused by seasonal Influenza is substantial due to the relatively high rate of infection. In a normal season, Influenza can cause between 3-5 million cases of severe illness and is associated with 200,000 to 500,000 deaths worldwide (World Health Organization (April, 2009) Influenza (Seasonal) Fact Sheet 211). In the United States, Influenza viruses infect an estimated 10-15% of the population (Glezen and Couch R B (1978) Interpandemic Influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated With Influenza and Respiratory Syncytial Virus in the United States. JAMA 289: 179-186; Belshe (2007) Translational research on vaccines: Influenza as an example. Clin Pharmacol Ther 82: 745-749).

In addition to annual epidemics, Influenza viruses are the cause of infrequent pandemics. For example, Influenza A viruses can cause pandemics such as those that occurred in 1918, 1957 and 1968. Due to the lack of pre-formed immunity against the major viral antigen, hemagglutinin (HA), pandemic Influenza viruses can affect greater than 50% of the population in a single year and often cause more severe disease than seasonal Influenza viruses. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 Influenza virus in the late 1990s (Claas et al. (1998) Human Influenza A H5N1 virus related to a highly pathogenic avian Influenza virus. Lancet 351: 472-7), there have been concerns that the virus may become transmissible between humans and cause a major pandemic.

An effective way to protect against Influenza virus infection is through vaccination; however, current vaccination approaches rely on achieving a good match between circulating strains and the isolates included in the vaccine formulation. Such a match is often difficult to attain due to a combination of factors. First, Influenza viruses are constantly undergoing change: every 3-5 years the predominant strain of Influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the Influenza season. Occasionally, the predictions of the vaccine strain selection committee are inaccurate, resulting in a substantial drop in the efficacy of vaccination.

The possibility of a novel subtype of Influenza A virus entering the human population also presents a significant challenge to current vaccination strategies. Since it is impossible to predict what subtype and strain of Influenza virus will cause the next pandemic, current, strain-specific approaches cannot be used to prepare a pandemic Influenza vaccine.

3. SUMMARY

Provided herein are methods for generating monoclonal antibodies that bind to an Influenza virus antigen. Such monoclonal antibodies may bind to an Influenza virus antigen on an Influenza virus particle, e.g., hemagglutinin (HA). In another specific embodiment, the monoclonal antibodies bind to an Influenza virus particle. In another specific embodiment, the monoclonal antibodies selectively bind to hemagglutinin expressed by one, two, three or more strains of Influenza virus relative to a non-Influenza virus hemagglutinin antigen as assessed by techniques known in the art, e.g., ELISA, Western blot, FACs or BIACore. In other words, the monoclonal antibodies bind to hemagglutinin expressed by one, two, three or more strains of Influenza virus with a higher affinity than a non-Influenza virus hemagglutinin antigen as assessed by techniques known in the art, e.g., ELISA, Western blot, FACs or BIACore. In a specific embodiment, the monoclonal antibody binds to and neutralizes two or more strains of Influenza viruses that express antigenically distinct HA. In another embodiment, the monoclonal antibody binds to and neutralizes two or more strains of an Influenza A virus hemagglutinin (HA) subtype. In another embodiment, the monoclonal antibody binds to and neutralizes strains of Influenza A virus of two or more HA subtypes. In another specific embodiment, the monoclonal antibody binds to the long alpha-helix of the HA2 region of an Influenza virus.

In one aspect, a method for generating a monoclonal antibody that binds to and neutralizes two or more strains of Influenza viruses that express antigenically distinct HA is provided. In a specific embodiment, a method for generating a monoclonal antibody that binds to and neutralizes two or more strains of Influenza viruses that express antigenically distinct HA comprises administering two, three, four or more immunogenic compositions to a non-human subject with the administration of each immunogenic composition separated by a certain amount of time, and generating B-cell hybridomas from the subject that express a monoclonal antibody that binds to and neutralizes two or more strains of an Influenza virus that express antigenically distinct HA (e.g., two or more strains of an Influenza A virus subtype or two or more strains from distinct Influenza A subtypes), wherein each immunogenic composition comprises an inactivated Influenza virus, an attenuated Influenza virus, a live Influenza virus other than an attenuated Influenza virus (e.g., naturally occurring Influenza virus), an antigen derived or obtained from an Influenza virus (e.g., HA), or a nucleic acid encoding an antigen derived or obtained from an Influenza virus, and wherein one immunogenic composition differs from another immunogenic composition in that the Influenza virus, or the Influenza virus from which the antigen or fragment thereof or the nucleic acid encoding the antigen or fragment thereof is derived or obtained are antigenically distinct. In specific embodiments, the method comprises selecting for B-cell hybridoma clones that express a monoclonal antibody that binds to and neutralizes two or more strains of an Influenza virus which express antigenically distinct HA. In particular embodiments, the two or more strains of Influenza virus which express antigenically distinct HA are two or more strains of an Influenza A virus subtype. In certain aspects, the methods for producing a monoclonal antibody that binds to two or more strains of Influenza virus which express antigenically distinct HA can be used to produce hybridomas that express such an antibody.

In one embodiment, a method for generating a monoclonal antibody that binds to and neutralizes two or more strains of an Influenza A virus HA subtype comprises: (i) administering to a non-human subject a first immunogenic composition comprising an inactivated first Influenza virus, an attenuated first Influenza virus, a live first Influenza virus other than an attenuated Influenza virus, an HA derived or obtained from a first Influenza virus or fragment thereof, or a nucleic acid encoding an HA derived or obtained from a first Influenza virus or fragment thereof; (ii) after a first period of time, administering to the subject a second immunogenic composition comprising an inactivated second Influenza virus, an attenuated second Influenza virus, a live second Influenza virus other than an attenuated Influenza virus, an HA derived or obtained from a second Influenza virus or fragment thereof, or a nucleic acid encoding an HA derived or obtained from a second Influenza virus or fragment thereof, wherein the second Influenza virus is antigenically distinct from the first Influenza virus; and (iii) after a second period of time, generating B-cell hybridomas from the subject that express a monoclonal antibody that binds to and neutralizes two or more strains of an Influenza A virus HA subtype. In certain embodiments, the method comprises selecting for clones that express a monoclonal antibody that binds to and neutralizes two or more strains of an Influenza A virus subtype. In certain embodiments, the method further comprises isolating the monoclonal antibody. In some embodiments, the method further comprises screening for the cross-reactive neutralizing monoclonal antibody. In specific embodiments, the Influenza A virus subtype is H3. In specific embodiments, the Influenza A virus is a Group 2 Influenza virus (e.g., an Influenza virus that is an H4, H14, H3, H15, H7, or H10 subtype). In specific embodiments, the Influenza A virus is a Group 1 Influenza virus (e.g., an Influenza virus that is an H1 subtype such as A/South Carolina/1918 (H1), A/USSR/92/77 (H1), A/California/04/09 (H1), or A/Brisbane/59/07-like (H1).

In another embodiment, a method for generating a monoclonal antibody that binds to and neutralizes two or more strains of an Influenza A virus HA subtype comprises: (i) administering to a non-human subject a first immunogenic composition comprising an inactivated first Influenza virus, an attenuated first Influenza virus, a live first Influenza virus other than an attenuated Influenza virus, an HA derived or obtained from a first Influenza virus or fragment thereof, or a nucleic acid encoding an HA derived or obtained from a first Influenza virus or fragment thereof; (ii) after a first period of time, administering to the subject a second immunogenic composition comprising an inactivated second Influenza virus, an attenuated second Influenza virus, a live second Influenza virus other than an attenuated Influenza virus, an HA derived or obtained from a second Influenza virus or fragment thereof, or a nucleic acid encoding an HA derived or obtained from a second Influenza virus or fragment thereof, wherein the second Influenza virus is antigenically distinct from the first Influenza virus; (iii) after a second period of time, administering to the subject a third immunogenic composition comprising an inactivated third Influenza virus, an attenuated third Influenza virus, a live third Influenza virus other than an attenuated Influenza virus, an HA derived or obtained from a third Influenza virus or fragment thereof, or a nucleic acid encoding an HA derived or obtained from a third Influenza virus or fragment thereof, wherein the third Influenza virus is antigenically distinct from the first and the second Influenza viruses; and (iv) after a third period of time, generating B-cell hybridomas from the subject and further selecting for hybridoma clones that express a monoclonal antibody that binds to and neutralizes two or more strains of an Influenza A virus HA subtype. In certain embodiments, the method comprises selecting for hybridoma clones that express a monoclonal antibody that binds to and neutralizes two or more strains of an Influenza A virus subtype. In some embodiments, the method further comprises isolating the monoclonal antibody. In other embodiments, the method further comprises screening for the cross-reactive neutralizing monoclonal antibody. In specific embodiments, the Influenza A virus subtype is H3. In specific embodiments, the Influenza A virus is characterized as a Group 2 Influenza virus (e.g., an Influenza virus that is an H4, H14, H3, H15, H17, or H10 subtype). In specific embodiments, the Influenza A virus is a Group 1 Influenza virus (e.g., an Influenza virus that is an H1 subtype such as A/South Carolina/1918 (H1), A/USSR/92/77 (H1), A/California/04/09 (H1), or A/Brisbane/59/07-like (H1).

In another embodiment, a method for generating a monoclonal antibody that binds to and neutralizes two or more strains of an Influenza A virus HA subtype comprises: (i) administering to a non-human subject a first immunogenic composition comprising an inactivated first Influenza virus, an attenuated first Influenza virus, a live first Influenza virus other than an attenuated Influenza virus, an HA derived or obtained from a first Influenza virus or fragment thereof, or a nucleic acid encoding an HA derived or obtained from a first Influenza virus or fragment thereof; (ii) after a first period of time, administering to the subject a second immunogenic composition comprising an inactivated second Influenza virus, an attenuated second Influenza virus, a live second Influenza virus other than an attenuated Influenza virus, an HA derived or obtained from a second Influenza virus or fragment thereof, or a nucleic acid encoding an HA derived or obtained from a second Influenza virus or fragment thereof, wherein the second Influenza virus is antigenically distinct from the first Influenza virus; (iii) after a second period of time, administering to the subject a third immunogenic composition comprising an inactivated third Influenza virus, an attenuated third Influenza virus, a live third Influenza virus other than an attenuated Influenza virus, an HA derived or obtained from a third Influenza virus or fragment thereof, or a nucleic acid encoding an HA derived or obtained from a third Influenza virus or fragment thereof, wherein the third Influenza virus is antigenically distinct from the first and the second Influenza viruses; (iv) after a third period of time, administering to the subject a fourth immunogenic composition comprising an inactivated fourth Influenza virus, an attenuated fourth Influenza virus, a live fourth Influenza virus other than an attenuated Influenza virus, an HA derived or obtained from a fourth Influenza virus or fragment thereof, or a nucleic acid encoding an HA derived or obtained from a fourth Influenza virus or fragment thereof, wherein the fourth Influenza virus is antigenically distinct from the first, second and third Influenza viruses; and (v) after a fourth period of time, generating B-cell hybridomas from the subject that express a monoclonal antibody that binds to and neutralizes two or more strains of an Influenza A virus HA subtype. In certain embodiments, the method further comprises isolating the monoclonal antibody. In certain embodiments, the method comprises selecting hybridoma clones that express a monoclonal antibody that binds to and neutralizes two or more strains of an Influenza A virus subtype. In some embodiments, the method further comprises screening for the cross-reactive neutralizing monoclonal antibody. In specific embodiments, the Influenza A virus is characterized as a Group 2 Influenza virus (e.g., an Influenza virus that is an H4, H14, H3, H15, H17, or H10 subtype). In specific embodiments, the Influenza A virus subtype is H3. In specific embodiments, the first Influenza virus is A/Hong Kong/1/1968, the second Influenza virus is A/Alabama/1/1981, the third Influenza virus is A/Beijing/47/1992, and the fourth Influenza virus is A/Wyoming/3/2003. In specific embodiments, the Influenza A virus is a Group 1 Influenza virus (e.g., an Influenza virus that is an H1 (H1a/H1b) or H9 subtype). In specific embodiments, the Influenza A virus subtype is H1. In specific embodiments, the first Influenza virus is A/South Carolina/1918 (H1), the second Influenza virus is A/USSR/92/77 (H1), the third Influenza virus is A/California/04/09 (H1), and the fourth Influenza virus is A/Brisbane/59/07-like (H1).

In another aspect, a method for generating a monoclonal antibody that binds to and neutralizes strains of two or more Influenza A virus HA subtypes is provided. In a specific embodiment, a method for generating a monoclonal antibody that binds to and neutralizes strains of two or more Influenza A virus HA subtypes comprises administering two, three, four or more immunogenic compositions to a non-human subject with the administration of each immunogenic composition separated by a certain amount of time, and generating B-cell hybridomas from the subject that express a monoclonal antibody that binds to and neutralizes strains of two or more Influenza A virus HA subtypes, wherein each immunogenic composition comprises an inactivated Influenza virus, an attenuated Influenza virus, a live Influenza virus other than an attenuated Influenza virus (e.g., naturally occurring Influenza virus), an antigen derived or obtained from an Influenza virus, or a nucleic acid encoding an antigen derived or obtained from an Influenza virus, and wherein one immunogenic composition differs from another immunogenic composition in that the Influenza virus, or the Influenza virus from which the antigen or the nucleic acid encoding the antigen is derived or obtained are antigenically distinct. In some embodiments, the method comprises selecting hybridoma clones that express a monoclonal antibody that binds to and neutralizes strains of Influenza A virus of two or more HA subtypes. In certain embodiments, the method comprises selecting hybridoma clones that express a monoclonal antibody that binds to and neutralizes two or more strains of an Influenza A virus subtype.

In one embodiment, a method for generating a monoclonal antibody that binds to and neutralizes strains of Influenza A virus of two or more HA subtypes comprises: (i) administering to a non-human subject a first immunogenic composition comprising an inactivated first Influenza virus, an attenuated first Influenza virus, a live first Influenza virus other than an attenuated Influenza virus, an HA derived or obtained from a first Influenza virus or fragment thereof, or a nucleic acid encoding an HA derived or obtained from a first Influenza virus or fragment thereof; (ii) after a first period of time, administering to the subject a second immunogenic composition comprising an inactivated second Influenza virus, an attenuated second Influenza virus, a live second Influenza virus other than an attenuated Influenza virus, an HA derived or obtained from a second Influenza virus or fragment thereof, or a nucleic acid encoding an HA derived or obtained from a second Influenza virus or fragment thereof, wherein the second Influenza virus is antigenically distinct from the first Influenza virus; and (iii) after a second period of time, generating B-cell hybridomas from the subject that express a monoclonal antibody that binds to and neutralizes strains of Influenza A virus of two or more HA subtypes. In some embodiments, the method comprises selecting hybridoma clones that express a monoclonal antibody that binds to and neutralizes strains of Influenza A virus of two or more HA subtypes. In certain embodiments, the method comprises selecting hybridoma clones that express a monoclonal antibody that binds to and neutralizes two or more strains of an Influenza A virus subtype. In certain embodiments, the method further comprises isolating the monoclonal antibody. In some embodiments, the method further comprises screening for the cross-reactive neutralizing monoclonal antibody. In specific embodiments, the Influenza A virus subtypes are H1 and H3.

In another embodiment, a method for generating a monoclonal antibody that binds to and neutralizes strains of Influenza A virus of two or more HA subtypes comprises: (i) administering to a non-human subject a first immunogenic composition comprising an inactivated first Influenza virus, an attenuated first Influenza virus, a live first Influenza virus other than an attenuated Influenza virus, an HA derived or obtained from a first Influenza virus or fragment thereof, or a nucleic acid encoding an HA derived or obtained from a first Influenza virus or fragment thereof; (ii) after a first period of time, administering to the subject a second immunogenic composition comprising an inactivated second Influenza virus, an attenuated second Influenza virus, a live second Influenza virus other than an attenuated Influenza virus, an HA derived or obtained from a second Influenza virus or fragment thereof, or a nucleic acid encoding an HA derived or obtained from a second Influenza virus or fragment thereof, wherein the second Influenza virus is antigenically distinct from the first Influenza virus; (iii) after a second period of time, administering to the subject a third immunogenic composition comprising an inactivated third Influenza virus, an attenuated third Influenza virus, a live third Influenza virus other than an attenuated Influenza virus, an HA derived or obtained from a third Influenza virus or fragment thereof, or a nucleic acid encoding an HA derived or obtained from a third Influenza virus or fragment thereof, wherein the third Influenza virus is antigenically distinct from the first and the second Influenza viruses; and (iv) after a third period of time, generating B-cell hybridomas from the subject that express a monoclonal antibody that binds to and neutralizes strains of Influenza A virus of two or more HA subtypes. In some embodiments, the method comprises selecting hybridoma clones that express a monoclonal antibody that binds to and neutralizes strains of Influenza A virus of two or more HA subtypes. In certain embodiments, the method comprises selecting hybridoma clones that express a monoclonal antibody that binds to and neutralizes two or more strains of an Influenza A virus subtype. In certain embodiments, the method further comprises isolating the monoclonal antibody. In some embodiments, the method further comprises screening for the cross-reactive neutralizing monoclonal antibody. In specific embodiments, the Influenza A virus subtypes are H1 and H3.

In another embodiment, a method for generating a monoclonal antibody that binds to and neutralizes strains of Influenza A virus of two or more HA subtypes comprises: (i) administering to a non-human subject a first immunogenic composition comprising an inactivated first Influenza virus, an attenuated first Influenza virus, a live first Influenza virus other than an attenuated Influenza virus, an HA derived or obtained from a first Influenza virus or fragment thereof, or a nucleic acid encoding an HA derived or obtained from a first Influenza virus or fragment thereof; (ii) after a first period of time, administering to the subject a second immunogenic composition comprising an inactivated second Influenza virus, an attenuated second Influenza virus, a live second Influenza virus other than an attenuated Influenza virus, an HA derived or obtained from a second Influenza virus or fragment thereof, or a nucleic acid encoding an HA derived or obtained from a second Influenza virus or fragment thereof, wherein the second Influenza virus is antigenically distinct from the first Influenza virus; (iii) after a second period of time, administering to the subject a third immunogenic composition comprising an inactivated third Influenza virus, an attenuated third Influenza virus, a live third Influenza virus other than an attenuated Influenza virus, an HA derived or obtained from a third Influenza virus or fragment thereof, or a nucleic acid encoding an HA derived or obtained from a third Influenza virus or fragment thereof, wherein the third Influenza virus is antigenically distinct from the first and the second Influenza viruses; (iv) after a third period of time, administering to the subject a fourth immunogenic composition comprising an inactivated fourth Influenza virus, an attenuated fourth Influenza virus, a live fourth Influenza virus other than an attenuated Influenza virus, an HA derived or obtained from a fourth Influenza virus or fragment thereof, or a nucleic acid encoding an HA derived or obtained from a fourth Influenza virus or fragment thereof, wherein the fourth Influenza virus is antigenically distinct from the first, second and third Influenza viruses; and (v) after a fourth period of time, generating B-cell hybridomas from the subject and further selecting for hybridoma clones that express a monoclonal antibody that binds to and neutralizes strains of Influenza A virus of two or more HA subtypes. In some embodiments, the method comprises selecting hybridoma clones that express a monoclonal antibody that binds to and neutralizes strains of Influenza A virus of two or more HA subtypes. In certain embodiments, the method comprises selecting hybridoma clones that express a monoclonal antibody that binds to and neutralizes two or more strains of an Influenza A virus subtype. In certain embodiments, the method further comprises isolating the monoclonal antibody. In some embodiments, the method further comprises screening for the cross-reactive neutralizing monoclonal antibody. In specific embodiments, the Influenza A virus subtypes are H1 and H3.

In another embodiment, a method for generating a monoclonal antibody that binds to and neutralizes strains of Influenza A virus of two or more HA subtypes comprises: (i) administering to a non-human subject a first immunogenic composition comprising an inactivated first Influenza virus of a first HA subtype, an attenuated first Influenza virus of a first HA subtype, a live first Influenza virus of a first HA subtype other than an attenuated Influenza virus, an HA of a first HA subtype derived or obtained from a first Influenza virus of a first HA subtype of a first HA subtype or fragment thereof, or a nucleic acid encoding an HA of a first HA subtype derived or obtained from a first Influenza virus or fragment thereof; (ii) after a first period of time, administering to the subject a second immunogenic composition comprising an inactivated second Influenza virus of a second HA subtype, an attenuated second Influenza virus of a second HA subtype, a live second Influenza virus of a second HA subtype other than an attenuated Influenza virus, an HA of a second HA subtype derived or obtained from a second Influenza virus or fragment thereof, or a nucleic acid encoding an HA of a second HA subtype derived or obtained from a second Influenza virus or fragment thereof, wherein the second Influenza virus is antigenically distinct from the first Influenza virus; (iii) after a second period of time, administering to the subject a third immunogenic composition comprising an inactivated third Influenza virus of a third HA subtype, an attenuated third Influenza virus of a third HA subtype, a live third Influenza virus of a third HA subtype other than an attenuated Influenza virus, an HA of a third HA subtype derived or obtained from a third Influenza virus or fragment thereof, or a nucleic acid encoding an HA of a third HA subtype derived or obtained from a third Influenza virus or fragment thereof, wherein the third Influenza virus is antigenically distinct from the first and the second Influenza viruses; (iv) after a third period of time, administering to the subject a fourth immunogenic composition comprising an inactivated fourth Influenza virus of a fourth HA subtype, an attenuated fourth Influenza virus of a fourth HA subtype, a live fourth Influenza virus of a fourth HA subtype other than an attenuated Influenza virus, an HA of a fourth HA subtype derived or obtained from a fourth Influenza virus or fragment thereof, or a nucleic acid encoding an HA of a fourth HA subtype derived or obtained from a fourth Influenza virus or fragment thereof, wherein the fourth Influenza virus is antigenically distinct from the first, second and third Influenza viruses; (v) after a fourth period of time, administering to the subject a fifth immunogenic composition comprising (a) an inactivated fifth Influenza virus of a fifth HA subtype, an attenuated fifth Influenza virus of a fifth HA subtype, a live fifth Influenza virus of a fifth HA subtype other than an attenuated Influenza virus, an HA of a fifth HA subtype derived or obtained from a fifth Influenza virus or fragment thereof, or a nucleic acid encoding an HA of a fifth HA subtype derived or obtained from a fifth Influenza virus or fragment thereof and (b) an inactivated sixth Influenza virus of a sixth HA subtype, an attenuated sixth Influenza virus of a sixth HA subtype, a live sixth Influenza virus of a sixth HA subtype other than an attenuated Influenza virus, an HA of a sixth HA subtype derived or obtained from a sixth Influenza virus or fragment thereof, or a nucleic acid encoding an HA of a sixth HA subtype derived or obtained from a sixth Influenza virus or fragment thereof, wherein the fifth Influenza virus is antigenically distinct from the first, second, third, and fourth Influenza viruses and wherein the sixth Influenza virus is antigenically distinct from the first, second, third, fourth, and fifth Influenza viruses; and (vi) after a fifth period of time, generating B-cell hybridomas from the subject and further selecting for hybridoma clones that express a monoclonal antibody that binds to and neutralizes strains of Influenza A virus of two or more HA subtypes. In certain embodiments, the first, third, and fifth HA subtypes are the same (e.g., the subtypes are all H3 subtypes) and the second, fourth, and sixth HA subtypes are the same (e.g., the subtypes are all H1 subtypes). In specific embodiments, the Influenza A virus subtypes are H1 and H3. In specific embodiments, the first Influenza virus is A/Hong Kong/1/68 (H3), the second Influenza virus is A/USSR/92/77 (H1), the third Influenza virus is A/California/1/88 (H3), the fourth Influenza virus is A/California/04/09 (H1), the fifth Influenza virus is A/Brisbane/59/07-like (H1), and the sixth Influenza virus is A/Brisbane/10/07-like (H3). In some embodiments, the first, second, third, fourth, fifth, and sixth HA subtypes are 2, 3, or more different subtypes. In some embodiments, the method comprises selecting hybridoma clones that express a monoclonal antibody that binds to and neutralizes strains of Influenza A virus of two or more HA subtypes. In certain embodiments, the method comprises selecting hybridoma clones that express a monoclonal antibody that binds to and neutralizes two or more strains of an Influenza A virus subtype. In certain embodiments, the method further comprises isolating the monoclonal antibody. In some embodiments, the method further comprises screening for the cross-reactive neutralizing monoclonal antibody.

In certain embodiments, the non-human subject referenced in the methods described herein is a transgenic animal (e.g., a transgenic mouse) capable of producing human antibodies. Examples of transgenic mice that are capable of producing human antibodies are those available from Abgenix, Inc. (Freemont, Calif.), Genpharm (San Jose, Calif.), or Medarex, Inc. (Princeton, N.J.).

In another aspect, provided herein are isolated antibodies (e.g., monoclonal antibodies and antigen-binding fragments thereof) that bind to and neutralize two or more strains of an Influenza A virus. In a specific embodiment, the strains are from the same Influenza A virus HA subtype. In another specific embodiment, the strains are Influenza A viruses belonging to different HA subtypes. In certain embodiments, such monoclonal antibodies are humanized.

In a specific embodiment, provided herein are the antibody 7A7, 12D1, 39A4, 66A6 or a fragment thereof (in particular, an antigen-binding fragment thereof). In another specific embodiment, provided herein is an antibody that binds to Influenza virus HA, wherein the antibody comprises the variable heavy (VH) domain of the antibody 7A7, 12D1, 39A4, or 66A6. In another specific embodiment, provided herein is an antibody that binds to Influenza virus HA, wherein the antibody comprises the variable light (VL) domain of the antibody 7A7, 12D1, 39A4, or 66A6. In another specific embodiment, provided herein is an antibody that binds to Influenza virus HA, wherein the antibody comprises the VH and VL domain of the antibody 7A7, 12D1, 39A4, or 66A6. In another specific embodiment, provided herein is an antibody that binds to Influenza virus HA, wherein the antibody comprises 1, 2, or 3 VH CDRs and/or 1, 2, or 3 VL CDRs of the antibody 7A7, 12D1, 39A4, or 66A6. In certain embodiments, the antibody not only binds to Influenza virus HA, but also neutralizes the Influenza virus.

Also provided herein are nucleic acids encoding the antibodies provided herein or generated in accordance with the methods provided herein. In a specific embodiment, a nucleic acid(s) provided herein encodes for the antibody 7A7, 12D1, 39A4, 66A6 or a fragment thereof (in particular, an antigen-binding fragment thereof). In another specific embodiment, a nucleic acid(s) provided herein encodes for an antibody that binds to Influenza virus HA, wherein the antibody comprises the VH domain of the antibody 7A7, 12D1, 39A4, or 66A6. In another specific embodiment, a nucleic acid(s) provided herein encodes for an antibody that binds to Influenza virus HA, wherein the antibody comprises the VL domain of the antibody 7A7, 12D1, 39A4, or 66A6. In another specific embodiment, a nucleic acid(s) provided herein encodes for an antibody that binds to Influenza virus HA, wherein the antibody comprises the VH and VL domain of the antibody 7A7, 12D1, 39A4, or 66A6. In another specific embodiment, a nucleic acid(s) provided herein encodes for an antibody that binds to Influenza virus HA, wherein the antibody comprises 1, 2, or 3 VH CDRs and/or 1, 2, or 3 VL CDRs of the antibody 7A7, 12D1, 39A4, or 66A6. In certain embodiments, the nucleic acid encodes an antibody that not only binds to Influenza virus HA, but also neutralizes the Influenza virus.

In another aspect, provided herein are hybridomas produced in accordance with the methods described herein. In one embodiment, provided herein is a hybridoma designated 7A7 deposited under provisions of the Budapest Treaty with the American Type Culture Collection (ATCC, 10801 University Blvd., Manassas, Va. 20110-2209) on May 22, 2009 (ATCC Accession No. PTA-10058). In another embodiment, provided herein is a hybridoma designated 12D1 deposited under provisions of the Budapest Treaty with the American Type Culture Collection (ATCC, 10801 University Blvd., Manassas, Va. 20110-2209) on May 22, 2009 (ATCC Accession No. PTA-10059). In another embodiment, provided herein is a hybridoma designated 39A4 deposited under provisions of the Budapest Treaty with the American Type Culture Collection (ATCC, 10801 University Blvd., Manassas, Va. 20110-2209) on May 22, 2009 (ATCC Accession No. PTA-10060). In another embodiment, provided herein is a hybridoma designated 66A6 deposited under provisions of the Budapest Treaty with the American Type Culture Collection (ATCC, 10801 University Blvd., Manassas, Va. 20110-2209) on May 26, 2010 (ATCC Accession No. PTA-11046).

In another aspect, provided herein are isolated monoclonal antibodies or antigen-binding fragments thereof produced by the hybridomas generated in the accordance with the methods described herein. In a specific embodiment, the isolated monoclonal antibody is the antibody 7A7, 12D1 or 39A4. In certain embodiments, such monoclonal antibodies are humanized.

In another aspect, provided herein are isolated antibodies that bind to SEQ ID NO:1 and neutralize two or more strains of an Influenza A virus HA subtype. In another aspect, provided herein are compositions as well as kits comprising an antibody described herein. In a specific embodiment, such compositions are pharmaceutical compositions suitable for administration to a patient.

In another aspect, provided herein are methods of preventing and/or treating an Influenza virus disease comprising administering to a subject an antibody described herein or a pharmaceutical composition thereof. In a specific embodiment, provided herein are methods for preventing and/or treating Influenza virus infection comprising administering to a subject an antibody described herein or a pharmaceutical composition thereof.

In another aspect, provided herein are methods for detecting an Influenza virus, or detecting, diagnosing or monitoring an Influenza virus infection in a subject using an antibody described herein. In a specific embodiment, a method of detecting a strain of Influenza A virus comprises: (a) assaying for the level of an Influenza virus HA in cells or a tissue sample of a subject using an antibody; and (b) comparing the level of the Influenza virus HA assayed in (a) with the level of the Influenza virus HA in cells or tissue samples not infected with Influenza virus (e.g., a control level), wherein an increase in the assayed level of Influenza virus HA compared to the control level of the Influenza virus antigen is indicative of the presence of a strain of Influenza A virus. In specific embodiments, the strain of Influenza A virus detected belongs to the H3 subtype. In a specific embodiment, the strain of Influenza A virus detected is Influenza virus is A/Hong Kong/1/1968, A/Alabama/1/1981, A/Beijing/47/1992, or A/Wyoming/3/2003.

3.1 Terminology

As used herein, the term "about" or "approximately" when used in conjunction with a number refers to any number within 0.25%, 0.5%, 1%, 5% or 10% of the referenced number. The terms "about" or "approximate," when used in reference to an amino acid position refer to the particular amino acid position in a sequence or any amino acid that is within five, four, three, two or one residues of that amino acid position, either in an N-terminal direction or a C-terminal direction.

As used herein, the term "administer" or "administration" refers to the act of injecting or otherwise physically delivering a substance as it exists outside the body (e.g., an anti-Influenza A virus antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

Antibodies encompassed herein include, but are not limited to, synthetic antibodies, monoclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, F(ab')$_2$ fragments, disulfide-linked Fvs (sdFv), anti-idiotypic (anti-Id) antibodies, and epitope-binding fragments of any of the above. In particular, antibodies encompassed herein include immunoglobulin molecules and immunologically active portions of immunoglobulin molecules, i.e., antigen binding domains or molecules that contain an antigen-binding site that immunospecifically binds to an Influenza virus antigen (e.g., one or more complementarity determining regions (CDRs) of an anti-Influenza virus antibody). The antibodies encompassed herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduction or amelioration the severity of an Influenza virus infection, an Influenza virus disease or a symptom associated therewith; (ii) reduction in the duration of an Influenza virus infection, an Influenza virus disease or a symptom associated therewith; (iii) prevention of the progression of an Influenza virus infection, an Influenza virus disease or a symptom associated therewith; (iv) regression of an Influenza virus infection, an Influenza virus disease or a symptom associated therewith; (v) prevention of the development or onset of an Influenza virus infection, an Influenza virus disease or a symptom associated therewith; (vi) prevention of the recurrence of an Influenza virus infection, an Influenza virus disease or a symptom associated therewith; (vii) reduction or prevention of the spread of an Influenza virus from one cell to another cell, one tissue to another tissue, or one organ to another organ; (viii) prevention or reduction of the spread/transmission of an Influenza virus from one subject to another subject; (ix) reduction in organ failure associated with an Influenza virus infection or Influenza virus disease; (x) reduction in the hospitalization of a subject; (xi) reduction in the hospitalization length; (xii) an increase in the survival of a subject with an Influenza virus infection or a disease associated therewith; (xiii) elimination of an Influenza virus infection or a disease associated therewith; (xiv) inhibition or reduction in Influenza virus replication; (xv) inhibition or reduction in the binding or fusion of Influenza virus to a host cell(s); (xvi) inhibition or reduction in the entry of an Influenza virus into a host cell(s); (xvii) inhibition or reduction of replication of the Influenza virus genome; (xviii) inhibition or reduction in the synthesis of Influenza virus proteins; (xix) inhibition or reduction in the assembly of Influenza virus particles; (xx) inhibition or reduction in the release of Influenza virus particles from a host cell(s); (xxi) reduction in Influenza virus titer; (xxii) the reduction in the number of symptoms associated with an Influenza virus infection or an Influenza virus disease; (xxiii) enhancement, improvement, supplementation, complementation, or augmentation of the prophylactic or therapeutic effect(s) of another therapy; (xxiv) prevention of the onset or progression of a secondary infection associated with an Influenza virus infection; and/or (xxv) prevention of the onset or diminution of disease severity of bacterial pneumonias occurring secondary to Influenza virus infections. In some embodiments, the "effective amount" of a therapy has a beneficial effect but does not cure an Influenza virus infection or a disease associated therewith. In certain embodiments, the "effective amount" of a therapy may encompass the administration of multiple doses of a therapy at a certain frequency to achieve an amount of the therapy that has a prophylactic and/or therapeutic effect. In other situations, the "effective amount" of a therapy may encompass the administration of a single dose of a therapy at a certain amount. Exemplary doses of an effective amount are provided in Section 5.5.2 infra.

In certain embodiments, the effective amount does not result in complete protection from an Influenza virus disease, but results in a lower titer or reduced number of Influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of Influenza virus relative to an untreated subject. In some embodiments, the effective amount results in a reduction in titer of Influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs. Benefits of a reduction in the titer, number or total burden of Influenza virus include, but are not limited to, less severe symptoms of the infection, fewer symptoms of the infection, reduction in the length of the disease associated with the infection, and prevention of the onset or diminution of disease severity of bacterial pneumonias occurring secondary to Influenza virus infections.

As used herein, the term "fragment" refers to a sequence comprising at least 2 consecutive amino acids or nucleotides from a parent sequence. In a specific embodiment, it refers to 2 to 10, 2 to 15, 2 to 30, 5 to 30, 10 to 60, 25 to 50, 25 to 100, 100 to 175, 150 to 250, 150 to 300 or more consecutive amino acids or nucleotides from a parent sequence.

As used herein, the terms "hemagglutinin" and "HA" refer to any Influenza hemagglutinin known to those of skill in the art. In certain embodiments, the hemagglutinin is Influenza hemagglutinin, such as an Influenza A hemagglutinin, an Influenza B hemagglutinin or an Influenza C hemagglutinin. A typical hemagglutinin comprises domains known to those of skill in the art including a signal peptide, a stem domain, a globular head domain, a luminal domain, a transmembrane domain and a cytoplasmic domain. In certain embodiments, a hemagglutinin consists of a single polypeptide chain, such as HA0. In certain embodiments, a hemagglutinin consists of more than one polypeptide chain in quaternary association, e.g. HA1 and HA2. In certain embodiments, a hemagglutinin consists of an hemagglutinin monomer (HA0 or HA1/HA2). In certain embodiments, a hemagglutinin consists of a trimeric hemagglutinin molecule as it is expressed on the viral surface. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

As used herein, the term "host cell" refers to any type of cell, e.g., a primary cell or a cell from a cell line. In specific embodiments, the term "host cell" refers a cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus. In certain embodiments, an infection refers to the presence of a virus in a cell or a subject, or the invasion of a cell or subject by the virus, without a resulting pathological state.

As used herein, the term "Influenza virus antigen" refers to any antigen obtained or derived from an Influenza virus. In a specific embodiment, the antigen is a protein, polypeptide or peptide expressed by an Influenza virus or a fragment thereof. In another specific embodiment, the antigen is a protein, polypeptide or peptide found on the surface of an Influenza virus particle or a fragment thereof (e.g., hemagglutinin or a fragment thereof, or neuraminidase or a fragment thereof). In a preferred embodiment, the antigen is an Influenza virus hemagglutinin or a fragment thereof.

As used herein, the terms "Influenza virus disease" and a disease associated with an Influenza virus infection refer to the pathological state resulting from the presence of an Influenza virus (e.g., Influenza A or B virus) in a cell or subject or the invasion of a cell or subject by an Influenza virus. In specific embodiments, the term refers to a respiratory illness caused by an Influenza virus.

The terms "Kabat numbering," and like terms are recognized in the art and refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3.

An "isolated" or "purified" protein (e.g., an antibody) is substantially free of cellular material or other contaminating proteins from the cell or tissue source from which the protein is derived, or substantially free of chemical precursors or other chemicals when chemically synthesized. The language "substantially free of cellular material" includes preparations of a protein (e.g., an antibody) in which the protein is separated from cellular components of the cells from which it is isolated or recombinantly produced. Thus, a protein (e.g., an antibody) that is substantially free of cellular material includes preparations of protein having less than about 30%, 20%, 10%, or 5% (by dry weight) of heterologous protein (also referred to herein as a "contaminating protein"). When the protein is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the protein of interest. In a specific embodiment, an antigen derived or obtained from an Influenza virus is purified. In another specific embodiment, antibodies encompassed herein are purified.

As used herein, the numeric term "log" refers to $\log_{10}$.

As used herein, the terms "manage," "managing," and "management" refer to the beneficial effects that a subject derives from a therapy (e.g., a prophylactic or therapeutic agent), which does not result in a cure of the infection or disease associated therewith. In certain embodiments, a subject is administered one or more therapies (e.g., prophylactic or therapeutic agents, such as an antibody encompassed herein) to "manage" an Influenza virus disease, or one or more symptoms thereof, so as to prevent the progression or worsening of the disease.

As used herein, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogues of natural nucleotides, for example, peptide nucleic acids ("PNA"s), that have similar binding properties as the reference nucleic acid. In some embodiments, nucleic acid refers to deoxyribonucleic acids (e.g., cDNA or DNA). In other embodiments, nucleic acid refers to ribonucleic acid (e.g., mRNA or RNA).

As used herein, the terms "prevent," "preventing" and "prevention" in the context of the administration of a therapy(ies) to a subject to prevent an Influenza virus disease refer to one or more of the following effects resulting from the administration of a therapy or a combination of therapies: (i) the inhibition or reduction in the development or onset of an Influenza virus disease or a symptom thereof (e.g., fever, myalgia, edema, inflammatory infiltrates); (ii) the inhibition or reduction in the recurrence of an Influenza virus disease or a symptom associated therewith; and (iii) the reduction or inhibition in Influenza virus infection and/or replication.

As used herein, the terms "prevent", "preventing" and "prevention" in the context of the administration of a therapy(ies) to a subject to prevent an Influenza virus infection refer to one or more of the following: (i) the reduction or inhibition of the spread of Influenza virus from one cell to another cell; (ii) the reduction or inhibition of the spread of Influenza virus from one organ or tissue to another organ or tissue; (iii) the reduction or inhibition of the spread of Influenza virus from one region of an organ or tissue to another region of the organ or tissue (e.g., the reduction in the spread of Influenza virus from the upper to lower respiratory tract); (iv) the prevention of an initial infection after exposure to an Influenza virus; and/or (v) prevention of the onset or development of one or more symptoms associated with Influenza virus disease or infection.

As used herein, the terms "subject" and "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In another embodiment, a subject is a human. In another embodiment, a subject is a human infant. In another embodiment, a subject is a human child. In another embodiment, the subject is a human adult. In another embodiment, a subject is an elderly human.

As used herein, the term "human infant" refers to a newborn to 1 year old human.

As used herein, the term "human child" refers to a human that is 1 year to 18 years old.

As used herein, the term "human toddler" refers to a human that is 1 years to 3 years old.

As used herein, the term "human adult" refers to a human that is 18 years or older.

As used herein, the term "elderly human" refers to a human 65 years or older.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to an antibody that binds an Influenza virus of the hemagglutinin 3 ("H3") subtype. In other embodiments, the term "therapy" refers to an immunogenic composition (e.g., an Influenza virus vaccine).

As used herein, the terms "treat," "treatment," and "treating" in the context of administration of a therapy(ies) to a subject to treat an Influenza virus disease or Influenza virus infection refer to a beneficial or therapeutic effect of a therapy or a combination of therapies. In specific embodiments, such terms refer to one, two, three, four, five or more of the following effects resulting from the administration of a therapy or a combination of therapies: (i) reduction or amelioration in the severity of an Influenza virus infection, an Influenza virus disease or a symptom associated therewith; (ii) reduction in the duration of an Influenza virus infection, an Influenza virus disease or a symptom associated therewith; (iii) prevention of the progression of an Influenza virus infection, an Influenza virus disease or a symptom associated therewith; (iv) regression of an Influenza virus infection, an Influenza virus disease or a symptom associated therewith; (v) prevention of the development or onset of an Influenza virus infection, an Influenza virus disease or a symptom associated therewith; (vi) prevention of the recurrence of an Influenza virus infection, an Influenza virus disease or a symptom associated therewith; (vii) reduction or prevention of the spread of an Influenza virus from one cell to another cell, one tissue to another tissue, or one organ to another organ; (viii) prevention or reduction of the spread/transmission of an Influenza virus from one subject to another subject; (ix) reduction in organ failure associated with an Influenza virus infection or Influenza virus disease; (x) reduction in the hospitalization of a subject; (xi) reduction in the hospitalization length; (xii) an increase in the survival of a subject with an Influenza virus infection or a disease associated therewith; (xiii) elimination of an Influenza virus infection or a disease associated therewith; (xiv) inhibition or reduction in Influenza virus replication; (xv) inhibition or reduction in the binding or fusion of Influenza virus to a host cell(s); (xvi) inhibition or reduction in the entry of an Influenza virus into a host cell(s); (xvii) inhibition or reduction of replication of the Influenza virus genome; (xviii) inhibition or reduction in the synthesis of Influenza virus proteins; (xix) inhibition or reduction in the assembly of Influenza virus particles; (xx) inhibition or reduction in the release of Influenza virus particles from a host cell(s); (xxi) reduction in Influenza virus titer; (xxii) the reduction in the number of symptoms associated with an Influenza virus infection or an Influenza virus disease; (xxiii) enhancement, improvement, supplementation, complementation, or augmentation of the prophylactic or therapeutic effect(s) of another therapy; (xxiv) prevention of the onset or progression of a secondary infection associated with an Influenza virus infection; and/or (xxv) prevention of the onset or diminution of disease severity of bacterial pneumonias occurring secondary to Influenza virus infections.

4 DESCRIPTION OF THE FIGURES

FIG. 1. Characteristics of anti-Influenza virus antibodies. (A) Monoclonal antibodies 7A7 and 39A4 react with Influenza virus A/HK/1/1968 hemagglutinin as measured by ELISA; and monoclonal antibody 12D1 reacts with A/HK/1/1968 hemagglutinin as measured by Western blot. (B) Monoclonal antibody 12D1 binds hemagglutinin of Influenza virus strain A/Pan/2007/1999 (H3) in the HA2 region as measured by Western Blot. (C) Monoclonal antibody 7A7 binds Influenza virus strains A/HK/1/1968, A/Pan/2007/1999, and A/Wisc/67/2005 as measured by ELISA. (D) Monoclonal antibody 39A4 binds Influenza virus strains A/HK/1/1968, A/Pan/2007/1999, and A/Wisc/67/2005 as measured by ELISA.

Figure 2:
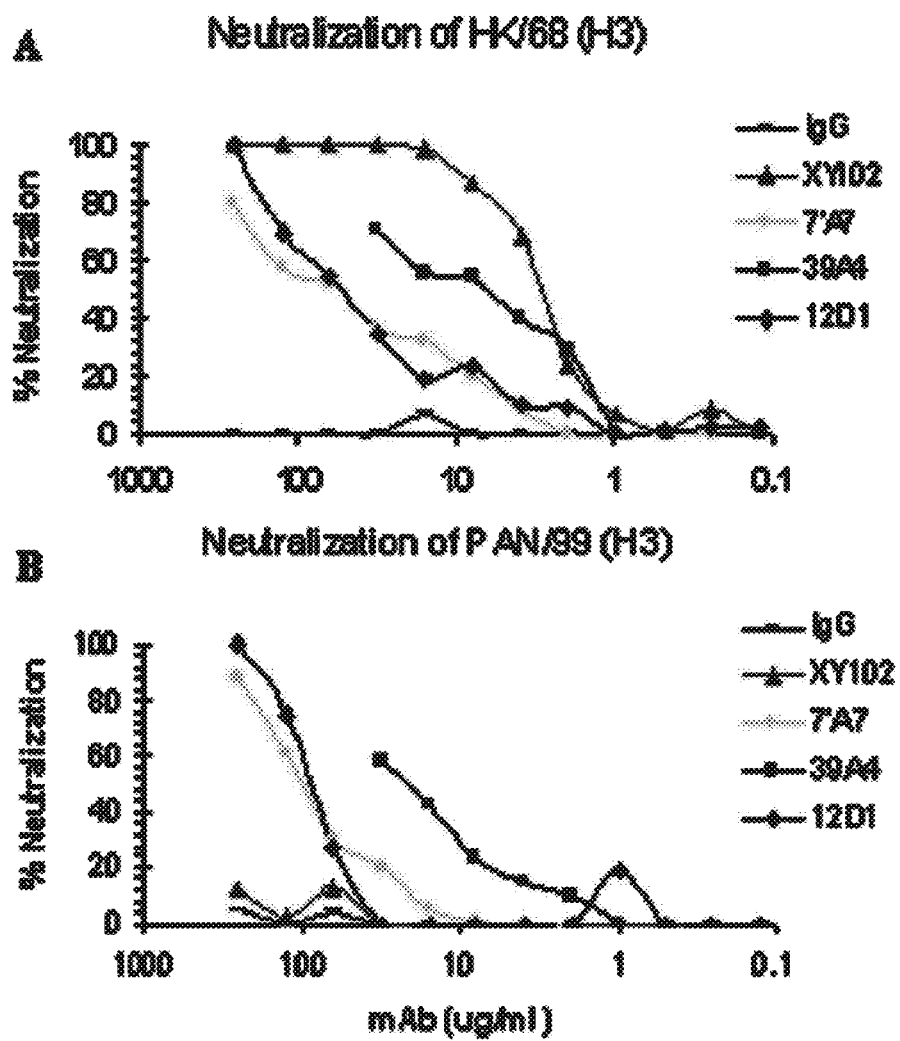

FIG. 2. Neutralization of Influenza virus strains by monoclonal antibodies 7A7, 12D1, and 39A4. (A) Monoclonal antibodies 7A7, 12D1, and 39A4 neutralize Influenza virus strain A/HK/1/1968 (H3) as measured by microneutralization assay. IgG represents isotype control antibody; XY102 represents a monoclonal antibody specific to Influenza virus strain A/HK/1/1968 (H3). (B) Monoclonal antibodies 7A7, 12D1, and 39A4 neutralize Influenza virus strain A/Pan/2007/1999 (H3) as measured by microneutralization assay. IgG represents isotype control antibody; XY102 represents a monoclonal antibody specific to Influenza virus strain A/HK/1/1968 (H3).

Figure 3:
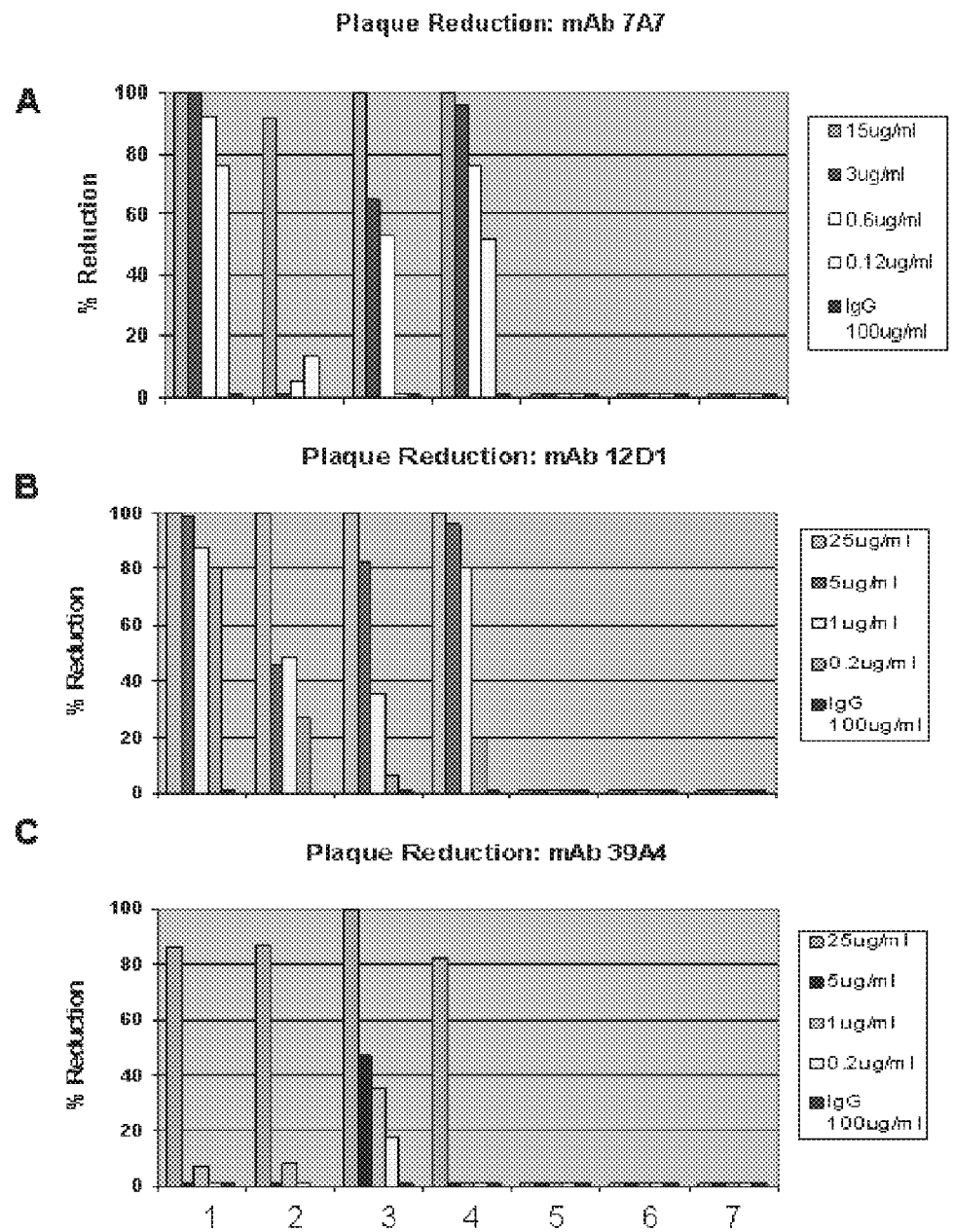

FIG. 3. Monoclonal antibodies 7A7, 12D1, and 39A4 specifically neutralize Influenza virus H3 strains. (A) Neutralization by monoclonal antibody 7A7 as measured by plaque reduction assay. (B) Neutralization by monoclonal antibody 12D1 as measured by plaque reduction assay. (C) Neutralization by monoclonal antibody 39A4 as measured by plaque reduction assay. (A-C) A/Hong Kong/1/1968 (H3), lane 1; A/Beijing/47/1992 (H3), lane 2; A/Pan/2007/1999 (H3), lane 3; A/Brisbane/10/2007 (H3), lane 4; A/New Caledonia20/1999 (H1), lane 5; A/DK/1964 (H4), lane 6; A/TKY/1963 (H7), lane 7.

Figure 4:
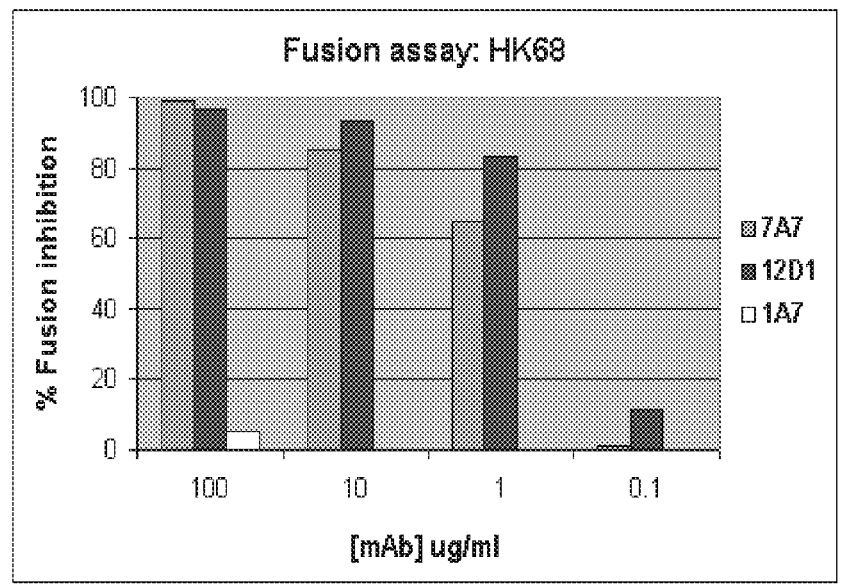

FIG. 4. Monoclonal antibodies 7A7 and 12D1 inhibit low-pH fusion of Influenza virus strain A/Hong Kong/1/1968 (H3) hemagglutinin as measured by red blood cell fusion assay. Monoclonal antibody 1A7 (IgG) is specific for the Influenza A virus protein NS 1 and does not affect viral fusion.

Figure 5:
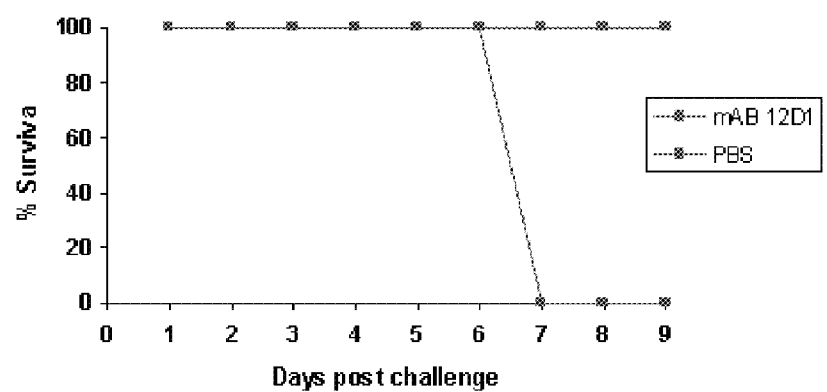

FIG. 5. Mice injected with monoclonal antibody 12D1 one hour prior to challenge with Influenza virus strain X31 survive longer than mice injected with PBS alone. X31 is a chimeric virus expressing the hemagglutinin and neuraminidase proteins from A/Hong Kong/1/1968 (H3N2) on an A/PR/8 background (mouse-adapted H1N1 virus).

Figure 6:
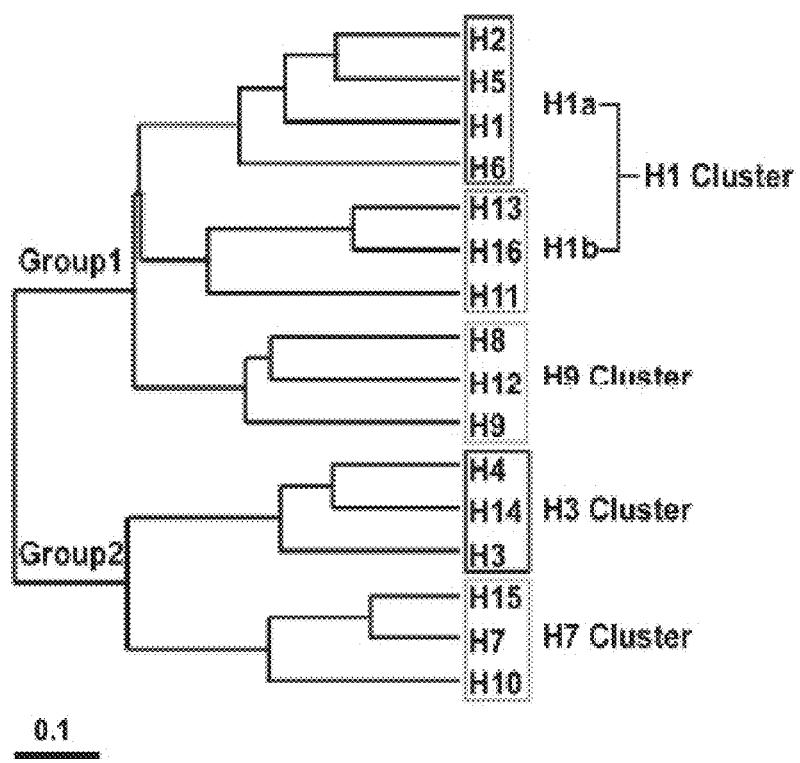

FIG. 6. Phylogenetic relationships among Influenza virus HA subtypes from Sui et al., 2009, Nat. Struct. Mol. Biol 16(3): 265-273.

Figure 7:
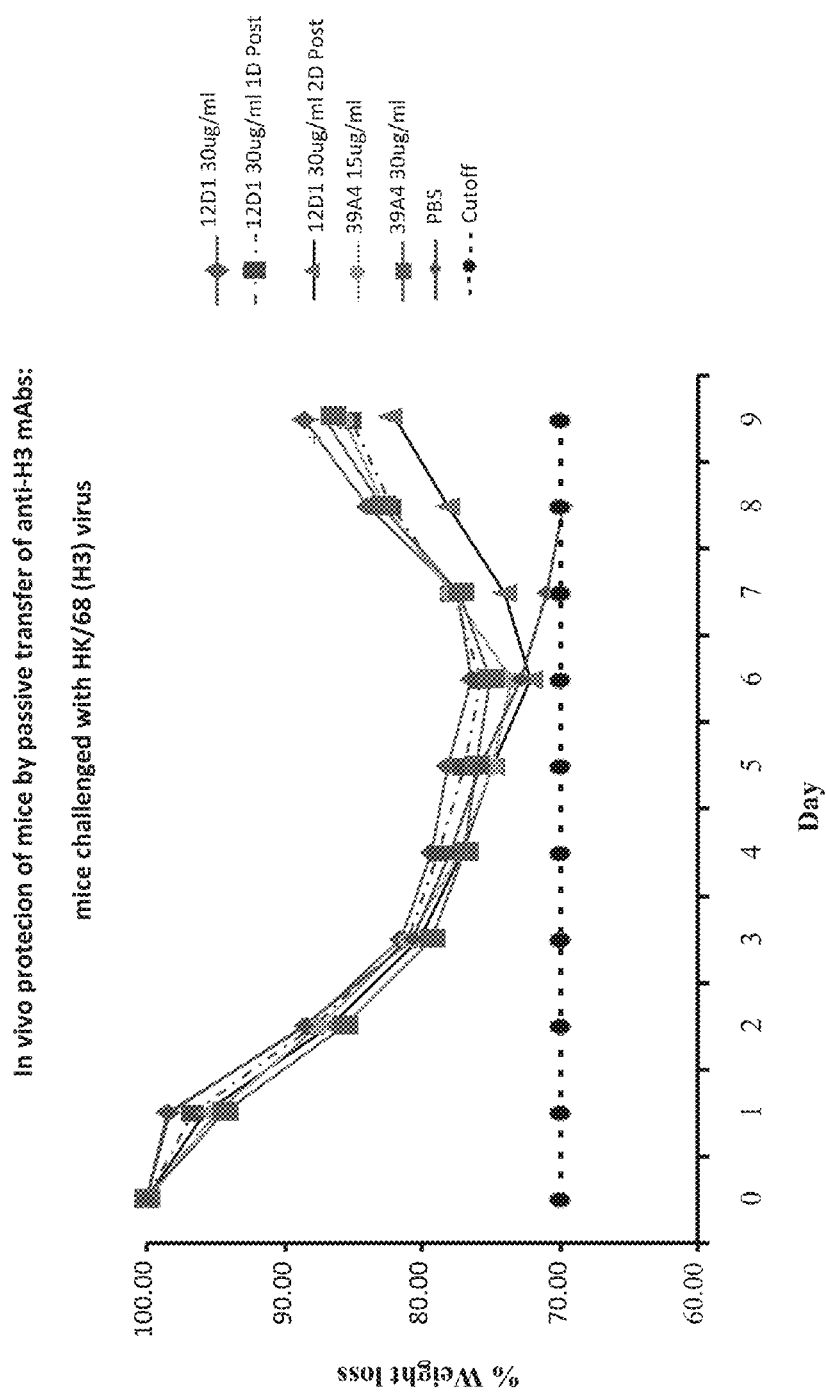

FIG. 7. Passive transfer of monoclonal antibodies 12D1 and 39A4 results in decreased weight loss in mice challenged with Influenza A virus strain A/Hong Kong/1/1968 (H3) as compared to mice administered PBS, rather than antibody.

Figure 8:
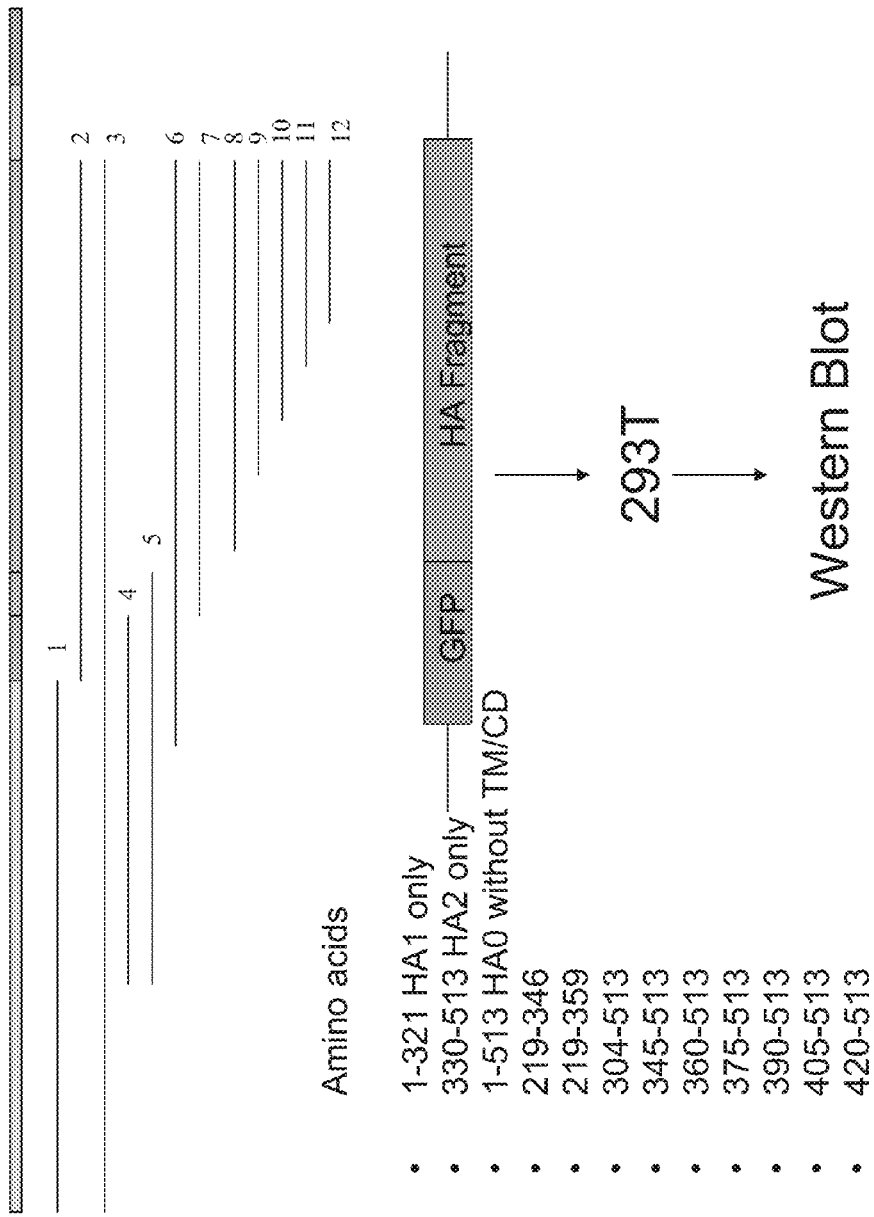

FIG. 8. Diagram of fusion protein encoded by nucleic acid constructs: hemagglutinin truncation mutants fused to green fluorescent protein.

Figure 9:
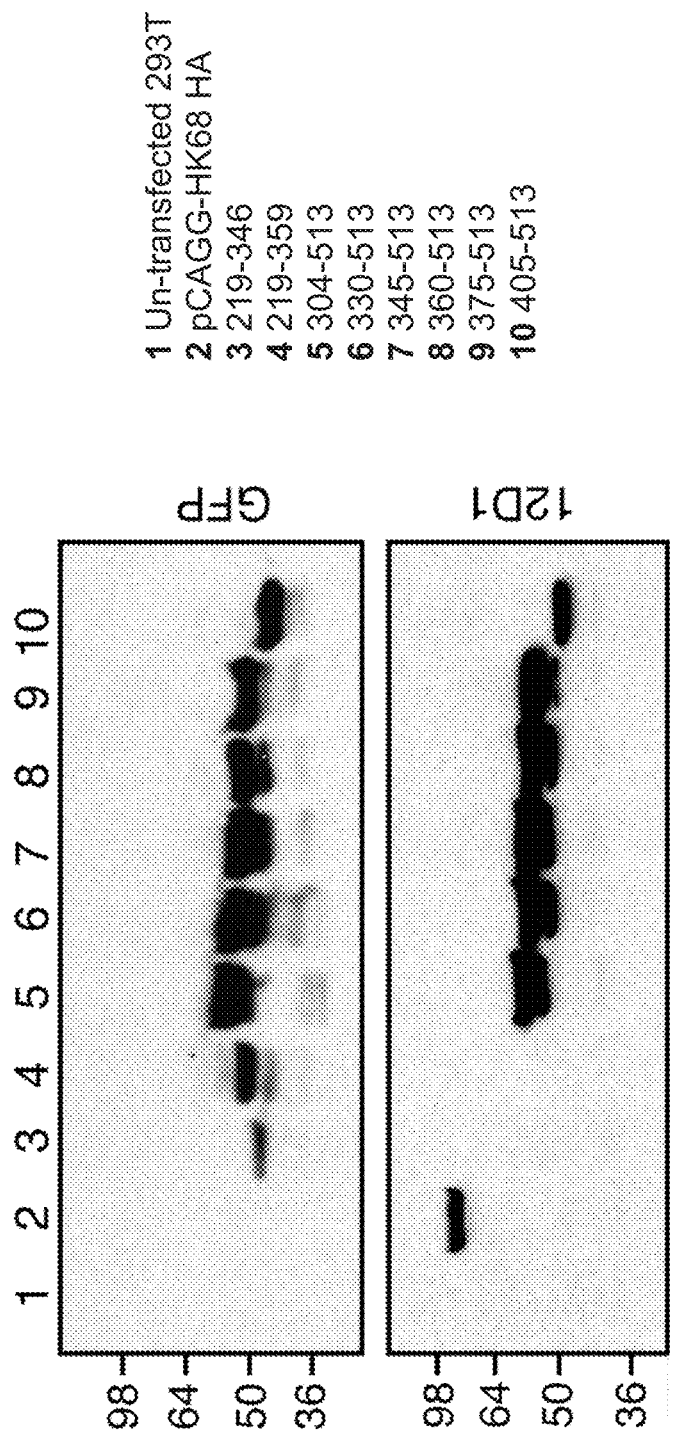

FIG. 9. Western blot assessing the ability of the monoclonal antibody 12D1 to bind to fragments of the hemagglutinin protein of Influenza A virus strain A/Hong Kong/1/1968 (H3).

Figure 10:
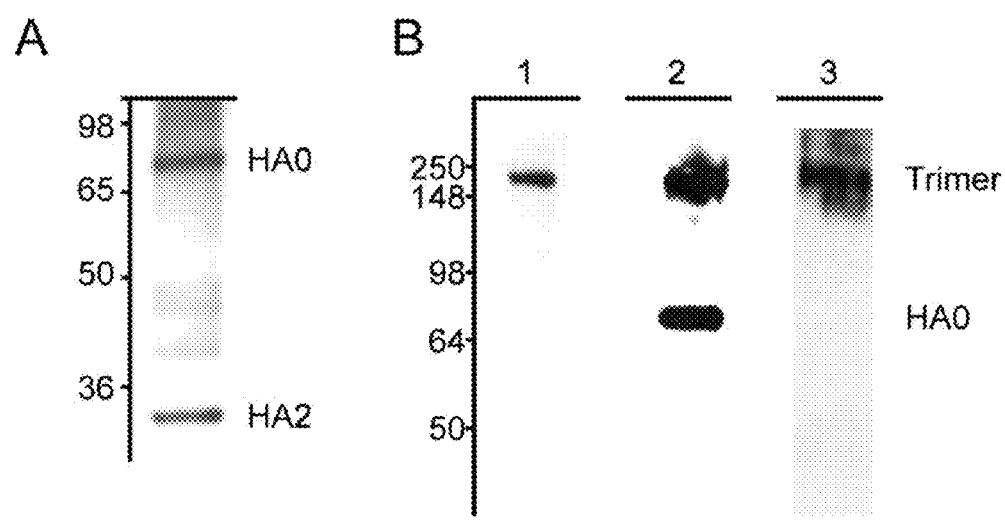

FIG. 10. Monoclonal antibodies 7A7, 12D1 and 39A4 react with H3 hemagglutinin by Western blot. (A) MAb 12D1 binds the A/Pan/2007/1999 hemagglutinin within the HA2 subunit. Monoclonal antibodies 7A7 and 39A4 do not react with hemagglutinin under reducing conditions. (B) Monoclonal antibodies 7A7, 12D1 and 39A4 react with the A/HK/1/1968 hemagglutinin under non-reducing conditions. Monoclonal antibodies 7A7 (lane 1) and 39A4 (lane 3) bind HA trimer complexes. mAb 12D1 (lane 2) binds HA trimer complexes and HA0.

Figure 11:
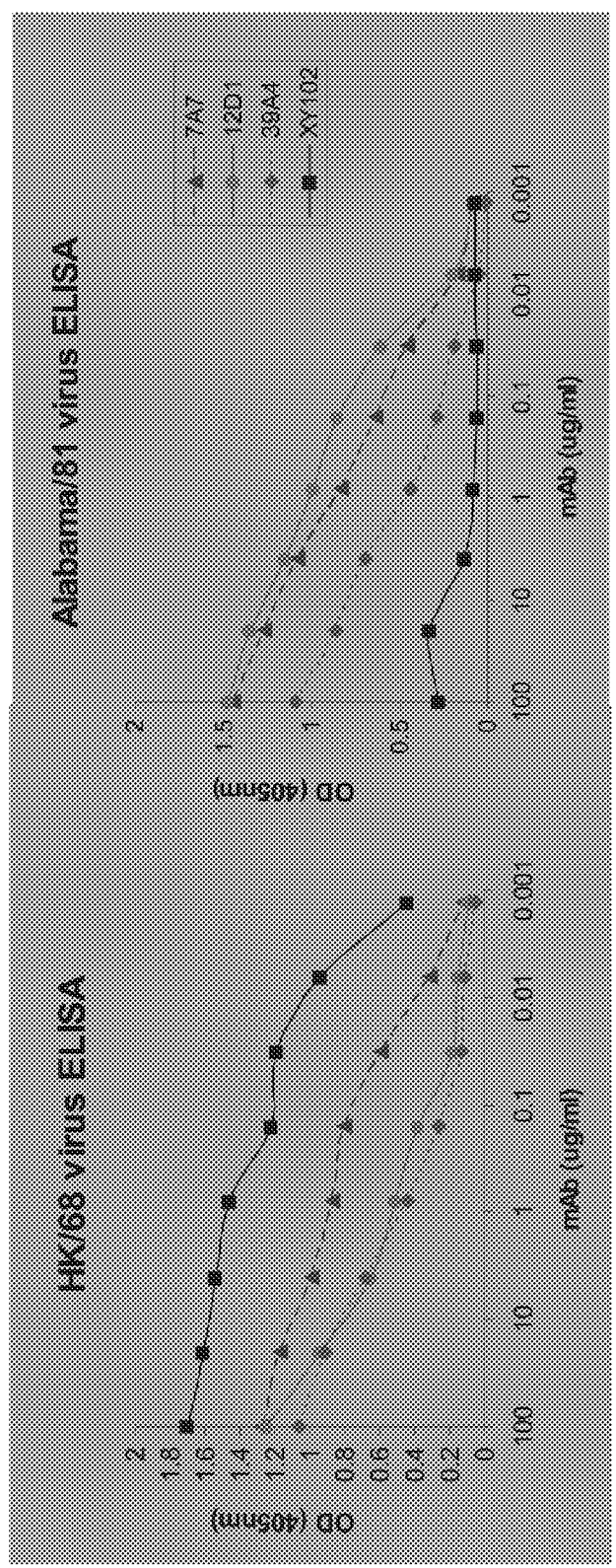

FIG. 11. Reactivity of anti-H3 mAbs by ELISA. (A) Monoclonal antibodies 7A7 and 39A4 react with purified A/HK/1968 (H3) virus. (B) Monoclonal antibodies 7A7, 12D1 and 39A4 react with purified A/Alabama/1981 (H3) virus. Monoclonal antibody XY102 is specific for the hemagglutinin of A/HK/1968 virus.

Figure 12:
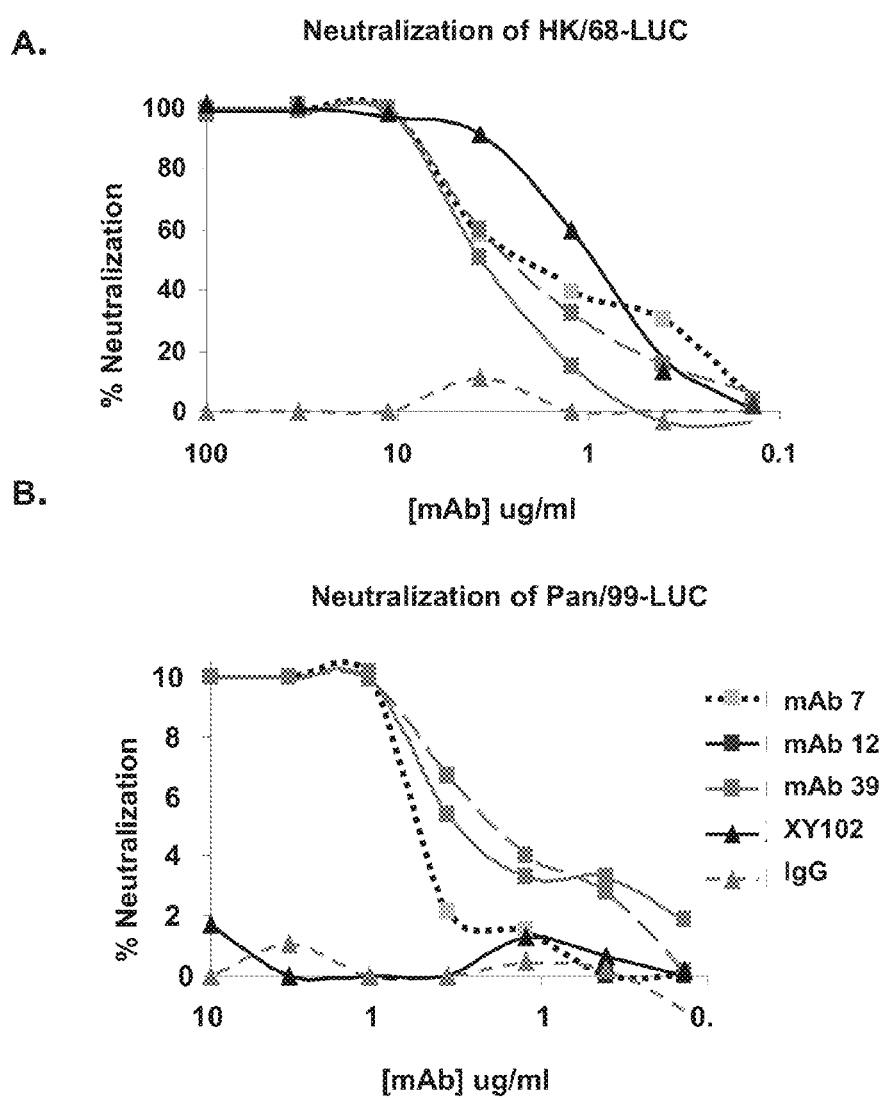

FIG. 12. Anti-H3 monoclonal antibodies in microneutralization assay. Neutralization of virus expressing the HA from either (A) A/Hong Kong/1/1968 virus or (B) A/Panama/2007/1999 virus by monoclonal antibodies 7A7, 12D1 and 39A4. Monoclonal antibody XY102 is specific for A/HK/1968 virus. Purified mouse IgG was used for the negative control.

Figure 13:
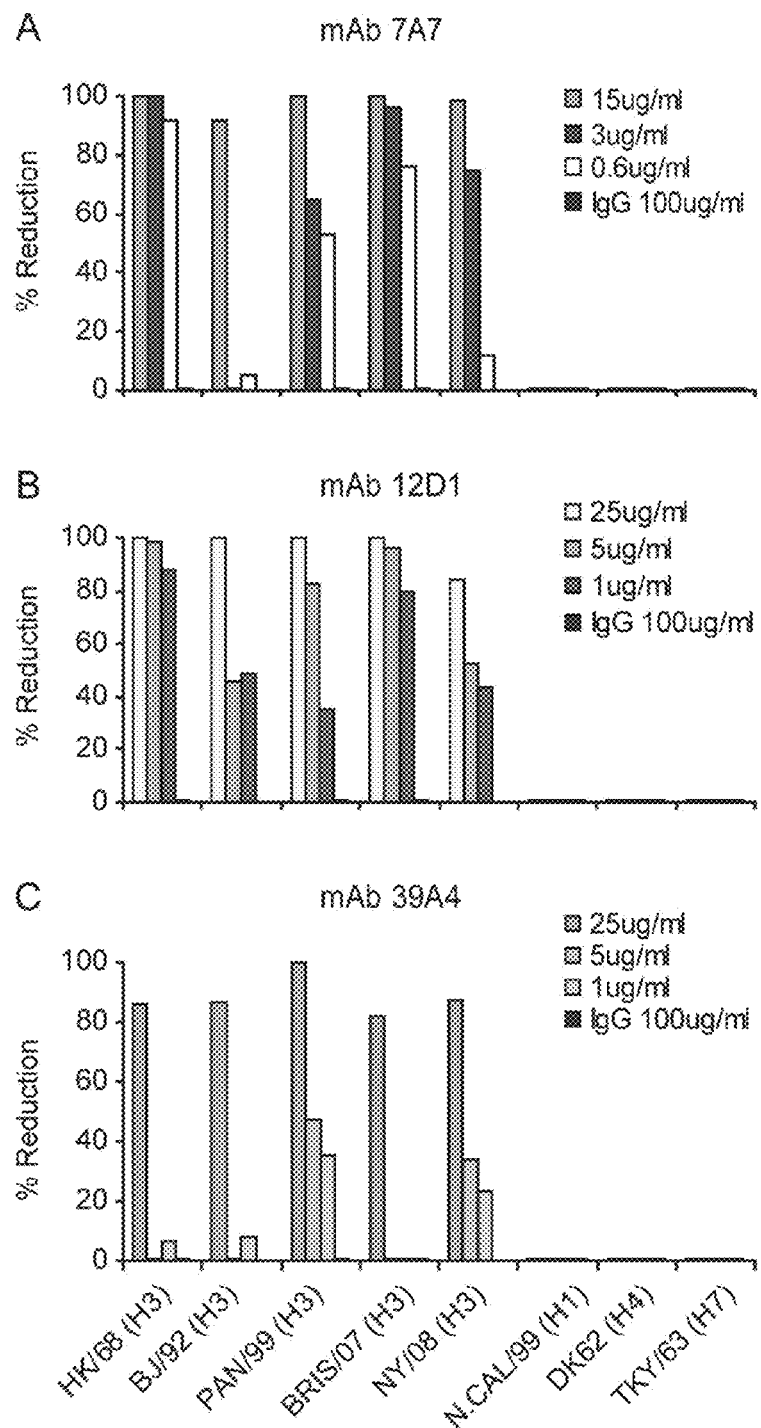

FIG. 13. Activity of anti-H3 mabs in plaque reduction assay on MDCK cells. Monoclonal antibodies 7A7 (A), 12D1 (B) and 39A4 (C) neutralize all H3 viruses tested by plaque reduction assay but not representative H1, H4 or H7 viruses. Purified mouse IgG was used for the negative control. The plaque reduction assays were performed multiple times and with each new antibody preparation.

Figure 14:
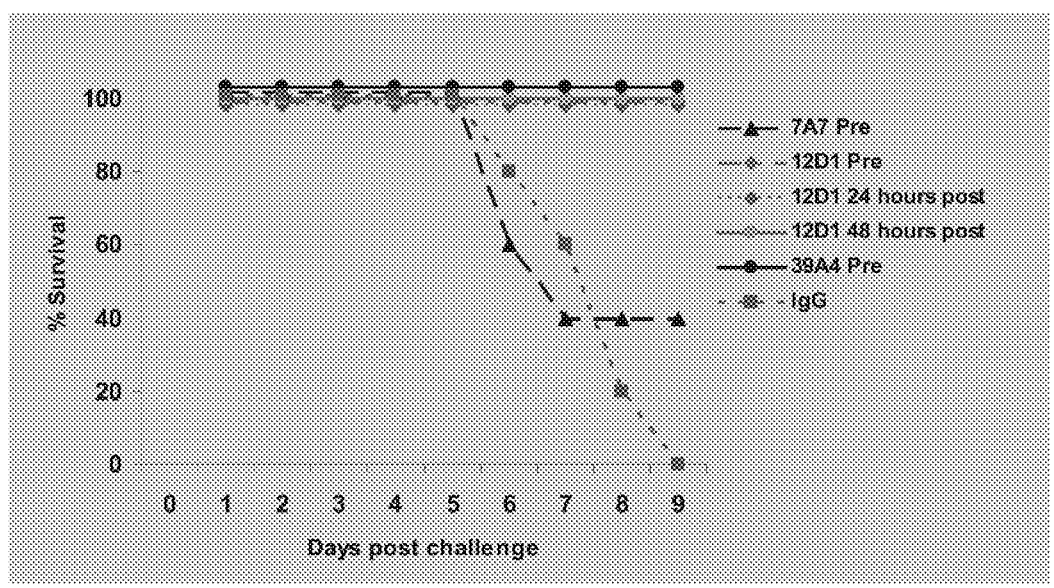

FIG. 14. Anti-H3 monoclonal antibodies protect against H3 virus in vivo. Mice were given 30 mg/kg mAb 7A7, 12D1, 39A4 or isotype control by intraperitoneal injection 1 hour prior, 24 hours post (12D1 only) or 48 hours post (12D1 only) challenge with X31. N=5 per group.

Figure 15:
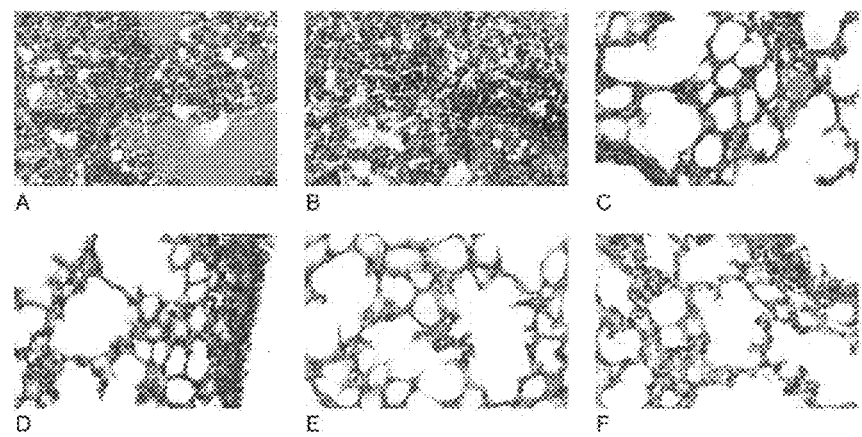

FIG. 15. Treatment with anti-H3 monoclonal antibodies diminishes lung damage associated with viral pneumonia caused by X31 virus. (A,B) Untreated (C,D) mice treated with monoclonal antibody 39A4 (E,F) mice treated with mAb 12D1. 40× magnification.

Figure 16:
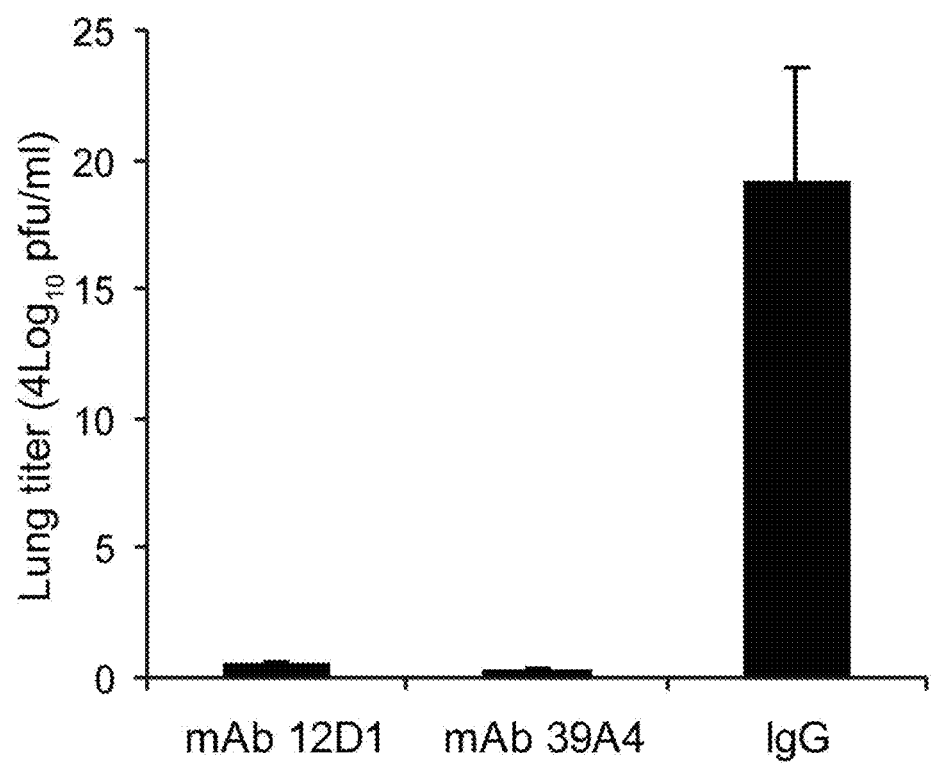

FIG. 16. Anti-H3 monoclonal antibodies protect against replication of H3 virus in lungs. Mice were given 30 mg/kg monoclonal antibody 12D1, 39A4 or isotype control by intraperitoneal injection 1 hour prior to infection with A/Georgia/1981 virus. Data represent lung titers from groups of 5 mice, 2 days post infection.

Figure 17:
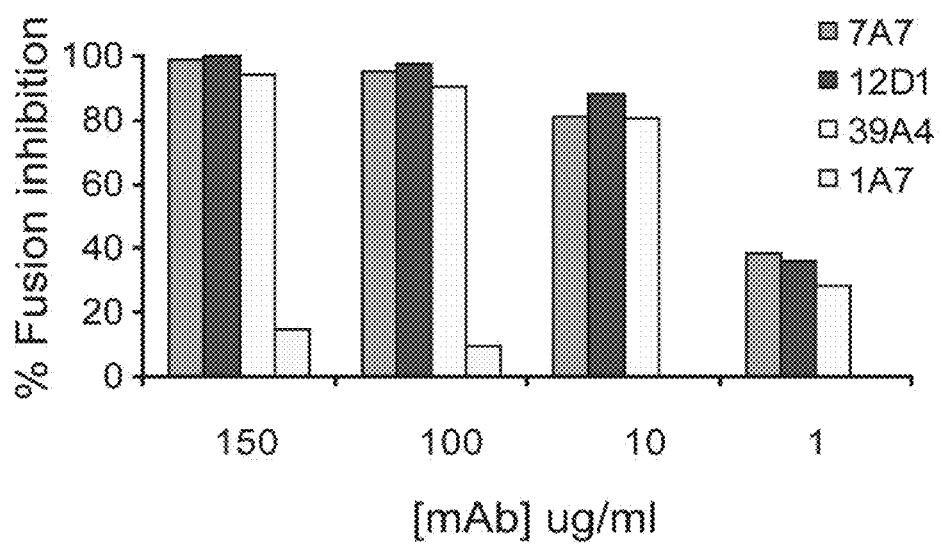

FIG. 17. Red blood cell fusion assay. Anti-H3 monoclonal antibodies inhibit low-pH induced fusion of HK/68 hemagglutinin with chicken red blood cells. All monoclonal antibodies are negative for hemagglutinin-inhibition activity. Monoclonal antibody 1A7 is specific for Influenza virus NS1 protein.

Figure 18:
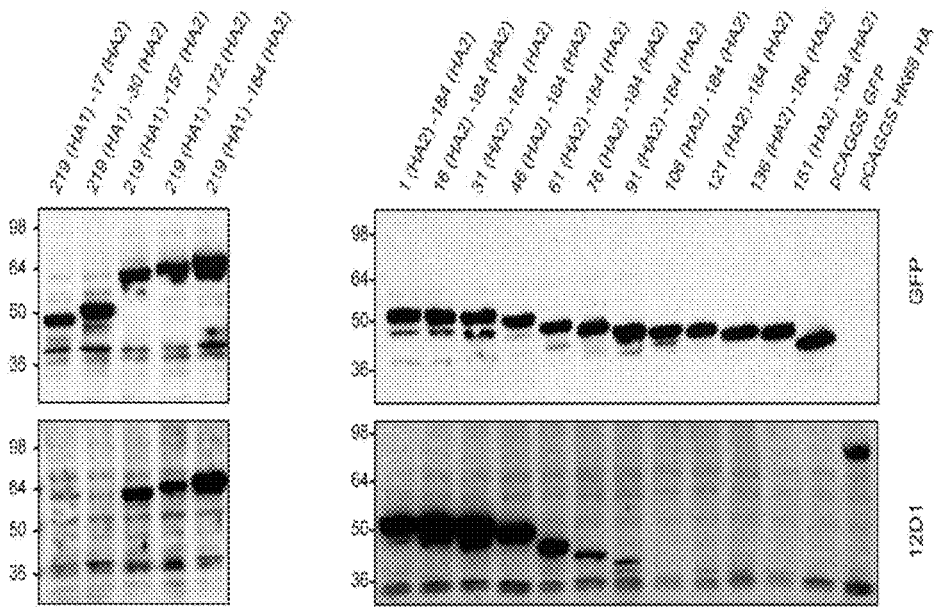

FIG. 18. MAb 12D1 reacts by Western blot with hemagglutinin truncation mutants. 12D1 makes dominant contacts with the HA2 subunit in the region of amino acids 30 to 106 (H3 numbering (see, e.g., Wilson et al., Nature 1981; 289 (5796):366-73)). Diminished 12D1 binding without diminished GFP expression in the HA2 76-184 and HA2 91-184 truncations along with loss of binding with the HA2 106-184 truncation suggests that the binding epitope lies in the region from amino acids HA2 76-106. These 30 amino acids fall within the membrane distal half of the long alpha-helix of HA2.

FIG. 19. The deduced nucleotide sequences of the VH and VL chains of the antibody 7A7. Framework regions are shown in bold. CDR regions are underlined.

FIG. 20. The deduced amino acid sequences of the VH and VL chains of the antibody 7A7. Framework regions are shown in bold. CDR regions are underlined.

FIG. 21. The deduced nucleotide sequences of the VH and VL chains of the antibody 12D1. Framework regions are shown in bold. CDR regions are underlined.

FIG. 22. The deduced amino acid sequences of the VH and VL chains of the antibody 12D1. Framework regions are shown in bold. CDR regions are underlined.

Figure 23:
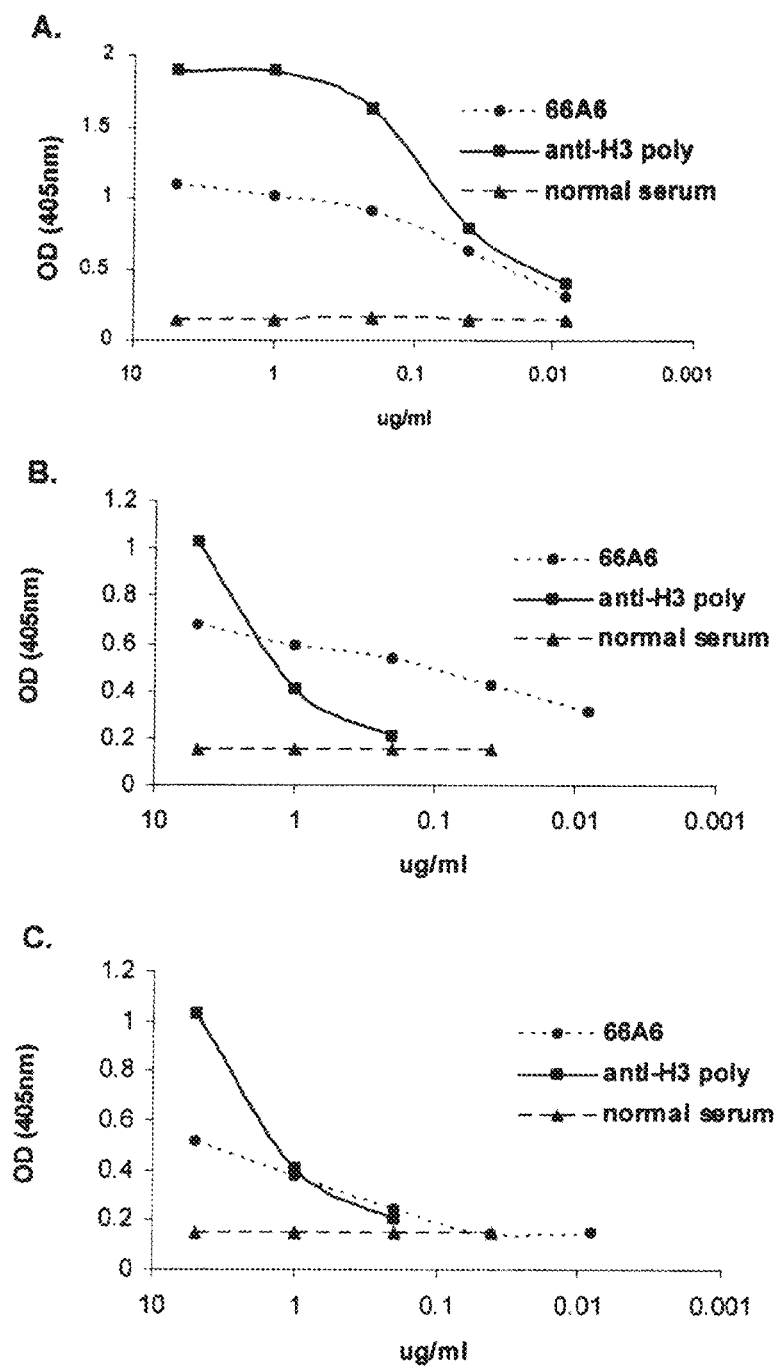

FIG. 23. Reactivity of monoclonal antibody 66A6 by ELISA. (A) Monoclonal antibody 66A6 reacts with purified A/HK/1968 (H3) virus. (B) Monoclonal antibody 66A6 reacts with purified A/Panama/2007/1999 (H3) virus. (C) Monoclonal antibody 66A6 reacts with purified A/Brisbane/10/2007 (H3) virus.

Figure 24:
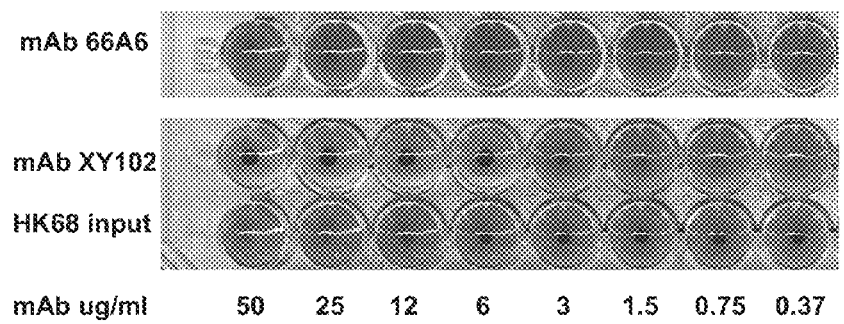

FIG. 24. Red blood cell fusion assay. Monoclonal antibody 66A6 is negative for hemagglutinin-inhibition activity against purified A/HK/1968 (H3) virus. Monoclonal antibody XY102 is specific for A/HK/1968 virus.

Figure 25:
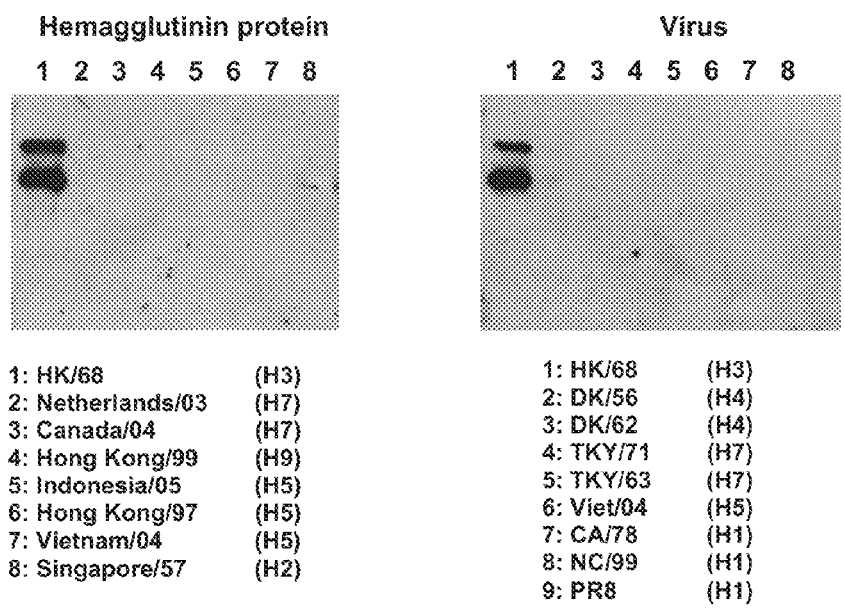

FIG. 25. Monoclonal antibody 66A6 reacts with the hemagglutinin protein of A/HK/1968 (H3) virus by Western blot, but does not react with non-H3 viruses or recombinantly-expressed non-H3 hemagglutinins.

Figure 26:
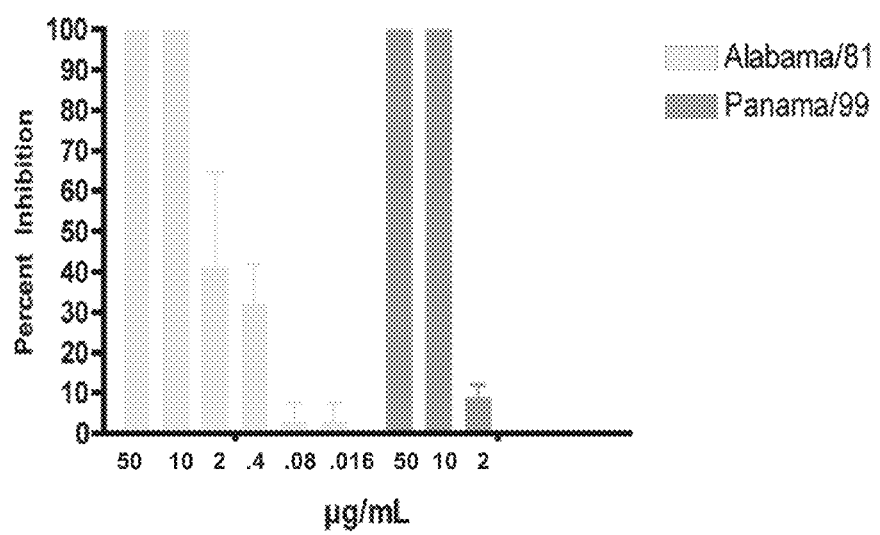

FIG. 26. Activity of monoclonal antibody 66A6 in plaque reduction assay on MDCK cells. Monoclonal antibody 66A6 neutralizes A/Panama/2007/1999 (H3) and A/Alabama/1/1981 (H3) Influenza viruses by plaque reduction assay.

Figure 27:
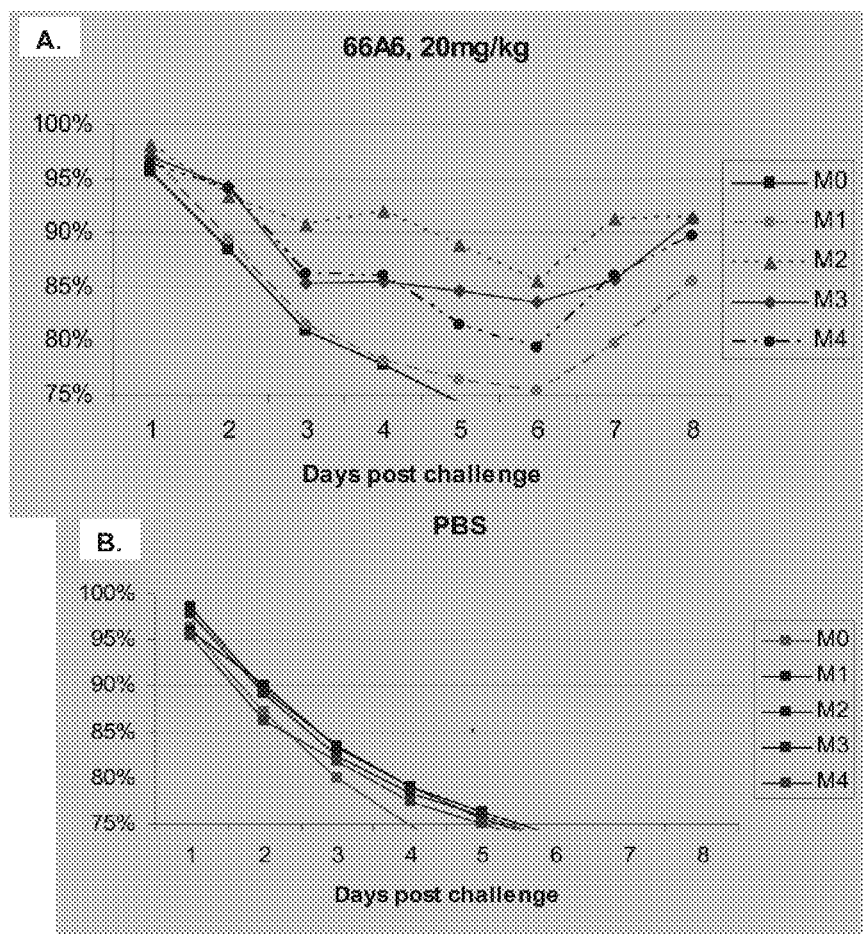

FIG. 27. Passive transfer of monoclonal antibody 66A6 results in decreased weight loss in mice challenged with Influenza X31 virus as compared to mice administered PBS, rather than antibody. "M" represent mouse.

FIG. 28. The deduced nucleotide sequences of the VH and VL chains of the antibody 66A6. Framework regions are shown in bold. CDR regions are underlined.

FIG. 29. The deduced amino acid sequences of the VH and VL chains of the antibody 66A6. Framework regions are shown in bold. CDR regions are underlined.

Figure 30:
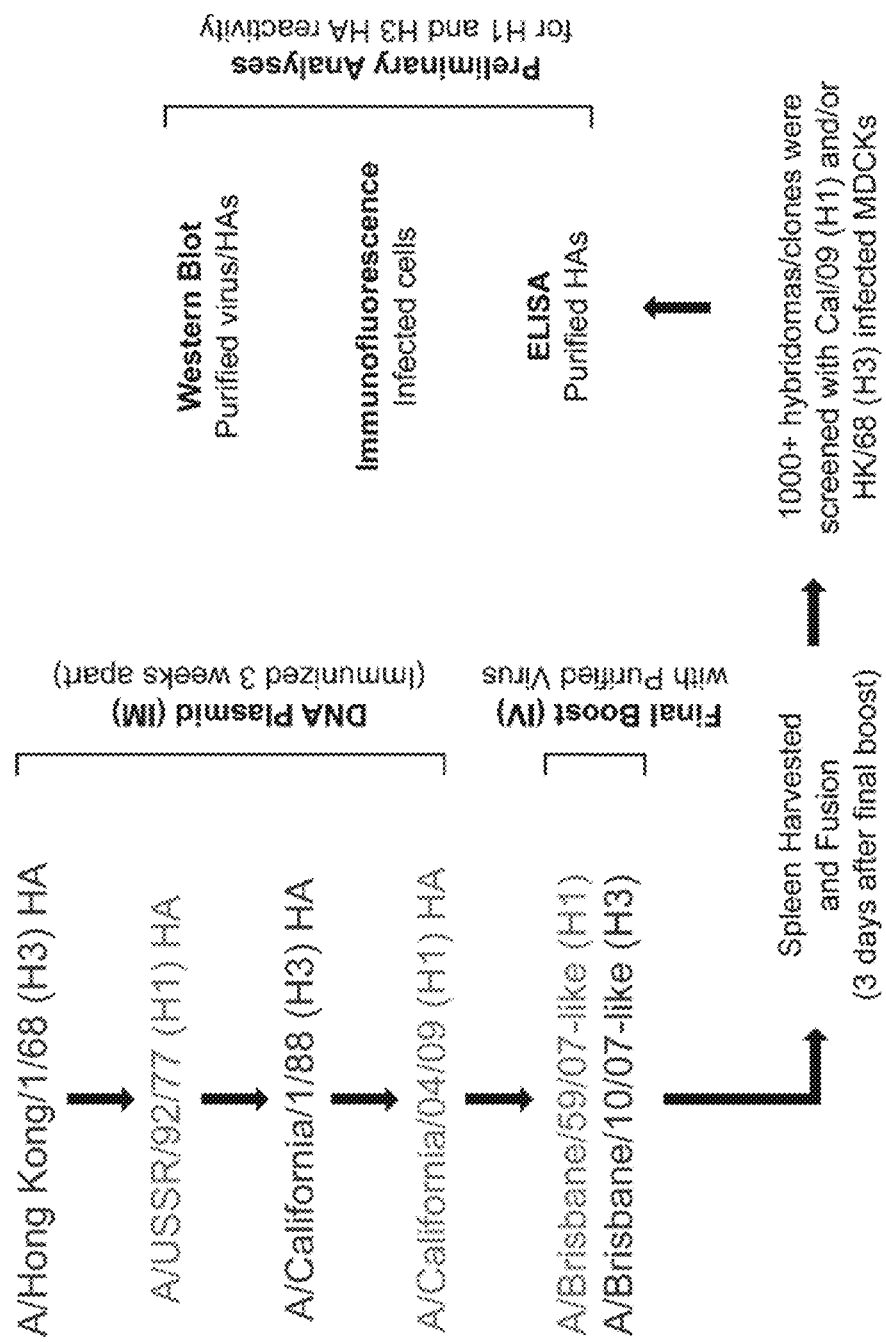

FIG. 30. Immunization strategy for cross-reactive anti-H1/H3 antibodies.

Figure 31:
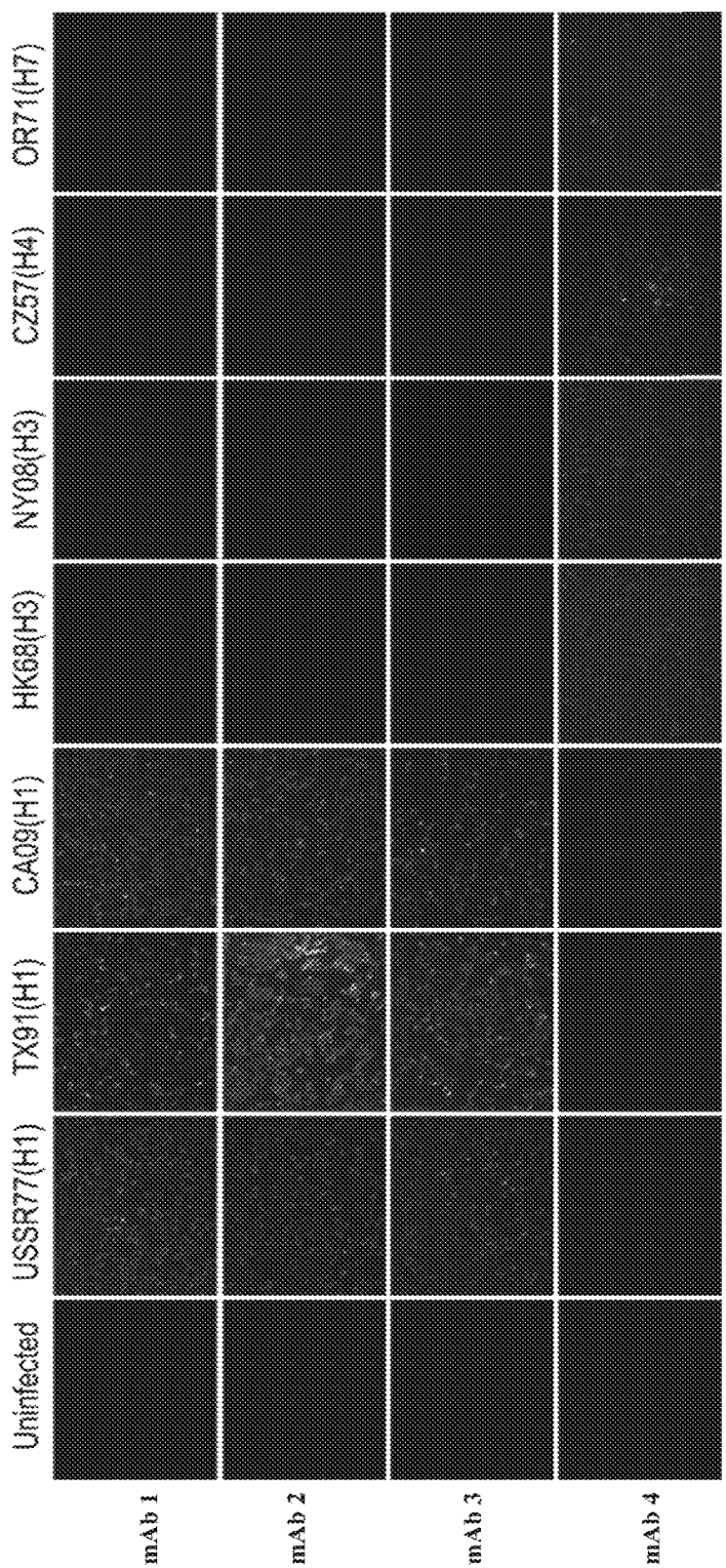

FIG. 31. Antibodies 1, 2, and 3 recognize the hemagglutinin protein of three H1N1 viruses, namely A/USSR/77 (H1), A/Texas/91 (H1), and A/California/09 (H1), by immunofluorescence. Antibody 4 recognizes the hemagglutinin protein of two H3N2 viruses, namely A/HK/1968 (H3) virus and A/NY/08 (H3) virus, by immunofluorescence.

Figure 32:
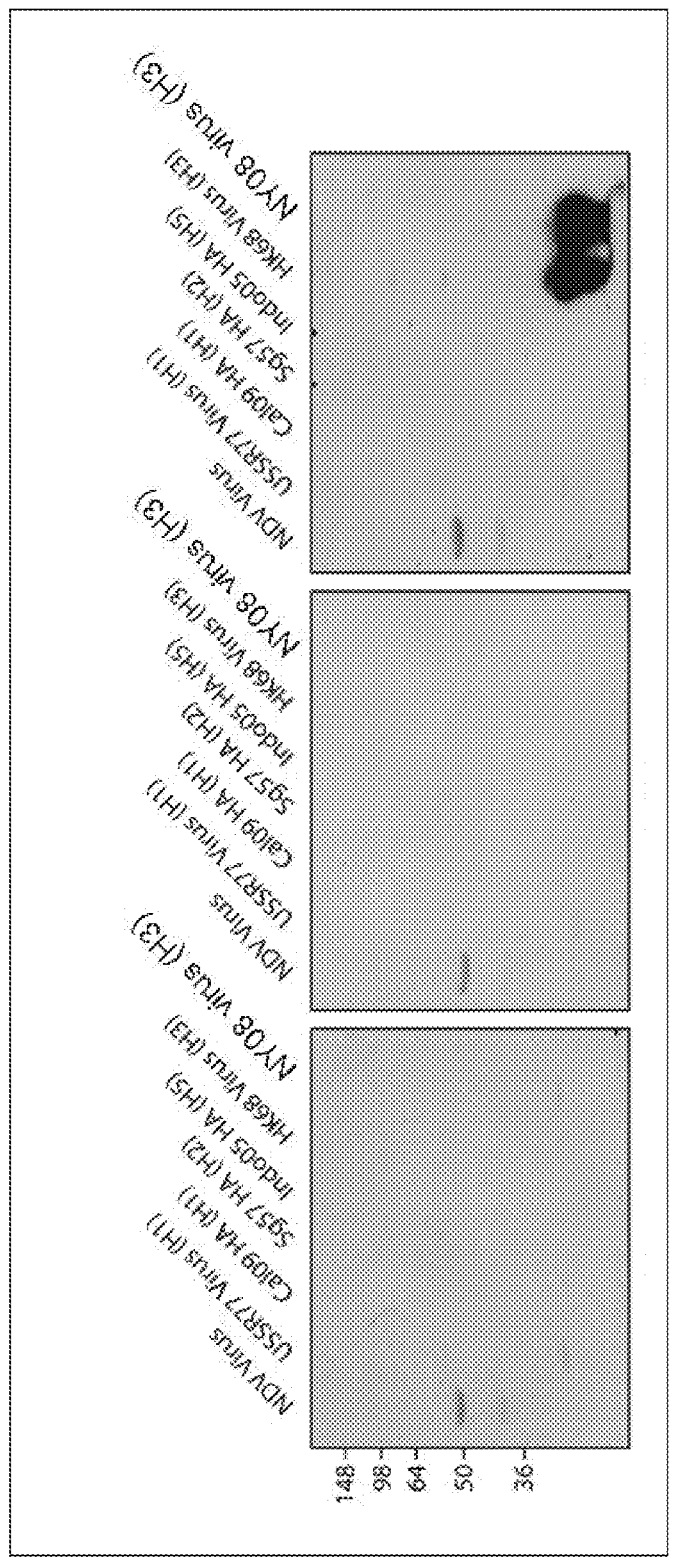

FIG. 32. Western blot results for Antibodies 1, 3, and 4: Antibodies 1 and 3 do not recognize hemagglutinin protein under denaturing and reducing conditions. Antibody 4 recognizes the hemagglutinin protein of H3 viruses under denaturing and reducing conditions.

Figure 33:
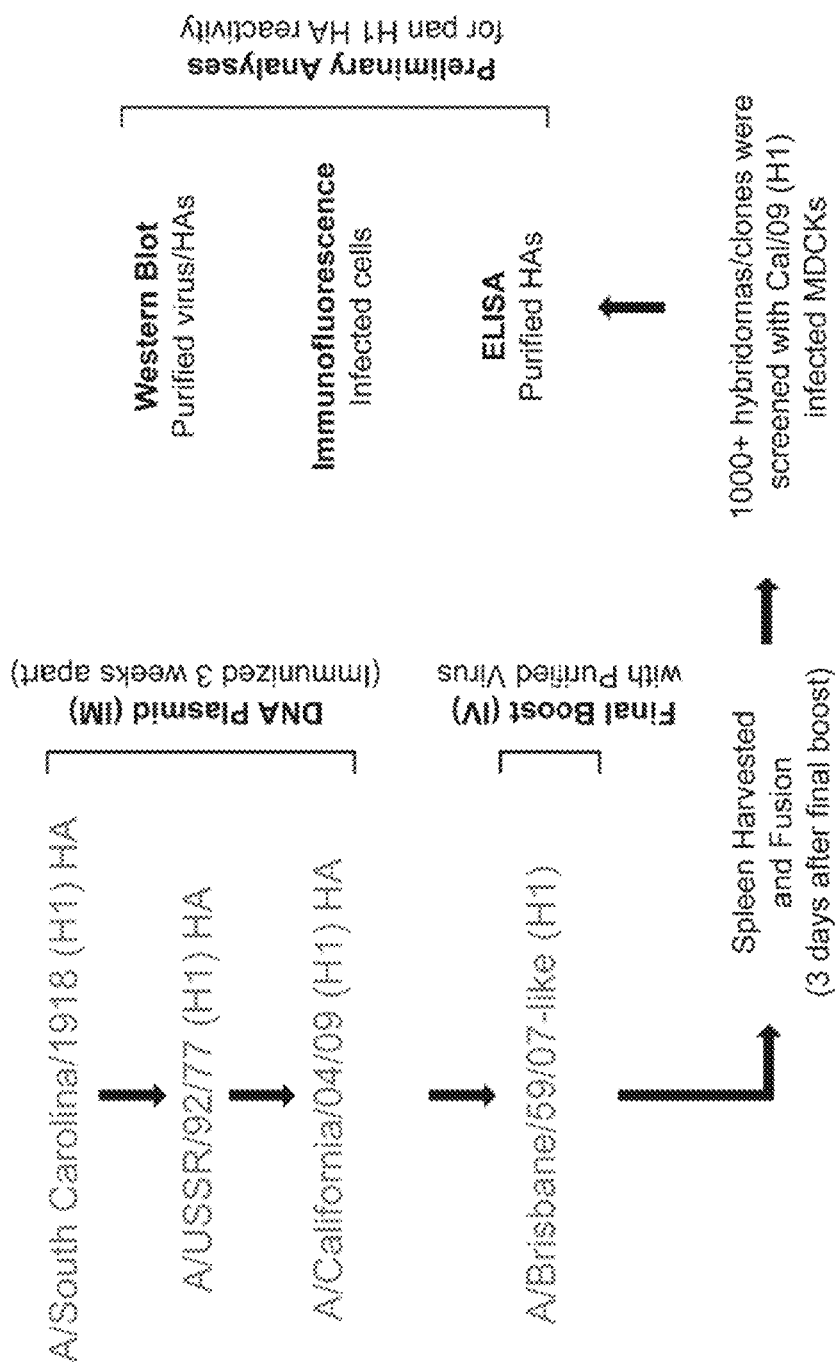

FIG. 33. Immunization strategy for cross-reactive anti-H1 antibodies.

Figure 34:
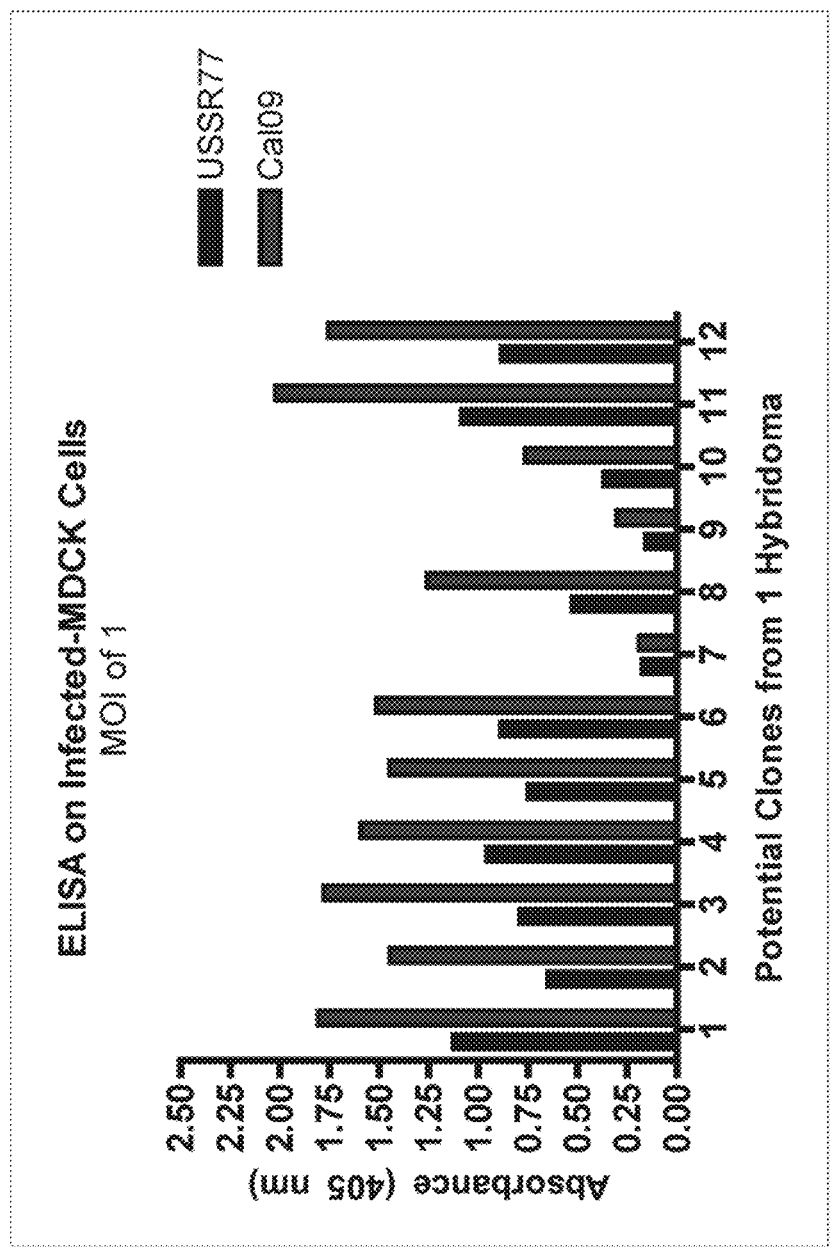

FIG. 34. Reactivity of potential clones from one hybridoma generated using the immunization strategy for cross-reactive anti-H1 antibodies by ELISA.

5. DETAILED DESCRIPTION

5.1 Generation of Antibodies

Provided herein are methods for generating monoclonal antibodies that bind to an Influenza virus antigen. Such monoclonal antibodies may bind to an Influenza virus antigen on an Influenza virus particle, e.g., hemagglutinin. In a specific embodiment, the monoclonal antibodies bind to an Influenza virus particle. In another specific embodiment, the monoclonal antibodies selectively bind to hemagglutinin expressed by one, two, three or more strains of Influenza virus relative to a non-Influenza virus hemagglutinin antigen as assessed by techniques known in the art, e.g., ELISA, Western blot, FACs or BIACore. In other words, the monoclonal antibodies bind to hemagglutinin expressed by one, two, three or more strains of Influenza virus with a higher affinity than a non-Influenza virus hemagglutinin antigen as assessed by techniques known in the art, e.g., ELISA, Western blot, FACs or BIACore.

In a specific embodiment, a monoclonal antibody that binds to an Influenza virus antigen, which is generated in accordance with a method provided herein, neutralizes a strain(s) of Influenza virus. In another specific embodiment, a monoclonal antibody that binds to an Influenza virus antigen, which is generated in accordance with a method provided herein, neutralizes antigenically distinct strains of Influenza virus (i.e., a cross-reactive neutralizing monoclonal antibody), as measured by an assay known to those of skill in the art, e.g., a hemagglutination inhibition assay. The antigenically distinct strains of Influenza virus may be of the same subtype or a different subtype as determined by, e.g., the phylogenetic relationships among hemagglutinin and/or neuraminidase subtypes. For example, a monoclonal antibody generated in accordance with a method provided herein may neutralize two, three or more strains of the same Influenza virus hemagglutinin subtype (e.g., the H3 subtype). In addition, a monoclonal antibody generated in accordance with a method provided herein may neutralize strains of different Influenza virus hemagglutinin subtypes (e.g., Influenza virus strains of the H1 and H3 subtypes) or may neutralize Influenza virus hemagglutinin subtypes of 1, 2, or more clusters. A monoclonal antibody generated in accordance with a method provided herein may neutralize an Influenza virus as a result of:

inhibiting or reducing the binding of the Influenza virus to a host cell; and/or inhibiting or reducing the fusion of the Influenza virus with a host cell.

In a specific embodiment, a monoclonal antibody generated in accordance with a method described herein binds to amino acid residues within the range of 330 to 513, 359 to 513, 360 to 513, 375 to 513, 390 to 513, and/or 405 to 513 of a hemagglutinin polypeptide numbered according to the HA0 polypeptide of the H3 subtype of Influenza virus. In another embodiment, a monoclonal antibody generated in accordance with a method described herein binds to amino acid residues within the range of 1-184, 16-184, 30-184, 31-184, 46-184, 61-184, 70-110, 76-106, and/or 76-184 of a hemagglutinin polypeptide numbered according to the classic H3 subtype numbering system (see, Wilson I A, Skehel J J, Wiley DC (1981) Structure of the haemagglutinin membrane glycoprotein of influenza virus at 3 A resolution. Nature 289:366-373 for classic H3 subtype numbering system).

In a specific embodiment an antibody generated in accordance with a method described herein binds to the HA2 region of the hemagglutinin polypeptide of the Influenza virus strain A/Hong Kong/1/1968 (H3) (see Genbank Accession No. AAK51718 for the amino acid sequence of the hemagglutinin polypeptide of A/Hong Kong/1/1968 (H3)). In another specific embodiment, an antibody generated in accordance with a method described herein binds to the long alpha-helix of HA2 of an Influenza virus (e.g., the hemagglutinin polypeptide of the Influenza virus strain A/Hong Kong/1/1968 (H3)). In a specific embodiment, an antibody generated in accordance with a method described herein binds to the long alpha-helix of the hemagglutinin polypeptide of the Influenza virus strain A/Hong Kong/1/1968 (H3) (i.e., amino acids 76-130, numbered according to the classic H3 subtype numbering system), i.e., the antibody binds an epitope within the following amino acid sequence: RIQDLEKYVEDT-KIDLWSYNAELLVALENQHTIDLTD-SEMNKLFEKTRRQLRENA (SEQ ID NO:125). In another specific embodiment, a monoclonal antibody generated in accordance with a method described herein binds to amino acid residues within the range of 304 to 513, 330 to 513, 345 to 513, 360 to 513, 375 to 513, 390 to 513, and/or 405-513 of the hemagglutinin polypeptide of the Influenza virus strain A/Hong Kong/1/1968 (H3). In another specific embodiment, a monoclonal antibody generated in accordance with a method described herein binds to amino acid residues within the range of 330 to 513, 359 to 513, 360 to 513, 375 to 513, 390 to 513, and/or 405 to 513 of the hemagglutinin polypeptide of the Influenza virus strain A/Hong Kong/1/1968 (H3) numbered according to the HA0 polypeptide of the H3 subtype of Influenza virus. In another specific embodiment, a monoclonal antibody generated in accordance with a method described herein binds to amino acid residues within the range of 1-184, 16-184, 30-184, 31-184, 46-184, 61-184, 70-110, 76-106, and/or 76-184 of the hemagglutinin polypeptide of the Influenza virus strain A/Hong Kong/1/1968 (H3) numbered according to the classic H3 subtype numbering system (see, Wilson I A, Skehel J J, Wiley DC (1981) Structure of the haemagglutinin membrane glycoprotein of influenza virus at 3 A resolution. Nature 289:366-373 for classic H3 subtype numbering system). In another specific embodiment, a monoclonal antibody generated in accordance with a method described herein binds to an epitope in the hemagglutinin polypeptide of A/Hong Kong/1/1968 (H3) located within amino acids 405 to 513 of the hemagglutinin polypeptide (i.e., within amino acids 76-183 in the classic H3 subtype numbering system), i.e., the antibody binds an epitope within the following amino acid sequence: RIQDLEKYVE DTKIDLWSYN AELLVALENQ HTIDLTDSEM NKLFEK-TRRQ LRENAEDMGN GCFKIYHKCD NACIESIRNG TYDHDVYRDE ALNNRFQIKG VELKSGYKD (SEQ ID NO:1).

In one aspect, a method for generating a monoclonal antibody that binds to an Influenza virus antigen involves the administration of two, three, four or more immunogenic compositions to a non-human subject with the administration of each immunogenic composition separated by a certain amount of time (e.g., about 2 to 4 weeks, about 2 to 6 weeks, about 4 to 6 weeks, about 2 to 8 weeks or about 4 to 8 weeks), wherein each immunogenic composition comprises an inactivated Influenza virus, an attenuated Influenza virus (e.g., a live Influenza virus that has been attenuated), a live Influenza virus other than an attenuated Influenza virus (e.g., naturally occurring Influenza virus), an antigen derived or obtained from an Influenza virus, or a nucleic acid encoding an antigen derived or obtained from an Influenza virus, and wherein one immunogenic composition differs from another immunogenic composition in that the Influenza virus, or the Influenza virus from which the antigen or the nucleic acid sequence encoding the antigen is derived or obtained are antigenically distinct. In one embodiment, such immunogenic compositions differ from each other because at a minimum the Influenza virus, or the Influenza virus from which the antigen or the nucleic acid sequence encoding the antigen is derived or obtained that is included in each composition are from antigenically distinct strains of one subtype (e.g., the H3 subtype). In another embodiment, such immunogenic compositions differ from each other because at a minimum the Influenza virus, or the Influenza virus from which the antigen or the nucleic acid sequence encoding the antigen is derived or obtained that is included in each composition are from antigenically distinct strains of two, three, four, five or more subtypes (e.g., the H1 and H3 subtypes). A certain period of time after the administration of the last immunogenic composition (e.g., about 2 to 5 days, about 5 to 10 days, or about 8 to 14 days), cells which can be used to produce hybridomas, e.g., splenocytes or lymph node cells, may be harvested from the subject for the production of hybridomas. Any technique known in the art may be used to produce hybridomas (see, for example, the techniques taught in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563 681 (Elsevier, N.Y., 1981) (said references incorporated by reference in their entireties)). Supernatants from hybridomas generated may be screened for binding to different strains of Influenza virus of the same and/or different subtypes as well as neutralization activity in a microneutralization assay such as described in Example 6 infra. Monoclonal antibodies may then be isolated from the hybridomas. In a specific embodiment, a monoclonal antibody that binds to and neutralizes two, three or more strains of Influenza virus of the same subtype and/or different subtypes is generated in accordance with such a method. In some embodiments, the immunogenic composition comprises more than one inactivated Influenza virus, attenuated Influenza virus (e.g., a live Influenza virus that has been attenuated), live Influenza virus other than an attenuated Influenza virus, antigen derived or obtained from an Influenza virus, or nucleic acid encoding an antigen derived or obtained from an Influenza virus.

In one embodiment, a method for generating a monoclonal antibody that binds to an Influenza virus antigen comprises: (i) immunizing a non-human subject (e.g., a mouse, rabbit, rat, guinea pig, etc.) with an inactivated first Influenza virus, an attenuated first Influenza virus, a live first Influenza virus other than an attenuated Influenza virus, an antigen (e.g., hemagglutinin) derived or obtained from a first Influenza virus, or a nucleic acid encoding an antigen derived or obtained from a first Influenza virus; (ii) after a specified period of time, immunizing the subject with an inactivated second Influenza virus, an attenuated second Influenza virus, a live second Influenza virus other than an attenuated Influenza virus, an antigen (e.g., hemagglutinin) derived or obtained from a second Influenza virus, or a nucleic acid encoding an antigen derived or obtained from a second Influenza virus, wherein the second Influenza virus is antigenically distinct from the first Influenza virus; and (iii) after a specified period of time, generating B-cell hybridomas from the subject and further selecting for hybridoma clones that express monoclonal antibodies that bind to the Influenza virus antigen. In certain embodiments, the method comprises selecting hybridoma clones that express a monoclonal antibody that binds to the Influenza virus antigen. In specific embodiments, the monoclonal antibodies are isolated from the hybridomas. In certain embodiments, before monoclonal antibodies are isolated, the hybridomas may be screened for binding to different strains of Influenza virus of the same and/or different subtypes as well as neutralization activity in a microneutralization assay such as described in Example 6 infra. In some embodiments, only monoclonal antibodies that bind to and neutralize different strains of Influenza virus of the same and/or different subtypes are isolated. In certain embodiments, immunization (i) above involves the administration of an antigen or nucleic acid construct, and immunization (ii) involves the administration of inactivated or attenuated Influenza virus. In other embodiments, immunization (i) above involves the administration of inactivated or attenuated Influenza virus, and immunization (ii) involves the administration of an antigen or nucleic acid construct. In a specific embodiment, a monoclonal antibody generated in accordance with such a method binds to and neutralizes two, three or more strains of Influenza virus of the same subtype and/or different subtypes.

In another embodiment, a method for generating a monoclonal antibody that binds to an Influenza virus antigen comprises: (i) immunizing a non-human subject (e.g., a mouse, rabbit, rat, guinea pig, etc.) with an inactivated first Influenza virus, an attenuated first Influenza virus, a live first Influenza virus other than an attenuated Influenza virus, an antigen (e.g., hemagglutinin) derived or obtained from a first Influenza virus, or nucleic acid encoding an antigen derived or obtained from a first Influenza virus; (ii) after a specified period of time, immunizing the subject with an inactivated second Influenza virus, an attenuated second Influenza virus, a live second Influenza virus other than an attenuated Influenza virus, an antigen derived or obtained from a second Influenza virus, or a nucleic acid encoding an antigen from a second Influenza virus, wherein the second Influenza virus is antigenically distinct from the first Influenza virus; (iii) after a specified period of time, immunizing the subject with an inactivated third Influenza virus, an attenuated third Influenza virus, a live third Influenza virus other than an attenuated Influenza virus, an antigen derived or obtained from a third Influenza virus, or a nucleic acid encoding an antigen derived or obtained from a third Influenza virus, wherein the third Influenza virus is antigenically distinct from the second and first Influenza viruses; and (iv) after a specified period of time, generating B-cell hybridomas from the subject that express monoclonal antibodies that bind to an Influenza virus antigen. In certain embodiments, the method comprises selecting hybridoma clones that express a monoclonal antibody that binds to the Influenza virus antigen. In specific embodiments, the monoclonal antibodies are isolated from the hybridomas. In certain embodiments, before monoclonal antibodies are isolated, the hybridomas may be screened for binding to different strains of Influenza virus of the same and/or different subtypes as well as neutralization activity in a microneutralization assay such as described in Example 6 infra. In some embodiments, only monoclonal antibodies that bind to and neutralize different strains of Influenza virus of the same and/or different subtypes are isolated. In certain embodiments, the immunizations (i) and (ii) above involve the administration of an antigen or nucleic acid construct, and immunization (iii) involves the administration of inactivated or attenuated Influenza virus. In other embodiments, the immunizations (i) and (ii) above involve the administration of inactivated or attenuated Influenza virus, and immunization (iii) involves the administration of an antigen or nucleic acid construct. In a specific embodiment, a monoclonal antibody generated in accordance with such a method binds to and neutralizes two, three or more strains of Influenza virus of the same subtype and/or different subtypes.

In another embodiment, a method for generating a monoclonal antibody that binds to an Influenza virus antigen comprises: (i) immunizing a non-human subject (e.g., a mouse, rabbit, rat, guinea pig, etc.) with an inactivated first Influenza virus, an attenuated first Influenza virus other than an attenuated Influenza virus, a live first Influenza virus, an antigen (e.g., hemagglutinin) derived or obtained from a first Influenza virus, or a nucleic acid encoding an antigen obtained or derived from a first Influenza virus; (ii) after a specified period of time, immunizing the subject with an inactivated second Influenza virus, an attenuated second Influenza virus, a live second Influenza virus other than an attenuated Influenza virus, an antigen derived or obtained from a second Influenza virus, or a nucleic acid encoding an antigen derived or obtained from a second Influenza virus, wherein the second Influenza virus is antigenically distinct from the first Influenza virus; (iii) after a specified period of time, immunizing the subject with an inactivated third Influenza virus, an attenuated third Influenza virus, a live third Influenza virus other than an attenuated Influenza virus, an antigen derived or obtained from a third Influenza virus, or a nucleic acid encoding an antigen derived or obtained from a third Influenza virus, wherein the third Influenza virus is antigenically distinct from the second and first Influenza viruses; (iv) after a specified period of time, immunizing the subject with an inactivated fourth Influenza virus, an attenuated fourth Influenza virus, a live fourth Influenza virus other than an attenuated Influenza virus, an antigen derived or obtained from a fourth Influenza virus, or a nucleic acid encoding an antigen derived or obtained from a fourth Influenza virus, wherein the fourth Influenza virus is antigenically distinct from the third, second, and first Influenza viruses; and (v) after a specified period of time, generating B-cell hybridomas from the subject that express monoclonal antibodies that bind to an Influenza virus antigen. In certain embodiments, the method comprises selecting hybridoma clones that express a monoclonal antibody that binds to an Influenza virus antigen. In specific embodiments, the monoclonal antibodies are isolated from the hybridomas. In certain embodiments, before monoclonal antibodies are isolated, the hybridomas may be screened for binding to different strains of Influenza virus of the same and/or different subtypes as well as neutralization activity in a microneutralization assay such as described in Example 6 infra. In some embodiments, only monoclonal antibodies that bind to and neutralize different strains of Influenza virus of the same and/or different subtypes are isolated. In certain embodiments, the immunizations (i), (ii) and (iii) above involve the administration of an antigen or nucleic acid construct, and immunization (iv) involves the administration of inactivated or attenuated Influenza virus. In other embodiments, the immunizations (i), (ii) and (iii) above involve the administration of inactivated or attenuated Influenza virus, and immunization (iv) involves the administration of an antigen or nucleic acid construct. In a specific embodiment, a monoclonal antibody generated in accordance with such a method binds to and neutralizes two, three or more strains of Influenza virus of the same subtype and/or different subtypes.

Once a monoclonal antibody has been produced in accordance with the methods described herein, it can be screened for its ability to bind to Influenza viruses using methods known in the art and described herein. The monoclonal antibodies produced in accordance with the methods described herein can also be tested for their ability to neutralize Influenza virus using methods known in the art, e.g., microneutralization assay, plaque reduction assay, and/or cell fusion assay, and described herein (see Section 5.7 and Example 6, infra).

According to methods provided herein, the specified period of time between immunizations of a non-human subject (e.g., a mouse, rabbit, rat, guinea pig, etc.) with inactivated Influenza virus, attenuated Influenza virus, live Influenza virus (e.g., naturally occurring Influenza virus), an antigen (e.g., hemagglutinin) derived or obtained from an Influenza virus, or a nucleic acid encoding an antigen derived or obtained from an Influenza virus can be any time period sufficient to allow the subject to generate an antibody response to the Influenza virus or the Influenza virus antigen. In some embodiments, the specified period of time between immunizations is 1 week, 10 days, 12 days, 2 weeks, 3 weeks, 4 weeks, 5 weeks, 6 weeks, 7 weeks, 8 weeks, 10 weeks, 12 weeks, 14 weeks, 16 weeks, or greater than 16 weeks. In other embodiments, the specified period of time between immunizations ranges from about 2-4 weeks, about 2-6 weeks, about 2-8 weeks, about 3-4 weeks, about 3-5 weeks, about 3-7 weeks, about 4-6 weeks, about 4-8 weeks, about 4-12 weeks, and/or about 4-16 weeks. In certain embodiments, the specified period of time between immunizations is not 10 days.

In some embodiments, the specified period of time between the final immunization of the non-human subject (e.g., a mouse, rabbit, rat, guinea pig, etc.) and the generation of B-cell hybridomas is 1 day, 2 days, 3 days, 4 days, 5 days, 6 days, 7 days, 8 days, 10 days, 12 days, 14 days, or more than 14 days. In other embodiments, the specified period of time between the final immunization of the non-human subject and the generation of B-cell hybridomas is about 1-3 days, about 2-5 days, about 3-7 days, about 4-8 days, about 5-10 days, or about 7-14 days. In certain embodiments, the specified period of time between the final immunization of the non-human subject (e.g., a mouse, rabbit, rat, guinea pig, etc.) and the generation of B-cell hybridomas is not 3 days.

In a specific embodiment, a method for generating a monoclonal antibody that binds to an Influenza virus antigen comprises: (i) immunizing a mouse with a nucleic acid encoding hemagglutinin from Influenza A virus strain A/Hong Kong/1/1968 (H3); (ii) after three weeks, immunizing the mouse with a nucleic acid encoding hemagglutinin from Influenza A virus strain A/Alabama/1/1981 (H3); (iii) after three weeks, immunizing the mouse with a nucleic acid encoding hemagglutinin from Influenza A virus strain A/Beijing/47/1992 (H3); (iv) after three weeks, immunizing the mouse with Influenza A virus strain A/Wyoming/3/2003 (H3); and (v) after three days, generating hybridomas from splenocytes harvested from the mouse. In specific embodiments, the monoclonal antibodies are harvested/isolated from hybridoma supernatants. In certain embodiments, before monoclonal antibodies are isolated, the hybridomas may be screened for binding to different strains of Influenza virus of the same and/or different subtypes as well as neutralization activity in a microneutralization assay such as described in Example 6 infra. In some embodiments, only monoclonal antibodies that bind to and neutralize different strains of Influenza virus of the same and/or different subtypes are isolated. In a specific embodiment, a monoclonal antibody generated in accordance with such a method binds to and neutralizes two, three or more strains of Influenza virus of the same subtype and/or different subtypes.

In a specific embodiment, a method for generating a monoclonal antibody that binds to an Influenza virus antigen comprises: (i) immunizing a mouse with a nucleic acid encoding hemagglutinin from Influenza A virus strain A/Hong Kong/1/1968 (H3); (ii) after three weeks, immunizing the mouse with a nucleic acid encoding hemagglutinin from Influenza A virus strain A/USSR/92/77 (H1); (iii) after three weeks, immunizing the mouse with a nucleic acid encoding hemagglutinin from Influenza A virus strain A/California/1/88 (H3); (iv) after three weeks, immunizing the mouse with Influenza A virus strain A/California/04/09 (H1); (v) after three weeks, immunizing the mouse with a composition comprising Influenza A virus strain A/Brisbane/59/07-like (H1) and Influenza A virus strain A/Brisbane/10/07-like (H3); and (vi) after three days, generating hybridomas from splenocytes harvested from the mouse. In specific embodiments, the monoclonal antibodies are harvested/isolated from hybridoma supernatants. In certain embodiments, before monoclonal antibodies are isolated, the hybridomas may be screened for binding to different strains of Influenza virus of the same and/or different subtypes as well as neutralization activity in a microneutralization assay such as described in Example 6 infra. In some embodiments, only monoclonal antibodies that bind to and neutralize different strains of Influenza virus of the same and/or different subtypes are isolated. In a specific embodiment, a monoclonal antibody generated in accordance with such a method binds to and neutralizes two, three or more strains of Influenza virus of the same subtype and/or different subtypes.

In a specific embodiment, a method for generating a monoclonal antibody that binds to an Influenza virus antigen comprises: (i) immunizing a mouse with a nucleic acid encoding hemagglutinin from Influenza A virus strain A/South Carolina/1918 (H1); (ii) after three weeks, immunizing the mouse with a nucleic acid encoding hemagglutinin from Influenza A virus strain A/USSR/92/77 (H1); (iii) after three weeks, immunizing the mouse with a nucleic acid encoding hemagglutinin from Influenza A virus strain A/California/04/09 (H1); (iv) after three weeks, immunizing the mouse with Influenza A virus strain A/Brisbane/59/07-like (H1); and (v) after three days, generating hybridomas from splenocytes harvested from the mouse. In specific embodiments, the monoclonal antibodies are harvested/isolated from hybridoma supernatants. In certain embodiments, before monoclonal antibodies are isolated, the hybridomas may be screened for binding to different strains of Influenza virus of the same and/or different subtypes as well as neutralization activity in a microneutralization assay such as described in Example 6 infra. In some embodiments, only monoclonal antibodies that bind to and neutralize different strains of Influenza virus of the same and/or different subtypes are isolated. In a specific embodiment, a monoclonal antibody generated in accordance with such a method binds to and neutralizes two, three or more strains of Influenza virus of the same subtype and/or different subtypes.

In certain embodiments, the non-human subjects administered an immunogenic composition(s) in accordance with the methods described herein are transgenic animals (e.g., transgenic mice) that are capable of producing human antibodies. Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. Companies such as Abgenix, Inc. (Freemont, Calif.), Genpharm (San Jose, Calif.), and Medarex, Inc. (Princeton, N.J.) can be engaged to provide human antibodies directed against a selected antigen.

In addition, the non-human subjects administered an immunogenic composition(s) described herein may be transplanted with human peripheral blood leukocytes, splenocytes, or bone marrow (e.g., Trioma Techniques XTL) so that human antibodies that bind to an Influenza virus antigen are generated.

The steps of the methods provided herein for generating monoclonal antibodies are not limited to immunization with any particular number of Influenza virus strains and the immunization of the non-human subject can be repeated using any number of Influenza virus strains that are antigenically distinct from one another, e.g., 2 antigenically distinct Influenza virus strains, 3 antigenically distinct Influenza virus strains, 4 antigenically distinct Influenza virus strains, 5 antigenically distinct Influenza virus strains, or 6 or more antigenically distinct Influenza virus strains.

In certain embodiments, the antigenically distinct Influenza virus strains used in accordance with the methods provided herein for generating monoclonal antibodies are selected based on the difference in time between the emergence of the Influenza virus strains. For example, Influenza viruses of the same subtype are likely to be antigenically distinct from one another as the difference in time between their emergence becomes greater, i.e., an Influenza A virus of subtype H3 that emerged in 1960 would have a high likelihood of being antigenically distinct from an Influenza A virus of subtype H3 that emerged in 1980. In a specific embodiment, antigenically distinct Influenza virus strains include strains that have emerged over a period of about 10 years, about 15 years, about 20 years, about 25 years, about 30 years, about 40 years or about 50 years. In another specific embodiment, antigenically distinct Influenza virus strains include strains that have emerged over a period of about 10 to 100 years, about 10 to 75 years, about 10 to 50 years, about 10 to 40 years, about 10 to 30 years, about 10 to 25 years, or about 10 to 20 years. In certain embodiments, Influenza virus strains, or Influenza virus antigens or nucleic acids encoding Influenza virus antigens used in accordance with the methods provided herein for generating monoclonal antibodies are selected from virus strains that have emerged about every 5 years, about every 10 years, or about every 20 years over a 40 year period, or over a 40 to 50 year period. In other embodiments, Influenza virus strains, or Influenza virus antigens or nucleic acids encoding Influenza virus antigen used in accordance with the methods provided herein for generating monoclonal antibodies are selected from virus strains that have emerged about every 5 years, about every 10 years, about every 20 years, about every 25 years, or about every 30 years over a 75 to 100 year period.

In certain embodiments, Influenza virus strains, or Influenza virus antigens or nucleic acids encoding Influenza virus antigen used in accordance with the methods provided herein for generating monoclonal antibodies are selected from virus strains that have emerged over a period of about 7 years. In other embodiments, Influenza virus strains, or Influenza virus antigens or nucleic acids encoding Influenza virus antigen used in accordance with the methods provided herein for generating monoclonal antibodies are not selected from virus strains that have emerged over a period of about 7 years. In certain embodiments, Influenza virus strains, or Influenza virus antigens or nucleic acids encoding Influenza virus antigen used in accordance with the methods provided herein for generating monoclonal antibodies are selected from virus strains that have emerged over a period of about 6-8 years. In other embodiments, Influenza virus strains, or Influenza virus antigens or nucleic acids encoding Influenza virus antigen used in accordance with the methods provided herein for generating monoclonal antibodies are not selected from virus strains that have emerged over a period of about 6-8 years.

In other embodiments, the antigenically distinct Influenza virus strains used in accordance with the methods provided herein for generating monoclonal antibodies are selected from viruses that emerged at or around the same time, e.g., within the same year, but are antigenically distinct from each other.

In certain embodiments, the Influenza viruses, or the Influenza viruses that antigens or nucleic acids encoding antigens are derived or obtained from are strains of Influenza A viruses. In one embodiment, the Influenza viruses, or the Influenza viruses that antigens or nucleic acids encoding antigens are derived or obtained from are strains of Influenza A viruses from a single subtype. In another embodiment, the Influenza viruses, or the Influenza viruses that antigens or nucleic acids encoding antigens are derived or obtained from are strains of Influenza A viruses from two, three or more subtypes. In another embodiment, the Influenza viruses, or the Influenza viruses that antigens or nucleic acids encoding antigens are derived or obtained from are strains of Influenza A viruses from one, two, or more clusters (e.g., the H1 cluster of H1a Influenza viruses (H2, H5, H1, and H6) and H1b Influenza viruses (H13, H16, and H11), the H9 cluster of Influenza viruses (H8, H12, and H9), the H3 cluster of Influenza viruses (H4, H14, and H3), or the H7 cluster of Influenza viruses (H15, H7, and H10)). Non-limiting examples of Influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of Influenza A virus include, but are not limited to: A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06

(H16N3); A/sw/Netherlands/25/80 (H1N1); A/sw/Germany/ 2/81 (H1N1); A/sw/Hannover/1/81 (H1N1); A/sw/Potsdam/ 1/81 (H1N1); A/sw/Potsdam/15/81 (H1N1); A/sw/Potsdam/ 268/81 (H1N1); A/sw/Finistere/2899/82 (H1N1); A/sw/ Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/ 103/89 (H1N1); A/turkey/Germany/3/91 (H1N1); A/sw/Germany/8533/91 (H1N1); A/sw/Belgium/220/92 (H3N2); A/sw/GentN230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/ 419440/94 (H1N2); A/sw/Bakum/5/95 (H1N1); A/sw/Best/ 5C/96 (H1N1); A/sw/England/17394/96 (H1N2); A/sw/Jena/ 5/96 (H3N2); A/sw/Oedenrode/7C/96 (H3N2); A/sw/Lohne/ 1/97 (H3N2); A/sw/Cote d'Armor/790/97 (H1N2); A/sw/ Bakum/1362/98 (H3N2); A/sw/Italy/1521/98 (H1N2); A/sw/ Italy/1553-2/98 (H3N2); A/sw/Italy/1566/98 (H1N1); A/sw/ Italy/1589/98 (H1N1); A/sw/Bakum/8602/99 (H3N2); A/sw/ Cotes d'Armor/604/99 (H1N2); A/sw/Cote d'Armor/1482/99 (H1N1); A/sw/Gent/7625/99 (H1N2); A/Hong Kong/1774/ 99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/ 00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/ 9296/01 (H3N2); A/sw/Hong Kong/9745/01 (H3N2); A/sw/ Spain/33601/01 (H3N2); A/sw/Hong Kong/1144/02 (H3N2); A/sw/Hong Kong/1197/02 (H3N2); A/sw/Spain/ 39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/ IDT2570/03 (H1N2); A/sw/Gescher/IDT2702/03 (H1N2); A/sw/Haselünne/2617/03 hp (H1N1); A/sw/Löningen/ IDT2530/03 (H1N2); A/sw/IVD/IDT2674/03 (H1N2); A/sw/ Nordkirchen/IDT1993/03 (H3N2); A/sw/Nordwalde/ IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/swNisbek/ IDT2869/03 (H1N2); A/sw/Waltersdorf/IDT2527/03 (H1N2); A/sw/Damme/IDT2890/04 (H3N2); A/sw/Geldern/ IDT2888/04 (H1N1); A/sw/Granstedt/IDT3475/04 (H1N2); A/sw/Greven/IDT2889/04 (H1N1); A/sw/Gudensberg/ IDT2930/04 (H1N2); A/sw/Gudensberg/IDT2931/04 (H1N2); A/sw/Lohne/IDT3357/04 (H3N2); A/sw/Nortrup/ IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/ IDT2965/04 (H1N1); A/sw/Bad Griesbach/IDT4191/05 (H3N2); A/sw/Cloppenburg/IDT4777/05 (H1N2); A/sw/ Dötlingen/IDT3780/05 (H1N2); A/sw/Dötlingen/IDT4735/ 05 (H1N2); A/sw/Egglham/IDT5250/05 (H3N2); A/sw/ Harkenblek/IDT4097/05 (H3N2); A/sw/Hertzen/IDT4317/ 05 (H3N2); A/sw/Krogel/IDT4192/05 (H1N1); A/sw/Laer/ IDT3893/05 (H1N1); A/sw/Laer/IDT4126/05 (H3N2); A/sw/Merzen/IDT4114/05 (H3N2); A/sw/Mueslingen-S./ IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/swNoglarn/IDT4096/05 (H1N1); A/sw/Wohlerst/IDT4093/05 (H1N1); A/sw/Bad Griesbach/IDT5604/06 (H1N1); A/sw/Herzlake/IDT5335/ 06 (H3N2); A/sw/Herzlake/IDT5336/06 (H3N2); A/sw/Herzlake/IDT5337/06 (H3N2); and A/wild boar/Germany/R169/ 2006 (H3N2).

Other specific examples of strains of Influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/ 2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/ 2009 (H1N1); A/Stockholm/45/2009 (H1N1); A/swine/Alberta/OTH-33-1/2009 (H1N1); A/swine/Alberta/OTH-33- 14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33- 23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/ OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/ 2009 (H1N1); A/Catalonia/385/2009 (H1N1); A/Catalonia/ 386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/ 2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1N1); A/Sao Paulo/2303/ 2009 (H1N1); A/Sapporo/1/2009 (H1N1); A/Stockholm/30/ 2009 (H1N1); A/Stockholm/31/2009 (H1N1); A/Stockholm/ 32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/ 2009 (H1N1); A/Stockholm/39/2009 (H1N1); A/Stockholm/ 40/2009 (H1N1;) A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

In certain embodiments, the Influenza viruses, or the Influenza viruses that antigens or nucleic acids encoding antigens are derived or obtained from are not subtype H3N2. In some embodiments, the Influenza viruses, or the Influenza viruses that antigens or nucleic acids encoding antigens are derived or obtained from are H3N2 strain A/Aichi/2/68, H3N2 strain A/Victoria/3/75, or H3N2 strain A/Philippines/2/82. In other embodiments, the Influenza viruses, or the Influenza viruses that antigens or nucleic acids encoding antigens are derived or obtained from are not H3N2 strain A/Aichi/2/68, H3N2 strain A/Victoria/3/75, or H3N2 strain A/Philippines/2/82.

In other embodiments, the Influenza viruses, or the Influenza viruses that antigens or nucleic acids encoding antigens are derived or obtained from are A/Hong Kong/1/1968 (HK/ 68) (H3), A/Alabama/1/1981 (AL/81) (H3), A/Georgia/1981 (H3), A/Beijing/47/1992 (BJ/92) (H3), A/Wyoming/3/2003 (H3), A/Wisconsin/67/2005 (WI/05) (H3), A/Brisbane/10/ 2007 (BR/07) (H3), A/New York/2008 (NY08) (H3), A/Texas/36/1991 (TX/91) (H1), A/New Caledonia/20/99 (N.Cal/99) (H1), A/Duck/England/1962 (Dk/62) (H4), A/Turkey/England/1963 (Tky/63) (H7), A/Equine/Kentucky/2002 (e/KY/02) (H3), A/Ann Arbor/6/1960 (AA/60) (H2), A/Fort Monmouth/1/1947 (FM/47) (H1), A/USSR/92/ 77 (H1), A/California/1/88 (H3), A/California/04/09 (H1), A/Brisbane/59/07-like (H1), A/Brisbane/10/07-like (H3) and/or A/South Carolina/1918 (H1).

There are currently 16 hemagglutinin subtypes of Influenza viruses that fall into two different groups and any one, two or more of such subtypes may be used in accordance with the methods provided herein. See FIG. 6 for a table of the phylogenetic relationships among hemagglutinin subtypes. In a specific embodiment, the Influenza viruses, or the Influenza viruses that antigens or nucleic acids encoding antigens are derived or obtained from strains of Influenza A viruses from a single hemagglutinin subtype (e.g., H1 or H3). In a specific embodiment, the Influenza viruses, or the Influenza viruses that antigens or nucleic acids encoding antigens are derived or obtained from are strains of Influenza A viruses from two, three or more hemagglutinin subtypes (e.g., H1 and H3). In another specific embodiment, the Influenza viruses, or the Influenza viruses that antigens or nucleic acids encoding antigens are derived or obtained from are strains of Influenza A viruses from one, two, or more clusters (e.g., the H1 cluster of H1a Influenza viruses (H2, H5, H1, and H6) and H1b Influenza viruses (H13, H16, and H11), the H9 cluster of Influenza viruses (H8, H12, and H9), the H3 cluster of Influenza viruses (H4, H14, and H3), or the H7 cluster of Influenza viruses (H15, H7, and H10)).

In certain embodiments, the Influenza viruses, or the Influenza viruses that antigens or nucleic acids encoding antigens are derived or obtained are from strains of Influenza B viruses. Specific examples of Influenza B viruses include strain Aichi/5/88, strain Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos AiresNL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, and strain Rochester/02/2001.

In certain embodiments, the Influenza viruses, or the Influenza viruses that antigens or nucleic acids encoding antigens are derived or obtained from are strains of Influenza C viruses. Specific examples of Influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/

2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/ 1167/54, strain JJ/50, strain PIG/BEIJING/10/81, strain PIG/ BEIJING/439/82), strain TAYLOR/1233/47, and strain C/YAMAGATA/10/81.

In certain embodiments, the Influenza viruses, or the Influenza viruses that antigens or nucleic acids encoding antigens are derived or obtained from are strains of Influenza A virus and strains of Influenza B virus. In some embodiments, the Influenza viruses, or the Influenza viruses that antigens or nucleic acids encoding antigens are derived or obtained from are strains of Influenza A virus, strains of Influenza B virus, and strains of Influenza C virus.

In certain embodiments, the Influenza viruses, or the Influenza viruses that antigens or nucleic acids encoding antigens are derived or obtained from are treated with bromelain. In other embodiments, the Influenza viruses, or the Influenza viruses that antigens or nucleic acids encoding antigens are derived or obtained from are not treated with bromelain.

In a specific embodiment, the Influenza viruses administered to a non-human subject are isolated or purified. The Influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In a specific embodiment, antigens derived or obtained from a strain(s) of Influenza virus that are administered to a non-human subject are isolated. In another specific embodiment, nucleic acids encoding antigens derived or obtained from a strain(s) of Influenza virus that are administered to a non-human subject are isolated.

An "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In accordance with the methods described herein, Influenza virus (live, inactivated or attenuated (e.g., a live Influenza virus that has been attenuated)), antigens (e.g., hemagglutinin) derived or obtained from Influenza virus, or a nucleic acid encoding an antigen derived or obtained from an Influenza virus may be delivered to a non-human subject by a variety of routes. Such routes include, but are not limited to, intranasal, intratracheal, oral, intradermal, transdermal, intramuscular, intraperitoneal, transdermal, intravenous, conjunctival and subcutaneous routes. In a specific embodiment, the Influenza virus, antigen derived or obtained from Influenza virus, or a nucleic acid encoding an antigen derived or obtained from an Influenza virus is formulated in a composition containing excipients or carriers and the composition is administered to the non-human subject. Such compositions are preferably suited for the route of administration to a non-human subject.

In cases where Influenza virus, or a viral vector or viral-like particle is used to administer a nucleic acid encoding an antigen derived or obtained from an Influenza virus, it may be preferable to introduce the virus, viral vector or viral-like particle via the natural route of infection for the virus, viral vector or viral-like particle. Alternatively, it may be preferable to introduce the viral vector or virus-like particle via the natural route of infection of the Influenza virus from which nucleic acid encoding the antigen is derived. The ability of an antigen, particularly a viral vector, to induce a vigorous secretory and cellular immune response can be used advantageously. For example, infection of the respiratory tract by Influenza virus or a viral vector may induce a strong secretory immune response, for example in the urogenital system, with concomitant protection against an Influenza virus. In addition, in a preferred embodiment it may be desirable to introduce the Influenza virus into the lungs by any suitable route. Pulmonary administration can also be employed, e.g., by use of an inhaler or nebulizer, and formulation with an aerosolizing agent for use as a spray.

The amount of Influenza virus (live, inactivated or attenuated (e.g., a live Influenza virus that has been attenuated)), antigen (e.g., hemagglutinin) derived or obtained from an Influenza virus, or a nucleic acid encoding an antigen derived or obtained from an Influenza virus used to immunize a non-human subject in accordance with the methods provided herein for generating monoclonal antibodies can be determined by methods known in the art. In certain embodiments, where the non-human subject is administered Influenza virus (live, inactivated or attenuated (e.g., a live Influenza virus that has been attenuated)) or a viral vector containing a nucleic acid encoding an antigen derived or obtained from an Influenza virus, approximately $10^4$ pfu, approximately $10^5$ pfu, approximately $10^6$ pfu or approximately $10^7$ may be administered to the subject. In certain embodiments, wherein the non-human subject is administered an antigen derived or obtained from an Influenza virus, approximately 1 mg/kg, approximately 1.5 mg/kg, approximately 2 mg/kg, approximately 3 mg/kg or approximately 4 mg/kg may be administered to the subject. In certain embodiments, wherein the non-human subject is administered an antigen derived or obtained from an Influenza virus, about 0.1 μg to about 1,000 μg; about 0.1 μg to about 500 μg; about 0.1 μg to about 250 μg; about 0.1 μg to about 100 μg; about 0.1 μg to about 50 μg, about 0.1 μg to about 25 μg or about 0.1 μg to about 10 μg of the antigen may be administered to the subject. In certain embodiments, wherein the non-human subject is administered a nucleic acid encoding an antigen derived or obtained from an Influenza virus, about 10 ng to 1 g, 100 ng to 100 mg, 1 μg to 10 mg or 30-300 μg of the nucleic acid may be administered to the subject.

5.1.1 Influenza Viruses

In certain embodiments, the Influenza viruses administered to a non-human subject are inactivated. Techniques known to one of skill in the art may be used to inactivate viruses. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In certain embodiments, the Influenza viruses administered to a non-human subject are attenuated (e.g., a live Influenza virus that has been attenuated). In specific embodiments, attenuation of Influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a non-human subject to induce an immune response. Attenuation of the Influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses). Alternatively, naturally occurring attenuated Influenza viruses may be used as Influenza virus backbones for the Influenza virus vectors.

In some embodiments, an Influenza virus may be attenuated, at least in part, by engineering the Influenza virus to express a mutated NS1 gene that impairs the ability of the virus to antagonize the cellular interferon (IFN) response. Examples of the types of mutations that can be introduced into the Influenza virus NS1 gene include deletions, substitutions, insertions and combinations thereof. One or more mutations can be introduced anywhere throughout the NS1 gene (e.g., the N-terminus, the C-terminus or somewhere in between) and/or the regulatory element of the NS1 gene. In one embodiment, an attenuated Influenza virus comprises a genome having a mutation in an Influenza virus NS 1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated Influenza virus comprises a genome having a mutation in an Influenza virus NS1 gene such that it encodes an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and Influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety.

5.1.2 Expression of Influenza Virus Antigen

A nucleic acid encoding an antigen derived or obtained from an Influenza virus may be administered to a non-human subject as part of a vector, such as, e.g., an expression vector. In addition, an antigen derived or obtained from an Influenza virus may be produced by transfecting a host cell with a nucleic acid encoding such antigen, and such nucleic acid may be part of a vector. In a specific embodiment, the vector is an expression vector that is capable of directing the expression of a nucleic acid encoding an antigen derived or obtained from an Influenza virus. Non-limiting examples of expression vectors include, but are not limited to, plasmids and viral vectors, such as replication defective retroviruses, adenoviruses, adeno-associated viruses, Newcastle disease virus, vaccinia virus and baculoviruses. Standard molecular biology techniques may be used to introduce a nucleic acid encoding an antigen derived or obtained from an Influenza virus into an expression vector.

An expression vector comprises a nucleic acid encoding an antigen derived or obtained from an Influenza virus in a form suitable for expression of the nucleic acid in a host cell or non-human subject. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as, e.g., the choice of the host cell to be transformed, the level of expression of protein desired, etc.

Expression vectors can be designed for expression of an antigen derived or obtained from an Influenza virus using prokaryotic (e.g., *E. coli*) or eukaryotic cells (e.g., insect cells (using baculovirus expression vectors), yeast cells or mammalian cells). Examples of mammalian host cells include, but are not limited to, Crucell Per.C6 cells, Vero cells, CHO cells, VERY cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g., Chinese hamster ovary or baby hamster kidney cells) is used for expression of an Influenza hemagglutinin stem domain polypeptide.

In some embodiments, a plant cell culture system is used for expression of an antigen derived or obtained from an Influenza virus. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems.

In certain embodiments, plants (e.g., plants of the genus *Nicotiana*) may be engineered to express an antigen derived or obtained from an Influenza virus. In specific embodiments, plants are engineered to express an antigen derived or obtained from an Influenza virus via an agroinfiltration procedure using methods known in the art. For example, nucleic acids encoding a gene of interest, e.g., a gene encoding an antigen derived or obtained from an Influenza virus, are introduced into a strain of *Agrobacterium*. Subsequently the strain is grown in a liquid culture and the resulting bacteria are washed and suspended into a buffer solution. The plants are then exposed (e.g., via injection or submersion) to the *Agrobacterium* that comprises the nucleic acids encoding an antigen derived or obtained from an Influenza virus such that the *Agrobacterium* transforms the gene of interest to a portion of the plant cells. The antigen derived or obtained from an Influenza virus is then transiently expressed by the plant and can isolated using methods known in the art and described herein. (For specific examples see Shoji et al., 2008, Vaccine, 26(23): 2930-2934; and D'Aoust et al., 2008, J. Plant Biotechnology, 6(9):930-940). In a specific embodiment, the plant is a tobacco plant (i.e., *Nicotiana tabacum*). In another specific embodiment, the plant is a relative of the tobacco plant (e.g., *Nicotiana benthamiana*). In other embodiments, algae (e.g., *Chlamydomonas reinhardtii*) may be engineered to express an antigen derived or obtained from an Influenza virus (see, e.g., Rasala et al., 2010, Plant Biotechnology Journal (Published online Mar. 7, 2010)).

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding an antigen derived or obtained from an Influenza virus. In other embodiments, a host cell is stably transfected with an expression vector containing a nucleic acid encoding an antigen derived or obtained from an Influenza virus.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

As an alternative to recombinant expression of an antigen derived or obtained from an Influenza virus using a host cell, an expression vector containing a nucleic acid encoding an antigen derived or obtained from an Influenza virus can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce an antigen derived or obtained from an Influenza virus.

Once an antigen derived or obtained from an Influenza virus has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins.

5.2 Antibodies

Provided herein are monoclonal antibodies generated in accordance with the methods described herein that bind to and neutralize antigenically distinct strains of Influenza virus. In a specific embodiment, provided herein are monoclonal antibodies generated in accordance with the methods described herein that bind to and neutralize antigenically distinct strains of the H3 subtype of the Influenza A virus as measured by techniques known to one of skill in the art, e.g., ELISA or Western blot for binding and a microneutralization assay, such as described in Example 6 infra.

In a specific embodiment, provided herein are monoclonal antibodies generated in accordance with the methods described herein that bind to the HA region of a certain group, cluster or subtype of Influenza virus, e.g., Group 2 Influenza virus or the H3 subtype of the Influenza A virus. In certain embodiments, the monoclonal antibodies generated in accordance with the methods described herein have a higher affinity for a certain group, cluster or subtype of Influenza virus (e.g., Group 2 Influenza virus or the H3 subtype of the Influenza A virus) than to another group or subtype of Influenza virus. In specific embodiments, the affinity of a monoclonal antibody generated in accordance with the methods described herein for a certain group, cluster or subtype of Influenza virus (e.g., Group 2 Influenza virus or the H3 subtype of the Influenza A virus) is 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater than the affinity of the monoclonal antibody to another group, cluster or subtype of Influenza virus. In specific embodiments, the affinity of a monoclonal antibody generated in accordance with the methods described herein for a certain group, cluster or subtype of Influenza virus (e.g., Group 2 Influenza virus or the H3 subtype of the Influenza A virus) is 0.5 log, 1 log, 1.5 log, 2 log, 2.5 log, 3 log, 3.5 log, or 4 log greater than the affinity of the monoclonal antibody to another group, cluster or subtype of Influenza virus.

In a specific embodiment, the monoclonal antibodies selectively bind to hemagglutinin expressed by one, two, three or more strains of Influenza virus relative to a non-Influenza virus hemagglutinin antigen as assessed by techniques known in the art, e.g., ELISA, Western blot, FACs or BIACore. In other words, the monoclonal antibodies bind to hemagglutinin expressed by one, two, three or more strains of Influenza virus with a higher affinity than a non-Influenza virus hemagglutinin antigen as assessed by techniques known in the art, e.g., ELISA, Western blot, FACs or BIACore. In specific embodiments, the monoclonal antibodies bind to hemagglutinin expressed by one, two, three or more strains of Influenza virus with a 1-fold, 1.5-fold, 2-fold, 3-fold, 4-fold, 5-fold, 6-fold, 7-fold, 8-fold, 9-fold, 10-fold, greater than 10-fold, 1- to 2-fold, 1- to 5-fold, 1- to 10-fold, 2- to 5-fold, 2- to 10-fold, 5- to 10-fold, 10- to 15-fold, or 10- to 20-fold greater affinity than that which they bind to a non-Influenza virus hemagglutinin antigen. In specific embodiments, the monoclonal antibodies bind to hemagglutinin expressed by one, two, three or more strains of Influenza virus with a 0.5 log, 1 log, 1.5 log, 2 log, 2.5 log, 3 log, 3.5 log, or 4 log greater affinity than that which they bind to a non-Influenza virus hemagglutinin antigen.

In a specific embodiment, a monoclonal antibody generated in accordance with the methods described herein is capable of binding to the HA2 region of the hemagglutinin polypeptide of the Influenza virus strain A/Hong Kong/1/

1968 (H3). In another specific embodiment, an antibody generated in accordance with a method described herein is capable of binding to the long alpha-helix of the HA2 region of, e.g., the Influenza virus strain A/Hong Kong/1/1968 (H3). In a specific embodiment, an antibody generated in accordance with a method described herein binds to the long alpha-helix of the hemagglutinin polypeptide of the Influenza virus strain A/Hong Kong/1/1968 (H3) (i.e., amino acids 76-130, numbered according to the classic H3 subtype numbering system), i.e., the antibody binds an epitope within the following amino acid sequence: RIQDLEKYVEDTKIDLWSYNAELLVALENQHTIDLTDSEMNKLFEKTRRQLRENA (SEQ ID NO:125). In another specific embodiment, a monoclonal antibody generated in accordance with a method described herein binds to amino acid residues within the range of 304 to 513, 330 to 513, 345 to 513, 360 to 513, 375 to 513, 390 to 513, and/or 405-513 of the hemagglutinin polypeptide of the Influenza virus strain A/Hong Kong/1/1968 (H3). In another specific embodiment, a monoclonal antibody generated in accordance with a method described herein is capable of binding to amino acid residues within the range of 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In another specific embodiment, a monoclonal antibody generated in accordance with the methods described herein is capable of binding to an epitope in the hemagglutinin polypeptide of A/Hong Kong/1/1968 (H3) located within amino acids 405 to 513 of the hemagglutinin polypeptide, i.e., the antibody binds an epitope within the following amino acid sequence: RIQDLEKYVE DTKIDLWSYN AELLVALENQ HTIDLTDSEM NKLFEKTRRQ LRENAEDMGN GCFKIYHKCD NACIESIRNG TYDHDVYRDE ALNNRFQIKG VELKSGYKD (SEQ ID NO:1).

In another specific embodiment, a monoclonal antibody generated in accordance with the methods described herein is capable of binding to an epitope in the hemagglutinin polypeptide of A/Hong Kong/1/1968 (H3) located within amino acids 76-106, numbered according to the classic H3 subtype numbering system (see, Wilson I A, Skehel J J, Wiley DC (1981) Structure of the haemagglutinin membrane glycoprotein of influenza virus at 3 A resolution. Nature 289: 366-373 for classic H3 subtype numbering system), i.e., the antibody binds an epitope within the following amino acid sequence: RIQDLEKYVEDTKIDLWSYNAELLVALENQH (SEQ ID NO:124). In another specific embodiment, a monoclonal antibody generated in accordance with the methods described herein is capable of binding to an epitope in the hemagglutinin polypeptide of A/Hong Kong/1/1968 (H3) located within amino acids 73-103, 73-104, 73-105, 73-106, 73-107, 73-108, 73-109, 74-103, 74-104, 74-105, 74-106, 74-107, 74-108, 74-109, 75-103, 75-104, 75-105, 75-106, 75-107, 75-108, 75-109, 76-103, 76-104, 76-105, 76-107, 76-108, 76-109, 77-103, 77-104, 77-105, 77-106, 77-107, 77-108, 77-109, 78-103, 78-104, 78-105, 78-106, 78-107, 78-108, 78-109, 79-103, 79-104, 79-105, 79-106, 79-107, 79-108, or 79-109 numbered according to the classic H3 subtype numbering system.

In a specific embodiment, a monoclonal antibody provided herein is the antibody designated 7A7. In another embodiment, a monoclonal antibody provided herein is the antibody designated 12D1. In another embodiment, a monoclonal provided is the antibody designated 39A4. In another embodiment, a monoclonal provided is the antibody designated 66A6. Encompassed herein are antigen-binding fragments (e.g., Fab fragments, F(ab') fragments, $F(ab')_2$ fragments) of the antibody designated 7A7, the antibody designated 12D1, the antibody designated 39A4, and the antibody designated 66A6. Hybridomas that produce each of the 7A7, 12D1, and 39A4 antibodies were deposited under provisions of the Budapest Treaty with the American Type Culture Collection (ATCC, 10801 University Blvd., Manassas, Va. 20110-2209) on May 22, 2009 under ATCC Accession Nos. PTA-10058, PTA-10059, and PTA 10060, respectively, and are herein incorporated by reference. A hybridoma that produces the 66A6 antibody was deposited under provisions of the Budapest Treaty with the American Type Culture Collection (ATCC, 10801 University Blvd., Manassas, Va. 20110-2209) on May 26, 2010 under ATCC Accession Nos. PTA No. PTA-11046, and is herein incorporated by reference.

Provided herein are antibodies (such as monoclonal antibodies) that compete with the 7A7 antibody, 12D1 antibody, 39A4 antibody, or 66A6 antibody for binding to a strain of the H3 subtype of Influenza A virus as determined using techniques known to one of skill in the art. In a specific embodiment, an antibody competes with the antibody 7A7, 12D1, 39A4, or 66A6 for binding to the Influenza A virus strain A/Hong Kong/1/1968 (H3) as determined using techniques known to one of skill in the art. In another specific embodiment, an antibody competes with the antibody 7A7, 12D1, 39A4, or 66A6 for binding to the Influenza A strain A/Alabama/1/1981 (H3) as determined using techniques known to one of skill in the art. In another specific embodiment, an antibody competes with the antibody 7A7, 12D1, 39A4, or 66A6 for binding to the Influenza A virus strain A/Beijing/47/1992 (H3) as determined using techniques known to one of skill in the art. In another specific embodiment, an antibody competes with the antibody 7A7, 12D1, 39A4, or 66A6 for binding to the Influenza A virus strain A/Wyoming/3/2003 (H3) as determined using techniques known to one of skill in the art. Competition assays known to one of skill in the art may be used to assess the competition of an antibody with the antibody 7A7, 12D1, 39A4, or 66A6 for binding to a strain of the H3 subtype of Influenza virus. For example, an immunoassay (e.g., an ELISA) in competitive format may be used.

Provided herein are antibodies that bind to a strain of Influenza A virus which comprise a variable light (VL) chain and/or a variable heavy (VH) chain of the antibody 7A7, 12D1, 39A4, or 66A6. In one embodiment, an antibody that binds to a strain of Influenza A virus comprises the VL chain or VH chain of the antibody 7A7, 12D1, 39A4, or 66A6. In another embodiment, an antibody that binds to a strain of Influenza A virus comprises the VL chain of the antibody 7A7, 12D1, 39A4, or 66A6 and the VH chain of another antibody. In another embodiment, an antibody that binds to a strain of Influenza A virus comprises the VH chain of the antibody 7A7, 12D1, 39A4, or 66A6 and the VL chain of another antibody. In a specific embodiment, an antibody that binds to a strain of the Influenza A virus comprises the VL chain of the antibody 7A7 and the VH chain of the antibody 12D1, 39A4, or 66A6; the VL chain of the antibody 12D1 and the VH chain of the antibody 7A7, 39A4, or 66A6; the VL chain of the antibody 39A4 and the VH chain of the antibody 7A7, 12D1, or 66A6; the VH chain of the antibody 66A6 and the VL chain of the antibody 7A7, 12D1, or 39A4; or the VL chain of the antibody 66A6 and the VH chain of the antibody 7A7, 12D1, or 39A4. In specific embodiments, such antibodies bind to a strain of the H3 subtype of Influenza A virus and in certain embodiments, such antibodies neutralize a strain of the H3 subtype of Influenza A virus.

Provided herein are antibodies that bind to a strain of Influenza A virus which comprise a VL domain and/or a VH domain of the antibody 7A7, 12D1, 39A4, or 66A6. In one embodiment, an antibody that binds to a strain of Influenza A virus comprises the VL domain or VH domain of the antibody 7A7, 12D1, 39A4, or 66A6. In another embodiment, an antibody that binds to a strain of Influenza A virus comprises the VL domain of the antibody 7A7, 12D1, 39A4, or 66A6 and the VH domain of another antibody. In another embodiment, an antibody that binds to a strain of Influenza A virus comprises the VH domain of the antibody 7A7, 12D1, 39A4, or 66A6 and the VL domain of another antibody. In a specific embodiment, an antibody that binds to a strain of the Influenza A virus comprises the VL domain of the antibody 7A7 and the VH domain of the antibody 12D1, 39A4, or 66A6; the VL domain of the antibody 12D1 and the VH domain of the antibody 7A7, 39A4, or 66A6; the VL domain of the antibody 39A4 and the VH domain of the antibody 7A7, 12D1, or 66A6; the VH domain of the antibody 66A6 and the VL domain of the antibody 7A7, 12D1, or 39A4; or the VL domain of the antibody 66A6 and the VH domain of the antibody 7A7, 12D1, or 39A4. In specific embodiments, such antibodies bind to a strain of the H3 subtype of Influenza A virus and in certain embodiments, such antibodies neutralize a strain of the H3 subtype of Influenza A virus. A VH domain or VL domain refers to the variable region of the variable heavy chain or variable light chain, respectively.

Provided herein are antibodies that bind to a strain of Influenza A virus which comprise a VL chain of the antibody 7A7, 12D1, 39A4, or 66A6 and a VH domain of the antibody 7A7, 12D1, 39A4, or 66A6, or VL domain of the antibody 7A7, 12D1, 39A4, or 66A6 and a VH chain of the antibody 7A7, 12D1, 39A4, or 66A6. In one embodiment, an antibody that binds to a strain of Influenza A virus comprises the VL chain of the antibody 7A7, 12D1, 39A4, or 66A6 and the VH domain of another antibody. In another embodiment, an antibody that binds to a strain of Influenza A virus comprises the VL domain of the antibody 7A7, 12D1, 39A4, or 66A6 and the VH chain of another antibody. In a specific embodiment, an antibody that binds to a strain of the Influenza A virus comprises the VL chain of the antibody 7A7 and the VH domain of the antibody 12D1, 39A4, or 66A6; the VL domain of the antibody 7A7 and the VH chain of the antibody 12D1, 39A4, or 66A6; the VL chain of the antibody 12D1 and the VH domain of the antibody 7A7, 39A4, or 66A6; the VL domain of the antibody 12D1 and the VH chain of the antibody 7A7, 39A4, or 66A6; the VL chain of the antibody 39A4 and the VH domain of the antibody 7A7, 12D1, or 66A6; the VL domain of the antibody 39A4 and the VH chain of the antibody 7A7, 12D1, or 66A6; the VL chain of the antibody 66A6 and the VH domain of the antibody 7A7, 12D1, or 39A4; or the VL domain of the antibody 66A6 and the VH chain of the antibody 7A7, 12D1, or 39A4. In specific embodiments, such antibodies bind to a strain of the H3 subtype of Influenza A virus and in certain embodiments, such antibodies neutralize a strain of the H3 subtype of Influenza A virus.

Provided herein are antibodies that bind to a strain of Influenza A virus comprising one, two or three complementarity determining regions (CDRs) of the variable heavy chain (VH CDRs) of the antibody 7A7, 12D1, 39A4, or 66A6 and one, two or three CDRs of the variable light chain (VL CDRs) of the antibody 7A7, 12D1, 39A4, or 66A6. In certain embodiments, an antibody that binds to a strain of Influenza A virus, comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; a VH CDR1, VH CDR2, a VH CDR3, a VL CDR1, a VL CDR2, and a VL CDR3; or any combination thereof of the VH CDRs and VL CDRs of the antibodies 7A7, 12D1, 39A4, or 66A6. In specific embodiments, such antibodies bind to a strain of the H3 subtype of Influenza A virus and in certain embodiments, such antibodies neutralize a strain of the H3 subtype of Influenza A virus.

The sequence of the antibody 7A7, 12D1, 39A4, and/or 66A6 can be determined using standard techniques known to one skilled in the art and the VH chain, VL chain, VH domain, VL domain, VH CDRs, and VL CDRs can be determined using, e.g., the Kabat numbering system (such as the EU index in Kabat).

The deduced nucleotide sequences of the VH and VL chains of the antibody 7A7 are shown in FIG. 19. The deduced amino acid sequences of the VH and VL chains of the antibody 7A7 are shown in FIG. 20. The deduced nucleotide sequences of the VH and VL chains of the antibody 12D1 are shown in FIG. 21. The deduced amino acid sequences of the VH and VL chains of the antibody 12D1 are shown in FIG. 22. The deduced nucleotide sequences of the VH and VL chains of the antibody 66A6 are shown in FIG. 28. The deduced amino acid sequences of the VH and VL chains of the antibody 66A6 are shown in FIG. 29. In FIGS. 19, 20, 21, 22, 28, and 29, the framework and CDR regions corresponding to the nucleic acid sequences are shown in bold and underlined, respectively. One of skill in the art can readily determine the location of the framework regions and CDRs in amino acid sequences using techniques known in the art (e.g., using the program provided at the following website www.expasy.ch/tools/dna.html).

The antibodies provided herein or generated in accordance with the methods provided herein include derivatives that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies provided herein or generated in accordance with the methods provided herein can comprise a framework region known to those of skill in the art (e.g., a human or non-human fragment). The framework region may be naturally occurring or consensus framework regions (see, e.g., Sui et al., 2009, Nature Structural & Molecular Biology 16:265-273).

Also provided herein are nucleic acids encoding the antibodies provided herein or generated in accordance with the methods provided herein. In some embodiments, a nucleic acid molecule(s) encoding an antibody provided herein or generated in accordance with the methods provided herein is isolated. In other embodiments, a nucleic acid(s) encoding an antibody provided herein or generated in accordance with the methods provided herein is not isolated. In yet other embodiments, a nucleic acid(s) encoding an antibody provided herein or generated in accordance with the methods provided herein is integrated, e.g., into chromosomal DNA or an expression vector. In a specific embodiment, a nucleic acid(s) provided herein encodes for the antibody 7A7, 12D1, 39A4, 66A6 or a fragment thereof (in particular, an antigen-binding fragment thereof). In another specific embodiment, a nucleic acid(s) provided herein encodes for an antibody that binds to Influenza virus HA, wherein the antibody comprises the VH domain of the antibody 7A7, 12D1, 39A4, or 66A6. In another specific embodiment, a nucleic acid(s) provided herein encodes for an antibody that binds to Influenza virus HA, wherein the antibody comprises the VL domain of the antibody 7A7, 12D1, 39A4, or 66A6. In another specific embodiment, a nucleic acid(s) provided herein encodes for an antibody that binds to Influenza virus HA, wherein the antibody comprises the VH and VL domain of the antibody 7A7, 12D1, 39A4, or 66A6. In another specific embodiment, a nucleic acid(s) provided herein encodes for an antibody that binds to Influenza virus HA, wherein the antibody comprises 1, 2, or 3 VH CDRs and/or 1, 2, or 3 VL CDRs of the antibody 7A7, 12D1, 39A4, or 66A6. In certain embodiments, the nucleic acid encodes an antibody that not only binds to Influenza virus HA, but also neutralizes the Influenza virus.

The antibodies described herein or generated in accordance with the methods provided herein can be affinity matured using techniques known to one of skill in the art. The monoclonal antibodies described herein or generated in accordance with the methods provided herein can be chimerized using techniques known to one of skill in the art. A chimeric antibody is a molecule in which different portions of the antibody are derived from different immunoglobulin molecules. Methods for producing chimeric antibodies are known in the art. See, e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

The monoclonal antibodies described herein or generated in accordance with the methods provided herein can be humanized. A humanized antibody is an antibody which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fab, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments include, but are not limited to, C-kappa and C-gamma-1 (nG1m) described in Johnson et al. (1997) *J. Infect. Dis.* 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16): 10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.

5.2.1 Antibodies with Increased Half-Lives

Provided herein are antibodies, wherein said antibodies are modified to have an extended (or increased) half-life in vivo. In particular, provided herein are modified antibodies which have a half-life in a subject, preferably a mammal and most preferably a human, of from about 3 days to about 180 days (or more), and in some embodiments greater than 3 days, greater than 7 days, greater than 10 days, greater than 15 days, greater than 20 days, greater than 25 days, greater than 30 days, greater than 35 days, greater than 40 days, greater than 45 days, greater than 50 days, at least about 60 days, greater than 75 days, greater than 90 days, greater than 105 days, greater than 120 days, greater than 135 days, greater than 150 days, greater than 165 days, or greater than 180 days.

In a specific embodiment, modified antibodies having an increased half-life in vivo are generated by introducing one or more amino acid modifications (i.e., substitutions, insertions or deletions) into an IgG constant domain, or FcRn-binding fragment thereof (preferably a Fc or hinge-Fc domain fragment). See, e.g., International Publication Nos. WO 02/060919; WO 98/23289; and WO 97/34631; and U.S. Pat. No. 6,277,375; each of which is incorporated herein by reference in its entirety. In a specific embodiment, the modified antibodies may have one or more amino acid modifications in the second constant CH2 domain (residues 231-340 of human IgG1) and/or the third constant CH3 domain (residues 341-447 of human IgG1), with numbering according to the Kabat numbering system (e.g., the EU index in Kabat).

In some embodiments, to prolong the in vivo serum circulation of antibodies, inert polymer molecules such as high molecular weight polyethyleneglycol (PEG) are attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

In another embodiment, antibodies are conjugated to albumin in order to make the antibody more stable in vivo or have a longer half-life in vivo. The techniques are well-known in the art, see, e.g., International Publication Nos. WO 93/15199, WO 93/15200, and WO 01/77137; and European Patent No. EP 413,622, all of which are incorporated herein by reference.

5.2.2 Antibody Conjugates

In some embodiments, antibodies are conjugated or recombinantly fused to a diagnostic, detectable or therapeutic agent or any other molecule. When in vivo half-life is desired to be increased, said antibodies can be modified antibodies. The conjugated or recombinantly fused antibodies can be useful, e.g., for monitoring or prognosing the onset, development, progression and/or severity of an Influenza virus disease as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, strepta-vidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{187}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Encompassed herein are antibodies recombinantly fused or chemically conjugated (including both covalent and non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, provided herein are fusion proteins comprising an antigen-binding fragment of a monoclonal antibody (e.g., a Fab fragment, Fd fragment, Fv fragment, F(ab)$_2$ fragment, a VH domain, a VH CDR, a VL domain or a VL CDR) and a heterologous protein, polypeptide, or peptide. In a specific embodiment, the heterologous protein, polypeptide, or peptide that the antibody is fused to is useful for targeting the antibody to a particular cell type.

In one embodiment, a fusion protein provided herein comprises the 7A7, 12D1, 39A4, or 66A6 antibody and a heterologous polypeptide. In another embodiment, a fusion protein provided herein comprises an antigen-binding fragment of the 7A7, 12D1, 39A4, or 66A6 antibody and a heterologous polypeptide. In another embodiment, a fusion protein provided herein comprises one, two, or more VH domains having the amino acid sequence of any one of the VH domains of the 7A7, 12D1, 39A4, or 66A6 antibody or one or more VL domains having the amino acid sequence of any one of the VL domains of the 7A7, 12D1, 39A4, or 66A6 antibody and a heterologous polypeptide. In another embodiment, a fusion protein provided herein comprises one, two, or more VH CDRs having the amino acid sequence of any one of the VH CDRs of the 7A7, 12D1, 39A4, or 66A6 antibody and a heterologous polypeptide. In another embodiment, a fusion protein comprises one, two, or more VL CDRs having the amino acid sequence of any one of the VL CDRs of the 7A7, 12D1, 39A4, or 66A6 antibody and a heterologous polypeptide. In another embodiment, a fusion protein provided herein comprises at least one VH domain and at least one VL domain of the 7A7, 12D1, 39A4, or 66A6 antibody and a heterologous polypeptide. In yet another embodiment, a fusion protein provided herein comprises at least one VH CDR and at least one VL CDR of the 7A7, 12D1, 39A4, or 66A6 antibody and a heterologous polypeptide. In certain embodiments, the above-referenced antibodies comprise a modified IgG (e.g., IgG1) constant domain, or FcRn binding fragment thereof (e.g., the Fc domain or hinge-Fc domain), described herein.

Encompassed herein are uses of the antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, β-interferon, γ-interferon, α-interferon, interleukin-2 ("IL-2"), interleukin-4 ("IL-4"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-18 ("IL-18"), interleukin-23 ("IL-23"), granulocyte macrophage colony stimulating factor ("GM-CSF"), granulocyte colony stimulating factor ("G-CSF")), a growth factor, or a defensin. The therapeutic moiety or drug conjugated or recombinantly fused to an antibody should be chosen to achieve the desired prophylactic or therapeutic effect(s). In certain embodiments, an antibody conjugate may be used for the prophylactic or therapeutic uses described herein. In certain embodiments, the antibody is a modified antibody. A clinician or other medical personnel should consider the following when deciding on which therapeutic moiety or drug to conjugate or recombinantly fuse to an antibody: the nature of the disease, the severity of the disease, and the condition of the subject.

Moreover, antibodies can be fused to marker sequences, such as a peptide to facilitate purification. In preferred embodiments, the marker amino acid sequence is a hexa-histidine peptide (i.e., His-tag), such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the Influenza hemagglutinin protein (Wilson et al., 1984, Cell 37:767), and the "flag" tag.

Methods for fusing or conjugating therapeutic moieties (including polypeptides) to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; —C—U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154: 5590-5600, 1995; Vil et al., Proc. Natl. Acad. Sci. USA, 89:11337-11341, 1992; which are incorporated herein by reference in their entireties.

In particular, fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the monoclonal antibodies described herein or generated in accordance with the methods provided herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding a monoclonal antibody described herein or generated in accordance with the methods provided herein may be recombined with one or more components, motifs, sections, parts, domains, fragments, etc. of one or more heterologous molecules.

An antibody can also be conjugated to a second antibody to form an antibody heteroconjugate as described by Segal in U.S. Pat. No. 4,676,980, which is incorporated herein by reference in its entirety.

An antibody can also linked directly or indirectly to one or more antibodies to produce bispecific/multispecific antibodies.

An antibody can also be attached to solid supports, which are particularly useful for immunoassays or purification of an antigen. Such solid supports include, but are not limited to, glass, cellulose, polyacrylamide, nylon, polystyrene, polyvinyl chloride or polypropylene.

5.3 Production of Antibody

The antibodies described herein can be produced by any method known in the art for the synthesis of antibodies, in particular, by chemical synthesis or preferably, by recombinant expression techniques. The methods provided herein encompass, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Recombinant expression of an antibody requires construction of an expression vector containing a polynucleotide that encodes the antibody. Once a polynucleotide encoding an antibody has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Thus, provided herein are replicable vectors comprising a nucleotide sequence encoding an antibody operably linked to a promoter. Such vectors may include the nucleotide sequence encoding the constant region of the antibody and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce a monoclonal antibody described herein or generated in accordance with the methods provided herein. Thus, provided herein are host cells containing a polynucleotide encoding a monoclonal antibody described herein or generated in accordance with the methods provided herein or fragments thereof, or a heavy or light chain thereof, or fragment thereof, or a single chain monoclonal antibody described herein or generated in accordance with the methods provided herein, operably linked to a heterologous promoter. In preferred embodiments for the expression of double-chained antibodies, vectors encoding both the heavy and light chains may be co-expressed in the host cell for expression of the entire immunoglobulin molecule, as detailed below.

In a specific embodiment, a host cell provided herein comprises a nucleic acid encoding the antibody 7A7, 12D1, 39A4, or 66A6. In another specific embodiment, a host cell provided herein comprises a nucleic acid encoding an antibody that binds to Influenza virus HA, the antibody comprising the VH chain or VH domain and/or the VL chain or VL domain of the antibody 7A7, 12D1, 39A4, or 66A6. In another specific embodiment, a host cell provided herein comprises a nucleic acid encoding an antibody that binds to Influenza virus HA, the antibody comprising the 1, 2, or 3 VH CDRs and/or 1, 2, or 3 VL CDRs of the antibody 7A7, 12D1, 39A4, or 66A6. In specific embodiments, the antibody not only binds to Influenza virus HA, but also neutralizes the Influenza virus.

A variety of host-expression vector systems may be utilized to express an antibody (see, e.g., U.S. Pat. No. 5,807, 715). Such host-expression systems represent vehicles by which the coding sequences of interest may be produced and subsequently purified, but also represent cells which may, when transformed or transfected with the appropriate nucleotide coding sequences, express an antibody in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (including plant cell systems described in Section 5.3) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding the monoclonal antibodies described herein or generated in accordance with the methods provided herein is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, Vero, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule. Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors provided herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains may comprise cDNA or genomic DNA.

Once an antibody has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies may be fused to heterologous polypeptide sequences described herein or otherwise known in the art to facilitate purification.

In addition, human antibodies could be generated using the antibodies described herein. Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

5.4 Compositions

Provided herein are compositions comprising an antibody having the desired degree of purity in a physiologically acceptable carrier, excipient or stabilizer (*Remington's Pharmaceutical Sciences* (1990) Mack Publishing Co., Easton, Pa.). In a specific embodiment, the compositions comprise an antibody conjugated to a moiety such as described in Section 5.2.2. In certain embodiments, the compositions comprise an antibody that has been modified to increase its half-life. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an antibody, and optionally one or more additional prophylactic or therapeutic agents, in a pharmaceutically acceptable carrier. In a specific embodiment, pharmaceutical compositions comprise an effective amount of an antibody, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in the prevention or treatment of Influenza virus infection. Further, pharmaceutical compositions described herein can be useful in the prevention, treatment or management of Influenza virus disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parental. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody can be formulated as an aerosol for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody is a lyophilized powder, which can be reconstituted for administration as solutions, emulsions and other mixtures. It may also be reconstituted and formulated as solids or gels. The lyophilized powder is prepared by dissolving an antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

An antibody can also, for example, be formulated in liposomes. Liposomes containing the molecule of interest are prepared by methods known in the art, such as described in Epstein et al. (1985) *Proc. Natl. Acad. Sci. USA* 82:3688; Hwang et al. (1980) *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556. In one embodiment, liposomal suspensions may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound comprising monoclonal antibodies described herein or generated in accordance with the methods provided herein provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

An antibody can also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* (1990) Mack Publishing Co., Easton, Pa.

Sustained-release preparations can also be prepared. Suitable examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The compositions to be used for in vivo administration can be sterile. This is readily accomplished by filtration through, e.g., sterile filtration membranes.

In a specific embodiment, nucleic acids comprising sequences encoding an antibody are administered to a subject by way of gene therapy. Gene therapy refers to therapy performed by the administration to a subject of an expressed or expressible nucleic acid. Encompassed herein are any of the methods for gene therapy available in the art. For general review of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

5.5 Prophylactic and Therapeutic Uses

In one aspect, provided herein are methods of preventing, managing, and/or treating an Influenza virus disease in a subject by administering neutralizing antibodies described herein. In a specific embodiment, a method for preventing or treating an Influenza virus disease in a subject comprises administering to a subject an effective amount of a neutralizing antibody described herein, or a pharmaceutical composition thereof. In another embodiment, a method for preventing, managing, or treating an Influenza virus disease in a subject comprises administering to a subject an effective amount of a neutralizing antibody described herein, or a pharmaceutical composition thereof and another therapy. In particular embodiments, the neutralizing antibody is a monoclonal antibody. In a specific embodiment, the Influenza virus disease that is prevented, managed, or treated is caused by an Influenza virus that is characterized as a Group 2 Influenza virus. In another specific embodiment, the Influenza virus disease that is prevented, managed, or treated is caused by an Influenza virus that is characterized as an Influenza virus of the H3 subtype.

In one aspect, provided herein are methods of preventing or treating an Influenza virus infection in a subject by administering neutralizing antibodies described herein. In a specific embodiment, a method for preventing or treating an Influenza virus infection in a subject comprises administering to a subject an effective amount of a neutralizing antibody described herein, or a pharmaceutical composition thereof. In another embodiment, a method for preventing or treating an Influenza virus infection in a subject comprises administering to a subject an effective amount of a neutralizing antibody described herein, or a pharmaceutical composition thereof and another therapy. In particular embodiments, the neutralizing antibody is a monoclonal antibody.

In a specific embodiment, administration of an antibody(ies) prevents or inhibits Influenza virus from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus binding to its host cell receptor in the absence of said antibody(ies) or in the presence of a negative control in an assay known to one of skill in the art or described herein.

In a specific embodiment, administration of an antibody (ies) prevents or inhibits Influenza virus-induced fusion by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus-induced fusion in the absence of said antibody(ies) or in the presence of a negative control in an assay known to one of skill in the art or described herein.

In a specific embodiment, administration of an antibody(ies) prevents or inhibits Influenza virus-induced fusion after viral attachment to cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus-induced fusion after viral attachment to cells in the absence of said antibody(ies) or in the presence of a negative control in an assay known to one of skill in the art or described herein.

In a specific embodiment, administration of an antibody(ies) inhibits or reduces Influenza virus replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to replication of Influenza virus in the absence of said antibody(ies) or in the presence of a negative control in an assay known to one of skill in the art or described herein. Inhibition of Influenza virus replication can be determined by detecting the Influenza virus titer in a biological specimens from a subject using methods known in the art (e.g., Northern blot analysis, RT-PCR, Western Blot analysis, etc.).

In a specific embodiment, administration of an antibody(ies) results in reduction of about 1-fold, about 1.5-fold, about 2-fold, about 3-fold, about 4-fold, about 5-fold, about 8-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 105 fold, about 110-fold, about 115-fold, about 120 fold, about 125-fold or higher in Influenza virus titer in the subject. The fold-reduction in Influenza virus titer may be as compared to a negative control, as compared to another treatment, or as compared to the titer in the patient prior to antibody administration.

In a specific embodiment, administration of an antibody(ies) results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs in Influenza virus titer in the subject. The log-reduction in Influenza virus titer may be as compared to a negative control, as compared to another treatment, or as compared to the titer in the patient prior to antibody administration.

In a specific embodiment, administration of an antibody(ies) inhibits or reduces Influenza virus infection of a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to Influenza virus infection of a subject in the absence of said antibody(ies) or in the presence of a negative control in an assay known to one of skill in the art or described herein.

In a specific embodiment, administration of an antibody(ies) inhibits or reduces the spread of Influenza virus in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of Influenza virus in a subject in the absence of said an antibody(ies) or in the presence of a negative control in an assay known to one of skill in the art or described herein.

In a specific embodiment, administration of an antibody(ies) inhibits or reduces the spread of Influenza virus between a subject and at least one other subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the spread of Influenza virus between a subject and at least one other subject in the absence of said antibody(ies) or in the presence of a negative control in an assay known to one of skill in the art or described herein.

In a specific embodiment, administration of an antibody(ies) reduces the number of and/or the frequency of symptoms of Influenza virus disease or infection in a subject (exemplary symptoms of influenza virus disease include, but are not limited to, body aches (especially joints and throat), fever, nausea, headaches, irritated eyes, fatigue, sore throat, reddened eyes or skin, and abdominal pain).

An antibody(ies) may be administered alone or in combination with another/other type of therapy known in the art to reduce Influenza virus infection, to reduce titers of Influenza virus in a subject, to reduce the spread of Influenza virus between subjects, to inhibit Influenza virus replication, to inhibit Influenza virus-induced fusion, and/or to inhibit binding of Influenza virus to its host cell receptor.

One or more of the antibodies may be used locally or systemically in the body as a prophylactic or therapeutic agent. The antibodies may also be advantageously utilized in combination with other antibodies (e.g., monoclonal or chimeric antibodies), or with lymphokines or hematopoietic growth factors (such as, e.g., IL-2, IL-3 and IL-7), which, for example, serve to increase the number or activity of effector cells which interact with the antibodies.

One or more antibodies may also be advantageously utilized in combination with one or more agents used to treat Influenza virus infection such as, for example anti-viral agents. Specific anti-viral agents include: oseltamavir (Tamiflu®), zanamivir (Relenza®), nucleoside analogs (e.g., zidovudine, acyclovir, gangcyclovir, vidarabine, idoxuridine, trifluridine, and ribavirin), foscarnet, amantadine, rimantadine (Flumadine®), saquinavir, indinavir, ritonavir, alpha-interferons and other interferons, AZT, Influenza virus vaccines (e.g., Fluarix®, FluMist®, Fluvirin®, and Fluzone®).

In some embodiments, an antibody acts synergistically with the one or more other therapies. Generally, administration of products of a species origin or species reactivity (in the case of antibodies) that is the same species as that of the patient is preferred. Thus, in a preferred embodiment, human or humanized antibodies are administered to a human patient for treatment or prophylaxis of an Influenza virus infection or a disease associated therewith.

In one embodiment, provided herein are methods of prevention, management, treatment and/or amelioration of an Influenza virus disease, and/or a symptom relating thereto as alternatives to current therapies. In a specific embodiment, the current therapy has proven or may prove to be too toxic (i.e., results in unacceptable or unbearable side effects) for the patient. In another embodiment, a monoclonal antibody described herein or generated in accordance with the methods provided herein decreases the side effects as compared to the current therapy. In another embodiment, the patient has proven refractory to a current therapy. In such embodiments, encompassed herein is the administration of one or more monoclonal antibodies described herein or generated in accordance with the methods provided herein without any other anti-infection therapies.

Suitable regimens can be selected by one skilled in the art by considering such factors and by following, for example, dosages reported in the literature and recommended in the Physician's Desk Reference ($58^{th}$ ed., 2004). See Section 5.5.2 for exemplary dosage amounts and frequencies of administration of the monoclonal antibodies described herein or generated in accordance with the methods provided herein.

In accordance with the methods encompassed herein, a monoclonal antibody described herein or generated in accordance with the methods provided herein may be used as any line of therapy, including, but not limited to, a first, second, third, fourth and/or fifth line of therapy. Further, in accordance with the methods encompassed herein, a monoclonal antibody described herein or generated in accordance with the methods provided herein can be used before or after any adverse effects or intolerance of the therapies other than a monoclonal antibody described herein or generated in accordance with the methods provided herein occurs. Encompassed herein are methods for administering one or more a monoclonal antibody described herein or generated in accordance with the methods provided herein to prevent the onset of an Influenza virus disease and/or to treat or lessen the recurrence of an Influenza virus disease.

In a specific embodiment, administration of an antibody(ies) reduces the incidence of hospitalization by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the incidence of hospitalization in the absence of administration of said antibody(ies).

In a specific embodiment, administration of an antibody(ies) reduces mortality by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the mortality in the absence of administration of said antibody(ies).

Further encompassed herein are methods for preventing, managing, treating and/or ameliorating an Influenza virus disease and/or a symptom relating thereto for which no other anti-viral therapy is available.

5.5.1 Patient Population

In one embodiment, a patient treated or prevented in accordance with the methods provided herein is a naïve subject, i.e., a subject that does not have a disease caused by Influenza virus infection or has not been and is not currently infected with an Influenza virus infection. In another embodiment, a patient treated or prevented in accordance with the methods provided herein is a subject that is at risk of acquiring an Influenza virus infection. In another embodiment, a patient treated or prevented in accordance with the methods provided herein is a naïve subject that is at risk of acquiring an Influenza virus infection. In another embodiment, a patient treated or prevented in accordance with the methods provided herein is a patient suffering from or expected to suffer from an Influenza virus disease. In another embodiment, a patient treated or prevented in accordance with the methods provided herein is a patient diagnosed with an Influenza virus infection or a disease associated therewith. In some embodiments, a patient treated or prevented in accordance with the methods provided herein is a patient infected with an Influenza virus that does not manifest any symptoms of Influenza virus disease.

In a specific embodiment, a patient treated or prevented in accordance with the methods provided herein is a subject that is at risk of an infection with a Group 2 Influenza virus. In another specific embodiment, a patient treated or prevented in accordance with the methods provided herein is a naïve subject that is at risk of an infection with a Group 2 Influenza virus. In another specific embodiment, a patient treated or prevented in accordance with the methods provided herein is a patient suffering from or expected to suffer from an Influenza virus disease caused by a Group 2 Influenza virus. In another specific embodiment, a patient treated or prevented in accordance with the methods provided herein is a patient diagnosed with a Group 2 Influenza virus infection or a disease associated therewith.

In another embodiment, a patient treated or prevented in accordance with the methods provided herein is a patient experiencing one or more symptoms of Influenza virus disease. Symptoms of Influenza virus disease include, but are not limited to, body aches (especially joints and throat), fever, nausea, headaches, irritated eyes, fatigue, sore throat, reddened eyes or skin, and abdominal pain. In another embodiment, a patient treated or prevented in accordance with the methods provided herein is a patient with Influenza virus disease who does not manifest symptoms of the disease that are severe enough to require hospitalization.

In another embodiment, a patient treated or prevented in accordance with the methods provided herein is a patient infected with an Influenza A virus, an Influenza B virus or Influenza C virus. In another embodiment, a patient treated or prevented in accordance with the methods provided herein is a patient infected with a particular subtype of Influenza A virus. In another embodiment, a patient treated or prevented in accordance with the methods provided herein is a patient infected with a Group 2 Influenza virus. In another embodiment, a patient treated or prevented in accordance with the methods provided herein is a patient infected with an Influenza virus characterized as an Influenza virus of the H3 subtype. In accordance with such embodiments, the patients that are infected with the virus may manifest symptoms of Influenza virus disease.

In some embodiments, a patient treated or prevented in accordance with the methods provided herein is an animal. In certain embodiments, the animal is a bird. In certain embodiments, the animal is a mammal, e.g., a horse, swine, mouse, or primate, preferably a human.

In a specific embodiment, a patient treated or prevented in accordance with the methods provided herein is a human. In certain embodiments, a patient treated or prevented in accordance with the methods provided herein is a human infant. In some embodiments, a patient treated or prevented in accordance with the methods provided herein is a human toddler. In certain embodiments, a patient treated or prevented in accordance with the methods provided herein is a human child. In other embodiments, a patient treated or prevented in accordance with the methods provided herein is a human adult. In some embodiments, a patient treated or prevented in accordance with the methods provided herein is an elderly human.

In certain embodiments, a patient treated or prevented in accordance with the methods provided herein is patient that is pregnant. In another embodiment, a patient treated or prevented in accordance with the methods provided herein is a patient who may or will be pregnant during the Influenza season (e.g., November to April in the Northern Hemisphere).

In some embodiments, a patient treated or prevented in accordance with the methods provided herein is any subject at increased risk of Influenza virus infection or disease resulting from Influenza virus infection (e.g., an immunocompromised or immunodeficient individual). In some embodiments, a patient treated or prevented in accordance with the methods provided herein is any subject in close contact with an individual with increased risk of Influenza virus infection or disease resulting from Influenza virus infection (e.g., immunocompromised or immunosuppressed individuals).

In some embodiments, a patient treated or prevented in accordance with the methods provided herein is a subject affected by any condition that increases susceptibility to Influenza virus infection or complications or disease resulting from Influenza virus infection. In other embodiments, a patient treated or prevented in accordance with the methods provided herein is a subject in which an Influenza virus infection has the potential to increase complications of another condition that the individual is affected by, or for which they are at risk. In particular embodiments, such conditions that increase susceptibility to Influenza virus complications or for which Influenza virus increases complications associated with the condition are, e.g., conditions that affect the lung, such as cystic fibrosis, asthma, emphysema, or bacterial infections; cardiovascular disease; or diabetes. Other conditions that may increase Influenza virus complications include kidney disorders; blood disorders (including anemia or sickle cell disease); or weakened immune systems (including immunosuppression caused by medications, malignancies such as cancer, organ transplant, or HIV infection).

In some embodiments, a patient treated or prevented in accordance with the methods provided herein is a subject that resides in a group home, such as a nursing home or orphanage. In some embodiments, a patient treated or prevented in accordance with the methods provided herein is subject that works in, or spends a significant amount of time in, a group home, e.g., a nursing home or orphanage. In some embodiments, a patient treated or prevented in accordance with the methods provided herein is a health care worker (e.g., a doctor or nurse). In some embodiments, a patient treated or prevented in accordance with the methods provided herein resides in a dormitory (e.g., a college dormitory). In some embodiments, a patient treated or prevented in accordance with the methods provided herein is a member of the military. In some embodiments, a patient treated or prevented in accordance with the methods provided herein is a child that attends school.

In some embodiments, a patient treated or prevented in accordance with the methods provided herein is a subject at increased risk of developing complications from Influenza virus infection including: any individual who can transmit Influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with Influenza).

In other embodiments, a patient treated or prevented in accordance with the methods provided herein includes healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where Influenza viruses are circulating; attend school or college and reside in dormitories, or reside in institutional settings; or wish to reduce their risk of becoming ill with Influenza virus disease.

In specific embodiments, a patient treated or prevented in accordance with the methods provided herein is an individual who is susceptible to adverse reactions to conventional therapies. In other embodiments, the patient may be a person who has proven refractory to therapies other than an antibody described herein or generated in accordance with the methods provided herein but are no longer on these therapies. In certain embodiments, a patient with an Influenza virus disease is refractory to a therapy when the infection has not significantly been eradicated and/or the symptoms have not been significantly alleviated. The determination of whether a patient is refractory can be made either in vivo or in vitro by any method known in the art for assaying the effectiveness of a therapy for infections, using art-accepted meanings of "refractory" in such a context. In various embodiments, a patient with an Influenza virus disease is refractory when viral replication has not decreased or has increased following therapy.

In certain embodiments, patients treated or prevented in accordance with the methods provided herein are patients already being treated with antibiotics, anti-virals, anti-fungals, or other biological therapy/immunotherapy. Among these patients are refractory patients, patients who are too young for conventional therapies, and patients with reoccurring Influenza virus disease or a symptom relating thereto despite treatment with existing therapies.

5.5.2 Route of Administration and Dosage

An antibody or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. Pulmonary administration can also be employed, e.g., by use of an inhaler or nebulizer, and formulation with an aerosolizing agent for use as a spray.

The amount of an antibody or composition which will be effective in the treatment and/or prevention of an Influenza virus infection or an Influenza virus disease will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For passive immunization with an antibody, the dosage ranges from about 0.0001 to 100 mg/kg, and more usually 0.01 to 5 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. In some embodiments, the dosage administered to the patient is about 3 mg/kg to about 60 mg/kg of the patient's body weight. Preferably, the dosage administered to a patient is between 0.025 mg/kg and 20 mg/kg of the patient's body weight, more preferably 1 mg/kg to 15 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies described herein or generated in accordance with the methods provided herein may be reduced by enhancing uptake and tissue penetration (e.g., into the nasal passages and/or lung) of the antibodies by modifications such as, for example, lipidation.

An exemplary treatment regime entails administration once per every two weeks or once a month or once every 3 to 6 months for a period of one year or over several years, or over several year-intervals. In some methods, two or more antibodies with different binding specificities are administered simultaneously to a subject. An antibody is usually administered on multiple occasions. Intervals between single dosages can be weekly, monthly, every 3 months, every 6 months or yearly. Intervals can also be irregular as indicated by measuring blood levels of antibody to the Influenza virus antigen (e.g., hemagglutinin) in the patient.

In a specific embodiment, an antibody described herein or generated in accordance with the methods provided herein, or a composition thereof is administered once a month just prior to (e.g., within three months, within two months, within one month) or during the Influenza season. In another embodiment, an antibody described herein or generated in accordance with the methods provided herein, or a composition thereof is administered every two months just prior to or during the Influenza season. In another embodiment, an antibody described herein or generated in accordance with the methods provided herein, or a composition thereof is administered every three months just prior to or during the Influenza season. In a specific embodiment, an antibody described herein or generated in accordance with the methods provided herein, or a composition thereof is administered once just prior to or during the Influenza season. In another specific embodiment, an antibody described herein or generated in accordance with the methods provided herein, or a composition thereof is administered twice, and most preferably once, during a Influenza season. In some embodiments, an antibody described herein or generated in accordance with the methods provided herein, or a composition thereof is administered just prior to the Influenza season and can optionally be administered once during the Influenza season. In some embodiments, an antibody described herein or generated in accordance with the methods provided herein, or a composition thereof is administered every 24 hours for at least three days, at least four days, at least five days, at least six days up to one week just prior to or during an Influenza season. In specific embodiments, the daily administration of the antibody or composition thereof occurs soon after Influenza virus infection is first recognized in a patient, but prior to presentation of clinically significant disease. The term "Influenza season" refers to the season when Influenza infection is most likely to occur. Typically, the Influenza season in the northern hemisphere commences in November and lasts through April.

In some embodiments, the plasma level of an antibody described herein or generated in accordance with the methods provided herein in a patient is measured prior to administration of a subsequent dose of an antibody described herein or generated in accordance with the methods provided herein, or a composition thereof. The plasma level of the antibody may be considered in determining the eligibility of a patient to receive a subsequent dose of an antibody described herein or generated in accordance with the methods provided herein. For example, a patient's plasma level of an antibody described herein or generated in accordance with the methods provided herein may suggest not administering an antibody described herein or generated in accordance with the methods provided herein; alternatively, a patient's plasma level of an antibody described herein or generated in accordance with the methods provided herein may suggest administering an antibody described herein or generated in accordance with the methods provided herein at a particular dosage, at a particular frequency, and/or for a certain period of time.

In certain embodiments, the route of administration for a dose of an antibody described herein or generated in accordance with the methods provided herein, or a composition thereof to a patient is intranasal, intramuscular, intravenous, or a combination thereof, but other routes described herein are also acceptable. Each dose may or may not be administered by an identical route of administration. In some embodiments, an antibody described herein or generated in accordance with the methods provided herein, or composition thereof, may be administered via multiple routes of administration simultaneously or subsequently to other doses of the same or a different antibody described herein or generated in accordance with the methods provided herein.

5.5.3 Combination Therapies

In various embodiments, an antibody described herein or generated in accordance with the methods provided herein or a nucleic acid encoding such an antibody may be administered to a subject in combination with one or more other therapies (e.g., antiviral or immunomodulatory therapies). In some embodiments, a pharmaceutical composition described herein may be administered to a subject in combination with one or more therapies. The one or more other therapies may be beneficial in the treatment or prevention of an Influenza virus disease or may ameliorate a condition associated with an Influenza virus disease.

In some embodiments, the one or more other therapies that are supportive measures, such as pain relievers, anti-fever medications, or therapies that alleviate or assist with breathing. Specific examples of supportive measures include humidification of the air by an ultrasonic nebulizer, aerolized racemic epinephrine, oral dexamethasone, intravenous fluids, intubation, fever reducers (e.g., ibuprofen, acetometaphin), and antibiotic and/or anti-fungal therapy (i.e., to prevent or treat secondary bacterial and/or fungal infections).

In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may be used in combination with an antibody or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, AZT, zanamivir, and oseltamivir. Other anti-viral agents include Influenza virus vaccines, e.g., Fluarix® (GlaxoSmithKline), FluMist® (MedImmune Vaccines), Fluvirin® (Chiron Corporation), Fluzone® (Aventis Pasteur), or those described in Section 5.6 infra.

In specific embodiments, the anti-viral agent is an immunomodulatory agent that is specific for a viral antigen. In particular embodiments, the viral antigen is an Influenza virus polypeptide other than a hemagglutinin polypeptide. In other embodiments, the viral antigen is an Influenza virus hemagglutinin polypeptide.

In a specific embodiment, one or more therapies that prevent or treat secondary responses to a primary Influenza virus infection are administered in combination with one or more antibodies described herein or generated in accordance with the methods provided herein. Examples of secondary responses to a primary Influenza virus infection include, but are not limited to, asthma-like responsiveness to mucosal stimuli, elevated total respiratory resistance, increased susceptibility to secondary viral, bacterial, and fungal infections, and development of conditions such as, but not limited to, bronchiolitis, pneumonia, croup, and febrile bronchitis.

In a specific embodiment, one or more antibodies described herein or generated in accordance with the methods provided herein is used in combination with another antibody (e.g., an anti-Influenza virus monoclonal antibody) or a set of other antibodies (e.g., a set of anti-Influenza virus monoclonal antibodies) in order to enhance the prophylactic and/or therapeutic effect of the other antibody or set of other antibodies.

In some embodiments, a combination therapy comprises the administration of one or more antibodies described herein or generated in accordance with the methods provided herein. In some embodiments, a combination therapy comprises administration of two or more antibodies described herein or generated in accordance with the methods provided herein. In a specific embodiment, a combination therapy comprises the administration of the 7A7 antibody and one or more of the antibody 12D1, 39A4, or 66A6. In another specific embodiment, a combination therapy comprises the administration of the 12D1 antibody and one or more of the antibody 7A7, 39A4, or 66A6. In another specific embodiment, a combination therapy comprises the administration of the 39A4 antibody and one or more of the antibody 7A7, 12D1, or 66A6. In another specific embodiment, a combination therapy comprises the administration of the 66A6 antibody and one or more of the antibody 7A7, 39A4, or 12D1.

5.6 Use of the Antibodies to Generate Vaccines

Provided herein are immunogenic compositions (e.g., vaccines) capable of generating immune responses against a plurality of Influenza virus strains. While not intending to be bound by any particular theory of operation, it is believed that the antibody binding regions within the Influenza antigens bound by an antibody described herein or generated by a process described herein are useful for presenting one or more relatively conserved antigenic regions to a host immune system in order to generate an immune response that is capable of cross-reacting with a plurality of Influenza strains. Since the one or more antigenic regions are well conserved across Influenza subtypes, such an immune response might cross-react with several subtypes of Influenza virus.

Advantageously, Influenza regions bound by an antibody described herein or generated by a process described herein might be useful to generate an immune response against multiple Influenza strains because they present one or more epitopes in a relatively conserved region of an Influenza virus antigen. As such, they might be used to generate a host immune response against multiple Influenza strains that carry the relatively conserved epitopes. Accordingly, the Influenza hemagglutinin regions bound by an antibody described herein or generated by a process described herein find use as antigens in compositions and vaccines. The Influenza hemagglutinin regions bound by an antibody described herein or generated by a process described herein might be useful for generating a host immune response against any one, two, three, four, five, six, seven, eight, nine, ten, eleven, twelve, thirteen, fourteen, fifteen or sixteen known Influenza A subtypes or a later identified Influenza A subtype. The Influenza hemagglutinin regions bound by an antibody described herein or generated by a process described herein might be useful for generating a host immune response against any one, two, three, four, five, six, seven, eight, nine, ten, eleven, twelve, thirteen, fourteen, fifteen or sixteen known Influenza A strains or a later identified Influenza A strain. The Influenza regions bound by an antibody described herein or generated by a process described herein might also be useful for generating a host immune response against any Influenza B subtype now known or later identified. Additionally, the antibodies described herein or generated in accordance with the methods described herein can be utilized to identify Influenza hemagglutinin regions that mediate a broadly-protective immune response against Influenza viruses.

The binding regions of an antibody can be identified using methods known in the art, e.g., Western blot, and described herein (see Section 6.3). Once an antibody binding region has been identified, the specific epitopes bound by the antibodies can be identified using methods known in the art, e.g., alanine scanning mutagenesis (see, e.g., Cunningham et al., "High-Resolution Epitope Mapping of hGH-Receptor Interactions by Alanine-Scanning Mutagenesis" Science 244:1081-1085).

Generally, the Influenza virus binding regions and epitopes provided herein are polypeptides that comprise or consist essentially of the binding regions and epitopes of an Influenza hemagglutinin polypeptide bound by an antibody described herein or generated by a process described herein.

The Influenza virus binding regions and epitopes provided herein can be prepared according to any technique deemed suitable to one of skill, including techniques described below. In certain embodiments, the Influenza virus binding regions and epitopes provided herein are isolated. In certain embodiments, the Influenza virus binding regions and epitopes provided herein comprise a carbohydrate moiety.

In a specific embodiment, the Influenza virus binding region comprises the long alpha-helix of the HA2 region of a hemagglutinin polypeptide of an Influenza virus of the H3 subtype.

In a specific embodiment, an Influenza virus binding region comprises the long alpha-helix of the HA2 region of a hemagglutinin polypeptide of an Influenza A virus, such as the Influenza A virus strain A/Hong Kong/1/1968 (H3).

In a specific embodiment, the Influenza virus binding region comprises amino acid residues 304 to 513, 330 to 513, 345 to 513, 359 to 513, 360 to 513, 375 to 513, 359 to 514, and/or 360 to 514 of the hemagglutinin polypeptide of an Influenza virus of the H3 subtype. In a specific embodiment, the Influenza virus binding region comprises amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, the Influenza virus binding region comprises amino acid residues 76-106 of the hemagglutinin polypeptide numbered according to the classic H3 subtype numbering system. In another specific embodiment, the Influenza virus binding region comprises amino acid residues 73-103, 73-104, 73-105, 73-106, 73-107, 73-108, 73-109, 74-103, 74-104, 74-105, 74-106, 74-107, 74-108, 74-109, 75-103, 75-104, 75-105, 75-106, 75-107, 75-108, 75-109, 76-103, 76-104, 76-105, 76-107, 76-108, 76-109, 77-103, 77-104, 77-105, 77-106, 77-107, 77-108, 77-109, 78-103, 78-104, 78-105, 78-106, 78-107, 78-108, 78-109, 79-103, 79-104, 79-105, 79-106, 79-107, 79-108, or 79-109 numbered according to the classic H3 subtype numbering system.

In a specific embodiment, an Influenza virus binding region comprises amino acid residues 304 to 513, 330 to 513, 345 to 513, 359 to 513, 360 to 513, 375 to 513, 359 to 514, and/or 360 to 514 of the hemagglutinin polypeptide of the Influenza virus strain A/Hong Kong/1/1968 (H3). In a specific embodiment, an Influenza virus binding region comprises amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In another specific embodiment, an Influenza virus binding region provided herein comprises the following amino acid sequence: RIQDLEKYVE DTKIDLWSYN AELLVALENQ HTIDLTDSEM NKLFEKTRRQ LRENAEDMGN GCFKIYHKCD NACIESIRNG TYDHDVYRDE ALNNRFQIKG VELKSGYKD (SEQ ID NO:1). In another specific embodiment, an Influenza virus binding region provided herein comprises an amino acid sequence that is at least 99%, at least 98%, and least 97%, at least 96%, at least 95%, at least 90%, at least 85%, at least 80%, at least 75%, at least 70%, at least 65%, at least 60%, at least 55% or at least 50% identical to the amino acid sequence in SEQ ID NO:1.

In another specific embodiment, an Influenza virus epitope provided herein comprises an epitope identified in SEQ ID NO:1 that is bound by an antibody described herein or generated in accordance with the methods provided herein. In another specific embodiment, an Influenza virus epitope provided herein comprises an amino acid sequence that is at least 99%, at least 98%, and least 97%, at least 96%, at least 95%, at least 90%, at least 85%, at least 80%, at least 75%, at least 70%, at least 65%, at least 60%, at least 55% or at least 50% identical to an amino acid epitope identified in SEQ ID NO:1.

In certain embodiments, the binding region or epitope may be conjugated or fused to a heterologous amino acid sequence. Such conjugated or fused polypeptides can be used in an immunogenic composition for the uses described herein.

In certain embodiments, the binding region or epitope may be coupled/linked (e.g., via directly linked by a linker) to a carrier protein, e.g., tetanus toxoid (CRM197—non-toxic diptheria toxoid point mutant) or keyhole limpet hemocyanin (KLH).

Also provided herein are nucleic acids that encode an Influenza binding region and/or epitope provided herein. In a specific embodiment, provided herein is a nucleic acid that encodes an Influenza virus binding region that comprises the long alpha-helix of the HA2 region of a hemagglutinin polypeptide of an Influenza A virus, such as the Influenza A virus strain A/Hong Kong/1/1968 (H3). In another specific embodiment, provided herein is a nucleic acid that encodes the long alpha-helix of the HA2 region of a hemagglutinin polypeptide of an Influenza virus of the H3 subtype. In another specific embodiment, provided herein is a nucleic acid that encodes amino acid residues 304 to 513, 330 to 513, 345 to 513, 359 to 513, 360 to 513, 375 to 513, 359 to 514, and/or 360 to 514 of the hemagglutinin polypeptide of the Influenza virus strain A/Hong Kong/1/1968 (H3). In another specific embodiment, provided herein is a nucleic acid that encodes amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, provided herein is a nucleic acid that encodes amino acid residues 76-106 of the hemagglutinin polypeptide numbered according to the classic H3 subtype numbering system. In another specific embodiment, provided herein is a nucleic acid that encodes amino acid residues 73-103, 73-104, 73-105, 73-106, 73-107, 73-108, 73-109, 74-103, 74-104, 74-105, 74-106, 74-107, 74-108, 74-109, 75-103, 75-104, 75-105, 75-106, 75-107, 75-108, 75-109, 76-103, 76-104, 76-105, 76-107, 76-108, 76-109, 77-103, 77-104, 77-105, 77-106, 77-107, 77-108, 77-109, 78-103, 78-104, 78-105, 78-106, 78-107, 78-108, 78-109, 79-103, 79-104, 79-105, 79-106, 79-107, 79-108, or 79-109 numbered according to the classic H3 subtype numbering system. In a specific embodiment, provided herein is a nucleic acid that encodes SEQ ID NO:1 or an epitope identified within SEQ ID NO:1. Due to the degeneracy of the genetic code, any nucleic acid that encodes SEQ ID NO:1 or an epitope identified within SEQ ID NO:1 is encompassed herein. In another specific embodiment, provided herein are nucleic acids that encode a binding region that is at least 99%, at least 98%, and least 97%, at least 96%, at least 95%, at least 90%, at least 85%, at least 80%, at least 75%, at least 70%, at least 65%, at least 60%, at least 55% or at least 50% identical to the amino acid sequence in SEQ ID NO:1. In another specific embodiment, provided herein are nucleic acids that encode an epitope that is at least 99%, at least 98%, and least 97%, at least 96%, at least 95%, at least 90%, at least 85%, at least 80%, at least 75%, at least 70%, at least 65%, at least 60%, at least 55% or at least 50% identical to an epitope identified in SEQ ID NO:1. In some embodiments, the nucleic acids encompassed herein are isolated. In accordance with the methods described herein, a nucleic acid that encodes an Influenza binding region and/or epitope provided herein can be administered to a patient to induce an immune response in the patient.

Also provided herein are vectors, including expression vectors, containing nucleic acids that encode the binding regions and epitopes encompassed herein. In a specific embodiment, the vector is an expression vector that is capable of directing the expression of a nucleic acid that encodes a binding region and/or epitope encompassed herein.

Non-limiting examples of expression vectors include, but are not limited to, plasmids and viral vectors, such as replication defective retroviruses, adenoviruses, adeno-associated viruses, Newcastle disease viruses, and baculoviruses. In certain embodiments, a binding region or epitope described herein is engineered into an influenza virus vector. In other embodiments, a binding region or epitope described herein is engineered into a non-Influenza virus. In certain embodiments, the binding regions and epitopes encompassed herein can be incorporated into viral-like particles or a virosome. Techniques known to one skilled in the art may be used to produce expression vectors. In addition, a nucleic acid encoding a binding region or epitope described herein, or an expression vector can be introduced into host cells using techniques known in the art (see, e.g., Sambrook et al., 1989, Molecular Cloning—A Laboratory Manual, 2nd Edition, Cold Spring Harbor Press, New York). The expression vector selected for expression of a binding region or epitope may vary depending on the host cells chosen. The host cells selected might be prokaryotic (*E. coli, Salmonella, Listeria, Shigella*, etc.) or eukaryotic (e.g., mammalian cells, insect cells, yeast cells, or plant cells). The host cells may be engineered to stably or transiently express a binding region or epitope (see, e.g., Section 5.1.2 for information regarding expression of antigens).

Accordingly, provided herein are methods for producing an Influenza virus binding region and/or epitope. In one embodiment, the method comprises culturing a host cell containing a nucleic acid encoding the binding region and/or epitope in a suitable medium such that the a binding region and/or epitope is produced. In some embodiments, the method further comprises isolating the binding region and/or epitope from the medium or the host cell.

In one embodiment, an immunogenic composition comprises an Influenza virus binding region and/or epitope provided herein, in an admixture with a pharmaceutically acceptable carrier. In another embodiment, an immunogenic composition comprises a nucleic acid encoding an Influenza virus binding region and/or epitope described herein, in an admixture with a pharmaceutically acceptable carrier. In another embodiment, an immunogenic composition comprises an expression vector comprising a nucleic acid encoding an Influenza virus binding region and/or epitope provided herein, in an admixture with a pharmaceutically acceptable carrier. In another embodiment, an immunogenic composition comprises an Influenza virus or non-Influenza virus containing an Influenza virus binding region and/or epitope provided herein, in an admixture with a pharmaceutically acceptable carrier. In another embodiment, an immunogenic composition comprises an Influenza virus or non-Influenza virus having a genome engineered to express an Influenza virus binding region and/or epitope provided herein, in admixture with a pharmaceutically acceptable carrier. In another embodiment, an immunogenic composition comprises a viral-like particle or virosome containing an Influenza virus binding region and/or epitope provided herein, in an admixture with a pharmaceutically acceptable carrier. In another embodiment, an immunogenic composition comprises a bacteria expressing or engineered to express an Influenza virus binding region and/or epitope provided herein, in an admixture with a pharmaceutically acceptable carrier. In another embodiment, an immunogenic composition comprises cells stimulated with an Influenza virus binding region and/or epitope provided herein, in an admixture with a pharmaceutically acceptable carrier. In a specific embodiment, such compositions are formulated for the intended route of administration. Such compositions may include a pharmaceutically acceptable carrier or excipient.

In one embodiment, provided herein are subunit vaccines comprising an Influenza virus binding region and/or epitope provided herein. In a specific embodiment, a subunit vaccine comprises amino acid residues 304 to 513, 330 to 513, 345 to 513, 359 to 513, 360 to 513, 375 to 513, 359 to 514, and/or 360 to 514 of the hemagglutinin polypeptide of the Influenza virus strain A/Hong Kong/1/1968 (H3). In a specific embodiment, a subunit vaccine comprises amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, a subunit vaccine comprises amino acid residues 76-106 of the hemagglutinin polypeptide numbered according to the classic H3 subtype numbering system. In another specific embodiment, a subunit vaccine comprises SEQ ID NO:1 or a nucleic acid encoding SEQ ID NO:1. In some embodiments, the subunit vaccine further comprises one or more surface glycoproteins (e.g., Influenza virus neuraminidase), other targeting moieties, carrier proteins, or adjuvants.

In another embodiment, encompassed herein is a live virus engineered to express an Influenza virus binding region and/or epitope provided herein. In a specific embodiment, provided herein are immunogenic compositions (e.g., vaccines) comprising live virus containing an Influenza virus binding region and/or epitope provided herein. In specific embodiments, the Influenza virus binding region and/or epitope provided herein is membrane-bound. In other specific embodiments, the Influenza virus binding region and/or epitope provided herein is not membrane-bound, i.e., soluble. In particular embodiments, the live virus is an Influenza virus. In other embodiments, the live virus is a non-Influenza virus. In some embodiments, the live virus is attenuated. In some embodiments, an immunogenic composition comprises two, three, four or more live viruses containing or engineered to express two, three, four or more different Influenza virus binding regions and/or epitopes provided herein. In a specific embodiment, an immunogenic composition comprising live virus comprises amino acid residues 304 to 513, 330 to 513, 345 to 513, 359 to 513, 360 to 513, 375 to 513, 359 to 514, and/or 360 to 514 of the hemagglutinin polypeptide of the Influenza virus strain A/Hong Kong/1/1968 (H3). In a specific embodiment, an immunogenic composition comprising live virus comprises amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, an immunogenic composition comprising live virus comprises amino acid residues 76-106 of the hemagglutinin polypeptide numbered according to the classic H3 subtype numbering system. In another specific embodiment, an immunogenic composition comprising live virus comprises amino acid residues 73-103, 73-104, 73-105, 73-106, 73-107, 73-108, 73-109, 74-103, 74-104, 74-105, 74-106, 74-107, 74-108, 74-109, 75-103, 75-104, 75-105, 75-106, 75-107, 75-108, 75-109, 76-103, 76-104, 76-105, 76-107, 76-108, 76-109, 77-103, 77-104, 77-105, 77-106, 77-107, 77-108, 77-109, 78-103, 78-104, 78-105, 78-106, 78-107, 78-108, 78-109, 79-103, 79-104, 79-105, 79-106, 79-107, 79-108, or 79-109 of the hemagglutinin polypeptide numbered according to the classic H3 subtype numbering system. In a specific embodiment, an immunogenic composition comprising live virus comprises SEQ ID NO:1 or a nucleic acid encoding SEQ ID NO:1.

In another embodiment, provided herein are immunogenic compositions (e.g., vaccines) comprising an inactivated virus containing an Influenza virus binding region and/or epitope provided herein. In specific embodiments, the Influenza virus binding region and/or epitope provided herein is membrane-bound. In particular embodiments, the inactivated virus is an Influenza virus. In other embodiments, the inactivated virus is a non-Influenza virus. In some embodiments, an immunogenic composition comprises two, three, four or more inactivated viruses containing two, three, four or more different Influenza virus binding regions and/or epitopes provided herein. In certain embodiments, the inactivated virus immunogenic compositions comprise one or more adjuvants. In a specific embodiment, an immunogenic composition comprising an inactivated virus comprises amino acid residues 304 to 513, 330 to 513, 345 to 513, 359 to 513, 360 to 513, 375 to 513, 359 to 514, and/or 360 to 514 of the hemagglutinin polypeptide of the Influenza virus strain A/Hong Kong/1/1968 (H3). In a specific embodiment, an immunogenic composition comprising an inactivated virus comprises amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, an immunogenic composition comprising an inactivated virus comprises amino acid residues 76-106 of the hemagglutinin polypeptide numbered according to the classic H3 subtype numbering system. In another specific embodiment, an immunogenic composition comprising an inactivated virus comprises amino acid residues 73-103, 73-104, 73-105, 73-106, 73-107, 73-108, 73-109, 74-103, 74-104, 74-105, 74-106, 74-107, 74-108, 74-109, 75-103, 75-104, 75-105, 75-106, 75-107, 75-108, 75-109, 76-103, 76-104, 76-105, 76-107, 76-108, 76-109, 77-103, 77-104, 77-105, 77-106, 77-107, 77-108, 77-109, 78-103, 78-104, 78-105, 78-106, 78-107, 78-108, 78-109, 79-103, 79-104, 79-105, 79-106, 79-107, 79-108, or 79-109 of the hemagglutinin polypeptide numbered according to the classic H3 subtype numbering system. In a specific embodiment, an immunogenic composition comprising an inactivated virus comprises SEQ ID NO:1 or a nucleic acid encoding SEQ ID NO:1.

In another embodiment, an immunogenic composition comprising an Influenza virus binding region and/or epitope provided herein is a split virus vaccine. In some embodiments, a split virus vaccine contains two, three, four or more different Influenza virus binding regions and/or epitopes provided herein. In certain embodiments, the Influenza virus binding region and/or epitope provided herein is/was membrane-bound. In certain embodiments, the split virus vaccines comprise one or more adjuvants. In a specific embodiment, a split virus vaccine comprises amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, a split virus vaccine comprises amino acid residues 76-106 of the hemagglutinin polypeptide numbered according to the classic H3 subtype numbering system. In another specific embodiment, a split virus vaccine comprises amino acid residues 73-103, 73-104, 73-105, 73-106, 73-107, 73-108, 73-109, 74-103, 74-104, 74-105, 74-106, 74-107, 74-108, 74-109, 75-103, 75-104, 75-105, 75-106, 75-107, 75-108, 75-109, 76-103, 76-104, 76-105, 76-107, 76-108, 76-109, 77-103, 77-104, 77-105, 77-106, 77-107, 77-108, 77-109, 78-103, 78-104, 78-105, 78-106, 78-107, 78-108, 78-109, 79-103, 79-104, 79-105, 79-106, 79-107, 79-108, or 79-109 of the hemagglutinin polypeptide numbered according to the classic H3 subtype numbering system. In another specific embodiment, a split virus vaccine comprises SEQ ID NO:1 or a nucleic acid encoding SEQ ID NO:1.

In certain embodiments, the binding regions and/or epitopes provided herein and/or immunogenic compositions comprising an Influenza virus binding region and/or epitope provided herein can be used to induce an immune response to an Influenza A virus (e.g., any subtype or strain of an Influenza A virus). In other embodiments, the binding regions and/or epitopes provided herein and/or immunogenic compositions comprising an Influenza virus binding region and/or epitope provided herein can be used to induce an immune response to an Influenza virus characterized as a Group 2 Influenza virus. In other embodiments, the binding regions and/or epitopes provided herein and/or immunogenic compositions comprising an Influenza virus binding region and/or epitope provided herein can be used to induce an immune response to an Influenza virus of the H3 subtype.

In certain embodiments, the binding regions and/or epitopes provided herein and/or immunogenic compositions comprising an Influenza virus binding region and/or epitope provided herein can be used to prevent and/or treat an Influenza virus disease.

In certain embodiments, the binding regions and/or epitopes provided herein and/or immunogenic compositions comprising an Influenza virus binding region and/or epitope provided herein can be used to prevent and/or treat an Influenza virus infection.

In certain embodiments, the binding regions and/or epitopes provided herein and/or immunogenic compositions comprising an Influenza virus binding region and/or epitope provided herein may be used in combination with another therapy (see, e.g., Section 5.5.3 for types of therapies that could be used in such a combination).

In certain embodiments, the binding regions and/or epitopes provided herein and/or immunogenic compositions comprising an Influenza virus binding region and/or epitope provided herein can be can be administered to patient by any route and maybe reference various routes. These include, but are not limited to, intranasal, intratracheal, oral, intradermal, intramuscular, intraperitoneal, transdermal, intravenous, conjunctival and subcutaneous routes. Pulmonary administration can also be employed, e.g., by use of an inhaler or nebulizer, and formulation with an aerosolizing agent for use as a spray. Compositions can be formulated for the route of delivery.

Exemplary doses for nucleic acids encoding binding regions and/or epitopes provided herein range from about 10 ng to 1 g, 100 ng to 100 mg, 1 µg to 10 mg, or 30-300 µg nucleic acid, e.g., DNA, per patient.

Exemplary doses for influenza the binding regions and/or epitopes provided herein range from about 5 µg to 100 mg, 15 µg to 50 mg, 15 µg to 25 mg, 15 µg to 10 mg, 15 µg to 5 mg, 15 µg to 1 mg, 15 µg to 100 µg, 15 µg to 75 µg, 5 µg to 50 µg, 10 µg to 50 µg, 15 µg to 45 µg, 20 µg to 40 µg, or 25 to 35 µg per kilogram of the patient.

Doses for infectious viral vectors may vary from 10-100, or more, virions per dose. In some embodiments, suitable dosages of a virus vector are $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu, and can be administered to a subject once, twice, three or more times with intervals as often as needed.

In one embodiment, an inactivated vaccine is formulated such that it contains about 5 µg to about 50 µg, about 10 µg to about 50 µg, about 15 µg to about 100 µg, about 15 µg to about 75 µg, about 15 µg to about 50 µg, about 15 µg to about 30 µg, about 20 µg to about 50 µg, about 25 µg to about 40 µg, about 25 µg to about 35 µg of a binding region and/or epitope provided herein. Such a vaccine may contain a combination of one or more different binding regions and/or epitopes provided herein.

Patients that can be administered the binding regions and/or epitopes provided herein and/or immunogenic compositions comprising an Influenza virus binding region and/or epitope provided herein include those identified in Section 5.5.1.

5.7 Diagnostic Uses

The antibodies described herein or generated in accordance with the methods provided herein can be used for diagnostic purposes to detect an Influenza virus as well as detect, diagnose, or monitor an Influenza virus infection. In specific embodiments, the antibodies can be used to determine whether a particular Influenza virus is present or a particular Influenza virus subtype is present in a biological specimen (e.g., sputum, nasal drippings, other fluids, cells, or tissue samples).

Provided herein are methods for the detection of an Influenza virus infection comprising: (a) assaying the expression of an Influenza virus antigen in a biological specimen (e.g., sputum, nasal drippings, cells or tissue samples) from a subject using one or more of the antibodies described herein or generated in accordance with the methods provided herein; and (b) comparing the level of the Influenza virus antigen with a control level, e.g., levels in a biological specimen from a subject not infected with Influenza virus, wherein an increase in the assayed level of Influenza virus antigen compared to the control level of the Influenza virus antigen is indicative of an Influenza virus infection.

In a specific embodiment, the subtype of the Influenza virus, e.g., the H3 subtype of Influenza A virus, can be detected in accordance with the methods for detecting an Influenza virus infection. According to this method, an antibody described herein or generated in accordance with the methods provided herein that is used in the assay is specifically reactive to the subtype to be detected.

Provided herein is a diagnostic assay for diagnosing an Influenza virus infection comprising: (a) assaying for the level of an Influenza virus antigen in a biological specimen from a subject using one or more of the antibodies described herein or generated in accordance with the methods provided herein; and (b) comparing the level of the Influenza virus antigen with a control level, e.g., levels in a biological specimen from a subject not infected with Influenza virus, wherein an increase in the assayed Influenza virus antigen level compared to the control level of the Influenza virus antigen is indicative of an Influenza virus infection. A more definitive diagnosis of an Influenza virus infection may allow health professionals to employ preventative measures or aggressive treatment earlier thereby preventing the development or further progression of the Influenza virus infection.

Diagnosis of infection with a specific Influenza virus subtype (by use of subtype-specific antibodies) may allow the prescription of anti-viral medications that are most appropriate for treatment of the particular subtype.

Antibodies described herein or generated in accordance with the methods provided herein can be used to assay Influenza virus antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Antibody-based methods useful for detecting protein expression include immunoassays, such as the enzyme linked immunosorbent assay (ELISA) and the radioimmunoassay (RIA). An antibody described herein or generated in accordance with the methods described herein may be labeled with a detectable label or a secondary antibody that binds to such an antibody may be labeled with a detectable label. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

Also provided herein is the detection and diagnosis of an Influenza virus infection in a human. In one embodiment, diagnosis comprises: a) administering (for example, parenterally, intranasally, subcutaneously, or intraperitoneally) to a subject an effective amount of a labeled monoclonal antibody described herein or generated in accordance with the methods provided herein; b) waiting for a time interval following the administering for permitting the labeled antibody to preferentially concentrate at sites in the subject (e.g., the nasal passages, lungs, mouth and ears) where the Influenza virus antigen is expressed (and for unbound labeled molecule to be cleared to background level); c) determining background level; and d) detecting the labeled antibody in the subject, such that detection of labeled antibody above the background level indicates that the subject has an Influenza virus infection or a symptom relating thereto. Background level can be determined by various methods, including comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours, or 6 to 24 hours or 6 to 12 hours. In another embodiment the time interval following administration is 5 to 20 days or 5 to 10 days.

In one embodiment, monitoring of an Influenza virus infection is carried out by repeating the method for diagnosing the Influenza virus infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.8 Biological Assays

5.8.1 Assays for Testing Antibody Activity

An antibody may be characterized in a variety of ways known to one of skill in the art (e.g., ELISA, surface plasmon resonance display (BIAcore kinetic), Western blot, immunofluorescence, immunostaining and/or microneutralization assays). In some embodiments, an antibody assayed for its ability to bind to an Influenza virus antigen (e.g., an hemagglutinin polypeptide), or an Influenza virus.

The specificity or selectivity of an antibody for an Influenza virus antigen (e.g., hemagglutinin polypeptide) or an Influenza virus and cross-reactivity with other antigens can be assessed by any method known in the art. Immunoassays which can be used to analyze specific binding and cross-reactivity include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an Influenza virus antigen (e.g., a hemagglutinin polypeptide) or an Influenza virus and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for an Influenza virus antigen or an Influenza virus and the binding off-rates can be determined from the data by Scatchard plot analysis. Competition with a second antibody can also be determined using radioimmunoassays. In this case, an Influenza virus antigen or an Influenza virus is incubated with the test antibody conjugated to a detectable labeled (e.g., $^3$H or $^{125}$I) in the presence of increasing amounts of an unlabeled second antibody.

In some embodiments, surface plasmon resonance (e.g., BIAcore kinetic) analysis is used to determine the binding on and off rates of an antibody to an Influenza virus antigen (e.g., hemagglutinin polypeptide), or an Influenza virus. BIAcore kinetic analysis comprises analyzing the binding and dissociation of Influenza virus antigen from chips with immobilized antibodies to an Influenza virus antigen on their surface. Briefly, a typical BIAcore kinetic study involves the injection of 250 μL of an antibody reagent (mAb, Fab) at varying concentration in HBS buffer containing 0.005% Tween-20 over a sensor chip surface, onto which has been immobilized the Influenza virus hemagglutinin polypeptide. The flow rate is maintained constant at 75 μL/min. Dissociation data is collected for 15 min or longer as necessary. Following each injection/dissociation cycle, the bound antibody is removed from the Influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-NH$_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The neutralizing activity of an antibody can be determined utilizing any assay known to one skilled in the art. Antibodies can be assayed for their ability to inhibit the binding of an Influenza virus, or any other composition comprising Influenza virus antigen, such as a hemagglutinin polypeptide (e.g., a virus-like particle (VLP), liposome, or detergent extract), to its host cell receptor (i.e., sialic acid) using techniques known to those of skill in the art. For example, cells expressing Influenza virus receptors can be contacted with a composition comprising Influenza virus antigen (e.g., a hemagglutinin polypeptide) in the presence or absence of the antibody and the ability of the antibody to inhibit the antigen's binding can measured by, for example, flow cytometry or a scintillation assay. The composition comprising an Influenza virus antigen or the antibody can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between the composition comprising an Influenza virus antigen and a cell receptor. Alternatively, the ability of an antibody to inhibit an Influenza virus antigen (e.g., a hemagglutinin polypeptide) from binding to its receptor can be determined in cell-free assays. For example, a composition comprising an Influenza virus antigen (e.g., a hemagglutinin polypeptide) can be contacted with an antibody and the ability of the antibody to inhibit the composition comprising an Influenza virus antigen from binding to a cell receptor can be determined. In a specific embodiment, the antibody is immobilized on a solid support and the composition comprising an Influenza virus antigen is labeled with a detectable compound. Alternatively, a composition comprising an Influenza virus antigen is immobilized on a solid support and the antibody is labeled with a detectable compound.

In a specific embodiment, the neutralizing activity of an antibody is assessed using a microneutralization assay as described in Section 6.1.4 infra. In another specific embodiment, the neutralizing activity of an antibody is assessed using a plaque reduction assay as described in Example 6.1.5 infra.

In other embodiments, an antibody suitable for use in a method described herein does not inhibit Influenza virus receptor binding, yet is still found to be neutralizing in an assay described herein. In some embodiments, an antibody suitable for use in accordance with a method described herein reduces or inhibits virus-host membrane fusion in an assay known in the art or described herein.

In one embodiment, virus-host membrane fusion is assayed in an in vitro assay using an Influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

In one embodiment, virus-host membrane fusion is detected using a model system of cell fusion. In an exemplary cell fusion assay, cells (e.g., HeLa cells) are transfected with a plasmid encoding an Influenza virus hemagglutinin polypeptide and contacted and exposed to a buffer that allows the hemagglutinin polypeptide fusion function (e.g., pH 5.0 buffer) in the presence of an antibody. An antibody is neutralizing if it reduces or inhibits syncytia formation compared to a negative control (e.g., syncytia formation in the presence of a control antibody or in the absence of antibody).

In a specific embodiment, virus-host membrane fusion is assayed using a red blood cell fusion assay as known in the art or described herein (see Section 6.1.6 infra).

In other embodiments, virus-host membrane fusion is assayed using an in vitro liposome-based assay. In an exemplary assay, the host cell receptor is reconstituted into liposomes containing one half of a reporter. Influenza hemagglutinin polypeptide is reconstituted into another set of liposomes containing another half of a reporter. When the two liposome populations are mixed together, fusion is detected by reconstitution of the reporter, for example, an enzymatic reaction that can be detected colorimetrically. An antibody inhibits fusion if reporter activity is reduced or inhibited compared to reporter activity in an assay conducted in the absence of antibody or in the presence of a control antibody.

5.8.2 Antiviral Assays

An antibody or a composition thereof can be assessed in vitro for antiviral activity. In one embodiment, an antibody or composition thereof is tested in vitro for its effect on growth of an Influenza virus. Growth of Influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented a monoclonal antibody described herein or generated in accordance with the methods provided herein Viral titers are determined in the supernatant by hemagglutinin plaques or any other viral assay described herein. Cells in which viral titers can be assessed include, but are not limited to, MDCK cells, EFK-2 cells, Vero cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of Influenza virus and subsequently cultured at 37° C. in the presence or absence of various dilutions of a monoclonal antibody described herein or generated in accordance with the methods provided herein (e.g., 0.1 µg/ml, 1 µg/ml, 5 µg/ml, or 10 µg/ml). Cultures are overlaid with agar and harvested 48 hours or 72 hours post infection and titered by standard plaque assays known in the art on the appropriate target cell line (e.g., MDCK cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibody is preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, an antibody or composition thereof is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments, an inhibitor reduces viral titer in this assay by 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 5 logs, 2 to 10 logs, 2 to 5 logs, or 2 to 10 logs.

5.8.3 Cytotoxicity Assays

Many assays well-known in the art can be used to assess viability of cells (infected or uninfected) or cell lines following exposure to an antibody or composition thereof and, thus, determine the cytotoxicity of the antibody or composition thereof. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes may be given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

An antibody or composition thereof can be tested for in vivo toxicity in animal models. For example, animal models, described herein and/or others known in the art, used to test the activities of an antibody or composition thereof can also be used to determine the in vivo toxicity of these antibodies. For example, animals are administered a range of concentrations of an antibody. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an antibody or composition thereof can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or composition thereof that exhibits large therapeutic indices is preferred. While an antibody or composition thereof that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an antibody or composition thereof for use in humans. The dosage of such antibodies lies preferably within a range of circulating concentrations that include the $ED_{50}$ with little or no toxicity. The dosage may vary within this range depending upon the dosage form employed and the route of administration utilized. For an antibody or composition thereof used in a method described herein, the effective dose can be estimated initially from cell culture assays. A dose may be formulated in animal models to achieve a circulating plasma concentration range that includes the $IC_{50}$ (i.e., the concentration of the antibody that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of an antibody or composition thereof, for example, by measuring viral infection or a condition or symptoms associated therewith.

5.8.4 Assays for Measuring Antiviral Activity In Vivo

Antibodies and compositions thereof are preferably assayed in vivo for the desired therapeutic or prophylactic activity prior to use in humans. For example, in vivo assays can be used to determine whether it is preferable to administer an antibody or composition thereof and/or another therapy. For example, to assess the use of an antibody or composition thereof to prevent an Influenza virus disease, the antibody or composition can be administered before the animal is infected with Influenza virus. Alternatively, or in addition, an antibody or composition thereof can be administered to the animal at the same time that the animal is infected with Influenza virus. To assess the use of an antibody or composition thereof to treat an Influenza virus infection or disease associated therewith, the antibody or composition may be administered after infecting the animal with Influenza virus. In a specific embodiment, an antibody or composition thereof is administered to the animal more than one time.

Antibodies and compositions thereof can be tested for antiviral activity in animal model systems including, but are not limited to, rats, mice, chicken, cows, monkeys, pigs, goats, sheep, dogs, rabbits, guinea pigs, etc. In a specific embodiment, an antibody or composition thereof is tested in a mouse model system. Such model systems are widely used and well-known to the skilled artisan. Non-limiting examples of animal models for Influenza virus are provided in this section.

In general, animals are infected with Influenza virus and concurrently or subsequently treated with an antibody or composition thereof, or placebo. Alternatively, animals are treated with an antibody or composition thereof or placebo and subsequently infected with Influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for a time period (e.g., 20 minutes or 1 hour) at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an antibody or composition thereof on the infectious disease process or pathogenicity of a given virus can also be determined using in vivo assays in which the titer of the virus in an infected subject administered an antibody or composition thereof, the length of survival of an infected subject administered an antibody or composition thereof, the immune response in an infected subject administered an antibody or composition thereof, the number, duration and/or severity of the symptoms in an infected subject administered an antibody or composition thereof, and/or the time period before onset of one or more symptoms in an infected subject administered an antibody or composition thereof, is assessed. Techniques known to one of skill in the art can be used to measure such effects.

Influenza virus animal models, such as ferret, mouse, guinea pig, and chicken, developed for use to test antiviral agents against Influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of Influenza, non-limiting examples of parameters that can be used to assay antiviral activity of antibodies administered to the Influenza-infected mice include pneumonia-associated death, serum α1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In yet other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+(diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

In a specific embodiment, the ability of an antibody or composition thereof to treat an Influenza virus infection or disease associated therewith is assessed by determining the ability of the antibody to confer passive immunity to an Influenza virus disease in a subject. The ability of a monoclonal antibody described herein or generated in accordance with the methods provided herein to confer passive immunity to an Influenza virus disease in a subject can be assessed using any methods known in the art or described herein (see, e.g., Section 6.2 infra).

5.8.5 Assays in Humans

In one embodiment, an antibody or composition thereof that modulates replication of an Influenza virus is assessed in infected human subjects. In accordance with this embodiment, an antibody or composition thereof is administered to the human subject, and the effect of the antibody and/or composition on viral replication is determined by, e.g., analyzing the level of the virus or viral nucleic acids in a biological sample (e.g., serum or plasma). An antibody or composition thereof that alters virus replication can be identified by comparing the level of virus replication in a subject or group of subjects treated with a control antibody to that in a subject or group of subjects treated with an antibody or composition thereof. Alternatively, alterations in viral replication can be identified by comparing the level of the virus replication in a subject or group of subjects before and after the administration of an antibody or composition thereof. Techniques known to those of skill in the art can be used to obtain the biological sample and analyze the mRNA or protein expression.

In another embodiment, the effect of an antibody or composition thereof on the severity of one or more symptoms associated with an Influenza virus infection/disease are assessed in an infected subject. In accordance with this embodiment, an antibody or composition thereof or a control antibody is administered to a human subject suffering from Influenza virus infection and the effect of the antibody or composition on one or more symptoms of the virus infection is determined. An antibody or composition thereof that reduces one or more symptoms can be identified by comparing the subjects treated with a control antibody to the subjects treated with the antibody or composition. Techniques known to physicians familiar with infectious diseases can be used to determine whether an antibody or composition thereof reduces one or more symptoms associated with the Influenza virus disease.

5.9 Kits

Provided herein is a pharmaceutical pack or kit comprising one or more containers filled with one or more of the ingredients of the pharmaceutical compositions described herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in the above methods. In one embodiment, a kit comprises an antibody described herein, preferably an isolated antibody, in one or more containers. In a specific embodiment, the kits encompassed herein contain an isolated Influenza virus antigen that the antibodies encompassed herein react with (e.g., the antibody binds to the antigen) as a control. In a specific embodiment, the kits provided herein further comprise a control antibody which does not react with an Influenza virus antigen (e.g., the antibody does not bind to the antigen) that an antibody encompassed herein reacts with. In another specific embodiment, the kits provided herein contain a means for detecting the binding of an antibody to an Influenza virus antigen that an antibody encompassed herein reacts with (e.g., the antibody may be conjugated to a detectable substrate such as a fluorescent compound, an enzymatic substrate, a radioactive compound, a luminescent compound, or another antibody that is conjugated to a detectable substrate (e.g., the antibody may be conjugated to a second antibody which recognizes/binds to the first antibody)). In specific embodiments, the kit may include a recombinantly produced or chemically synthesized Influenza virus antigen. In other specific embodiments, the kit may include as the Influenza virus antigen the long alpha-helix of HA2 of an Influenza virus (e.g., the hemagglutinin polypeptide of the Influenza virus strain A/Hong Kong/1/1968 (H3)). In certain specific embodiments, the kit may include as the Influenza virus antigen amino acid residues within the range of 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system). In a specific embodiment, a kit comprises amino acid residues 76-106 of the hemagglutinin polypeptide of the Influenza virus strain A/Hong Kong/1/1968 (H3) numbered according to the classic H3 subtype numbering system. In certain embodiments, a kit includes a virus vector comprising/generated to express amino acid residues 330 to 513, 345 to 513, 359 to 513, 360 to 513, 375 to 513, 390 to 513, 384 to 439, 405 to 435, and/or 405 to 513 of the hemagglutinin polypeptide of the Influenza virus strain A/Hong Kong/1/1968 (H3) (i.e., amino acids 1-184, 16-184, 30-184, 31-184, 46-184, 61-184, 70-110, 76-106, and/or 76-184 of the hemagglutinin polypeptide numbered according to the classic H3 subtype numbering system) and/or amino acid residues 76-106 of the hemagglutinin polypeptide of the Influenza virus strain A/Hong Kong/1/1968 (H3) numbered according to the classic H3 subtype numbering system. The Influenza virus antigen provided in the kit may also be attached to a solid support. In a more specific embodiment the detecting means of the above described kit includes a solid support to which an Influenza virus antigen is attached. Such a kit may also include a non-attached reporter-labeled anti-human antibody. In this embodiment, binding of the antibody to the Influenza virus antigen can be detected by binding of the said reporter-labeled antibody.

6. EXAMPLES

The following examples are offered by way of illustration, and not by way of limitation.

6.1 Generation of Cross-reactive Neutralizing Antibodies
6.1.1 Plasmid Preparation
Three DNA plasmids were generated encoding the hemagglutinin (HA) molecules from each of three antigenically distinct Influenza A virus H3 subtypes: A/Hong Kong/1/1968 (plasmid 1), A/Alabama/1/1981 (plasmid 2), and A/Beijing/47/1992 (plasmid 3). To do so, the open reading frame of HA from each virus was amplified from the parental virus strain and cloned into pCAGGS (Niwa et al., 1991, Gene 108: 1993-199), a mammalian expression vector containing a chicken actin promoter that supports protein expression in mammalian cells.

Competent cells were transformed with either plasmid 1, plasmid 2, or plasmid 3 and positive transformants, i.e., cells harboring either plasmid 1, plasmid 2, or plasmid 3, were selected via resistance to ampicillin. Positive transformants then were cultured and plasmids were purified using the Qiagen Maxiprep Plasmid Purification Kit (Qiagen, Inc., Valencia, Calif.) according to the manufacturer's instructions. Plasmid DNA then was sequenced using methods known in the art to confirm sequence identity of the HA molecule in each of plasmids 1-3.

Once it was confirmed that the nucleotide sequence coding for HA molecules in each of plasmids 1-3 was accurate, plasmid DNA was prepared at a concentration of 1.0 µg/µl in PBS (whole plasmid). This concentration of plasmid DNA was used in subsequent immunizations of mice.

6.1.2 Immunization
Ten C57/BL6 mice and ten Balb/c mice were immunized. Three days before the first immunization, mice were injected with 0.5% bupivacaine in the calf muscle. Each immunization took place three weeks apart and consisted of an intra-muscular (calf muscle) injection of 100 µl of each plasmid preparation (plasmids 1-3) according to the following immunization schedule:
1. Immunization with plasmid 1.
2. Immunization with plasmid 2.
3. Immunization with plasmid 3.

Three weeks after the immunization with plasmid 3, the mice were immunized with Influenza virus strain A/Wyoming/3/2003, prepared as follows: virus was grown in 10-day old chicken eggs and subsequently concentrated and purified by centrifugation through a sucrose cushion. Virus then was resuspended in PBS. Protein concentration was determined using the Bradford assay and total protein was diluted to a concentration of 250 µg/ml. Mice were injected with 200 µl of the virus in PBS, corresponding to 50 µg of inactivated virus. Two weeks after each immunization, serum from each mouse was evaluated to confirm effective immunization.

6.1.3 Monoclonal Antibody Generation
Monoclonal antibodies were produced using hybridoma techniques known in the art (see, e.g., Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563 681 (Elsevier, N.Y., 1981)). Briefly, spleens from the immunized mice were harvested and splenocytes were isolated. The splenocytes then were fused to myeloma cells. After fusion, hybridomas resulting from the fusion were distributed in 96-well plates (10 plates per mouse, approximately 5 viable hybridomas per well). Supernatants were harvested 1 week post-fusion (to allow for sufficient antibody production) and screened by blot and by ELISA for reactivity with Influenza A virus strain A/Hong Kong/1/1968. Screening took place in iterative rounds alternating with subcloning of positive wells until monoclonal cell populations were obtained that had activity against A/Hong Kong/1/1968 as measured by either blot assay or ELISA.

For the ELISA, wells of an ELISA plate were coated with 5 µg/ml of purified virus in PBS and the plate was incubated either for 3 hours at 37° C. or overnight at 4° C. Prior to the assay, the purified virus was removed from the wells and 1% BSA in PBS was added for 30 minutes at room temperature. The wells were subsequently washed three times with 0.05% Tween 20 in PBS, followed by addition of the hybridoma supernatant (diluted 1:2) and incubation for 3 hours at 37° C. or overnight at 4° C. The wells were subsequently washed three times with 0.05% Tween 20 in PBS and anti-mouse IgG conjugated to alkaline phosphatase diluted in 1% BSA in PBS was added to each well followed by incubation for 3 hours at 37° C. or overnight at 4° C. After incubation, the wells were washed three times with 0.05% Tween 20 in PBS, followed by addition of p-nitrophenylphospante substrate to each well. The reactions were allowed to develop in the wells and reactivity of the hybridoma supernatants with Influenza A virus strain A/Hong Kong/1/1968 was determined.

For assessment of reactivity by blot assay, purified virus was absorbed onto nitrocellulose membranes. The membranes then were blocked with 1% BSA in PBS for 30 minutes at room temperature followed by incubation of the membrane with the hybridoma supernatant (diluted 1:2) for 1 hour at room temperature, with rocking. The membrane then was washed three times with 0.05% Tween 20 in PBS followed by incubation of the membrane with anti-mouse IgG conjugated to horseradish peroxidase diluted in 1% BSA in PBS for 1 hour at room temperature. The membrane then was washed three times with 0.05% Tween 20 in PBS followed by addition of chemiluminescent substrate. The reactivity of the hybridoma supernatants with Influenza A virus strain A/Hong Kong/1/1968 was then assessed by Western blot using standard techniques (see, e.g., *Current Protocols in Protein Science*, Sean Gallagher, Hoefer Scientific Instruments, San Francisco, Calif., 1996).

Supernatants having activity in either assay against A/Hong Kong/1/1968 were subcloned and monoclonal antibodies were isolated.

The ability of the monoclonal antibodies to bind various Influenza A virus strains of the H3 subtype then was assessed by ELISA or Western blot. As shown in FIG. 1A, purified monoclonal antibodies 7A7 and 39A4 both bind to A/Hong Kong/1/1968 (H3) as assessed by ELISA. The purified monoclonal antibody 12D1 binds to A/Hong Kong/1/1968 (H3) as assessed by Western blot. In addition, the purified monoclonal antibody 12D1 binds strain A/Panama/2007/1999 (H3) (FIG. 1B) as assessed by Western blot; and monoclonal antibodies 7A7 and 39A4 bind strains A/Hong Kong/1/1968 (H3), A/Panama/2007/1999 (H3), and A/Wisconsin/67/2005 (H3) (FIGS. 1C and 1D) as assessed by ELISA.

6.1.4 Microneutralization Assay

The ability of the monoclonal antibodies generated in Section 6.1.3 to neutralize Influenza A viruses of the H3 subtype was assessed using a microneutralization assay.

Viruses for use as neutralization targets were generated as follows: three stable cell lines were generated using MDCK cells, each expressing the hemagglutinin of one of the following viruses: A/Hong Kong/1/1968, A/Panama/2007/1999, A/Wisconsin/67/2005. The cell lines were infected with a virus containing 7 segments (all but HA) from A/WSN/33 and one segment coding for renilla luciferase (i.e., pseudotyped virus). Infection of HA-expressing cells with the WSN-luciferase virus yielded virus expressing the HA from the stable cell line and coding for renilla luciferase (to be used as a readout for infection in the microneutralization assay).

The monoclonal antibodies then were evaluated for their ability to prevent infection of MDCK cells by the pseudotyped viruses; the readout being luciferase activity, as detailed below.

In a 96-well plate, the monoclonal antibodies were serially diluted in two-fold dilutions in PBS. The final volume of antibody/PBS in each well was 55 μl. Five μl of 50 pfu/ml of pseudotyped virus expressing either the hemagglutinin from A/Hong Kong/1/1968, A/Panama/2007/1999 or A/Wisconsin/67/2005 diluted in PBS was added to each well, and the virus/antibody mixture was incubated at 37° C. for 30 minutes. After the 30 minutes, 50 μl of the virus/antibody mixture was removed and added to a 96-well plate seeded to confluency with MDCK cells. The cells were cultured with the virus/antibody mixture for 8-20 hours at 37° C. Following culture, the wells were rinsed and the cells were lysed. Luciferase activity then was measured by reading the relative light units using a luminometer. According to this assay, lack of luminescence is indicative of no infection by the virus and therefore neutralization of the virus by the monoclonal antibody.

As shown in FIG. 2, monoclonal antibodies 7A7, 39A4, and 12D1 all are capable of neutralizing both the A/Hong Kong/1/1968 Influenza A virus strain (FIG. 2A) and the A/Panama/2007/1999 Influenza A virus strain (FIG. 2B).

6.1.5 Plaque Reduction Assay

The ability of the monoclonal antibodies generated in Section 6.1.3 to neutralize Influenza A viruses of the H3 subtype was further assessed using a plaque reduction assay.

Various dilutions of monoclonal antibody were incubated in a 96-well plate with virus (~50 pfu/well) for 1 hour, with rocking. The virus/antibody mixture (200 μl) was subsequently added to MDCK cells grown to confluency. The cells and virus/antibody mixture were incubated for 20 minutes at 37° C. and subsequently the virus/antibody mixture was aspirated from the cells and the cells were overlaid with agar having a concentration of antibody identical to the concentration of antibody in the virus/antibody mixture being analyzed. The plates then were incubated for 3 days at 37° C. to allow for plaque formation.

As shown in FIG. 3, monoclonal antibodies 7A7, 12D1, and 39A4 neutralize all Influenza A virus strains of the H3 subtype tested, i.e., A/Hong Kong/1/1968 (H3), A/Beijing/47/1992 (H3), A/Pan/2007/1999 (H3), and BRIS/07 (H3) but do not neutralize Influenza A virus strains of subtypes other than H3 that were tested, i.e., New CAL/99 (H1), DK/64 (H4), and TKY/63 (H7).

6.1.6 Red Blood Cell Fusion Assay

The ability of the monoclonal antibodies generated in Section 6.1.3 to inhibit fusion between Influenza A viruses of the H3 subtype and host cells was assessed using a red blood cell fusion assay.

Virus was incubated with chicken red blood cells (0.2% final concentration RBCs) for ten minutes on ice followed by addition of monoclonal antibody. The mixture of virus, cells, and antibody was incubated on ice for 30 minutes followed by addition of sodium citrate buffer, pH 4.4, and incubation at room temperature for 5-30 minutes. 200 μl of the virus, cells, and antibody mixture was removed at various time points, centrifuged for 3 minutes at 3000 rpm, and the supernatant was transferred to a 96-well ELISA plate and read at $OD_{410}$. Positive readings indicated the presence of heme in the supernatant, which indicates that lysis of red blood cells occurred due to a low-pH fusion reaction between the cells and virus, particularly between the hemagglutinin protein of the virus and the cell.

As shown in FIG. 4, monoclonal antibodies 7A7 and 12D1 inhibit low-pH fusion of A/Hong Kong/1/1968 (H3) hemagglutinin and red blood cells.

6.1.7 Conclusions

The method of generating cross-reactive neutralizing monoclonal antibodies provided herein successfully results in the generation of monoclonal antibodies that cross-react with hemagglutinin from Influenza A virus strains of the H3 subtype that are antigenically distinct from one another. Moreover, these antibodies are capable of neutralizing all of the Influenza A virus strains of the H3 subtype tested as determined by multiple assays.

6.2 In Vivo Protection by Passive Transfer of Cross-Reactive Neutralizing Antibodies The ability of the cross-reactive neutralizing monoclonal antibodies generated in accordance with the methods described herein to protect mice from challenge with Influenza A virus was assessed by passive transfer of the antibodies in mice.

The ability of the cross-reactive neutralizing monoclonal antibodies generated in accordance with the methods described herein to confer passive immunity can be determined by assessing the ability of the antibodies to prolong the survival of mice infected with an Influenza virus. According to this method, mice are administered a cross-reactive neutralizing monoclonal antibody prior to challenge with an Influenza virus, e.g., 1 hour prior to challenge. The duration of survival of the mice is then calculated and compared to the survival of similarly challenged mice that were administered a control, e.g., PBS, rather than a cross-reactive neutralizing monoclonal antibody.

As demonstrated in FIG. 5, male BALB/c mice, 5 mice per group, 6-8 weeks of age administered approximately 15 mg/kg monoclonal antibody 12D1 by intraperitoneal injection 1 hour prior to intranasal challenge with $10^5$ pfu/ml X31 virus survive the viral challenge, whereas mice administered PBS alone die seven days subsequent to viral challenge.

The ability of the cross-reactive neutralizing monoclonal antibodies generated in accordance with the methods described herein to confer passive immunity can be determined by assessing the ability of the antibodies to inhibit weight loss of mice infected with an Influenza virus. According to this method, mice are administered a cross-reactive neutralizing monoclonal antibody prior to challenge with an Influenza virus, e.g., 1 hour prior to challenge. The weight loss of the mice is then measured over time and compared to the weight loss of similarly challenged mice that were administered a control, e.g., PBS, rather than a cross-reactive neutralizing monoclonal antibody.

As demonstrated in FIG. 7, passive transfer of the cross-reactive neutralizing monoclonal antibodies 12D1 and 39A4 results in decreased weight loss in mice challenged with Influenza A virus strain A/Hong Kong/1/1968 (H3) as compared to mice administered PBS, rather than antibody, thus demonstrating generation of passive immunity in these mice against the A/Hong Kong/1/1968 (H3) strain. Different groups of mice (five mice per group) were administered monoclonal antibody 12D1 (30 mg/kg), monoclonal antibody 39A4 (15 mg/kg or 30 mg/kg), or PBS by intraperitoneal injection 1 hour prior to intranasal challenge with $10^5$ pfu/ml X31, a chimeric virus containing the hemagglutinin and neuramidase gene segments from A/Hong Kong/1/1968 (H3) and the six other Influenza virus genes segments (not hemagglutinin and neuramidase) from the murine Influenza A virus A/PR/8/34. The weights of the mice were measured each day and the average weight of the five mice in each group is plotted in FIG. 7.

6.2.1 Conclusions

The cross-reactive neutralizing monoclonal antibodies generated in accordance with the methods described herein are capable of conferring passive immunity in vivo.

6.3 Determination of the Binding Region the Cross-Reactive Neutralizing Antibodies To determine the binding region of the cross-reactive neutralizing monoclonal antibodies generated in accordance with the methods described herein, nucleic acid constructs were generated that encode a fusion protein comprising the coding sequence of the green fluorescent protein (GFP) fused to different fragments of the A/Hong Kong/1/1968 (H3) hemagglutinin. HA fragments were generated by polymerase chain reaction and were subsequently cloned into pCAGGS-GFP vector. See FIG. 8 for a diagram of the fusion proteins encoded by the various nucleic acid constructs. Each nucleic acid construct (50 ng/6-well dish) was transfected into 293T cells using Lipofectamine 2000 (Invitrogen) and the ability of a monoclonal antibody to bind to a fusion protein expressed by the cells was assessed by Western blot using standard techniques (see, e.g., *Current Protocols in Protein Science*, Sean Gallagher, Hoefer Scientific Instruments, San Francisco, Calif., 1996). Anti-GFP antibodies were used as a positive control for protein expression.

As shown in FIG. 9 the monoclonal antibody 12D1 binds to the HA2 region of the hemagglutinin protein of Influenza A virus strain A/Hong Kong/1/1968 (H3) as demonstrated by the antibody's ability to bind to the region of the A/Hong Kong/1/1968 (H3) hemagglutinin corresponding to amino acid residues 304 to 513 and small fragments thereof (FIG. 9B, lanes 5-10). In particular, the monoclonal antibody 12D1 is capable of binding to the region of A/Hong Kong/1/1968 (H3) hemagglutinin corresponding to amino acids 405 to 513 (FIG. 9B, lanes 10). As expected, the anti-GFP antibody bound to each construct having the GFP fusion (FIG. 9A, lanes 3-10), the anti-GFP antibody did not bind to the A/Hong Kong/1/1968 (H3) hemagglutinin (FIG. 9A, lane 2), and neither monoclonal antibody 12D1 or the anti-GFP antibody bound to cell lysates from untransfected cells (FIGS. 9A and 9B, lane 1).

6.4 Broadly Protective Anti-Influenza Antibodies

6.4.1 Materials and Methods

6.4.1.1 Animals

Six week old female BALB/c mice from Jackson Laboratory were used for all experiments.

6.4.1.2 Viruses and Cells

Madin Darby canine kidney cells from ATCC were used for all cell based assays. Cells were maintained in minimum essential medium supplemented with 10% fetal bovine serum, and 100 units/ml of penicillin-100 µg/ml of streptomycin. All viruses were propagated in eggs. Viruses used in various studies: A/Hong Kong/1/1968 (HK/68) (H3), A/Alabama/1/1981 (AL/81) (H3), A/Georgia/1981 (H3), A/Beijing/47/1992 (BJ/92) (H3), A/Wyoming/3/2003 (H3), A/Wisconsin/67/2005 (WI/05) (H3), A/Brisbane/102007 (BR/07) (H3), A/New York/2008 (NY08) (H3), A/Texas/36/1991 (TX/91) (H1), A/New Caledonia/20/99 (N.Cal/99) (H1), A/Duck/England/1962 (Dk/62) (H4), A/Turkey/England/1963 (Tky/63) (H7), A/Equine/Kentucky/2002 (e/KY/02) (H3), A/Ann Arbor/6/1960 (AA/60) (H2), A/Fort Monmouth/1/1947 (FM/47) (H1). Purified virus was prepared by high speed centrifugation (43,000 rpm, 1 hour) of allantoic fluid through a 20% sucrose cushion.

6.4.1.3 Antibody Preparations

Hybridoma supernatants were used for screening of mAbs for reactivity by enzyme-linked immunosorbent assay (ELISA) and by western blot. For other assays, purified monoclonal antibody or ascites preparations treated with receptor-destroying enzyme (see, e.g., Jordan et al., J Immunol, 1954; 72(3):229-35) were used. RDE—treated ascites was used for measurement of binding by ELISA, microneutralization, plaque reduction and fusion assays. Antibodies were purified by methods previously described (see, e.g., Harlow E, Lane D. Antibodies: a laboratory manual. Cold Spring Harbor, N.Y.: Cold Spring Harbor Laboratory; 1988. xiii, 726 p.). Because of differences in isotypes, Protein A-agarose (Roche) was used for purification of mAbs 7A7 and 39A4 while protein G-agarose (Roche) was used for purification of mAb 12D1.

6.4.1.4 Immunization of Mice and Hybridoma Production

Six-week old BALB/c mice were immunized with DNA constructs coding for the open-reading frame of Influenza virus hemagglutinin in the pCAGGS plasmid (see, e.g., Basler et al., Proc Natl Acad Sci USA 98: 2746-2751). Individual immunizations were given intramuscularly, 3-weeks apart and consisted of 100 ug DNA in 100 ul PBS. Hemagglutinins utilized in the immunization schedule were cloned from the following parental viruses—primary immunization: A/Hong Kong/1/1968, secondary immunization: A/Alabama/1/1981, tertiary immunization: A/Beijing/47/1992 HA. Three days prior to fusion, mice were boosted with 50 ug purified A/Wyoming/3/2003 virus. B cell hybridomas were produced by methods previously described (see, e.g., de StGroth et al., J Immunol Methods 35: 1-21).

6.4.1.5 Screening of Hybridoma Supernatants

Hybridoma supernatants were screened by blot and by ELISA for reactivity with A/Hong Kong/1/1968 virus. For the ELISA, direct binding to wells coated with 5 ug/ml purified virus, 50 ul per well was assessed. For the blot assay, 10 μg purified virus was adsorbed onto nitrocellulose strips and individual strips were incubated with hybridoma supernatants. For the ELISA and blot assays, binding of antibody to virus was detected using goat anti-mouse γ-chain horse radish peroxidase secondary antibody (SouthernBiotech, Birmingham, Ala.). All wells that had activity in either assay against A/Hong Kong/1/1968 virus were subcloned repeatedly to ensure the monoclonality of the hybridoma populations.

6.4.1.6 Western Blots

Blots were produced by methods previously described (see, e.g., Towbin et al., Proc Natl Acad Sci USA 1979; 76(9):4350-4). Samples were boiled for 5 minutes at 100° C. in loading buffer containing SDS and 0.6M DTT. SDS migration buffer was used for electrophoresis. For non-reducing gel conditions samples were prepared in loading buffer with SDS but without reducing agent and were not boiled.

6.4.1.7 Immunofluorescence Test

MDCK cells were infected with virus at a multiplicity of infection of 1 and incubated for 6 hours at 37° C. Infected and uninfected cells were incubated with 1 μg/ml mAb for 1 hour at room temperature. Goat anti-mouse fluorescein conjugate (SouthernBiotech) was used for detection of mAb binding.

6.4.1.8 Microneutralization Assay

Two stable cell lines were generated that expressed the HA of A/Hong Kong/1/1968 virus or A/Panama/2007/1999 virus. Pseudotyped viruses expressing the HA of either cell line were generated by infection of cells with a virus that carries seven segments from A/WSN/33 virus (all except the HA segment) and one segment encoding Renilla luciferase. Pseudotyped viruses expressing the HA of A/Hong Kong/1/1968 virus or A/Panama/2007/1999 virus were used as the neutralization target. Viruses were incubated with mAb at room temperature for 30 minutes, rocking Purified polyclonal mouse IgG (Invitrogen) was used for the negative control. The mixture containing virus and mAb was then transferred to wells of a 96-well plate seeded to confluency with MDCK cells and incubated for 12 hours at 37° C. Individual determinants were performed in triplicate. After incubation, luciferase activity in cell-lysates was measured as a read-out of virus infection (Renilla luciferase assay system, Promega).

6.4.1.9 Plaque Reduction Assay

Antibody and virus (~50 pfu/well) were co-incubated at room temperature for 30 minutes, rocking 6 well plates seeded with MDCK cells were washed once with PBS and 200 μl of virus and mAb was added to each well then incubated for 20 minutes, 37° C. Virus with mAb was aspirated from cells and an agar overlay containing antibody was added to each well. Plates were incubated for 3 days, 37° C. and plaques were counted by crystal violet staining Purified mouse IgG (Invitrogen) was used for the negative control.

6.4.1.10 Passive Transfer Experiments

Before infection, mice were anesthetized by intraperitoneal administration of a ketamine (75 mg/kg of body weight)/xylazine (15 mg/kg of body weight) mixture. 6 week old BALB/c mice were given 30 mg/kg mAb intraperitoneally either one hour before, 24 hours after or 48 hours after challenge with 10 $LD_{50}$ A/Hong Kong/1/1968, A/PR/8/34 reassortant virus or 2700 pfu A/Georgia/1981 virus (lung titer experiment). Purified mouse IgG (Invitrogen) was used for the negative control. Virus was suspended in PBS and administered intranasally in 50 μl (25 μl per nostril). Mice were weighed daily and sacrificed if they fell to 75% of starting weight. For the lung titer experiment, mouse lungs were harvested 4 days post infection with A/Georgia/1981 and virus titers in lung homogenates were determined by plaque assay. For histologic evaluation of lung damage, lungs were harvested 4 days post infection with A/Hong Kong/1/1968-A/PR/8/34 reassortant virus. Tissues were imbedded in paraffin and sections were stained with hematoxylin and eosin.

6.4.1.11 Hemaglutinin Inhibition Assay and Fusion Assay

MAbs were tested in a standard hemagglutination inhibition assay (see, e.g., Cohen et al., Virology 1963; 20:518-29) using chicken red blood cells and A/Hong Kong/1/1968 virus. For the red blood cell fusion assay, virus was incubated with chicken red blood cells (2% final red cell concentration) on ice for 10 minutes. Dilutions of antibody were added and samples were incubated on ice for 30 minutes. Sodium citrate buffer, pH 4.6 was then added to bring the final pH to 5.0 and samples were incubated for 30 minutes at room temperature. Samples were centrifuged for 3 minutes at 3000 rpm to pellet red blood cells and supernatants were then transferred to an ELISA plate for determination of NADPH content by optical density measurement (340 nm). NADPH was present in the supernatant as a function of fusion-induced red blood cell lysis.

6.4.1.12 Hemaglutinin Truncation Mutants

DNA constructs were generated in the pCAGGS plasmid that coded for truncations of the A/HK/1/68 virus hemagglutinin fused to green fluorescent protein. All constructs were sequenced and confirmed. 293T cells were then transfected using Lipofectamine 2000 (Invitrogen, Inc.) with the various pCAGGS encoding the HA-GFP fusion gene. Cell lysates were resolved in a 4-20% Tris-HCl SDS-PAGE gel (Bio-Rad Laboratories) and proteins were blotted onto a Protran nitrocellulose membrane (Whatman). GFP and truncated HA fragments were detected using rabbit anti-GFP (Santa Cruz Biotechnology, Inc.) and anti-H3 mAb 12D1 respectively. Secondary antibodies were anti-rabbit IgG HRP (Dako) and anti-mouse Ig HRP(GE Healthcare).

6.4.2 Results 6.4.2.1 Isolation of Broadly-Reactive Anti-H3 mAbs

In order to enhance the production of cross-reactive antibody specificities, mice were immunized by sequential administration with DNA coding for the hemagglutinin from H3 viruses arising approximately 10 years apart: A/Hong Kong/1/1968, A/Alabama/1/1981, A/Beijing/47/1992. Three days prior to fusion, mice were boosted with the H3 virus A/Wyoming/3/2003. By performing the fusion rapidly after virus boost it was ensured that only hemagglutinin-specific B cells were present in the spleen at time of fusion. The hemagglutinins chosen were from viruses that arose over several decades, thus representing multiple H3 antigenic clusters (see, e.g., Smith et al., Science 2004; 305(5682):371-6). Post-fusion, hybridoma supernatants were screened for the ability to bind A/Hong Kong/1/1968 by Western blot or by ELISA and successive rounds of subcloning were performed on positive supernatants until monoclonal hybridoma populations were isolated.

The immunization schedule utilized successfully elicited the production of antibodies with broad reactivity against H3 viruses. Approximately 120 clones were isolated that reacted with A/Hong Kong/1/1968; of those, eight mAbs were cross-reactive against all of the H3 hemagglutinins tested. The particular immunization protocol also preferentially elicited the production of antibodies specific for the HA2 subunit of the hemagglutinin. Of the 8 mAbs identified, 5 mAbs react with HA2 and 1 mAb reacts with HA1 by Western blot. The remaining 2 mAbs (7A7 and 39A4) bind conformational epitopes present in the HA trimer as detected by western blot of purified H3 virus proteins separated under non-reducing gel conditions. All mAbs were reactive in a purified H3 virus ELISA. Three of the mAbs, 7A7, 12D1, 39A4, had the highest activity by ELISA and were selected for thorough characterization (Table 1, FIG. 10).

TABLE 1

Pattern of reactivity of anti-H3 mAbs. All mAbs have activity by ELISA and all mAbs react by western blot under reducing conditions except mAbs 7A7 and 39A4 that react with the HA trimer under non-reducing conditions. All mAbs are negative for hemagglutination inhibition activity at 50 ug/ml.

| | Isotype | ELISA | WB | HI |
|---|---|---|---|---|
| 7A7 | IgG2b | + | Trimer | − |
| 12D1 | IgG1 | + | HA2 | − |
| 39A4 | IgG2a | + | Trimer | − |
| 62F11 | IgG2a | + | HA2 | − |
| 36A7 | IgG2b | + | HA2 | − |
| 66A6 | IgG1 | + | HA1 | − |
| 49E12 | IgG2b | + | HA2 | − |
| 21D12 | IgG1 | + | HA2 | − |

Antibodies 7A7, 12D1 and 39A4 react by ELISA with purified A/Alabama/1/1981 and purified A/Hong Kong/1/1968 viruses (FIG. 11). MAb XY102 is specific for the hemagglutinin of A/Hong Kong/1/1968 virus. 7A7, 12D1 and 39A4 show broad reactivity by immunofluorescence against cells infected with all H3 viruses spanning 40 drift years. MAbs 7A7 and 39A4 also react by immunofluorescence with other Influenza A viruses chosen at random, including representative H1, H2 and equine H3 viruses (Table 2).

TABLE 2

Reactivity of mAbs at 5 ug/ml by immunofluorescence against MDCK cells infected with a panel of randomly chosen viruses. MAb XY102 was generated by immunization with A/HK/1968 (H3) virus and mAb 10C4 was generated by immunization with A/TX/1991 (H1) virus.

| Virus | Subtype | 7A7 | 12D1 | 39A4 | 10C4 | XY102 |
|---|---|---|---|---|---|---|
| HK/68 | H3 | + | + | + | − | + |
| AL/81 | H3 | + | + | + | − | − |
| BJ/92 | H3 | + | + | + | − | − |
| WI/05 | H3 | + | + | + | − | − |
| BR/07 | H3 | + | + | + | − | − |
| NY/08 | H3 | + | + | + | − | − |
| TX/91 | H1 | + | − | + | + | − |
| FM/47 | H1 | + | − | + | − | − |
| AA/60 | H2 | + | − | + | − | − |
| Equine/ KY/02 | H3 | + | − | + | − | − |

6.4.2.2 mAbs Neutralize H3 Viruses Spanning 40 Drift Years

The anti-H3 mAbs were first evaluated for their ability to neutralize H3 Influenza viruses by microneutralization assay. Viruses used in this assay contain a gene segment coding for firefly luciferase in place of the viral hemagglutinin; a hemagglutinin is present on the viral envelope due to propagation of virus in cells stably expressing a particular H3 hemagglutinin protein. Luciferase viruses were generated that express the hemagglutinin of A/HK/1968 or A/Panama/99 viruses. Neutralization of viruses by anti-H3 mAbs was determined based on luciferase activity after single-cycle replication. By microneutralization, the three anti-H3 mAbs were determined to neutralize the hemagglutinin of both A/HK/1968 and A/Pan/99 (FIG. 12).

Next, neutralization activity by plaque reduction assay was evaluated. The anti-H3 mAbs were able to prevent infection (not simply reduce plaque size) of Madin Darby canine kidney cells by H3 viruses arising over 40 drift years: A/HK/1968, A/BJ/1992, A/Pan/99, A/Bris/07, A/NY/08 (FIG. 13). Monoclonal antibodies 7A7, 12D1 and 39A4 were tested against representative H4 and H7 viruses (Group 2) as well as an H1 virus (Group 1) and it was determined that they did not neutralize these non-H3 subtype viruses (FIG. 13).

6.4.2.3 Anti-H3 mAbs in the Treatment of Influenza in Mice

The three mAbs were tested in vivo for use as passive transfer therapies in disease caused by H3 virus infection. Mice were given 30 mg/kg mAb intraperitoneally either 1 hour before, 24 hours post or 48 hours post challenge with 10 mouse $LD_{50}$ reassortant H3 virus (The A/HK/68 reassortant virus contains the six non-hemagglutinin, non-neuraminidase segments from the mouse-adapted A/PR/8 virus). Mice were weighed daily and were sacrificed if they reached 75% of their starting weight. Treatment of mice with mAb 12D1 either prophylactically or therapeutically was 100% protective. mAb 39A4 was evaluated for efficacy by prophylactic treatment and was similarly 100% protective in vivo. Mice treated prophylactically with mAb 7A7 were only 40% protected against the A/HK/68 reassortant virus (FIG. 14).

Next, the effect of prophylactic treatment with mAb 12D1 or 39A4 on lung damage caused by H3 viral pneumonia was assessed by histologic evaluation of tissue taken 4 days post infection with the A/HK/68 reassortant virus. Without treatment, lungs showed degenerative changes with focal hemorrhaging, dense neutrophilic infiltrates and diffuse alveolar damage with edema. Treatment with either anti-H3 mAb significantly diminished pathologic changes (FIG. 15).

Having demonstrated protective activity in vivo against the A/HK/68 reassortant virus, cross-protection mediated by mAbs 12D1 and 39A4 against a second H3 virus, A/Georgia/1981, was evaluated. MAbs 12D1 and 39A4 were administered as described above to BALB/c mice one hour prior to infection. Mice were then infected intranasally with 2700 pfu A/Georgia/1981 and lung titers were evaluated two days post infection. The anti-H3 mAbs reduced lung titers by 97.75% (12D1) or 99.03% (39A4) (FIG. 16).

6.4.2.4 Anti-H3 mAbs Act by Inhibiting Viral Fusion

In order to determine the mechanism of virus neutralization by the anti-H3 mAbs, the ability of the mAbs to inhibit virus hemagglutination of chicken red blood cells was examined. None of the three mAbs had hemagglutination inhibition activity, suggesting that the mAbs did not act by obstructing the binding of virus to the host-cell.

Next, the effect of the anti-H3 mabs on virus fusion was tested. MAbs 7A7, 12D1 and 39A4 were determined to inhibit the low-pH fusion of A/HK/1968 virus with chicken red blood cells by at least 80% at 10 ug/ml (FIG. 17).

6.4.2.5 Binding Epitope of mAb 12D1

The identity of the region of the H3 hemagglutinin that might elicit antibodies with fine specificities mirroring those of 12D1 or 39A4 was examined. Sixteen passages of A/HK/1968 virus in the presence of the anti-H3 mAbs 12D1 or 39A4 did not yield escape variants which might have assisted in identification of the binding epitopes. The hemagglutinin of six plaques present after incubation of A/HK/1968 virus with 50 ug/ml mAb 12D1 or 39A4 in a plaque assay was sequenced and no changes from the wild-type hemagglutinin were found. Because mAb 12D1 mediates protection against Influenza disease in vivo and reacts with a continuous epitope of the viral hemagglutinin (no trimeric structure required), as evidenced by reactivity with the denatured hemagglutinin monomer by Western blot (FIG. 10), the 12D1 binding epitope was focused on. Hemagglutinin truncation mutants consisting of hemagglutinin segments of varying length fused to GFP were generated. GFP expression was utilized to assess expression of the constructs in transfected 293T cells. By analysis of the truncation mutants, it was determined that the 12D1 paratope makes dominant interactions with the HA2 subunit in the region of amino acids 30-106. Diminished 12D1 binding without diminished GFP expression in the 76-184 and 91-184 truncations along with loss of binding with the 106-184 truncation suggested that 12D1 binding is dependent on contacts with amino acids in the HA2 76-106 region (FIG. 18). These 30 amino acids fall within the membrane distal half of the long alpha-helix of HA2. The 12D1 paratope may have additional contacts with amino acids outside of this region (in HA1 or HA2) that are not required for binding by Western blot.

6.4.3 Conclusion

An immunization schedule was developed that elicited broadly-neutralizing antibodies against H3 Influenza viruses in vitro and in vivo.

6.5 Cross-Reactive Anti-H3 Monoclonal Antibody 66A6

Monoclonal antibody 66A6 was generated using the same approach used for the generation of antibodies 7A7, 12D1, and 39A4, as described in Section 6.1.

6.5.1 Antibody 66A6 Binds H3 Viruses

Using the ELISA approach described in Section 6.1.3., the ability of monoclonal antibody 66A6 to bind Influenza A virus strains A/Hong Kong/1/1968, A/Brisbane/10/2007, and A/Panama/2007/1999 was assessed. As shown in FIG. 23, monoclonal antibody 66A6 bound each of Influenza virus strains.

6.5.2 Hemaglutination-Inhibition Activity of Antibody 66A6

The ability of monoclonal antibody 66A6 to inhibit fusion of Influenza A virus strain A/Hong Kong/1/1968 was assessed as described in Section 6.1.6. As shown in FIG. 24, monoclonal antibody 66A6 does not inhibit the low-pH fusion of A/Hong Kong/1/1968 hemagglutinin and red blood cells.

6.5.3 Antibody 66A6 Binds the HA1 Portion of H3 Virus Hemaglutinin

The binding region of monoclonal antibody 66A6 was determined using the approach described in Section 6.3. As shown in FIG. 25, monoclonal antibody 66A6 binds to the HA1 region of the hemagglutinin protein of Influenza virus strain A/Hong Kong/1/1968 (H3) as assessed by Western blot.

6.5.4 Antibody 66A6 Neutralizes H3 Virus

A plaque reduction assay was used as described in Section 6.1.5 to assess the ability of monoclonal antibody 66A6 to neutralize Influenza A viruses of the H3 subtype. As shown in FIG. 26, monoclonal antibody 66A6 neutralizes Influenza A virus strains A/Panama/2007/1999 (H3) and A/Alabama/1/1981 (H3).

6.5.5 Passive Transfer of Antibody 66A6

The ability of monoclonal antibody 66A6 to protect mice from challenge with Influenza A virus was assessed. According to this method, BALB/c mice, in groups of five, were administered 20 mg of 66A6 monoclonal antibody (intraperitoneally—Group 1) or a control (PBS—Group 2) 1 hour prior to challenge with a 10LD50 X31 chimeric virus containing the hemagglutinin and neuramidase gene segments from A/Hong Kong/1/1968 (H3) and the six other Influenza virus genes segments (not hemagglutinin and neuramidase) from the murine Influenza A virus A/PR/8/34. The body weight of the mice was measured daily and the body weight of the mice administered the 66A6 monoclonal antibody was compared to the body weight of the mice that were administered a control (PBS).

As demonstrated in FIG. 27, passive transfer of the cross-reactive neutralizing monoclonal antibody 66A6 results in decreased weight loss in mice challenged with Influenza A virus strain X31 as compared to mice administered PBS alone. The result demonstrates the generation of passive immunity in these mice against the X31 strain. The average weight of the mice in each group is plotted in FIG. 27. Mice that fell to below 75% of their starting weight were sacrificed.

6.6 Cross-Reactive Anti-H1/H3 Monoclonal Antibodies 6.6.1 Immunization and Hybridoma Generation A cyclical immunization strategy was used to generate monoclonal antibodies that are cross-reactive to antigenically distinct H1 and H3 subtypes of Influenza A virus (FIG. 30). Six-week old BALB/c mice were immunized with DNA constructs coding for the open-reading frame of Influenza virus hemagglutinin in the pCAGGS plasmid (see, e.g., Basler et al., Proc Natl Acad Sci USA 98: 2746-2751). Individual immunizations were given intramuscularly, 3-weeks apart and consisted of 100 µg DNA in 100 µl PBS. Hemagglutinins utilized in the immunization schedule were cloned from the following parental viruses—primary immunization: A/Hong Kong/1/1968 (H3), secondary immunization: A/USSR/92/77 (H1), tertiary immunization: A/California/1/88 (H3), quaternary immunization: A/California/04/09 (H1). Three weeks after the final immunization and three days prior to generation of hybridomas, mice were boosted intravenously with a composition comprising 50 µg purified A/Brisbane/59/07-like (H1) virus and 50 µg purified A/Brisbane/10/07-like (H3) virus. B cell hybridomas were produced by methods previously described (see, e.g., de StGroth et al., J Immunol Methods 35: 1-21).

6.6.2 Screening of Hybridoma Supernatants

Hybridoma supernatants were screened for reactivity with A/Hong Kong/1/1968 virus and A/California/04/09 (H1) by ELISA as described in Section 6.4.1.5. Hybridomas that reacted with either strain were selected for, including those that produce Antibody 1, Antibody 2, Antibody 3, and Antibody 4.

6.6.3 Immunofluorescence Test

MDCK cells were infected with virus at a multiplicity of infection of 1 or 0.5, incubated for 12 hours at 37° C., and fixed in the absence of trypsin. Infected and uninfected cells were incubated with 1 μg/ml mAb for 1 hour at room temperature. Goat anti-mouse fluorescein conjugate (SouthernBiotech) was used for detection of mAb binding. Antibody 1 and Antibody 2 recognize HA from 3 H1 Influenza viruses by immunofluorescence (FIG. 31). Antibody 4 recognizes the HA from two H3 Influenza viruses by immunofluorescence (FIG. 31).

6.6.4 Western Blots

Western blots were produced by methods previously described (see, e.g., Towbin et al., Proc Natl Acad Sci USA 1979; 76(9):4350-4). Samples were boiled for 5 minutes at 100° C. in loading buffer containing SDS and 0.6M DTT. SDS migration buffer was used for electrophoresis. Under denaturing and reducing conditions, Antibody 1 and Antibody 3 do not recognize HA (FIG. 32). Antibody 4 recognizes the HA2 subunit of HA (FIG. 32).

6.7 Cross-Reactive Anti-H1 Monoclonal Antibodies 6.7.1 Immunization and Hybridoma Generation A cyclical immunization strategy was used to generate monoclonal antibodies that are cross-reactive to antigenically distinct Influenza A virus H1 subtypes (FIG. 33). Six-week old BALB/c mice were immunized with DNA constructs coding for the open-reading frame of Influenza virus hemagglutinin in the pCAGGS plasmid (see, e.g., Basler et al., Proc Natl Acad Sci USA 98: 2746-2751). Individual immunizations were given intramuscularly, 3-weeks apart and consisted of 100 μg DNA in 100 μl PBS. Hemagglutinins utilized in the immunization schedule were cloned from the following parental viruses—primary immunization: A/South Carolina/1918 (H1), secondary immunization: A/USSR/92/77 (H1), tertiary immunization: A/California/04/09 (H1). Three weeks after the final immunization and three days prior to generation of hybridomas, mice were boosted intravenously with 50 μg purified A/Brisbane/59/07-like (H1) virus. B cell hybridomas were produced by methods previously described (see, e.g., de StGroth et al., J Immunol Methods 35: 1-21).

6.7.2 Screening of Hybridoma Supernatants

Hybridoma supernatants were screened for reactivity with A/USSR/92/77 (H1) virus and A/California/04/09 (H1) virus by ELISA as described in Section 6.4.1.5. The reactivity of potential clones from one hybridoma with the two H1 viruses are shown in FIG. 34.

6.7.3 Western Blots

To assess binding of cross-reactive anti-H1 monoclonal antibodies, Western blot can be performed. Western blots can be produced by methods known in the art (see, e.g., Towbin et al., Proc Natl Acad Sci USA 1979; 76(9):4350-4). Samples can be boiled for 5 minutes at 100° C. in loading buffer containing SDS and 0.6M DTT. SDS migration buffer can be used for electrophoresis.

6.7.4 Immunofluorescence Test

To assess binding of cross-reactive anti-H1 monoclonal antibodies, immunofluorescence can be performed. MDCK cells can be infected with virus at a multiplicity of infection of 1 or 0.5, incubated for 12 hours at 37° C., and fixed in the absence of trypsin. Infected and uninfected cells can be incubated with 1 μg/ml mAb for 1 hour at room temperature. Goat anti-mouse fluorescein conjugate (SouthernBiotech) can be used for detection of mAb binding. The ability of the cross-reactive anti-H1 monoclonal antibodies to bind the virus can then be assessed using immunofluorescence approaches.

The foregoing is not to be limited in scope by the specific embodiments described herein. Indeed, various modifications of the antibodies and methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

SEQUENCE LISTING

```
<160> NUMBER OF SEQ ID NOS: 125

<210> SEQ ID NO 1
<211> LENGTH: 109
<212> TYPE: PRT
<213> ORGANISM: Artificial Sequence
<220> FEATURE:
<223> OTHER INFORMATION: Amino acids 405 to 513 of the hemagglutinin
      polypeptide of Influenza strain A/Hong Kong/1/1968
      (H3)

<400> SEQUENCE: 1

Arg Ile Gln Asp Leu Glu Lys Tyr Val Glu Asp Thr Lys Ile Asp Leu
 1               5                  10                  15

Trp Ser Tyr Asn Ala Glu Leu Leu Val Ala Leu Glu Asn Gln His Thr
            20                  25                  30

Ile Asp Leu Thr Asp Ser Glu Met Asn Lys Leu Phe Glu Lys Thr Arg
        35                  40                  45

Arg Gln Leu Arg Glu Asn Ala Glu Asp Met Gly Asn Gly Cys Phe Lys
    50                  55                  60
```

```
Ile Tyr His Lys Cys Asp Asn Ala Cys Ile Glu Ser Ile Arg Asn Gly
 65                  70                  75                  80

Thr Tyr Asp His Asp Val Tyr Arg Asp Glu Ala Leu Asn Asn Arg Phe
                 85                  90                  95

Gln Ile Lys Gly Val Glu Leu Lys Ser Gly Tyr Lys Asp
            100                 105
```

```
<210> SEQ ID NO 2
<211> LENGTH: 804
<212> TYPE: DNA
<213> ORGANISM: Mus musculus
<220> FEATURE:
<223> OTHER INFORMATION: mAB 7A7 HC sequence comprising variable region

<400> SEQUENCE: 2
atggactcca ggctcaattt agttttcctt gtccttattt taaaaggtgt ccagtgtgat    60
gtgcagctgg tggagtctgg gggaggctta gtgcagcctg agggtcccg gaaactctcc   120 tgtgcagcct ctggattcac tttcagtagc tttggaatgc actgggttcg tcaggctcca   180
gagaaggggc tggagtgggt cgcatacatt agtagtggca gtagtaccat ctactatgca   240
gacacagtga agggccgatt caccatctcc agagacaatc caagaacac cctgttcctg    300 caaatgacca gtctaaggtc tgaggacacg gccatgtatt actgtgcaag aaattacgac   360
gaggacttcg atgtctgggg cgcagggacc acggtcaccg tctcctcagc aaaacaaca   420 cccccatcag tctatccact ggcccctggg tgtggagata aactggttc ctccgtgact    480 ctgggatgcc tggtcaaggg ctacttccct gagtcagtga ctgtgacttg aactctgga    540 tccctgtcca gcagtgtgca caccttccca gctctcctgc agtctggact ctacactatg   600
agcagctcag tgactgtccc ctccagcacc tggccaagtc agaccgtcac ctgcagcgtt   660
gctcacccag ccagcagcac cacggtggac aaaaaacttg agcccagcgg gcccatttca   720
acaatcaacc cctgtcctcc atgcaaggag tgtcacaaat gcccagctcc taacctcgag   780
ggtggaccat ccgtcttcat cttc                                          804
```

```
<210> SEQ ID NO 3
<211> LENGTH: 12
<212> TYPE: PRT
<213> ORGANISM: Artificial Sequence
<220> FEATURE:
<223> OTHER INFORMATION: Junctional amino acid residues for mAB 7A7 HC

<400> SEQUENCE: 3

Cys Ala Arg Asn Tyr Asp Glu Asp Phe Asp Val Trp
  1               5                  10
```

```
<210> SEQ ID NO 4
<211> LENGTH: 716
<212> TYPE: DNA
<213> ORGANISM: Mus musculus
<220> FEATURE:
<223> OTHER INFORMATION: mAB 7A7 LC sequence comprising variable region

<400> SEQUENCE: 4
tgaagttgcc tgttaggctg ttggtgctga tgttctggat tctgcttcc agcagtgatg     60 ttgtgatgac ccaaactcca ctctccctgc ctgtcagtct tggagatcaa gcctccatct   120
cttgcagatc tagtcagagc cttgtacaca gtaatggaaa cacctattta cattggtacc   180
tgcagaagcc aggccagtct ccaaagctcc tgatctacaa agttccaac cgattttctg    240 gggtcccaga caggttcagt ggcagtggat cagggacaga tttcacactc aagatcagca   300
```

```
gagtggaggc tgaggatctg ggagtttatt tctgctctca agtacacat gttccgtgga    360 cgttcggtgg aggcaccaag ctggaaatca acgggctga tgctgcacca actgtatcca    420
tcttcccacc atccagtgag cagttaacat ctggaggtgc ctcagtcgtg tgcttcttga    480
acaacttcta ccccaaagac atcaatgtca agtggaagat tgatggcagt gaacgacaaa    540
atggcgtcct gaacagttgg actgatcagg acagcaaaga cagcacctac agcatgagca    600
gcaccctcac gttgaccaag gacgagtatg aacgacataa cagctatacc tgtgaggcca    660
ctcacaagac atcaacttca cccattgtca agagcttcaa caggaatgag tgttag       716
```

<210> SEQ ID NO 5
<211> LENGTH: 11
<212> TYPE: PRT
<213> ORGANISM: Artificial Sequence
<220> FEATURE:
<223> OTHER INFORMATION: Junctional amino acid residues for mAB 7A7 LC

<400> SEQUENCE: 5

```
Cys Ser Gln Ser Thr His Val Pro Trp Thr Phe
 1               5                  10
```

<210> SEQ ID NO 6
<211> LENGTH: 268
<212> TYPE: PRT
<213> ORGANISM: Mus musculus
<220> FEATURE:
<223> OTHER INFORMATION: mAB 7A7 HC sequence comprising variable region

<400> SEQUENCE: 6

```
Met Asp Ser Arg Leu Asn Leu Val Phe Leu Val Leu Ile Leu Lys Gly
 1               5                  10                  15

Val Gln Cys Asp Val Gln Leu Val Glu Ser Gly Gly Gly Leu Val Gln
                20                  25                  30

Pro Gly Gly Ser Arg Lys Leu Ser Cys Ala Ala Ser Gly Phe Thr Phe
            35                  40                  45

Ser Ser Phe Gly Met His Trp Val Arg Gln Ala Pro Glu Lys Gly Leu
        50                  55                  60

Glu Trp Val Ala Tyr Ile Ser Ser Gly Ser Ser Thr Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Asn Tyr Asp Glu Asp Phe Asp Val Trp Gly Ala
        115                 120                 125

Gly Thr Thr Val Thr Val Ser Ser Ala Lys Thr Thr Pro Pro Ser Val
    130                 135                 140

Tyr Pro Leu Ala Pro Gly Cys Gly Asp Thr Thr Gly Ser Ser Val Thr
145                 150                 155                 160

Leu Gly Cys Leu Val Lys Gly Tyr Phe Pro Glu Ser Val Thr Val Thr
                165                 170                 175

Trp Asn Ser Gly Ser Leu Ser Ser Val His Thr Phe Pro Ala Leu
            180                 185                 190

Leu Gln Ser Gly Leu Tyr Thr Met Ser Ser Val Thr Val Pro Ser
        195                 200                 205

Ser Thr Trp Pro Ser Gln Thr Val Thr Cys Ser Val Ala His Pro Ala
    210                 215                 220
```

```
Ser Ser Thr Thr Val Asp Lys Lys Leu Glu Pro Ser Gly Pro Ile Ser
225                 230                 235                 240

Thr Ile Asn Pro Cys Pro Pro Cys Lys Glu Cys His Lys Cys Pro Ala
            245                 250                 255

Pro Asn Leu Glu Gly Gly Pro Ser Val Phe Ile Phe
        260                 265
```

<210> SEQ ID NO 7
<211> LENGTH: 238
<212> TYPE: PRT
<213> ORGANISM: Mus musculus
<220> FEATURE:
<223> OTHER INFORMATION: mAB 7A7 LC sequence comprising variable region

<400> SEQUENCE: 7

```
Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 8
<211> LENGTH: 772
<212> TYPE: DNA
<213> ORGANISM: Mus musculus
<220> FEATURE:
<223> OTHER INFORMATION: mAB 12D1 HC sequence comprising variable region

<400> SEQUENCE: 8

```
atggctgtct tggggctgct cttctgcctg gtgacattcc caagctgtgt cctatcccag    60
gtgcacctgg agcagtcagg acctggccta gtgcagccct cacagagcct gtccatcacc   120
```

```
tgcacagtct ctggtttctc attaacaacg tatggtgtac actgggttcg ccagtctcca      180
ggaaagggtc tggagtggct gggagtgata tggagaggtg aagcataga ctataatgca      240 gctttcatat ccagactgag catcagcaag acaattccta agagccaagt tttctttaaa      300
atgaacagtc tgcaagctaa tgacacagcc atatattact gtgccagaaa ttggggtagg      360
tacggatact tcgatgtctg gggcgcaggg accacggtca ccgtctcctc agccaaaacg      420 acaccccat ctgtctatcc actggcccct ggatctgctg cccaaactaa ctccatggtg       480
accctgggat gcctggtcaa gggctatttc cctgagccag tgacagtgac ctggaactct      540
ggatccctgt ccagcggtgt gcacaccttc ccagctgtcc tgcagtctga cctctacact      600
ctgagcagct cagtgactgt cccctccagc acctggccca gcgagaccgt cacctgcaac      660
gttgcccacc cggccagcag caccaaggtg gacaagaaaa ttgtgcccag ggattgtggt      720
tgtaagcctt gcatatgtac agtcccagaa gtatcatctg tcttcatctt cc              772

<210> SEQ ID NO 9
<211> LENGTH: 14
<212> TYPE: PRT
<213> ORGANISM: Artificial Sequence
<220> FEATURE:
<223> OTHER INFORMATION: Junctional amino acid residues for mAB 12D1 HC

<400> SEQUENCE: 9

Cys Ala Arg Asn Trp Gly Arg Tyr Gly Tyr Phe Asp Val Trp
  1               5                  10

<210> SEQ ID NO 10
<211> LENGTH: 717
<212> TYPE: DNA
<213> ORGANISM: Mus musculus
<220> FEATURE:
<223> OTHER INFORMATION: mAB 12D1 HC sequence comprising variable region

<400> SEQUENCE: 10
atggagacag acacactcct gctatgggtg ctgctgctct gggttccagg ttccacaggt      60
gacattgtgc tgacccaatc tccagcttct ttggctgtgt ctctagggca gagggccacc     120
atatcctgca gagccagtga aagtgttgat agttatggca cagttttat gcactggtac      180 cagcagaaac caggacagcc acccaaagtc ctcatctatc gtgcatccaa cctagaatct     240
gggatccctg ccaggttcag tggcagtggg tctaggacag acttcaccct caccattaat     300
cctgtggagg ctgatgatgt tgcaacctat tactgtcagc aaagtaatgg ggatcctcgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata acagctatac ctgtgaggcc    660
actcacaaga catcaacttc acccattgtc aagagcttca caggaatga gtgttag       717

<210> SEQ ID NO 11
<211> LENGTH: 11
<212> TYPE: PRT
<213> ORGANISM: Artificial Sequence
<220> FEATURE:
<223> OTHER INFORMATION: Junctional amino acid residues for mAB 12D1 LC

<400> SEQUENCE: 11
```

```
Cys Gln Gln Ser Asn Gly Asp Pro Arg Thr Phe
 1               5                  10
```

<210> SEQ ID NO 12
<211> LENGTH: 257
<212> TYPE: PRT
<213> ORGANISM: Mus musculus
<220> FEATURE:
<223> OTHER INFORMATION: mAB 12D1 HC sequence comprising variable region

<400> SEQUENCE: 12

```
Met Ala Val Leu Gly Leu Leu Phe Cys Leu Val Thr Phe Pro Ser Cys
 1               5                  10                  15

Val Leu Ser Gln Val His Leu Glu Gln Ser Gly Pro Gly Leu Val Gln
             20                  25                  30

Pro Ser Gln Ser Leu Ser Ile Thr Cys Thr Val Ser Gly Phe Ser Leu
         35                  40                  45

Thr Thr Tyr Gly Val His Trp Val Arg Gln Ser Pro Gly Lys Gly Leu
     50                  55                  60

Glu Trp Leu Gly Val Ile Trp Arg Gly Gly Ser Ile Asp Tyr Asn Ala
 65                  70                  75                  80

Ala Phe Ile Ser Arg Leu Ser Ile Ser Lys Asp Asn Ser Lys Ser Gln
                 85                  90                  95

Val Phe Phe Lys Met Asn Ser Leu Gln Ala Asn Asp Thr Ala Ile Tyr
            100                 105                 110

Tyr Cys Ala Arg Asn Trp Gly Arg Tyr Gly Tyr Phe Asp Val Trp Gly
        115                 120                 125

Ala Gly Thr Thr Val Thr Val Ser Ser Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe
```

<210> SEQ ID NO 13
<211> LENGTH: 238
<212> TYPE: PRT
<213> ORGANISM: Mus musculus
<220> FEATURE:
<223> OTHER INFORMATION: mAB 12D1 LC sequence comprising variable region

<400> SEQUENCE: 13

```
Met Glu Thr Asp Thr Leu Leu Leu Trp Val Leu Leu Leu Trp Val Pro
 1               5                  10                  15

Gly Ser Thr Gly Asp Ile Val Leu Thr Gln Ser Pro Ala Ser Leu Ala
             20                  25                  30
```

```
Val Ser Leu Gly Gln Arg Ala Thr Ile Ser Cys Arg Ala Ser Glu Ser
         35                  40                  45
Val Asp Ser Tyr Gly Asn Ser Phe Met His Trp Tyr Gln Gln Lys Pro
 50                  55                  60
Gly Gln Pro Pro Lys Val Leu Ile Tyr Arg Ala Ser Asn Leu Glu Ser
 65                  70                  75                  80
Gly Ile Pro Ala Arg Phe Ser Gly Ser Gly Ser Arg Thr Asp Phe Thr
                 85                  90                  95
Leu Thr Ile Asn Pro Val Glu Ala Asp Asp Val Ala Thr Tyr Tyr Cys
                100                 105                 110
Gln Gln Ser Asn Gly Asp Pro Arg Thr Phe Gly Gly Gly Thr Lys Leu
                115                 120                 125
Glu Ile Lys Arg Ala Asp Ala Ala Pro Thr Val Ser Ile Phe Pro Pro
130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
                180                 185                 190
Lys Asp Ser Thr Tyr Ser Met Ser Ser Thr Leu Thr Leu Thr Lys Asp
                195                 200                 205
Glu Tyr Glu Arg His Asn Ser Tyr Thr Cys Glu Ala Thr His Lys Thr
210                 215                 220
Ser Thr Ser Pro Ile Val Lys Ser Phe Asn Arg Asn Glu Cys
225                 230                 235
```

<210> SEQ ID NO 14
<211> LENGTH: 765
<212> TYPE: DNA
<213> ORGANISM: Mus musculus
<220> FEATURE:
<223> OTHER INFORMATION: mAB 66A6 HC sequence comprising variable region

<400> SEQUENCE: 14

```
aagcttgcca ccatggaaac cgataccctg ctgctgtggg tgctgctgct gtgggtgccg      60
ggcagctggg cgcaggtgca gctgcagcag agcggcccgg aactgaaaaa accgggcgaa     120
accgtgaaaa ttagctgcaa agcgagcggc tataccttta ccaactatgg catgaactgg     180
gtgaaacagg cgccgggcaa agatctgaaa tggctgggct ggattaacac cgataccggc     240
gaaccgacct atgcggaaga atttaaaggc cgctttgcgt ttagcctgga aaccagcgcg     300
agcaccgcgt atctggaaat taacaacctg aaaaacgaag atgcggcgac ctatttttgc     360
gcgcgcaaca aaaaatatga agcgtggttt acccattggg gccagggcac cctggtgacc     420
gtgagcagcg cgaaaaccac cccgccgagc gtgtatccgc tggcgccggg cagcgcggcg     480
cagaccaaca gcatggtgac cctgggctgc ctggtgaaag ctatttttcc ggaaccggtg     540
accgtgacct ggaacagcgg cagcctgagc agcggcgtgc atacctttcc ggcggtgctg     600
cagagcgatc tgtatacccc tgagcagcag gtgaccgtgc cgagcagcac ctggccgagc     660
cagaccgtga cctgcaacgt ggcgcatccg gcgagcagca ccaaagtgga taaaaaaatt     720
gtgccgcgcg attgcggcca tcatcatcat catcattaag aattc                    765
```

<210> SEQ ID NO 15
<211> LENGTH: 731
<212> TYPE: DNA

```
<213> ORGANISM: Mus musculus
<220> FEATURE:
<223> OTHER INFORMATION: mAB 66A6 LC sequence comprising variable region

<400> SEQUENCE: 15
aagcttgcca ccatggaaac cgatacctg ctgctgtggg tgctgctgct gtgggtgccg      60
ggcagcaccg ggaacattgt gctgacccag agcccggcga gcctggcggt gagcctgggc    120
cagcgcgcga ccattagctg caaagcgagc gaaagcgtgg atagctatgg caccagcttt    180
atgcattggt atcagcagaa accgggccag ccgccgaaac tgctgattta tctggcgagc    240
aacctggaaa gcggcgtgcc ggcgcgcttt agcggcagcg gcagccgcac cgattttacc    300
ctgaccattg atccggtgga agcggatgat gcggcgacct attattgcca gcagaacaac    360
gaacatccga tgtttggcgg cggcaccaaa ctggaaatta aacgcgcgga tgcggcgccg    420
accgtgagca ttttttccgcc gagcagcgaa cagctgacca gcggcggcgc gagcgtggtg    480
tgctttctga caactttta tccgaaagat attaacgtga atggaaaat tgatggcagc     540 gaacgccaga acggcgtgct gaacagctgg accgatcagg atagcaaaga tagcaccta t   600 agcatgagca gcaccctgac cctgaccaaa gatgaatatg aacgccataa cagctatacc    660
tgcgaagcga cccataaaac cagcaccagc ccgattgtga gagctttaa ccgcaacgaa    720 tgctaagaat t                                                          731

<210> SEQ ID NO 16
<211> LENGTH: 247
<212> TYPE: PRT
<213> ORGANISM: Mus musculus
<220> FEATURE:
<223> OTHER INFORMATION: mAB 66A6 HC sequence comprising variable region

<400> SEQUENCE: 16

Ser Lys Leu Ala Thr Met Glu Thr Asp Thr Leu Leu Leu Trp Val Leu
  1               5                  10                  15

Leu Leu Trp Val Pro Gly Ser Trp Ala Gln Val Gln Leu Gln Gln Ser
             20                  25                  30

Gly Pro Glu Leu Lys Lys Pro Gly Glu Thr Val Lys Ile Ser Cys Lys
         35                  40                  45

Ala Ser Gly Tyr Thr Phe Thr Asn Tyr Gly Met Asn Trp Val Lys Gln
     50                  55                  60

Ala Pro Gly Lys Asp Leu Lys Trp Leu Gly Trp Ile Asn Thr Asp Thr
 65                  70                  75                  80

Gly Glu Pro Thr Tyr Ala Glu Glu Phe Lys Gly Arg Phe Ala Phe Ser
                 85                  90                  95

Leu Glu Thr Ser Ala Ser Thr Ala Tyr Leu Glu Ile Asn Asn Leu Lys
            100                 105                 110

Asn Glu Asp Ala Ala Thr Tyr Phe Cys Ala Arg Asn Lys Lys Tyr Glu
        115                 120                 125

Ala Trp Phe Thr His Trp Gly Gln Gly Thr Leu Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
```

```
                 195                 200                 205

Ser Ser Ser Val Thr Val Pro Ser Ser Thr Trp Pro Ser Gln Thr Val
        210                 215                 220

Thr Cys Asn Val Ala His Pro Ala Ser Ser Thr Lys Val Asp Lys Lys
225                 230                 235                 240

Ile Val Pro Arg Asp Cys Gly
                245

<210> SEQ ID NO 17
<211> LENGTH: 242
<212> TYPE: PRT
<213> ORGANISM: Mus musculus
<220> FEATURE:
<223> OTHER INFORMATION: mAB 66A6 LC sequence comprising variable region

<400> SEQUENCE: 17

Ser Lys Leu Ala Thr Met Glu Thr Asp Thr Leu Leu Leu Trp Val Leu
1               5                   10                  15

Leu Leu Trp Val Pro Gly Ser Thr Gly Asn Ile Val Leu Thr Gln Ser
                20                  25                  30

Pro Ala Ser Leu Ala Val Ser Leu Gly Gln Arg Ala Thr Ile Ser Cys
            35                  40                  45

Lys Ala Ser Glu Ser Val Asp Ser Tyr Gly Thr Ser Phe Met His Trp
        50                  55                  60

Tyr Gln Gln Lys Pro Gly Gln Pro Pro Lys Leu Leu Ile Tyr Leu Ala
65                  70                  75                  80

Ser Asn Leu Glu Ser Gly Val Pro Ala Arg Phe Ser Gly Ser Gly Ser
                85                  90                  95

Arg Thr Asp Phe Thr Leu Thr Ile Asp Pro Val Glu Ala Asp Asp Ala
            100                 105                 110

Ala Thr Tyr Tyr Cys Gln Gln Asn Asn Glu His Pro Met Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 18
<211> LENGTH: 75
<212> TYPE: DNA
<213> ORGANISM: Artificial Sequence
<220> FEATURE:
<223> OTHER INFORMATION: mAB 7A7 HC variable region FR1

<400> SEQUENCE: 18
gatgtgcagc tggtggagtc tgggggaggc ttagtgcagc ctggagggtc ccggaaactc    60
```

```
tcctgtgcag cctct                                               75

<210> SEQ ID NO 19
<211> LENGTH: 51
<212> TYPE: DNA
<213> ORGANISM: Artificial Sequence
<220> FEATURE:
<223> OTHER INFORMATION: mAB 7A7 HC variable region FR2

<400> SEQUENCE: 19
atgcactggg ttcgtcaggc tccagagaag gggctggagt gggtcgcata c       51

<210> SEQ ID NO 20
<211> LENGTH: 114
<212> TYPE: DNA
<213> ORGANISM: Artificial Sequence
<220> FEATURE:
<223> OTHER INFORMATION: mAB 7A7 HC variable region FR3

<400> SEQUENCE: 20
tactatgcag acacagtgaa gggccgattc accatctcca gagacaatcc caagaacacc   60
ctgttcctgc aaatgaccag tctaaggtct gaggacacgg ccatgtatta ctgt         114

<210> SEQ ID NO 21
<211> LENGTH: 36
<212> TYPE: DNA
<213> ORGANISM: Artificial Sequence
<220> FEATURE:
<223> OTHER INFORMATION: mAB 7A7 HC variable region FR4

<400> SEQUENCE: 21
tggggcgcag ggaccacggt caccgtctcc tcagcc                        36

<210> SEQ ID NO 22
<211> LENGTH: 24
<212> TYPE: DNA
<213> ORGANISM: Artificial Sequence
<220> FEATURE:
<223> OTHER INFORMATION: mAB 7A7 HC variable region CDR1

<400> SEQUENCE: 22
ggattcactt tcagtagctt tgga                                     24

<210> SEQ ID NO 23
<211> LENGTH: 24
<212> TYPE: DNA
<213> ORGANISM: Artificial Sequence
<220> FEATURE:
<223> OTHER INFORMATION: mAB 7A7 HC variable region CDR2

<400> SEQUENCE: 23
attagtagtg gcagtagtac catc                                     24

<210> SEQ ID NO 24
<211> LENGTH: 30
<212> TYPE: DNA
<213> ORGANISM: Artificial Sequence
<220> FEATURE:
<223> OTHER INFORMATION: mAB 7A7 HC variable region CDR3

<400> SEQUENCE: 24
gcaagaaatt acgacgagga cttcgatgtc                               30

<210> SEQ ID NO 25
```

```
<211> LENGTH: 57
<212> TYPE: DNA
<213> ORGANISM: Artificial Sequence
<220> FEATURE:
<223> OTHER INFORMATION: mAB 7A7 HC variable region leader sequence

<400> SEQUENCE: 25
atggactcca ggctcaattt agttttcctt gtccttattt taaaaggtgt ccagtgt      57

<210> SEQ ID NO 26
<211> LENGTH: 78
<212> TYPE: DNA
<213> ORGANISM: Artificial Sequence
<220> FEATURE:
<223> OTHER INFORMATION: mAB 7A7 LC variable region FR1

<400> SEQUENCE: 26
gatgttgtga tgacccaaac tccactctcc ctgcctgtca gtcttggaga tcaagcctcc   60
atctcttgca gatctagt                                                 78

<210> SEQ ID NO 27
<211> LENGTH: 51
<212> TYPE: DNA
<213> ORGANISM: Artificial Sequence
<220> FEATURE:
<223> OTHER INFORMATION: mAB 7A7 LC variable region FR2

<400> SEQUENCE: 27
ttacattggt acctgcagaa gccaggccag tctccaaagc tcctgatcta c             51

<210> SEQ ID NO 28
<211> LENGTH: 108
<212> TYPE: DNA
<213> ORGANISM: Artificial Sequence
<220> FEATURE:
<223> OTHER INFORMATION: mAB 7A7 LC variable region FR3

<400> SEQUENCE: 28
aaccgatttt ctggggtccc agacaggttc agtggcagtg gatcagggac agatttcaca   60
ctcaagatca gcagagtgga ggctgaggat ctgggagttt atttctgc                108

<210> SEQ ID NO 29
<211> LENGTH: 36
<212> TYPE: DNA
<213> ORGANISM: Artificial Sequence
<220> FEATURE:
<223> OTHER INFORMATION: mAB 7A7 LC variable region FR4

<400> SEQUENCE: 29
ttcggtggag gcaccaagct ggaaatcaaa cgggct                             36

<210> SEQ ID NO 30
<211> LENGTH: 33
<212> TYPE: DNA
<213> ORGANISM: Artificial Sequence
<220> FEATURE:
<223> OTHER INFORMATION: mAB 7A7 LC variable region CDR1

<400> SEQUENCE: 30
cagagccttg tacacagtaa tggaaacacc tat                                33

<210> SEQ ID NO 31
<211> LENGTH: 9
<212> TYPE: DNA
<213> ORGANISM: Artificial Sequence
```

-continued

```
<220> FEATURE:
<223> OTHER INFORMATION: mAB 7A7 LC variable region CDR2

<400> SEQUENCE: 31 aaagtttcc                                                                  9

<210> SEQ ID NO 32
<211> LENGTH: 27
<212> TYPE: DNA
<213> ORGANISM: Artificial Sequence
<220> FEATURE:
<223> OTHER INFORMATION: mAB 7A7 LC variable region CDR3

<400> SEQUENCE: 32
tctcaaagta cacatgttcc gtggacg                                             27

<210> SEQ ID NO 33
<211> LENGTH: 57
<212> TYPE: DNA
<213> ORGANISM: Artificial Sequence
<220> FEATURE:
<223> OTHER INFORMATION: mAB 7A7 LC variable region leader sequence

<400> SEQUENCE: 33
atgaagttgc ctgttaggct gttggtgctg atgttctgga ttcctgcttc cagcagt            57

<210> SEQ ID NO 34
<211> LENGTH: 25
<212> TYPE: PRT
<213> ORGANISM: Artificial Sequence
<220> FEATURE:
<223> OTHER INFORMATION: mAB 7A7 HC variable region FR1

<400> SEQUENCE: 34

Asp Val Gln Leu Val Glu Ser Gly Gly Gly Leu Val Gln Pro Gly Gly
 1               5                  10                  15

Ser Arg Lys Leu Ser Cys Ala Ala Ser
            20                  25

<210> SEQ ID NO 35
<211> LENGTH: 17
<212> TYPE: PRT
<213> ORGANISM: Artificial Sequence
<220> FEATURE:
<223> OTHER INFORMATION: mAB 7A7 HC variable region FR2

<400> SEQUENCE: 35

Met His Trp Val Arg Gln Ala Pro Glu Lys Gly Leu Glu Trp Val Ala
 1               5                  10                  15

Tyr

<210> SEQ ID NO 36
<211> LENGTH: 38
<212> TYPE: PRT
<213> ORGANISM: Artificial Sequence
<220> FEATURE:
<223> OTHER INFORMATION: mAB 7A7 HC variable region FR3

<400> SEQUENCE: 36

Tyr Tyr Ala Asp Thr Val Lys Gly Arg Phe Thr Ile Ser Arg Asp Asn
 1               5                  10                  15

Pro Lys Asn Thr Leu Phe Leu Gln Met Thr Ser Leu Arg Ser Glu Asp
            20                  25                  30

Thr Ala Met Tyr Tyr Cys
```

<210> SEQ ID NO 37
<211> LENGTH: 12
<212> TYPE: PRT
<213> ORGANISM: Artificial Sequence
<220> FEATURE:
<223> OTHER INFORMATION: mAB 7A7 HC variable region FR4

<400> SEQUENCE: 37

Trp Gly Ala Gly Thr Thr Val Thr Val Ser Ser Ala
1               5                   10

<210> SEQ ID NO 38
<211> LENGTH: 8
<212> TYPE: PRT
<213> ORGANISM: Artificial Sequence
<220> FEATURE:
<223> OTHER INFORMATION: mAB 7A7 HC variable region CDR1

<400> SEQUENCE: 38

Gly Phe Thr Phe Ser Ser Phe Gly
1               5

<210> SEQ ID NO 39
<211> LENGTH: 8
<212> TYPE: PRT
<213> ORGANISM: Artificial Sequence
<220> FEATURE:
<223> OTHER INFORMATION: mAB 7A7 HC variable region CDR2

<400> SEQUENCE: 39

Ile Ser Ser Gly Ser Ser Thr Ile
1               5

<210> SEQ ID NO 40
<211> LENGTH: 10
<212> TYPE: PRT
<213> ORGANISM: Artificial Sequence
<220> FEATURE:
<223> OTHER INFORMATION: mAB 7A7 HC variable region CDR3

<400> SEQUENCE: 40

Ala Arg Asn Tyr Asp Glu Asp Phe Asp Val
1               5                   10

<210> SEQ ID NO 41
<211> LENGTH: 19
<212> TYPE: PRT
<213> ORGANISM: Artificial Sequence
<220> FEATURE:
<223> OTHER INFORMATION: mAB 7A7 HC variable region leader sequence

<400> SEQUENCE: 41

Met Asp Ser Arg Leu Asn Leu Val Phe Leu Val Leu Ile Leu Lys Gly
1               5                   10                  15

Val Gln Cys

<210> SEQ ID NO 42
<211> LENGTH: 26
<212> TYPE: PRT
<213> ORGANISM: Artificial Sequence
<220> FEATURE:
<223> OTHER INFORMATION: mAB 7A7 LC variable region FR1

<400> SEQUENCE: 42

-continued

```
Asp Val Val Met Thr Gln Thr Pro Leu Ser Leu Pro Val Ser Leu Gly
1               5                   10                  15
Asp Gln Ala Ser Ile Ser Cys Arg Ser Ser
            20                  25
```

<210> SEQ ID NO 43
<211> LENGTH: 17
<212> TYPE: PRT
<213> ORGANISM: Artificial Sequence
<220> FEATURE:
<223> OTHER INFORMATION: mAB 7A7 LC variable region FR2

<400> SEQUENCE: 43

```
Leu His Trp Tyr Leu Gln Lys Pro Gly Gln Ser Pro Lys Leu Leu Ile
1               5                   10                  15
Tyr
```

<210> SEQ ID NO 44
<211> LENGTH: 36
<212> TYPE: PRT
<213> ORGANISM: Artificial Sequence
<220> FEATURE:
<223> OTHER INFORMATION: mAB 7A7 LC variable region FR3

<400> SEQUENCE: 44

```
Asn Arg Phe Ser Gly Val Pro Asp Arg Phe Ser Gly Ser Gly Ser Gly
1               5                   10                  15
Thr Asp Phe Thr Leu Lys Ile Ser Arg Val Glu Ala Glu Asp Leu Gly
            20                  25                  30
Val Tyr Phe Cys
        35
```

<210> SEQ ID NO 45
<211> LENGTH: 12
<212> TYPE: PRT
<213> ORGANISM: Artificial Sequence
<220> FEATURE:
<223> OTHER INFORMATION: mAB 7A7 LC variable region FR4

<400> SEQUENCE: 45

```
Phe Gly Gly Gly Thr Lys Leu Glu Ile Lys Arg Ala
1               5                   10
```

<210> SEQ ID NO 46
<211> LENGTH: 11
<212> TYPE: PRT
<213> ORGANISM: Artificial Sequence
<220> FEATURE:
<223> OTHER INFORMATION: mAB 7A7 LC variable region CDR1

<400> SEQUENCE: 46

```
Gln Ser Leu Val His Ser Asn Gly Asn Thr Tyr
1               5                   10
```

<210> SEQ ID NO 47
<211> LENGTH: 3
<212> TYPE: PRT
<213> ORGANISM: Artificial Sequence
<220> FEATURE:
<223> OTHER INFORMATION: mAB 7A7 LC variable region CDR2

<400> SEQUENCE: 47

```
Lys Val Ser
1
```

<210> SEQ ID NO 48
<211> LENGTH: 9
<212> TYPE: PRT
<213> ORGANISM: Artificial Sequence
<220> FEATURE:
<223> OTHER INFORMATION: mAB 7A7 LC variable region CDR3

<400> SEQUENCE: 48

Ser Gln Ser Thr His Val Pro Trp Thr
 1               5

<210> SEQ ID NO 49
<211> LENGTH: 19
<212> TYPE: PRT
<213> ORGANISM: Artificial Sequence
<220> FEATURE:
<223> OTHER INFORMATION: mAB 7A7 LC variable region leader sequence

<400> SEQUENCE: 49

Met Lys Leu Pro Val Arg Leu Leu Val Leu Met Phe Trp Ile Pro Ala
 1               5                  10                  15

Ser Ser Ser

<210> SEQ ID NO 50
<211> LENGTH: 75
<212> TYPE: DNA
<213> ORGANISM: Artificial Sequence
<220> FEATURE:
<223> OTHER INFORMATION: mAB 12D1 HC variable region FR1

<400> SEQUENCE: 50
caggtgcacc tggagcagtc aggacctggc ctagtgcagc cctcacagag cctgtccatc    60
acctgcacag tctct                                                    75

<210> SEQ ID NO 51
<211> LENGTH: 51
<212> TYPE: DNA
<213> ORGANISM: Artificial Sequence
<220> FEATURE:
<223> OTHER INFORMATION: mAB 12D1 HC variable region FR2

<400> SEQUENCE: 51
gtacactggg ttcgccagtc tccaggaaag ggtctggagt ggctgggagt g             51

<210> SEQ ID NO 52
<211> LENGTH: 114
<212> TYPE: DNA
<213> ORGANISM: Artificial Sequence
<220> FEATURE:
<223> OTHER INFORMATION: mAB 12D1 HC variable region FR3

<400> SEQUENCE: 52
gactataatg cagctttcat atccagactg agcatcagca aggacaattc caagagccaa    60
gttttcttta aaatgaacag tctgcaagct aatgacacag ccatatatta ctgt         114

<210> SEQ ID NO 53
<211> LENGTH: 36
<212> TYPE: DNA
<213> ORGANISM: Artificial Sequence
<220> FEATURE:
<223> OTHER INFORMATION: mAB 12D1 HC variable region FR4

<400> SEQUENCE: 53
tggggcgcag ggaccacggt caccgtctcc tcagcc                              36

<210> SEQ ID NO 54
<211> LENGTH: 24
<212> TYPE: DNA
<213> ORGANISM: Artificial Sequence
<220> FEATURE:
<223> OTHER INFORMATION: mAB 12D1 HC variable region CDR1

<400> SEQUENCE: 54
ggtttctcat taacaacgta tggt                                    24

<210> SEQ ID NO 55
<211> LENGTH: 21
<212> TYPE: DNA
<213> ORGANISM: Artificial Sequence
<220> FEATURE:
<223> OTHER INFORMATION: mAB 12D1 HC variable region CDR2

<400> SEQUENCE: 55
atatggagag gtggaagcat a                                       21

<210> SEQ ID NO 56
<211> LENGTH: 36
<212> TYPE: DNA
<213> ORGANISM: Artificial Sequence
<220> FEATURE:
<223> OTHER INFORMATION: mAB 12D1 HC variable region CDR3

<400> SEQUENCE: 56
gccagaaatt ggggtaggta cggatacttc gatgtc                       36

<210> SEQ ID NO 57
<211> LENGTH: 57
<212> TYPE: DNA
<213> ORGANISM: Artificial Sequence
<220> FEATURE:
<223> OTHER INFORMATION: mAB 12D1 HC variable region leader sequence

<400> SEQUENCE: 57
atggctgtct tggggctgct cttctgcctg gtgacattcc caagctgtgt cctatcc    57

<210> SEQ ID NO 58
<211> LENGTH: 78
<212> TYPE: DNA
<213> ORGANISM: Artificial Sequence
<220> FEATURE:
<223> OTHER INFORMATION: mAB 12D1 LC variable region FR1

<400> SEQUENCE: 58
gacattgtgc tgacccaatc tccagcttct ttggctgtgt ctctagggca gagggccacc    60
atatcctgca gagccagt                                           78

<210> SEQ ID NO 59
<211> LENGTH: 51
<212> TYPE: DNA
<213> ORGANISM: Artificial Sequence
<220> FEATURE:
<223> OTHER INFORMATION: mAB 12D1 LC variable region FR2

<400> SEQUENCE: 59
atgcactggt accagcagaa accaggacag ccacccaaag tcctcatcta t           51

<210> SEQ ID NO 60
<211> LENGTH: 108
<212> TYPE: DNA

```
<213> ORGANISM: Artificial Sequence
<220> FEATURE:
<223> OTHER INFORMATION: mAB 12D1 LC variable region FR3

<400> SEQUENCE: 60
aacctagaat ctgggatccc tgccaggttc agtggcagtg ggtctaggac agacttcacc      60
ctcaccatta atcctgtgga ggctgatgat gttgcaacct attactgt                  108

<210> SEQ ID NO 61
<211> LENGTH: 36
<212> TYPE: DNA
<213> ORGANISM: Artificial Sequence
<220> FEATURE:
<223> OTHER INFORMATION: mAB 12D1 LC variable region FR4

<400> SEQUENCE: 61
ttcggtggag gcaccaagct ggaaatcaaa cgggct                                36

<210> SEQ ID NO 62
<211> LENGTH: 30
<212> TYPE: DNA
<213> ORGANISM: Artificial Sequence
<220> FEATURE:
<223> OTHER INFORMATION: mAB 12D1 LC variable region CDR1

<400> SEQUENCE: 62
gaaagtgttg atagttatgg caacagtttt                                       30

<210> SEQ ID NO 63
<211> LENGTH: 9
<212> TYPE: DNA
<213> ORGANISM: Artificial Sequence
<220> FEATURE:
<223> OTHER INFORMATION: mAB 12D1 LC variable region CDR2

<400> SEQUENCE: 63 cgtgcatcc                                                               9

<210> SEQ ID NO 64
<211> LENGTH: 27
<212> TYPE: DNA
<213> ORGANISM: Artificial Sequence
<220> FEATURE:
<223> OTHER INFORMATION: mAB 12D1 LC variable region CDR3

<400> SEQUENCE: 64
cagcaaagta atggggatcc tcggacg                                          27

<210> SEQ ID NO 65
<211> LENGTH: 60
<212> TYPE: DNA
<213> ORGANISM: Artificial Sequence
<220> FEATURE:
<223> OTHER INFORMATION: mAB 12D1 LC variable region leader sequence

<400> SEQUENCE: 65
atggagacag acacactcct gctatgggtg ctgctgctct gggttccagg ttccacaggt      60

<210> SEQ ID NO 66
<211> LENGTH: 25
<212> TYPE: PRT
<213> ORGANISM: Artificial Sequence
<220> FEATURE:
<223> OTHER INFORMATION: mAB 12D1 HC variable region FR1

<400> SEQUENCE: 66
```

```
Gln Val His Leu Glu Gln Ser Gly Pro Gly Leu Val Gln Pro Ser Gln
 1               5                  10                  15

Ser Leu Ser Ile Thr Cys Thr Val Ser
                20                  25

<210> SEQ ID NO 67
<211> LENGTH: 17
<212> TYPE: PRT
<213> ORGANISM: Artificial Sequence
<220> FEATURE:
<223> OTHER INFORMATION: mAB 12D1 HC variable region FR2

<400> SEQUENCE: 67

Val His Trp Val Arg Gln Ser Pro Gly Lys Gly Leu Glu Trp Leu Gly
 1               5                  10                  15

Val

<210> SEQ ID NO 68
<211> LENGTH: 38
<212> TYPE: PRT
<213> ORGANISM: Artificial Sequence
<220> FEATURE:
<223> OTHER INFORMATION: - mAB 12D1 HC variable region FR3

<400> SEQUENCE: 68

Asp Tyr Asn Ala Ala Phe Ile Ser Arg Leu Ser Ile Ser Lys Asp Asn
 1               5                  10                  15

Ser Lys Ser Gln Val Phe Phe Lys Met Asn Ser Leu Gln Ala Asn Asp
                20                  25                  30

Thr Ala Ile Tyr Tyr Cys
            35

<210> SEQ ID NO 69
<211> LENGTH: 12
<212> TYPE: PRT
<213> ORGANISM: Artificial Sequence
<220> FEATURE:
<223> OTHER INFORMATION: mAB 12D1 HC variable region FR4

<400> SEQUENCE: 69

Trp Gly Ala Gly Thr Thr Val Thr Val Ser Ser Ala
 1               5                  10

<210> SEQ ID NO 70
<211> LENGTH: 8
<212> TYPE: PRT
<213> ORGANISM: Artificial Sequence
<220> FEATURE:
<223> OTHER INFORMATION: mAB 12D1 HC variable region CDR1

<400> SEQUENCE: 70

Gly Phe Ser Leu Thr Thr Tyr Gly
 1               5

<210> SEQ ID NO 71
<211> LENGTH: 6
<212> TYPE: PRT
<213> ORGANISM: Artificial Sequence
<220> FEATURE:
<223> OTHER INFORMATION: mAB 12D1 HC variable region CDR2

<400> SEQUENCE: 71

Ile Trp Arg Gly Gly Ser
 1               5
```

<210> SEQ ID NO 72
<211> LENGTH: 12
<212> TYPE: PRT
<213> ORGANISM: Artificial Sequence
<220> FEATURE:
<223> OTHER INFORMATION: mAB 12D1 HC variable region CDR3

<400> SEQUENCE: 72

Ala Arg Asn Trp Gly Arg Tyr Gly Tyr Phe Asp Val
1               5                   10

<210> SEQ ID NO 73
<211> LENGTH: 19
<212> TYPE: PRT
<213> ORGANISM: Artificial Sequence
<220> FEATURE:
<223> OTHER INFORMATION: mAB 12D1 HC variable region leader sequence

<400> SEQUENCE: 73

Met Ala Val Leu Gly Leu Leu Phe Cys Leu Val Thr Phe Pro Ser Cys
1               5                   10                  15

Val Leu Ser

<210> SEQ ID NO 74
<211> LENGTH: 26
<212> TYPE: PRT
<213> ORGANISM: Artificial Sequence
<220> FEATURE:
<223> OTHER INFORMATION: mAB 12D1 LC variable region FR1

<400> SEQUENCE: 74

Asp Ile Val Leu Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 75
<211> LENGTH: 17
<212> TYPE: PRT
<213> ORGANISM: Artificial Sequence
<220> FEATURE:
<223> OTHER INFORMATION: mAB 12D1 LC variable region FR2

<400> SEQUENCE: 75

Met His Trp Tyr Gln Gln Lys Pro Gly Gln Pro Pro Lys Val Leu Ile
1               5                   10                  15

Tyr

<210> SEQ ID NO 76
<211> LENGTH: 36
<212> TYPE: PRT
<213> ORGANISM: Artificial Sequence
<220> FEATURE:
<223> OTHER INFORMATION: mAB 12D1 LC variable region FR3

<400> SEQUENCE: 76

Asn Leu Glu Ser Gly Ile Pro Ala Arg Phe Ser Gly Ser Gly Ser Arg
1               5                   10                  15

Thr Asp Phe Thr Leu Thr Ile Asn Pro Val Glu Ala Asp Asp Val Ala
            20                  25                  30

Thr Tyr Tyr Cys
            35

<210> SEQ ID NO 77
<211> LENGTH: 12
<212> TYPE: PRT
<213> ORGANISM: Artificial Sequence
<220> FEATURE:
<223> OTHER INFORMATION: mAB 12D1 LC variable region FR4

<400> SEQUENCE: 77

Phe Gly Gly Gly Thr Lys Leu Glu Ile Lys Arg Ala
 1               5                  10

<210> SEQ ID NO 78
<211> LENGTH: 10
<212> TYPE: PRT
<213> ORGANISM: Artificial Sequence
<220> FEATURE:
<223> OTHER INFORMATION: mAB 12D1 LC variable region CDR1

<400> SEQUENCE: 78

Glu Ser Val Asp Ser Tyr Gly Asn Ser Phe
 1               5                  10

<210> SEQ ID NO 79
<211> LENGTH: 3
<212> TYPE: PRT
<213> ORGANISM: Artificial Sequence
<220> FEATURE:
<223> OTHER INFORMATION: mAB 12D1 LC variable region CDR2

<400> SEQUENCE: 79

Arg Ala Ser
 1

<210> SEQ ID NO 80
<211> LENGTH: 9
<212> TYPE: PRT
<213> ORGANISM: Artificial Sequence
<220> FEATURE:
<223> OTHER INFORMATION: mAB 12D1 LC variable region CDR3

<400> SEQUENCE: 80

Gln Gln Ser Asn Gly Asp Pro Arg Thr
 1               5

<210> SEQ ID NO 81
<211> LENGTH: 20
<212> TYPE: PRT
<213> ORGANISM: Artificial Sequence
<220> FEATURE:
<223> OTHER INFORMATION: mAB 12D1 LC variable region leader sequence

<400> SEQUENCE: 81

Met Glu Thr Asp Thr Leu Leu Leu Trp Val Leu Leu Leu Trp Val Pro
 1               5                  10                  15

Gly Ser Thr Gly
            20

<210> SEQ ID NO 82
<211> LENGTH: 24
<212> TYPE: DNA
<213> ORGANISM: Artificial Sequence
<220> FEATURE:
<223> OTHER INFORMATION: mAB 66A6 HC variable region CDR1

<400> SEQUENCE: 82
ggctatacct ttaccaacta tggc                                          24

<210> SEQ ID NO 83
<211> LENGTH: 24
<212> TYPE: DNA
<213> ORGANISM: Artificial Sequence
<220> FEATURE:
<223> OTHER INFORMATION: mAB 66A6 HC variable region CDR2

<400> SEQUENCE: 83
attaacaccg ataccggcga accg                                              24

<210> SEQ ID NO 84
<211> LENGTH: 36
<212> TYPE: DNA
<213> ORGANISM: Artificial Sequence
<220> FEATURE:
<223> OTHER INFORMATION: mAB 66A6 HC variable region CDR3

<400> SEQUENCE: 84
gcgcgcaaca aaaatatga agcgtggttt acccat                                  36

<210> SEQ ID NO 85
<211> LENGTH: 30
<212> TYPE: DNA
<213> ORGANISM: Artificial Sequence
<220> FEATURE:
<223> OTHER INFORMATION: mAB 66A6 LC variable region CDR1

<400> SEQUENCE: 85
gaaagcgtgg atagctatgg caccagcttt                                        30

<210> SEQ ID NO 86
<211> LENGTH: 9
<212> TYPE: DNA
<213> ORGANISM: Artificial Sequence
<220> FEATURE:
<223> OTHER INFORMATION: mAB 66A6 LC variable region CDR2

<400> SEQUENCE: 86 ctggcgagc                                                                9

<210> SEQ ID NO 87
<211> LENGTH: 24
<212> TYPE: DNA
<213> ORGANISM: Artificial Sequence
<220> FEATURE:
<223> OTHER INFORMATION: mAB 66A6 LC variable region CDR3

<400> SEQUENCE: 87
cagcagaaca cgaacatcc gatg                                               24

<210> SEQ ID NO 88
<211> LENGTH: 25
<212> TYPE: PRT
<213> ORGANISM: Artificial Sequence
<220> FEATURE:
<223> OTHER INFORMATION: mAB 66A6 HC variable region FR1

<400> SEQUENCE: 88

Gln Val Gln Leu Gln Gln Ser Gly Pro Glu Leu Lys Lys Pro Gly Glu
 1               5                  10                  15

Thr Val Lys Ile Ser Cys Lys Ala Ser
            20                  25

<210> SEQ ID NO 89

```
<211> LENGTH: 17
<212> TYPE: PRT
<213> ORGANISM: Artificial Sequence
<220> FEATURE:
<223> OTHER INFORMATION: mAB 66A6 HC variable region FR2

<400> SEQUENCE: 89

Met Asn Trp Val Lys Gln Ala Pro Gly Lys Asp Leu Lys Trp Leu Gly
 1               5                  10                  15

Trp

<210> SEQ ID NO 90
<211> LENGTH: 38
<212> TYPE: PRT
<213> ORGANISM: Artificial Sequence
<220> FEATURE:
<223> OTHER INFORMATION: mAB 66A6 HC variable region FR3

<400> SEQUENCE: 90

Thr Tyr Ala Glu Glu Phe Lys Gly Arg Phe Ala Phe Ser Leu Glu Thr
 1               5                  10                  15

Ser Ala Ser Thr Ala Tyr Leu Glu Ile Asn Asn Leu Lys Asn Glu Asp
            20                  25                  30

Ala Ala Thr Tyr Phe Cys
        35

<210> SEQ ID NO 91
<211> LENGTH: 12
<212> TYPE: PRT
<213> ORGANISM: Artificial Sequence
<220> FEATURE:
<223> OTHER INFORMATION: mAB 66A6 HC variable region FR4

<400> SEQUENCE: 91

Trp Gly Gln Gly Thr Leu Val Thr Val Ser Ser Ala
 1               5                  10

<210> SEQ ID NO 92
<211> LENGTH: 8
<212> TYPE: PRT
<213> ORGANISM: Artificial Sequence
<220> FEATURE:
<223> OTHER INFORMATION: mAB 66A6 HC variable region CDR1

<400> SEQUENCE: 92

Gly Tyr Thr Phe Thr Asn Tyr Gly
 1               5

<210> SEQ ID NO 93
<211> LENGTH: 8
<212> TYPE: PRT
<213> ORGANISM: Artificial Sequence
<220> FEATURE:
<223> OTHER INFORMATION: mAB 66A6 HC variable region CDR2

<400> SEQUENCE: 93

Ile Asn Thr Asp Thr Gly Glu Pro
 1               5

<210> SEQ ID NO 94
<211> LENGTH: 12
<212> TYPE: PRT
<213> ORGANISM: Artificial Sequence
<220> FEATURE:
<223> OTHER INFORMATION: mAB 66A6 HC variable region CDR3
```

```
<400> SEQUENCE: 94

Ala Arg Asn Lys Lys Tyr Glu Ala Trp Phe Thr His
1               5                   10

<210> SEQ ID NO 95
<211> LENGTH: 25
<212> TYPE: PRT
<213> ORGANISM: Artificial Sequence
<220> FEATURE:
<223> OTHER INFORMATION: mAB 66A6 HC variable region leader sequence

<400> SEQUENCE: 95

Ser Lys Leu Ala Thr Met Glu Thr Asp Thr Leu Leu Leu Trp Val Leu
1               5                   10                  15

Leu Leu Trp Val Pro Gly Ser Trp Ala
            20                  25

<210> SEQ ID NO 96
<211> LENGTH: 26
<212> TYPE: PRT
<213> ORGANISM: Artificial Sequence
<220> FEATURE:
<223> OTHER INFORMATION: mAB 66A6 LC variable region FR1

<400> SEQUENCE: 96

Asn Ile Val Leu Thr Gln Ser Pro Ala Ser Leu Ala Val Ser Leu Gly
1               5                   10                  15

Gln Arg Ala Thr Ile Ser Cys Lys Ala Ser
            20                  25

<210> SEQ ID NO 97
<211> LENGTH: 21
<212> TYPE: PRT
<213> ORGANISM: Artificial Sequence
<220> FEATURE:
<223> OTHER INFORMATION: mAB 66A6 LC variable region FR2

<400> SEQUENCE: 97

Gly Thr Ser Phe Met His Trp Tyr Gln Gln Lys Pro Gly Gln Pro Pro
1               5                   10                  15

Lys Leu Leu Ile Tyr
            20

<210> SEQ ID NO 98
<211> LENGTH: 36
<212> TYPE: PRT
<213> ORGANISM: Artificial Sequence
<220> FEATURE:
<223> OTHER INFORMATION: mAB 66A6 LC variable region FR3

<400> SEQUENCE: 98

Asn Leu Glu Ser Gly Val Pro Ala Arg Phe Ser Gly Ser Gly Ser Arg
1               5                   10                  15

Thr Asp Phe Thr Leu Thr Ile Asp Pro Val Glu Ala Asp Asp Ala Ala
            20                  25                  30

Thr Tyr Tyr Cys
        35

<210> SEQ ID NO 99
<211> LENGTH: 12
<212> TYPE: PRT
<213> ORGANISM: Artificial Sequence
<220> FEATURE:
<223> OTHER INFORMATION: mAB 66A6 LC variable region FR4
```

```
<400> SEQUENCE: 99

Phe Gly Gly Gly Thr Lys Leu Glu Ile Lys Arg Ala
1               5                   10

<210> SEQ ID NO 100
<211> LENGTH: 6
<212> TYPE: PRT
<213> ORGANISM: Artificial Sequence
<220> FEATURE:
<223> OTHER INFORMATION: mAB 66A6 LC variable region CDR1

<400> SEQUENCE: 100

Glu Ser Val Asp Ser Tyr
1               5

<210> SEQ ID NO 101
<211> LENGTH: 3
<212> TYPE: PRT
<213> ORGANISM: Artificial Sequence
<220> FEATURE:
<223> OTHER INFORMATION: mAB 66A6 LC variable region CDR2

<400> SEQUENCE: 101

Leu Ala Ser
1

<210> SEQ ID NO 102
<211> LENGTH: 8
<212> TYPE: PRT
<213> ORGANISM: Artificial Sequence
<220> FEATURE:
<223> OTHER INFORMATION: mAB 66A6 LC variable region CDR3

<400> SEQUENCE: 102

Gln Gln Asn Asn Glu His Pro Met
1               5

<210> SEQ ID NO 103
<211> LENGTH: 25
<212> TYPE: PRT
<213> ORGANISM: Artificial Sequence
<220> FEATURE:
<223> OTHER INFORMATION: mAB 66A6 LC variable region leader sequence

<400> SEQUENCE: 103

Ser Lys Leu Ala Thr Met Glu Thr Asp Thr Leu Leu Leu Trp Val Leu
1               5                   10                  15
Leu Leu Trp Val Pro Gly Ser Thr Gly
            20                  25

<210> SEQ ID NO 104
<211> LENGTH: 75
<212> TYPE: DNA
<213> ORGANISM: Artificial Sequence
<220> FEATURE:
<223> OTHER INFORMATION: mAB 66A6 HC variable region FR1

<400> SEQUENCE: 104
caggtgcagc tgcagcagag cggcccggaa ctgaaaaaac gggcgaaac cgtgaaaatt    60 agctgcaaag cgagc                                                    75

<210> SEQ ID NO 105
<211> LENGTH: 51
<212> TYPE: DNA
```

```
<213> ORGANISM: Artificial Sequence
<220> FEATURE:
<223> OTHER INFORMATION: mAB 66A6 HC variable region FR2

<400> SEQUENCE: 105
atgaactggg tgaaacaggc gccgggcaaa gatctgaaat ggctgggctg g      51

<210> SEQ ID NO 106
<211> LENGTH: 114
<212> TYPE: DNA
<213> ORGANISM: Artificial Sequence
<220> FEATURE:
<223> OTHER INFORMATION: mAB 66A6 HC variable region FR3

<400> SEQUENCE: 106
acctatgcgg aagaatttaa aggccgcttt gcgtttagcc tggaaaccag cgcgagcacc      60
gcgtatctgg aaattaacaa cctgaaaaac gaagatgcgg cgacctattt ttgc           114

<210> SEQ ID NO 107
<211> LENGTH: 36
<212> TYPE: DNA
<213> ORGANISM: Artificial Sequence
<220> FEATURE:
<223> OTHER INFORMATION: mAB 66A6 HC variable region FR4

<400> SEQUENCE: 107
tggggccagg gcaccctggt gaccgtgagc agcgcg                              36

<210> SEQ ID NO 108
<211> LENGTH: 78
<212> TYPE: DNA
<213> ORGANISM: Artificial Sequence
<220> FEATURE:
<223> OTHER INFORMATION: mAB 66A6 LC variable region FR1

<400> SEQUENCE: 108
aacattgtgc tgacccagag cccggcgagc ctggcggtga gcctgggcca gcgcgcgacc      60
attagctgca aagcgagc                                                   78

<210> SEQ ID NO 109
<211> LENGTH: 51
<212> TYPE: DNA
<213> ORGANISM: Artificial Sequence
<220> FEATURE:
<223> OTHER INFORMATION: mAB 66A6 LC variable region FR2

<400> SEQUENCE: 109
atgcattggt atcagcagaa accgggccag ccgccgaaac tgctgattta t              51

<210> SEQ ID NO 110
<211> LENGTH: 108
<212> TYPE: DNA
<213> ORGANISM: Artificial Sequence
<220> FEATURE:
<223> OTHER INFORMATION: mAB 66A6 LC variable region FR3

<400> SEQUENCE: 110
aacctggaaa gcggcgtgcc ggcgcgcttt agcggcagcg gcagccgcac cgatttacc      60 ctgaccattg atccggtgga agcggatgat gcggcgacct attattgc                 108

<210> SEQ ID NO 111
<211> LENGTH: 36
<212> TYPE: DNA
<213> ORGANISM: Artificial Sequence
```

<220> FEATURE:
<223> OTHER INFORMATION: mAB 66A6 LC variable region FR4

<400> SEQUENCE: 111

```
tttggcggcg gcaccaaact ggaaattaaa cgcgcg                                  36
```

<210> SEQ ID NO 112
<211> LENGTH: 354
<212> TYPE: DNA
<213> ORGANISM: Artificial Sequence
<220> FEATURE:
<223> OTHER INFORMATION: mAB 7A7 HC variable region

<400> SEQUENCE: 112

```
gatgtgcagc tggtggagtc tgggggaggc ttagtgcagc ctggagggtc ccggaaactc        60
tcctgtgcag cctctggatt cactttcagt agctttggaa tgcactgggt tcgtcaggct       120
ccagagaagg ggctggagtg ggtcgcatac attagtagtg cagtagtac catctactat        180
gcagacacag tgaagggccg attcaccatc tccagagaca atcccaagaa caccctgttc       240
ctgcaaatga ccagtctaag gtctgaggac acggccatgt attactgtgc aagaaattac       300
gacgaggact cgatgtctg gggcgcaggg accacggtca ccgtctcctc agcc              354
```

<210> SEQ ID NO 113
<211> LENGTH: 342
<212> TYPE: DNA
<213> ORGANISM: Artificial Sequence
<220> FEATURE:
<223> OTHER INFORMATION: mAB 7A7 LC variable region

<400> SEQUENCE: 113

```
gatgttgtga tgacccaaac tccactctcc ctgcctgtca gtcttggaga tcaagcctcc        60
atctcttgca gatctagtca gagccttgta cacagtaatg gaaacaccta tttacattgg       120
tacctgcaga agccaggcca gtctccaaag ctcctgatct acaaagtttc caaccgattt       180
tctggggtcc cagacaggtt cagtggcagt ggatcaggga cagatttcac actcaagatc       240
agcagagtgg aggctgagga tctgggagtt tatttctgct ctcaaagtac acatgttccg       300
tggacgttcg gtggaggcac caagctggaa atcaaacggg ct                          342
```

<210> SEQ ID NO 114
<211> LENGTH: 118
<212> TYPE: PRT
<213> ORGANISM: Artificial Sequence
<220> FEATURE:
<223> OTHER INFORMATION: mAB 7A7 HC variable region

<400> SEQUENCE: 114

```
Asp Val Gln Leu Val Glu Ser Gly Gly Gly Leu Val Gln Pro Gly Gly
  1               5                  10                  15

Ser Arg Lys Leu Ser Cys Ala Ala Ser Gly Phe Thr Phe Ser Ser Phe
             20                  25                  30

Gly Met His Trp Val Arg Gln Ala Pro Glu Lys Gly Leu Glu Trp Val
         35                  40                  45

Ala Tyr Ile Ser Ser Gly Ser Ser Thr Ile Tyr Tyr Ala Asp Thr Val
     50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95
```

Ala Arg Asn Tyr Asp Glu Asp Phe Asp Val Trp Gly Ala Gly Thr Thr
                100                 105                 110

Val Thr Val Ser Ser Ala
        115

<210> SEQ ID NO 115
<211> LENGTH: 114
<212> TYPE: PRT
<213> ORGANISM: Artificial Sequence
<220> FEATURE:
<223> OTHER INFORMATION: mAB 7A7 LC variable region

<400> SEQUENCE: 115

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Ala

<210> SEQ ID NO 116
<211> LENGTH: 357
<212> TYPE: DNA
<213> ORGANISM: Artificial Sequence
<220> FEATURE:
<223> OTHER INFORMATION: mAB 12D1 HC variable region

<400> SEQUENCE: 116
caggtgcacc tggagcagtc aggacctggc ctagtgcagc cctcacagag cctgtccatc        60
acctgcacag tctctggttt ctcattaaca acgtatggtg tacactgggt tcgccagtct       120
ccaggaaagg gtctggagtg gctgggagtg atatggagag tggaagcat agactataat        180 gcagctttca tatccagact gagcatcagc aaggacaatt ccaagagcca gttttctttt       240
aaaatgaaca gtctgcaagc taatgacaca gccatatatt actgtgccag aaattggggt       300
aggtacggat acttcgatgt ctggggcgca gggaccacgg tcaccgtctc ctcagcc         357

<210> SEQ ID NO 117
<211> LENGTH: 339
<212> TYPE: DNA
<213> ORGANISM: Artificial Sequence
<220> FEATURE:
<223> OTHER INFORMATION: mAB 12D1 LC variable region

<400> SEQUENCE: 117
gacattgtgc tgacccaatc tccagcttct ttggctgtgt ctctagggca gagggccacc        60
atatcctgca gagccagtga agtgttgat agttatggca acagtttat gcactggtac        120 cagcagaaac aggacagcc acccaaagtc ctcatctatc gtgcatccaa cctagaatct       180
gggatccctg ccaggttcag tggcagtggg tctaggacag acttcaccct caccattaat       240

```
cctgtggagg ctgatgatgt tgcaacctat tactgtcagc aaagtaatgg ggatcctcgg    300
acgttcggtg gaggcaccaa gctggaaatc aaacgggct                           339
```

<210> SEQ ID NO 118
<211> LENGTH: 119
<212> TYPE: PRT
<213> ORGANISM: Artificial Sequence
<220> FEATURE:
<223> OTHER INFORMATION: mAB 12D1 HC variable region

<400> SEQUENCE: 118

Gln Val His Leu Glu Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Ile Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Asn Trp Gly Arg Tyr Gly Tyr Phe Asp Val Trp Gly Ala Gly Thr
            100                 105                 110

Thr Val Thr Val Ser Ser Ala
        115

<210> SEQ ID NO 119
<211> LENGTH: 112
<212> TYPE: PRT
<213> ORGANISM: Artificial Sequence
<220> FEATURE:
<223> OTHER INFORMATION: mAB 12D1 LC variable region

<400> SEQUENCE: 119

Ile Val Leu Thr Gln Ser Pro Ala Ser Leu Ala Val Ser Leu Gly Gln
1               5                   10                  15

Arg Ala Thr Ile Ser Cys Arg Ala Ser Glu Ser Val Asp Ser Tyr Gly
            20                  25                  30

Asn Ser Phe Met His Trp Tyr Gln Gln Lys Pro Gly Gln Pro Pro Lys
        35                  40                  45

Val Leu Ile Tyr Arg Ala Ser Asn Leu Glu Ser Gly Ile Pro Ala Arg
    50                  55                  60

Phe Ser Gly Ser Gly Ser Arg Thr Asp Phe Thr Leu Thr Ile Asn Pro
65                  70                  75                  80

Val Glu Ala Asp Asp Val Ala Thr Tyr Tyr Cys Gln Gln Ser Asn Gly
                85                  90                  95

Asp Pro Arg Thr Phe Gly Gly Gly Thr Lys Leu Glu Ile Lys Arg Ala
            100                 105                 110

<210> SEQ ID NO 120
<211> LENGTH: 359
<212> TYPE: DNA
<213> ORGANISM: Artificial Sequence
<220> FEATURE:
<223> OTHER INFORMATION: mAB 66A6 HC variable region

<400> SEQUENCE: 120

```
aggtgcagct gcagcagagc ggcccggaac tgaaaaaacc gggcgaaacc gtgaaaatta    60
gctgcaaagc gagcggctat acctttacca actatggcat gaactgggtg aaacaggcgc   120
cgggcaaaga tctgaaatgg ctgggctgga ttaacaccga taccggcgaa ccgacctatg   180
cggaagaatt taaaggccgc tttgcgttta gcctggaaac cagcgcgagc accgcgtatc   240
tggaaattaa caacctgaaa aacgaagatg cggcgaccta ttttgcgcg cgcaacaaaa    300 aatatgaagc gtggtttacc cattggggcc agggcaccct ggtgaccgtg agcagcgcg   359

<210> SEQ ID NO 121
<211> LENGTH: 336
<212> TYPE: DNA
<213> ORGANISM: Artificial Sequence
<220> FEATURE:
<223> OTHER INFORMATION: mAB 66A6 LC variable region

<400> SEQUENCE: 121
aacattgtgc tgacccagag cccggcgagc ctggcggtga gcctgggcca gcgcgcgacc    60
attagctgca aagcgagcga aagcgtggat agctatggca ccagctttat gcattggtat   120
cagcagaaac cgggccagcc gccgaaactg ctgatttatc tggcgagcaa cctggaaagc   180
ggcgtgccgg cgcgctttag cggcagcggc agccgcaccg attttaccct gaccattgat   240
ccggtggaag cggatgatgc ggcgacctat tattgccagc agaacaacga acatccgatg   300
tttggcggcg gcaccaaact ggaaattaaa cgcgcg                              336

<210> SEQ ID NO 122
<211> LENGTH: 120
<212> TYPE: PRT
<213> ORGANISM: Artificial Sequence
<220> FEATURE:
<223> OTHER INFORMATION: mAB 66A6 HC variable region

<400> SEQUENCE: 122

Gln Val Gln Leu Gln Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Asp Leu Lys Trp Leu
        35                  40                  45

Gly Trp Ile Asn Thr Asp Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Glu Ile Asn Asn Leu Lys Asn Glu Asp Ala Ala Thr Tyr Phe Cys
                85                  90                  95

Ala Arg Asn Lys Lys Tyr Glu Ala Trp Phe Thr His Trp Gly Gln Gly
            100                 105                 110

Thr Leu Val Thr Val Ser Ser Ala
        115                 120

<210> SEQ ID NO 123
<211> LENGTH: 112
<212> TYPE: PRT
<213> ORGANISM: Artificial Sequence
<220> FEATURE:
<223> OTHER INFORMATION: mAB 66A6 LC variable region

<400> SEQUENCE: 123

Asn Ile Val Leu Thr Gln Ser Pro Ala Ser Leu Ala Val Ser Leu Gly
```

```
                1               5              10              15

Gln Arg Ala Thr Ile Ser Cys Lys Ala Ser Glu Ser Val Asp Ser Tyr
                    20              25              30

Gly Thr Ser Phe Met His Trp Tyr Gln Gln Lys Pro Gly Gln Pro Pro
            35              40              45

Lys Leu Leu Ile Tyr Leu Ala Ser Asn Leu Glu Ser Gly Val Pro Ala
        50              55              60

Arg Phe Ser Gly Ser Gly Ser Arg Thr Asp Phe Thr Leu Thr Ile Asp
65              70              75              80

Pro Val Glu Ala Asp Asp Ala Ala Thr Tyr Tyr Cys Gln Gln Asn Asn
                85              90              95

Glu His Pro Met Phe Gly Gly Gly Thr Lys Leu Glu Ile Lys Arg Ala
                100             105             110

<210> SEQ ID NO 124
<211> LENGTH: 31
<212> TYPE: PRT
<213> ORGANISM: Artificial Sequence
<220> FEATURE:
<223> OTHER INFORMATION: Amino acids 76 to 106 of the hemagglutinin
      polypeptide of Influenza strain A/Hong Kong/1/1968
      (H3) numbered with classical numbering system

<400

4. An isolated antibody that binds to SEQ ID NO:1, SEQ ID NO:124, or SEQ ID NO:125, and neutralizes two or more strains of an Influenza A virus HA subtype.

5. An isolated antibody that binds to Influenza A virus of the H3 subtype, the antibody comprising (a) the variable heavy (VH) domain of the antibody 7A7, 12D1, 39A4, or 66A6; (b) the variable light (VL) domain of the antibody 7A7, 12D1, 39A4, or 66A6; (c) the VH domain of the antibody 7A7, 12D1, 39A4, or 66A6 and the VL domain of the antibody 7A7, 12D1, 39A4, or 66A6; (d) the VH complementarity determining regions (CDRs) of the antibody 7A7, 12D1, 39A4, or 66A6; (e) the VL CDRs of the antibody 7A7, 12D1, 39A4, or 66A6; or (f) the VH CDRs of the antibody 7A7, 12D1, 39A4, or 66A6 and the VL CDRs of the antibody 7A7, 12D1, 39A4, or 66A6.

6. A composition comprising the antibody of claim 3.

7. A method of preventing an Influenza virus disease comprising administering to a subject the antibody of claim 3.

8. A method of detecting a strain of Influenza A virus H3 subtype comprising: (a) assaying for the level of an Influenza virus HA in cells or a tissue sample of a subject using the antibody of claim 2 or 3; and (b) comparing the level of the Influenza virus HA assayed in (a) with the level of the Influenza virus HA in normal tissue samples not infected with Influenza virus, wherein an increase in the assayed level of Influenza virus HA compared to the control level of the Influenza virus antigen is indicative of the presence of a strain of Influenza A virus H3 subtype.

9. A kit comprising, in a container, the antibody of claim 3.

10. An isolated nucleic acid encoding an antibody that binds to Influenza A virus of the H3 subtype, wherein the antibody comprises (a) the amino acid sequence of the VH domain of the antibody 7A7, 12D1, 39A4, or 66A6; (b) the amino acid sequence of the VL domain of the antibody 7A7, 12D1, 39A4, or 66A6; (c) the amino acid sequence of the VH domain of the antibody 7A7, 12D1, 39A4, or 66A6 and the VL domain of the antibody 7A7, 12D1, 39A4, or 66A6; (d) the amino acid sequence of the VH CDRs of the antibody 7A7, 12D1, 39A4, or 66A6; (e) the amino acid sequence of the VL CDRs of the antibody 7A7, 12D1, 39A4, or 66A6; or (f) the VH CDRs of the antibody 7A7, 12D1, 39A4, or 66A6 and the VL CDRs of the antibody 7A7, 12D1, 39A4, or 66A6.

11. A host cell genetically engineered to contain or express the nucleic acid of claim 10.

12. A method of producing an antibody, comprising culturing the host cell of claim 11 under conditions in which the nucleic acid is expressed and recovering the antibody from the host cell culture.

13. The method of claim 7, wherein the subject is a human.

14. An isolated antibody that binds to Influenza A virus of the H3 subtype, the antibody comprising
(a) a heavy chain variable region comprising a complementarity determining region (CDR)1 having the amino acid sequence of SEQ ID NO:38, a CDR2 having the amino acid sequence of SEQ ID NO:39, and a CDR3 having the amino acid sequence of SEQ ID NO:40; and a light chain variable region comprising a CDR1 having the amino acid sequence of SEQ ID NO:46, a CDR2 having the amino acid sequence of SEQ ID NO:47, and a CDR3 having the amino acid sequence of SEQ ID NO:48;
(b) a heavy chain variable region comprising a CDR1 having the amino acid sequence of SEQ ID NO:70, a CDR2 having the amino acid sequence of SEQ ID NO:71, and a CDR3 having the amino acid sequence of SEQ ID NO:72; and a light chain variable region comprising a CDR1 having the amino acid sequence of SEQ ID NO:78, a CDR2 having the amino acid sequence of SEQ ID NO:79, and a CDR3 having the amino acid sequence of SEQ ID NO:80;
(c) a heavy chain variable region comprising a CDR1 having the amino acid sequence of SEQ ID NO:92, a CDR2 having the amino acid sequence of SEQ ID NO:93, and a CDR3 having the amino acid sequence of SEQ ID NO:94; and a light chain variable region comprising a CDR1 having the amino acid sequence of SEQ ID NO:100, a CDR2 having the amino acid sequence of SEQ ID NO: 101, and a CDR3 having the amino acid sequence of SEQ ID NO:102; or
(d) a heavy chain variable region comprising a CDR1 of the antibody 39A4, a CDR2 of the antibody 39A4, and a CDR3 of the antibody 39A4; and a light chain variable region comprising a CDR1 of the antibody 39A4, a CDR2 of the antibody 39A4, and a CDR3 of the antibody 39A4.

15. The antibody of claim 14, wherein the antibody comprises a heavy chain variable region comprising a complementarity determining region (CDR)1 having the amino acid sequence of SEQ ID NO:38, a CDR2 having the amino acid sequence of SEQ ID NO:39, and a CDR3 having the amino acid sequence of SEQ ID NO:40; and a light chain variable region comprising a CDR1 having the amino acid sequence of SEQ ID NO:46, a CDR2 having the amino acid sequence of SEQ ID NO:47, and a CDR3 having the amino acid sequence of SEQ ID NO:48.

16. The antibody of claim 14, wherein the antibody comprises a heavy chain variable region comprising a CDR1 having the amino acid sequence of SEQ ID NO:70, a CDR2 having the amino acid sequence of SEQ ID NO:71, and a CDR3 having the amino acid sequence of SEQ ID NO:72; and a light chain variable region comprising a CDR1 having the amino acid sequence of SEQ ID NO:78, a CDR2 having the amino acid sequence of SEQ ID NO:79, and a CDR3 having the amino acid sequence of SEQ ID NO:80.

17. The antibody of claim 14, wherein the antibody comprises a heavy chain variable region comprising a CDR1 having the amino acid sequence of SEQ ID NO:92, a CDR2 having the amino acid sequence of SEQ ID NO:93, and a CDR3 having the amino acid sequence of SEQ ID NO:94; and a light chain variable region comprising a CDR1 having the amino acid sequence of SEQ ID NO:100, a CDR2 having the amino acid sequence of SEQ ID NO: 101, and a CDR3 having the amino acid sequence of SEQ ID NO:102.

18. The antibody of claim 14, wherein the antibody comprises a heavy chain variable region comprising a CDR1 of the antibody 39A4, a CDR2 of the antibody 39A4, and a CDR3 of the antibody 39A4; and a light chain variable region comprising a CDR1 of the antibody 39A4, a CDR2 of the antibody 39A4, and a CDR3 of the antibody 39A4.

19. The antibody of claim 15, wherein the heavy chain variable region comprises the amino acid sequence of SEQ ID NO:6, and the light chain variable region comprises the amino acid sequence of SEQ ID NO:7.

20. The antibody of claim 16, wherein the heavy chain variable region comprises the amino acid sequence of SEQ ID NO:12, and the light chain variable region comprising the amino acid sequence of SEQ ID NO:13.

21. The antibody of claim 17, wherein the heavy chain variable region comprising the amino acid sequence of SEQ ID NO:16, and the light chain variable region comprising the amino acid sequence of SEQ ID NO:17.

22. The antibody of claim 18, wherein the heavy chain variable region comprising the amino acid sequence of the heavy chain variable region of antibody 39A4, and the light chain variable region comprising the amino acid sequence of the heavy chain variable region of antibody 39A4.

23. The isolated antibody of claim 14, wherein the antibody is a humanized or chimeric antibody.

24. A method of preventing an Influenza virus disease comprising administering to a subject the antibody of claim 14.

25. The method of claim 24, wherein the subject is a human.

26. A method of detecting a strain of Influenza A virus H3 subtype comprising: (a) assaying for the level of an Influenza virus HA in cells or a tissue sample of a subject using the antibody of claim 14; and (b) comparing the level of the Influenza virus HA assayed in (a) with the level of the Influenza virus HA in normal tissue samples not infected with Influenza virus, wherein an increase in the assayed level of Influenza virus HA compared to the control level of the Influenza virus antigen is indicative of the presence of a strain of Influenza A virus H3 subtype.

27. An isolated nucleic acid encoding the antibody of claim 14.

28. A host cell genetically engineered to contain or express the nucleic acid of claim 26.

29. A method of producing an antibody, comprising culturing the host cell of claim 28 under conditions in which the nucleic acid is expressed and recovering the antibody from the host cell culture.

30. A method of preventing an Influenza virus disease comprising administering to a subject the antibody of claim 4.

31. The method of claim 28, wherein the subject is a human.

32. A method of detecting a strain of Influenza A virus H3 subtype comprising: (a) assaying for the level of an Influenza virus HA in cells or a tissue sample of a subject using the antibody of claim 4; and (b) comparing the level of the Influenza virus HA assayed in (a) with the level of the Influenza virus HA in normal tissue samples not infected with Influenza virus, wherein an increase in the assayed level of Influenza virus HA compared to the control level of the Influenza virus antigen is indicative of the presence of a strain of Influenza A virus H3 subtype.

33. The hybridoma of claim 1, which is designated 7A7 deposited under provisions of the Budapest Treaty with the American Type Culture Collection (ATCC, 10801 University Blvd., Manassas, Va. 20110-2209) on May 22, 2009 (ATCC Accession No. PTA-10058).

34. The hybridoma of claim 1, which is designated 12D1 deposited under provisions of the Budapest Treaty with the American Type Culture Collection (ATCC, 10801 University Blvd., Manassas, Va. 20110-2209) on May 22, 2009 (ATCC Accession No. PTA-10059).

35. The hybridoma of claim 1, which is designated 39A4 deposited under provisions of the Budapest Treaty with the American Type Culture Collection (ATCC, 10801 University Blvd., Manassas, Va. 20110-2209) on May 22, 2009 (ATCC Accession No. PTA-10060).

36. The hybridoma of claim 1, which is designated 66A6 deposited under provisions of the Budapest Treaty with the American Type Culture Collection (ATCC, 10801 University Blvd., Manassas, Va. 20110-2209) on May 26, 2010 (ATCC Accession No. PTA-11046).

* * * * *